(12) United States Patent
Ellmark et al.

(10) Patent No.: US 11,780,928 B2
(45) Date of Patent: Oct. 10, 2023

(54) POLYPEPTIDES

(71) Applicant: ALLIGATOR BIOSCIENCE AB, Lund (SE)

(72) Inventors: Peter Ellmark, Lund (SE); Christina Furebring, Lund (SE); Per Norlen, Lund (SE); Eva Dahlen, Lund (SE); Sara Fritzell, Lund (SE); Laura Von Schantz, Lund (SE); Niina Veitonmaki, Lund (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 214 days.

(21) Appl. No.: 17/229,130

(22) Filed: Apr. 13, 2021

(65) Prior Publication Data

US 2021/0238298 A1 Aug. 5, 2021

Related U.S. Application Data

(63) Continuation of application No. 15/567,163, filed as application No. PCT/EP2016/061420 on May 20, 2016, now Pat. No. 11,008,396.

(30) Foreign Application Priority Data

| May 21, 2015 | (GB) | ..................................... | 1508729 |
| Aug. 24, 2015 | (GB) | ..................................... | 1514994 |
| Mar. 31, 2016 | (GB) | ..................................... | 1605450 |

(51) Int. Cl.
| *C07K 16/30* | (2006.01) |
| *C07K 16/28* | (2006.01) |
| *A61K 39/395* | (2006.01) |
| *A61K 47/68* | (2017.01) |
| *A61P 35/02* | (2006.01) |
| *A61P 35/00* | (2006.01) |
| *A61K 39/00* | (2006.01) |
| *A61K 38/00* | (2006.01) |

(52) U.S. Cl.
CPC .... *C07K 16/2878* (2013.01); *A61K 39/39541* (2013.01); *A61K 47/6849* (2017.08); *A61P 35/00* (2018.01); *A61P 35/02* (2018.01); *C07K 16/2818* (2013.01); *C07K 16/30* (2013.01); *A61K 38/00* (2013.01); *A61K 2039/505* (2013.01); *A61K 2039/507* (2013.01); *C07K 2317/21* (2013.01); *C07K 2317/31* (2013.01); *C07K 2317/33* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/624* (2013.01); *C07K 2317/732* (2013.01); *C07K 2317/734* (2013.01); *C07K 2317/74* (2013.01); *C07K 2317/75* (2013.01); *C07K 2317/76* (2013.01); *C07K 2317/92* (2013.01); *C07K 2319/30* (2013.01); *C07K 2319/32* (2013.01); *C07K 2319/74* (2013.01)

(58) Field of Classification Search
None
See application file for complete search history.

(56) References Cited

U.S. PATENT DOCUMENTS

| 9,872,909 | B2 | 1/2018 | Traber et al. | |
| 11,180,568 | B2 * | 11/2021 | Gray | ........................ A61P 11/00 |
| 2010/0303811 | A1 | 12/2010 | Ochi | |
| 2014/0377255 | A1 | 12/2014 | Ahrens et al. | |

FOREIGN PATENT DOCUMENTS

| EP | 2399935 A2 | 12/2011 |
| WO | 2012/145183 A2 | 10/2012 |
| WO | 2015/095423 A2 | 6/2015 |

OTHER PUBLICATIONS

Chin, et al., "Structure of the 4-1BB/4-1BBL complex and distinct binding and functional properties of utomilumab and urelumab" Nature Communications (2018) 9:4679.
Almagro, et al. "Humanization of antibodies" Frontiers in Bioscience (2008) 13:1619-1633.
Hornig, et al., "Evaluating combinations of costimulatory antibody-ligand fusion proteins for targeted cancer immunotherapy" Cancer Immunol. Immunother. (2013) 62:1369-1380.
Houot, et al., "Therapeutic effect of CD137 immunomodulation in lymphoma and its enhancement by Treg depletion" Blood (2009) 114:3431-3438.
Husain, et al., "Expanding the Boundaries of Biotherapeutics with Bispecific Antibodies" BioDrugs (2018) 32:441-464.
Linch, et al., "Combined OX40 ligation plus CTLA-4 blockade" OncoImmunology (2014) 3:e28245.
Redmond, et al., "Combined Targeting of Costimulatory (OX40) and Coinhibitory (CTLA-4) Pathways Elicits Potent Effector T Cells Capable of Driving Robust Antitumor Immunity" Cancer Immunol. Res. (2014) 2(2):142-53.
International Search Report and Written Opinion for PCT/EP2016/061420, dated Sep. 26, 2016.

(Continued)

*Primary Examiner* — Meera Natarajan
(74) *Attorney, Agent, or Firm* — Robert C. Netter, Jr.; Dann, Dorfman, Herrell & Skillman

(57) ABSTRACT

The present invention provides a bispecific polypeptides, such as bispecific antibodies, comprising a first binding domain capable of specifically binding to a first T cell target, and a second binding domain capable of specifically binding to a second T cell target, wherein the first and second T cell targets are different targets. The invention further provides compositions of said bispecific polypeptides, as well as methods and uses of the same.

15 Claims, 32 Drawing Sheets

Specification includes a Sequence Listing.

(56) References Cited

OTHER PUBLICATIONS

Palazon, et al., "Agonist Anti-CD137 mAb Act on Tumor Endothelial Cells to Enhance Recruitment of Activated T Lymphocytes" Cancer Res. (2011) 71(3):801-11.

Li, et al., "Immunotherapy of melanoma with the immune costimulatory monoclonal antibodies targeting CD137" Clinical Pharmacology: Advances and Applications (2013) 5(Suppl 1):47-53.

Carter, et al., "Antibody-Drug Conjugates for Cancer Therapy" The Cancer Journal (2008) 14(3):154-169.

Doppalapudi, et al., "Chemical generation of bispecific antibodies" PNAS (2010) 107(52):22611-22616.

Stagg, et al., "Anti-ErbB-2 mAb therapy requires type I and II interferons and synergizes with anti-PD-1 or anti-CD137 mAb therapy" PNAS (2011) 108(17):7142-7147.

Bartkowiak, et al., "4-1BB agonists: multi-potent potentiators of tumor immunity" Front. Oncol. (2015) 5:117.

\* cited by examiner

FIGURE 1
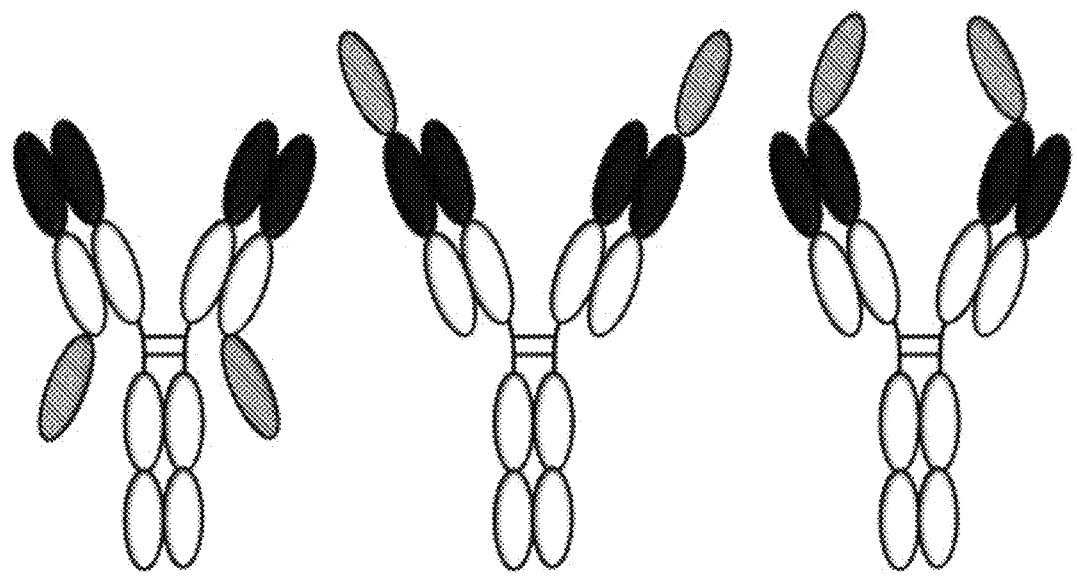
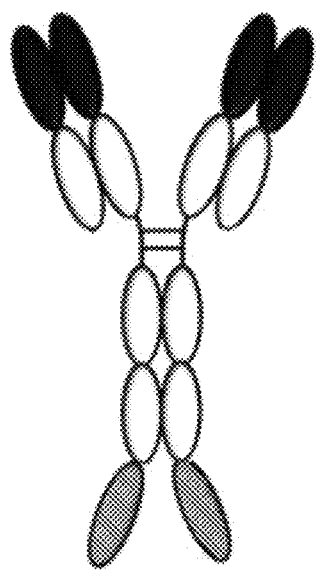

FIGURE 2
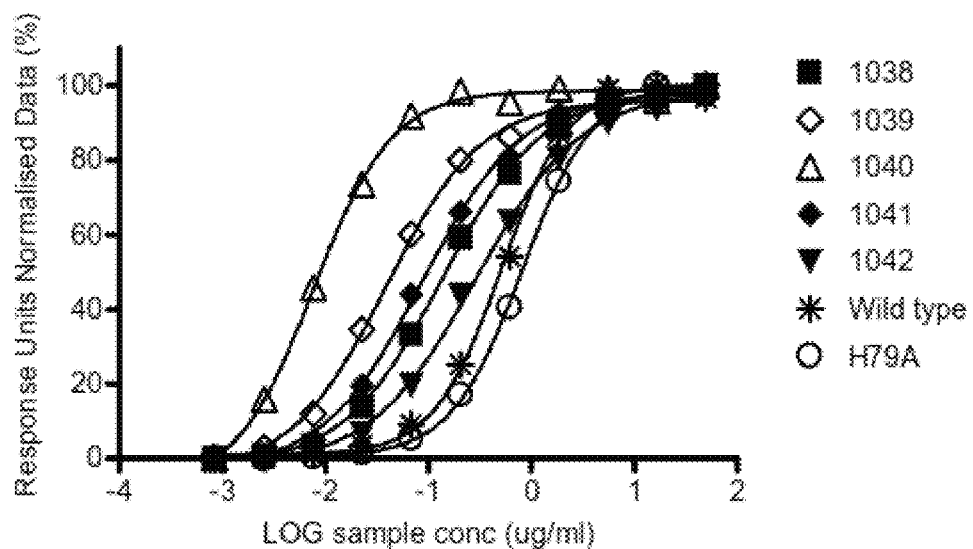
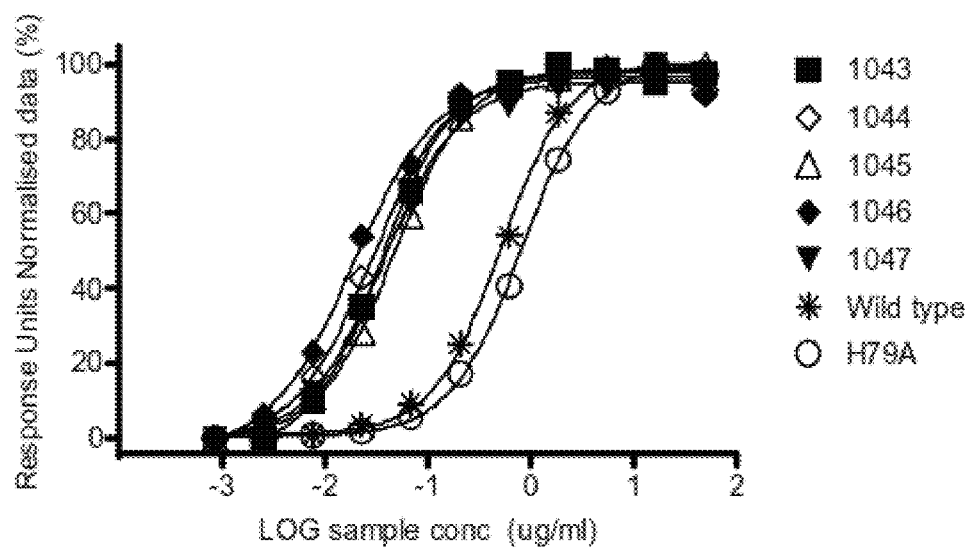

FIGURE 3
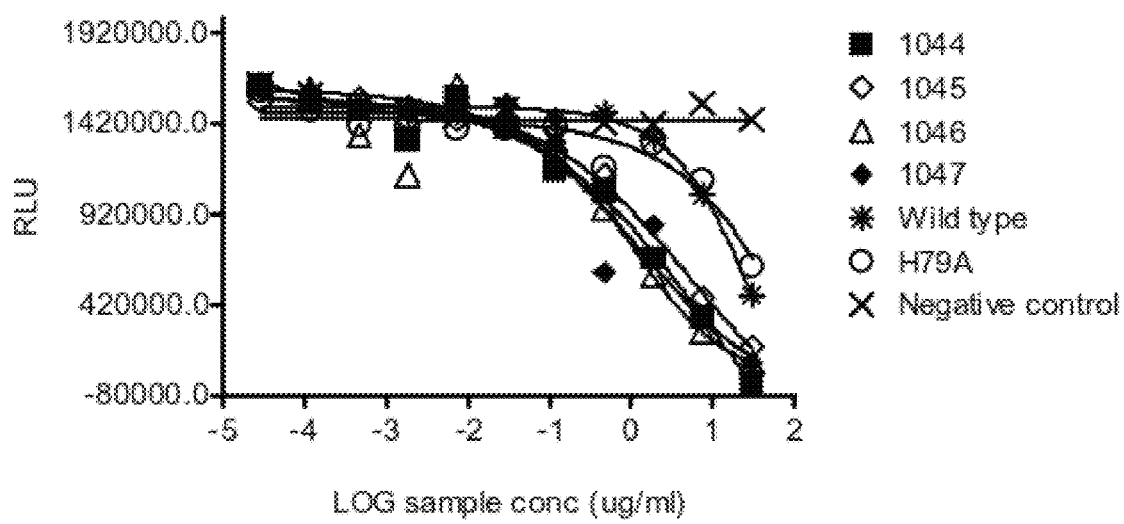
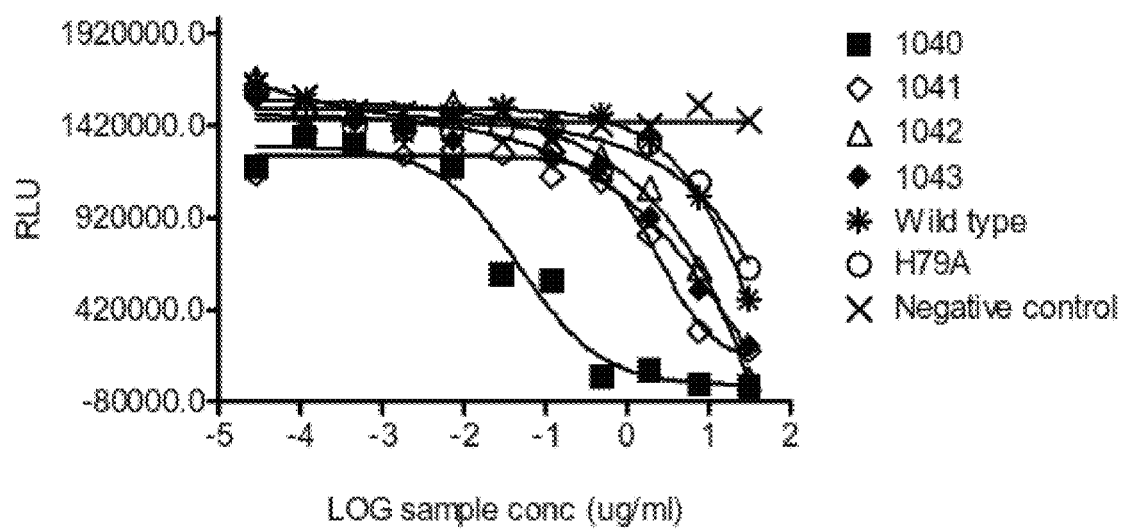

FIGURE 4

A      SEQ ID NO:3

```
                          24
                          |
                        APLKIQA YFNETADLPC QFANSQNQSL SELVVFWQDQ    60
ENLVLNEVYL GKEKFDSVHS KYMGRTSFDS DSWTLRLHNL QIKDKGLYQC IIHHKKPTGM  120
IRIHQMNSEL SVLA                                                    134
```

B      SEQ ID NO:4

```
MDPQCTMGLS NILFVMAFLL SGAAPLKIQA YFNETADLPC QFANSQNQSL SELVVFWQDQ   60
ENLVLNEVYL GKEKFDSVHS KYMGRTSFDS DSWTLRLHNL QIKDKGLYQC IIHHKKPTGM  120
IRIHQMNSEL SVLANFSQPE IVPISNITEN VYINLTCSSI HGYPEPKKMS VLLRTRNSTI  180
EYDGIMQKSQ DNVTELYDVS ISLSVSFPDV TSNMTIFCIL ETDKTRLLSS PFSIELEDPQ  240
PPPDRIP                                                            247
```

C      SEQ ID NO:44

```
MDPQCTMGLS NILFVMAFLL SGAAPLKIQA YFNETADLPC QFANSQNQSL SELVVFWQDQ   60
ENLVLNEVYL GKEKFDSVHS KYMGRTSFDS DSWTLRLHNL QIKDKGLYQC IIHHKKPTGM  120
IRIHQMNSEL SVLANFSQPE IVPISNITEN VYINLTCSSI HGYPEPKKMS VLLRTRNSTI  180
EYDGIMQKSQ DNVTELYDVS ISLSVSFPDV TSNMTIFCIL ETDKTRLLSS PFSIELEDPQ  240
PPPDRIPWIT AVLPTVIICV MVFCLILWKW KKKRPRNSY KCGTNTMERE ESEQTKKREK  300
IRIPERSDEA QRVFKSSKTS SCDKSDTCF                                    
```

FIGURE 7 continued
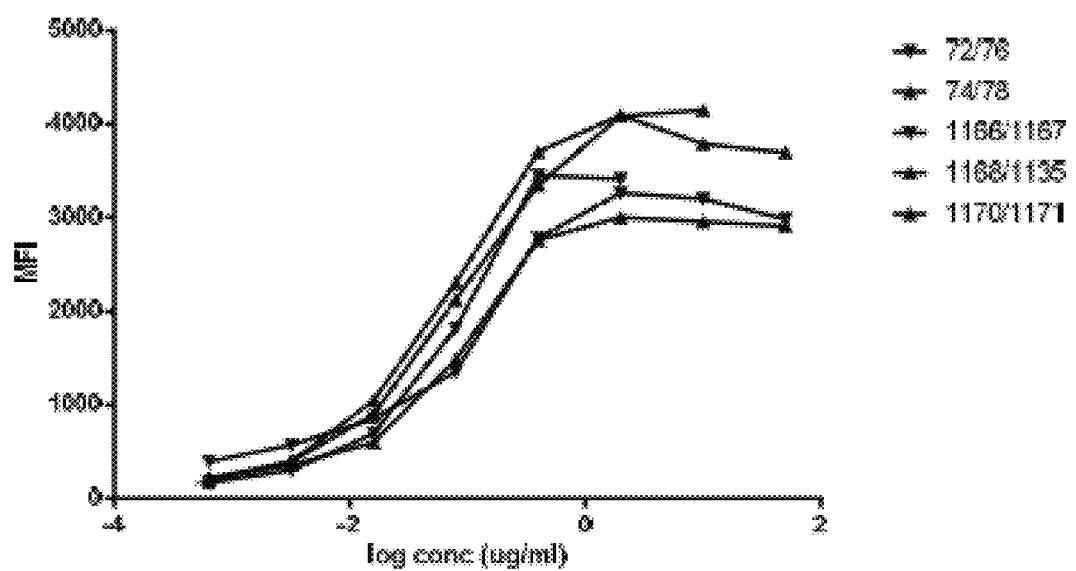
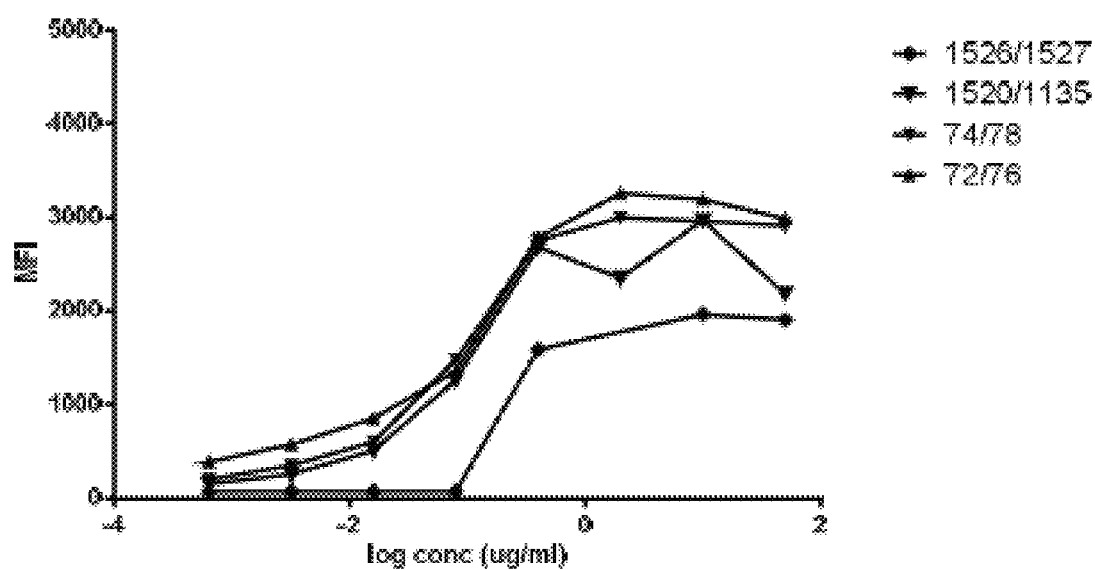

FIGURE 11
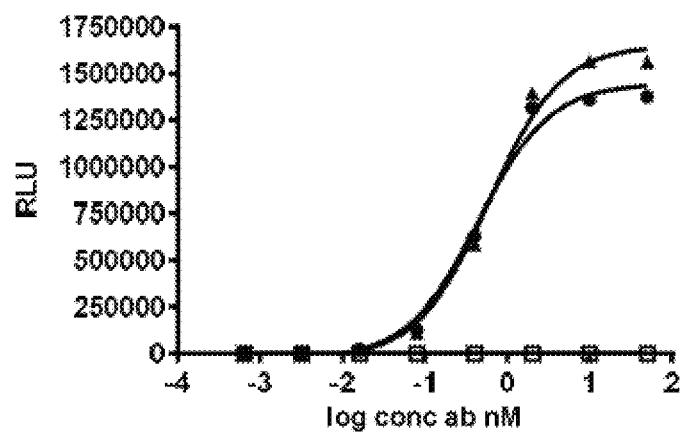
▲ 1164/1141
● 1168/1141
□ Negative control 1
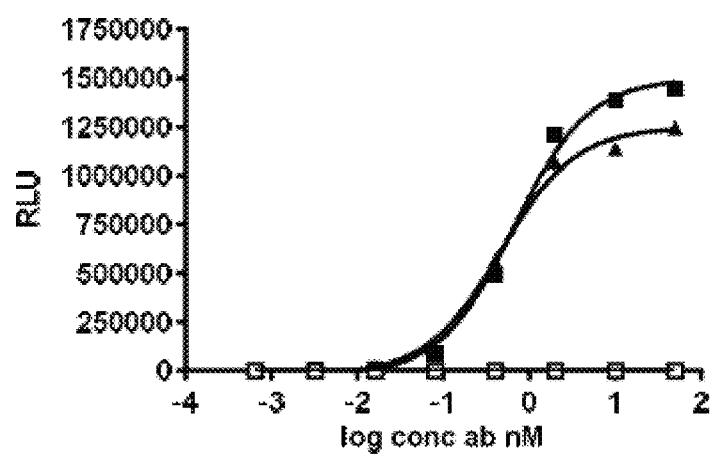
■ 1166/1261
▲ 1170/1263
□ Negative control

FIGURE 21

| Gene ID | Domain/Module diagram |
|---------|----------------------|
|         | Domain: 1, 2, 3, 4; Module: A, B, A, B, A, B; Signal peptide |
| 1407    | Modules 1, 2A, 2B filled (dark) |
| 1408    | Modules 2A, 2B, 3A filled |
| 1409    | Modules 2B, 3A, 3B filled |
| 1410    | Modules 3A, 3B, 4A filled |
| 1411    | Modules 3B, 4A, 4B filled |
| 1412    | Module 1 and 4B + C-terminal extension filled |

FIGURE 24
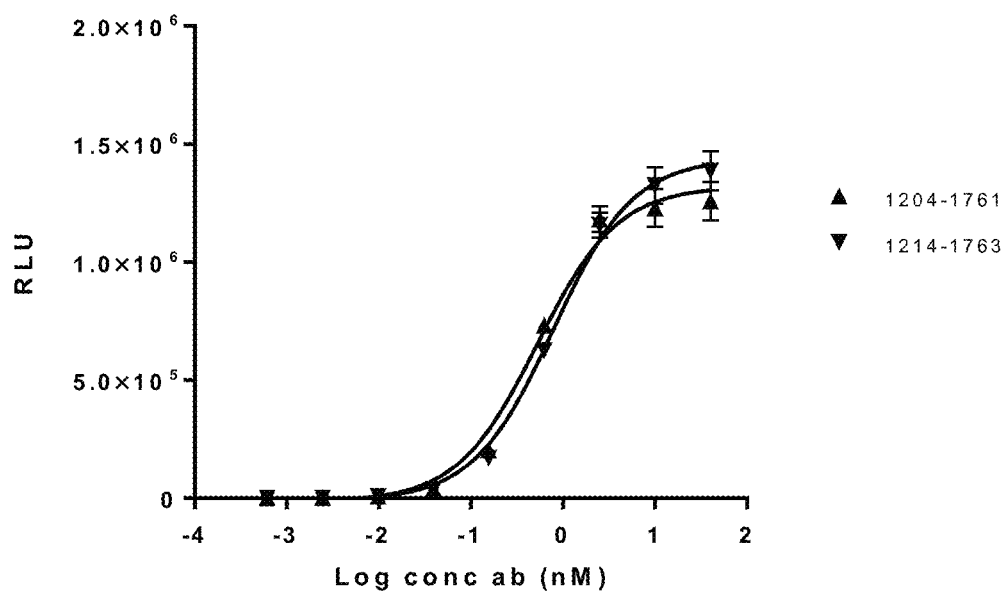
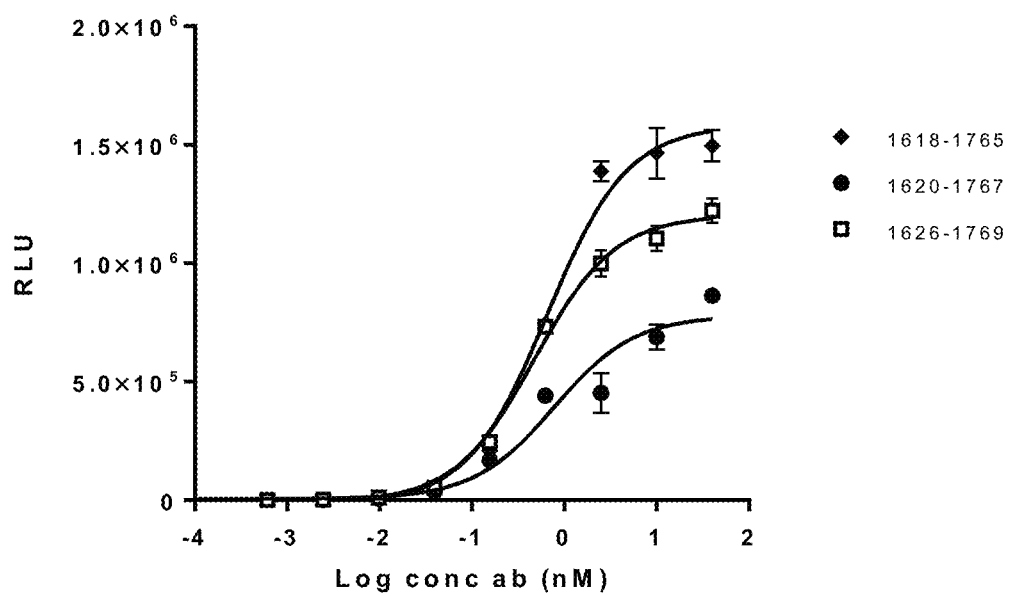

SEQUENCE LISTING

```
<160> NUMBER OF SEQ ID NOS: 226

<210> SEQ ID NO 1
<211> LENGTH: 137
<212> TYPE: PRT
<213> ORGANISM: Homo sapiens
<220> FEATURE:
<223> OTHER INFORMATION: CTLA-4

<400> SEQUENCE: 1

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Ala Lys Glu Lys Lys Pro Ser Tyr Asn Arg Gly Leu Cys
        115                 120                 125

Glu Asn Ala Pro Asn Arg Ala Arg Met
    130                 135

<210> SEQ ID NO 2
<211> LENGTH: 220
<212> TYPE: PRT
<213> ORGANISM: Homo sapiens
<220> FEATURE:
<223> OTHER INFORMATION: CD28
```

```
<400> SEQUENCE: 2

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
                35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
    210                 215                 220

<210> SEQ ID NO 3
<211> LENGTH: 111
<212> TYPE: PRT
<213> ORGANISM: Homo sapiens

<400> SEQUENCE: 3

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
            35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala
            100                 105                 110

<210> SEQ ID NO 4
<211> LENGTH: 247
<212> TYPE: PRT
<213> ORGANISM: Homo sapiens
```

<400> SEQUENCE: 4

```
Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro
            245
```

<210> SEQ ID NO 5
<211> LENGTH: 111
<212> TYPE: PRT
<213> ORGANISM: Homo sapiens

<400> SEQUENCE: 5

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val Ala Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala
            100                 105                 110
```

<210> SEQ ID NO 6
<211> LENGTH: 109
<212> TYPE: PRT
<213> ORGANISM: Artificial Sequence
<220> FEATURE:
<223> OTHER INFORMATION: Sequence of clone number 900

<400> SEQUENCE: 6

```
Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val Asp Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Ile Tyr Gln Cys Val Ile His His Lys Pro Ser Gly Leu Val
                85                  90                  95

Lys Ile His Glu Met Asn Ser Glu Leu Ser Val Leu Ala
            100                 105
```

<210> SEQ ID NO 7
<211> LENGTH: 109
<212> TYPE: PRT
<213> ORGANISM: Artificial Sequence
<220> FEATURE:
<223> OTHER INFORMATION: Sequence of clone number 901

<400> SEQUENCE: 7

```
Leu Lys Ile Gln Ala Tyr Phe Asn Glu Thr Ala Asp Leu Pro Cys Gln
1               5                   10                  15

Phe Ala Asn Ser Gln Asn Leu Thr Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val His Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Ile Tyr Gln Cys Val Ile His His Lys Pro Thr Gly Met Ile
                85                  90                  95

Lys Ile His Glu Met Asn Ser Glu Leu Ser Val Leu Thr
            100                 105
```

<210> SEQ ID NO 8
<211> LENGTH: 109
<212> TYPE: PRT
<213> ORGANISM: Artificial Sequence
<220> FEATURE:
<223> OTHER INFORMATION: Sequence of clone number 904

<400> SEQUENCE: 8

```
Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Ile Val Phe Trp
            20                  25                  30

Gln Asp Gln Glu Asn Leu Val Leu Asn Glu Val Tyr Leu Gly Lys Glu
```

```
                35                  40                  45
Arg Phe Asp Ala Val Asp Ser Lys Tyr Met Gly Arg Thr Ser Phe Asp
 50                  55                  60

Ser Asp Ser Trp Thr Leu Arg Leu His Asn Leu Gln Ile Lys Asp Lys
 65                  70                  75                  80

Gly Ile Tyr Gln Cys Ile Ile His His Lys Lys Pro Ser Gly Met Val
                 85                  90                  95

Lys Ile His Gln Met Asp Ser Glu Leu Ser Val Leu Ala
                100                 105
```

<210> SEQ ID NO 9
<211> LENGTH: 109
<212> TYPE: PRT
<213> ORGANISM: Artificial Sequence
<220> FEATURE:
<223> OTHER INFORMATION: Sequence of clone number number 906

<400> SEQUENCE: 9

```
Leu Lys Ile Gln Ala Tyr Ile Asn Glu Thr Ala Asp Leu Pro Cys Gln
 1               5                  10                  15

Phe Ala Asn Ser Gln Asn Leu Ser Leu Ser Glu Leu Val Val Phe Trp
                20                  25                  30

Gln Asp Gln Glu Asn Leu Val Leu Asn Glu Val Tyr Leu Gly Lys Glu
            35                  40                  45

Arg Phe Asp Ser Val Asp Ser Lys Tyr Met Gly Arg Thr Ser Phe Asp
 50                  55                  60

Ser Asp Ser Trp Thr Leu Arg Leu His Asn Leu Gln Ile Lys Asp Lys
 65                  70                  75                  80

Gly Phe Tyr Gln Cys Ile Ile His His Lys Lys Pro Thr Gly Leu Val
                 85                  90                  95

Lys Ile His Glu Met Asn Ser Glu Leu Ser Val Leu Ala
                100                 105
```

<210> SEQ ID NO 10
<211> LENGTH: 109
<212> TYPE: PRT
<213> ORGANISM: Artificial Sequence
<220> FEATURE:
<223> OTHER INFORMATION: Sequence of clone number 907

<400> SEQUENCE: 10

```
Leu Lys Ile Gln Ala Tyr Phe Asn Glu Thr Ala Asp Leu Pro Cys Gln
 1               5                  10                  15

Phe Ala Asn Ser Gln Asn Gln Ser Leu Ser Glu Leu Val Val Phe Trp
                20                  25                  30

Gln Asp Gln Glu Asn Leu Val Leu Asn Glu Val Tyr Leu Gly Lys Glu
            35                  40                  45

Lys Phe Asp Ser Val His Ser Lys Tyr Met Gly Arg Thr Ser Phe Asp
 50                  55                  60

Ser Asp Ser Trp Thr Leu Arg Leu His Asn Leu Gln Ile Lys Asp Lys
 65                  70                  75                  80

Gly Leu Tyr Gln Cys Ile Ile His His Lys Lys Pro Thr Gly Met Ile
                 85                  90                  95

Lys Ile His Glu Met Asn Ser Glu Leu Ser Val Leu Ala
                100                 105
```

<210> SEQ ID NO 11
<211> LENGTH: 109

-continued

```
<212> TYPE: PRT
<213> ORGANISM: Artificial Sequence
<220> FEATURE:
<223> OTHER INFORMATION: Sequence of clone number 908

<400> SEQUENCE: 11

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val His Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Ile Tyr Gln Cys Ile Ile His His Lys Lys Pro Thr Gly Met Val
                85                  90                  95

Lys Ile His Glu Met Asn Ser Glu Leu Ser Val Leu Ala
            100                 105

<210> SEQ ID NO 12
<211> LENGTH: 109
<212> TYPE: PRT
<213> ORGANISM: Artificial Sequence
<220> FEATURE:
<223> OTHER INFORMATION: Sequence of clone number 910

<400> SEQUENCE: 12

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val Asp Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Ile Tyr Gln Cys Ile Ile His His Lys Lys Pro Thr Gly Met Val
                85                  90                  95

Lys Ile His Glu Met Asn Ser Glu Leu Ser Val Leu Ala
            100                 105

<210> SEQ ID NO 13
<211> LENGTH: 109
<212> TYPE: PRT
<213> ORGANISM: Artificial Sequence
<220> FEATURE:
<223> OTHER INFORMATION: Sequence of clone number 915

<400> SEQUENCE: 13

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30

Gln Asp Gln Glu Asn Leu Ile Leu Asn Glu Val Tyr Leu Gly Lys Glu
        35                  40                  45

Lys Phe Asp Ser Val Asp Ser Lys Tyr Met Gly Arg Thr Ser Phe Asp
```

```
                 50                  55                  60
Ser Asp Ser Trp Thr Leu Arg Leu His Asn Leu Gln Ile Lys Asp Lys
 65                  70                  75                  80

Gly Phe Tyr Gln Cys Ile Ile His Lys Lys Pro Ser Gly Leu Ile
                 85                  90                  95

Lys Ile His Gln Met Asp Ser Glu Leu Ser Val Leu Ala
                100                 105

<210> SEQ ID NO 14
<211> LENGTH: 109
<212> TYPE: PRT
<213> ORGANISM: Artificial Sequence
<220> FEATURE:
<223> OTHER INFORMATION: Sequence of clone number 938

<400> SEQUENCE: 14

Leu Lys Ile Gln Ala Tyr Phe Asn Glu Thr Ala Asp Leu Pro Cys Gln
 1               5                  10                  15

Phe Ala Asn Ser Gln Asn Gln Ser Leu Ser Glu Leu Val Val Phe Trp
                20                  25                  30

Gln Asp Gln Glu Asn Leu Ile Leu Asn Glu Val Tyr Leu Gly Lys Glu
            35                  40                  45

Lys Phe Asp Ser Val His Ser Lys Tyr Met Gly Arg Thr Ser Phe Asp
        50                  55                  60

Ser Asp Ser Trp Thr Leu Arg Leu His Asn Leu Gln Ile Lys Asp Lys
 65                  70                  75                  80

Gly Ile Tyr Gln Cys Ile Ile His His Lys Lys Pro Thr Gly Met Val
                 85                  90                  95

Lys Ile His Gln Met Asn Ser Glu Leu Ser Val Leu Ala
                100                 105

<210> SEQ ID NO 15
<211> LENGTH: 111
<212> TYPE: PRT
<213> ORGANISM: Artificial Sequence
<220> FEATURE:
<223> OTHER INFORMATION: Sequence of clone number 1038

<400> SEQUENCE: 15

Ala Pro Leu Lys Ile Gln Ala Tyr Phe Asn Glu Thr Ala Asp Leu Pro
 1               5                  10                  15

Cys Gln Phe Ala Asn Ser Gln Asn Leu Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val Asp Ser Lys Tyr Met Gly Arg Thr Ser
        50                  55                  60

Phe Asp Ser Asp Ser Trp Thr Leu Arg Leu His Asn Leu Gln Ile Lys
 65                  70                  75                  80

Asp Lys Gly Ile Tyr Gln Cys Ile Ile His His Lys Lys Pro Thr Gly
                 85                  90                  95

Met Val Lys Ile His Glu Met Asn Ser Glu Leu Ser Val Leu Ala
                100                 105                 110

<210> SEQ ID NO 16
<211> LENGTH: 111
<212> TYPE: PRT
<213> ORGANISM: Artificial Sequence
<220> FEATURE:
```

<223> OTHER INFORMATION: Sequence of clone number 1039

<400> SEQUENCE: 16

```
Ala Pro Leu Lys Ile Gln Ala Tyr Phe Asn Glu Thr Ala Asp Leu Pro
1               5                   10                  15
Cys Gln Phe Ala Asn Ser Gln Asn Leu Ser Leu Ser Glu Leu Val Val
            20                  25                  30
Phe Trp Gln Asp Gln Glu Asn Leu Val Leu Asn Glu Val Tyr Leu Gly
        35                  40                  45
Lys Glu Lys Phe Asp Ser Val Ser Ser Lys Tyr Met Gly Arg Thr Ser
    50                  55                  60
Phe Asp Ser Asp Ser Trp Thr Leu Arg Leu His Asn Leu Gln Ile Lys
65                  70                  75                  80
Asp Lys Gly Ile Tyr Gln Cys Ile Ile His His Lys Lys Pro Ser Gly
                85                  90                  95
Met Val Lys Ile His Gln Met Asp Ser Glu Leu Ser Val Leu Ala
            100                 105                 110
```

<210> SEQ ID NO 17
<211> LENGTH: 111
<212> TYPE: PRT
<213> ORGANISM: Artificial Sequence
<220> FEATURE:
<223> OTHER INFORMATION: Sequence of clone number 1040

<400> SEQUENCE: 17

```
Ala Pro Leu Lys Ile Gln Ala Tyr Phe Asn Glu Thr Ala Asp Leu Pro
1               5                   10                  15
Cys Gln Phe Ala Asn Ser Gln Asn Leu Ser Leu Ser Glu Leu Val Val
            20                  25                  30
Phe Trp Gln Asp Gln Glu Asn Leu Val Leu Asn Glu Val Tyr Leu Gly
        35                  40                  45
Lys Glu Arg Phe Asp Ser Val Asp Ser Lys Tyr Met Gly Arg Thr Ser
    50                  55                  60
Phe Asp Ser Asp Ser Trp Thr Leu Arg Leu His Asn Leu Gln Ile Lys
65                  70                  75                  80
Asp Lys Gly Arg Tyr Gln Cys Ile Ile His His Lys Lys Pro Thr Gly
                85                  90                  95
Met Ile Asn Ile His Gln Met Asn Ser Glu Leu Ser Val Leu Ala
            100                 105                 110
```

<210> SEQ ID NO 18
<211> LENGTH: 111
<212> TYPE: PRT
<213> ORGANISM: Artificial Sequence
<220> FEATURE:
<223> OTHER INFORMATION: Sequence of clone number 1041

<400> SEQUENCE: 18

```
Ala Pro Leu Lys Ile Gln Ala Tyr Leu Asn Glu Thr Ala Asp Leu Pro
1               5                   10                  15
Cys Gln Phe Ala Asn Ser Gln Asn Leu Ser Leu Ser Glu Leu Val Val
            20                  25                  30
Phe Trp Gln Asp Gln Glu Asn Leu Val Leu Asn Glu Val Tyr Leu Gly
        35                  40                  45
Lys Glu Lys Phe Asp Ser Val Asp Ser Lys Tyr Met Gly Arg Thr Ser
    50                  55                  60
Phe Asp Ser Asp Ser Trp Thr Leu Arg Leu His Asn Leu Gln Ile Lys
```

```
                65                  70                  75                  80
Asp Lys Gly Ile Tyr Gln Cys Ile Ile His His Lys Pro Thr Gly
                    85                  90                  95

Leu Val Lys Ile His Glu Met Asn Ser Glu Leu Ser Val Leu Ala
            100                 105                 110
```

<210> SEQ ID NO 19
<211> LENGTH: 111
<212> TYPE: PRT
<213> ORGANISM: Artificial Sequence
<220> FEATURE:
<223> OTHER INFORMATION: Sequence of clone number 1042

<400> SEQUENCE: 19

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Ile Phe Asp Ser Val Ser Ser Lys Tyr Met Gly Arg Thr Ser
        50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His Lys Lys Pro Ser Gly
                    85                  90                  95

Met Val Lys Ile His Gln Met Asp Ser Glu Leu Ser Val Leu Ala
            100                 105                 110
```

<210> SEQ ID NO 20
<211> LENGTH: 111
<212> TYPE: PRT
<213> ORGANISM: Artificial Sequence
<220> FEATURE:
<223> OTHER INFORMATION: Sequence of clone number 1043

<400> SEQUENCE: 20

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val Asp Ser Lys Tyr Met Gly Arg Thr Ser
        50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Lys Pro Thr Gly
                    85                  90                  95

Met Ile Lys Ile His Glu Met Asn Ser Glu Leu Ser Val Leu Ala
            100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: Sequence of clone number 1044

<400> SEQUENCE: 21

Ala Pro Leu Lys Ile Gln Ala Tyr Phe Asn Glu Thr Ala Asp Leu Pro
1               5                   10                  15

Cys Gln Phe Ala Asn Ser Gln Asn Leu Thr Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val Ser Ser Lys Tyr Met Gly Arg Thr Ser
50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Lys Pro Thr Gly
                85                  90                  95

Met Ile Lys Ile His Glu Met Ser Ser Glu Leu Ser Val Leu Ala
                100                 105                 110

<210> SEQ ID NO 22
<211> LENGTH: 111
<212> TYPE: PRT
<213> ORGANISM: Artificial Sequence
<220> FEATURE:
<223> OTHER INFORMATION: Sequence of clone number 1045

<400> SEQUENCE: 22

Ala Pro Leu Lys Ile Gln Ala Tyr Phe Asn Glu Thr Ala Asp Leu Pro
1               5                   10                  15

Cys Gln Phe Ala Asn Ser Gln Asn Leu Thr Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val Asp Ser Lys Tyr Met Gly Arg Thr Ser
50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Leu Val Lys Ile His Glu Met Asn Ser Glu Leu Ser Val Leu Ala
                100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Sequence of clone number 1046

<400> SEQUENCE: 23

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val Asp Ser Lys Tyr Met Gly Arg Thr Ser
50                  55                  60

Phe Asp Ser Asp Ser Trp Thr Leu Arg Leu His Asn Leu Gln Ile Glu
65                  70                  75                  80

Asp Lys Gly Ile Tyr Gln Cys Ile Ile His His Lys Lys Pro Ser Gly

```
                85                  90                  95
Met Val Lys Ile His Gln Met Asp Ser Glu Leu Ser Val Leu Ala
            100                 105                 110
```

<210> SEQ ID NO 24
<211> LENGTH: 111
<212> TYPE: PRT
<213> ORGANISM: Artificial Sequence
<220> FEATURE:
<223> OTHER INFORMATION: Sequence of clone number 1047

<400> SEQUENCE: 24

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val Asp Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Ile Tyr Gln Cys Ile Ile His His Lys Lys Pro Thr Gly
                85                  90                  95

Leu Val Lys Ile His Glu Met Asn Ser Glu Leu Ser Val Leu Ala
            100                 105                 110
```

<210> SEQ ID NO 25
<211> LENGTH: 327
<212> TYPE: DNA
<213> ORGANISM: Artificial Sequence
<220> FEATURE:
<223> OTHER INFORMATION: Sequence of clone number 900

<400> SEQUENCE: 25

```
ctcaaaatcc aagcgtactt caacgaaact gcagacttac cgtgtcagtt tgccaattcg      60
cagaatcaaa gcctgagcga actggtggtt ttctggcagg atcaggagaa cctggttctg     120
aacgaagtct atctgggcaa agagaaattc gacagcgtgg acagcaagta tatgggccgc     180
accagctttg atagcgacag ctggaccctg cgtctgcaca atctgcaaat caaagataag     240
ggtatctacc agtgcgtgat ccaccataag aagccgagcg gtctggtgaa gattcacgag     300
atgaactccg agttgtctgt cctggcg                                         327
```

<210> SEQ ID NO 26
<211> LENGTH: 327
<212> TYPE: DNA
<213> ORGANISM: Artificial Sequence
<220> FEATURE:
<223> OTHER INFORMATION: Sequence of clone number 901

<400> SEQUENCE: 26

```
ctcaaaatcc aagcgtactt caacgaaact gcagacttac cgtgtcagtt tgccaattcg      60
cagaatctga ccctgagcga actggtggtt ttctggcagg atcaggagaa cctggttctg     120
aacgaagtct atctgggcaa agagaaattc gacagcgtgc atagcaagta tatgggccgc     180
accagctttg atagcgacag ctggaccctg cgtctgcaca atctgcaaat caaagataag     240
ggtatctacc agtgcgtgat ccaccataag aagccgacgg gtatgattaa gattcacgag     300
atgaactccg agttgtctgt cctgacc                                         327
```

<210> SEQ ID NO 27
<211> LENGTH: 327
<212> TYPE: DNA
<213> ORGANISM: Artificial Sequence
<220> FEATURE:
<223> OTHER INFORMATION: Sequence of clone number 904

<400> SEQUENCE: 27

```
ctcaaaatcc aagcgtactt caacgaaact gcagacttac cgtgtcagtt tgccaattcg      60
cagaatcaaa gcctgagcga actgatcgtt ttctggcagg atcaggagaa cctggttctg     120
aacgaagtct atctgggcaa agagcggttc gacgccgtgg acagcaagta tatgggccgc     180
accagctttg atagcgacag ctggaccctg cgtctgcaca atctgcaaat caaagataag     240
ggtatctacc agtgcattat ccaccataag aagccgagcg gtatggtgaa gattcaccaa     300
atggactccg agttgtctgt cctggcg                                         327
```

<210> SEQ ID NO 28
<211> LENGTH: 327
<212> TYPE: DNA
<213> ORGANISM: Artificial Sequence
<220> FEATURE:
<223> OTHER INFORMATION: Sequence of clone number 906

<400> SEQUENCE: 28

```
ctcaaaatcc aagcgtacat caacgaaact gcagacttac cgtgtcagtt tgccaattcg      60
cagaatctga gcctgagcga actggtggtt ttctggcagg atcaggagaa cctggttctg     120
aacgaagtct atctgggcaa agagcggttc gacagcgtgg acagcaagta tatgggccgc     180
accagctttg atagcgacag ctggaccctg cgtctgcaca atctgcaaat caaagataag     240
ggtttctacc agtgcattat ccaccataag aagccgacgg gtctggtgaa gattcacgag     300
atgaactccg agttgtctgt cctggcg                                         327
```

<210> SEQ ID NO 29
<211> LENGTH: 327
<212> TYPE: DNA
<213> ORGANISM: Artificial Sequence
<220> FEATURE:
<223> OTHER INFORMATION: Sequence of clone number 907

<400> SEQUENCE: 29

```
ctcaaaatcc aagcgtactt caacgaaact gcagacttac cgtgtcagtt tgccaattcg      60
cagaatcaaa gcctgagcga actggtggtt ttctggcagg atcaggagaa cctggttctg     120
aacgaagtct atctgggcaa agagaaattc gacagcgtgc atagcaagta tatgggccgc     180
accagctttg atagcgacag ctggaccctg cgtctgcaca atctgcaaat caaagataag     240
ggtctgtacc agtgcattat ccaccataag aagccgacgg gtatgattaa gattcacgag     300
atgaactccg agttgtctgt cctggcg                                         327
```

<210> SEQ ID NO 30
<211> LENGTH: 327
<212> TYPE: DNA
<213> ORGANISM: Artificial Sequence
<220> FEATURE:
<223> OTHER INFORMATION: Sequence of clone number 908

<400> SEQUENCE: 30

```
ctcaaaatcc aagcgtactt caacgaaact gcagacttac cgtgtcagtt tgccaattcg      60
```

```
cagaatcaaa gcctgagcga actggtggtt ttctggcagg atcaggagaa cctggttctg    120
aacgaagtct atctgggcaa agagaaattc gacagcgtgc atagcaagta tatgggccgc    180
accagctttg atagcgacag ctggaccctg cgtctgcaca atctgcaaat caaagataag    240
ggtatctacc agtgcattat ccaccataag aagccgacgg gtatggtgaa gattcacgag    300
atgaactccg agttgtctgt cctggcg                                        327

<210> SEQ ID NO 31
<211> LENGTH: 327
<212> TYPE: DNA
<213> ORGANISM: Artificial Sequence
<220> FEATURE:
<223> OTHER INFORMATION: Sequence of clone number 910

<400> SEQUENCE: 31
ctcaaaatcc aagcgtactt caacgaaact gcagacttac cgtgtcagtt tgccaattcg     60
cagaatcaaa gcctgagcga actggtggtt ttctggcagg atcaggagaa cctggttctg    120
aacgaagtct atctgggcaa agagaaattc gacagcgtgg acagcaagta tatgggccgc    180
accagctttg atagcgacag ctggaccctg cgtctgcaca atctgcaaat caaagataag    240
ggtatctacc agtgcattat ccaccataag aagccgacgg gtatggtgaa gattcacgag    300
atgaactccg agttgtctgt cctggcg                                        327

<210> SEQ ID NO 32
<211> LENGTH: 327
<212> TYPE: DNA
<213> ORGANISM: Artificial Sequence
<220> FEATURE:
<223> OTHER INFORMATION: Sequence for clone number 915

<400> SEQUENCE: 32
ctcaaaatcc aagcgtactt caacgaaact gcagacttac cgtgtcagtt tgccaattcg     60
cagaatcaaa gcctgagcga actggtggtt ttctggcagg atcaggagaa cctgatcctg    120
aacgaagtct atctgggcaa agagaaattc gacagcgtgg acagcaagta tatgggccgc    180
accagctttg atagcgacag ctggaccctg cgtctgcaca atctgcaaat caaagataag    240
ggtttctacc agtgcattat ccaccataag aagccgagcg gtctgattaa gattcaccaa    300
atggactccg agttgtctgt cctggcg                                        327

<210> SEQ ID NO 33
<211> LENGTH: 327
<212> TYPE: DNA
<213> ORGANISM: Artificial Sequence
<220> FEATURE:
<223> OTHER INFORMATION: Sequence of clone number 938

<400> SEQUENCE: 33
ctcaaaatcc aagcgtactt caacgaaact gcagacttac cgtgtcagtt tgccaattcg     60
cagaatctga gcctgagcga actggtggtt ttctggcagg atcaggagaa cctgatcctg    120
aacgaagtct atctgggcaa agagcggttc gacagcgtgc atagcaagta tatgggccgc    180
accagctttg atagcgacag ctggaccctg cgtctgcaca atctgcaaat caaagataag    240
ggtctgtacc agtgcattat ccaccataag aagccgagcg gtatggtgaa gattcacgag    300
atgaactccg agttgtctgt cctggcg                                        327

<210> SEQ ID NO 34
<211> LENGTH: 333
```

```
<212> TYPE: DNA
<213> ORGANISM: Artificial Sequence
<220> FEATURE:
<223> OTHER INFORMATION: Sequence of clone number 1038

<400> SEQUENCE: 34
gcccccctca aaatccaagc gtacttcaac gaaactgcag acttaccgtg tcagtttgcc      60
aattcgcaga atctgagcct gagcgaactg gtggttttct ggcaggatca ggagaacctg     120
gttctgaacg aagtctatct gggcaaagag aaattcgaca gcgtggacag caagtatatg     180
ggccgcacca gctttgatag cgacagctgg accctgcgtc tgcacaatct gcaaatcaaa     240 gataaggggta tctaccagtg cattatccac cataagaagc cgacgggtat ggtgaagatt     300
cacgagatga actccgagtt gtctgtcctg gcg                                  333

<210> SEQ ID NO 35
<211> LENGTH: 333
<212> TYPE: DNA
<213> ORGANISM: Artificial Sequence
<220> FEATURE:
<223> OTHER INFORMATION: Sequence of clone number 1039

<400> SEQUENCE: 35
gcccccctca aaatccaagc gtacttcaac gaaactgcag acttaccgtg tcagtttgcc      60
aattcgcaga atctgagcct gagcgaactg gtggttttct ggcaggatca ggagaacctg     120
gttctgaacg aagtctatct gggcaaagag aaattcgaca gcgtgagtag caagtatatg     180
ggccgcacca gctttgatag cgacagctgg accctgcgtc tgcacaatct gcaaatcaaa     240
gataagggta tctaccagtg cattatccac cataagaagc cgagcggtat ggtgaagatt     300
caccaaatgg actccgagtt gtctgtcctg gcg                                  333

<210> SEQ ID NO 36
<211> LENGTH: 333
<212> TYPE: DNA
<213> ORGANISM: Artificial Sequence
<220> FEATURE:
<223> OTHER INFORMATION: Sequence of clone number 1040

<400> SEQUENCE: 36
gcccccctca aaatccaagc gtacttcaac gaaactgcag acttaccgtg tcagtttgcc      60
aattcgcaga atctgagcct gagcgaactg gtggttttct ggcaggatca ggagaacctg     120
gttctgaacg aagtctatct gggcaaagag cggttcgaca gcgtggacag caagtatatg     180
ggccgcacca gctttgatag cgacagctgg accctgcgtc tgcacaatct gcaaatcaaa     240
gataagggta ggtaccagtg cattatccac cataagaagc cgacgggtat gattaatatt     300
caccaaatga actccgagtt gtctgtcctg gcg                                  333

<210> SEQ ID NO 37
<211> LENGTH: 333
<212> TYPE: DNA
<213> ORGANISM: Artificial Sequence
<220> FEATURE:
<223> OTHER INFORMATION: Sequence of clone number 1041

<400> SEQUENCE: 37
gcccccctca aaatccaagc gtacctcaac gaaactgcag acttaccgtg tcagtttgcc      60
aattcgcaga atctgagcct gagcgaactg gtggttttct ggcaggatca ggagaacctg     120
gttctgaacg aagtctatct gggcaaagag aaattcgaca gcgtggacag caagtatatg     180
```

```
ggccgcacca gctttgatag cgacagctgg accctgcgtc tgcacaatct gcaaatcaaa      240
gataagggta tctaccagtg cattatccac cataagaagc cgacgggtct ggtgaagatt      300
cacgagatga actccgagtt gtctgtcctg gcg                                   333
```

<210> SEQ ID NO 38
<211> LENGTH: 333
<212> TYPE: DNA
<213> ORGANISM: Artificial Sequence
<220> FEATURE:
<223> OTHER INFORMATION: Sequence of clone number 1042

<400> SEQUENCE: 38

```
gccccctca aaatccaagc gtacttcaac gaaactgcag acttaccgtg tcagtttgcc       60
aattcgcaga atctgagcct gagcgaactg gtggttttct ggcaggatca ggagaacctg     120
gttctgaacg aagtctatct gggcaaagag attttcgaca gcgtgagtag caagtatatg     180
ggccgcacca gctttgatag tgacagctgg accctgcgtc tgcacaatct gcaaatcaaa     240
gataagggta tctaccagtg cattatccac cataagaagc cgagcggtat ggtgaagatt     300
caccaaatgg actccgagtt gtctgtcctg gcg                                  333
```

<210> SEQ ID NO 39
<211> LENGTH: 333
<212> TYPE: DNA
<213> ORGANISM: Artificial Sequence
<220> FEATURE:
<223> OTHER INFORMATION: Sequence of clone number 1043

<400> SEQUENCE: 39

```
gccccctca aaatccaagc gtacttcaac gaaactgcag acttaccgtg tcagtttgcc       60
aattcgcaga atctgagcct gagcgaactg gtggttttct ggcaggatca ggagaacctg     120
gttctgaacg aagtctatct gggcaaagag aaattcgaca gcgtggatag caagtatatg     180
ggccgcacca gctttgatag cgacagctgg accctgcgtc tgcacaatct gcaaatcaaa     240
gataagggta tctaccagtg cattatccac cataagaagc cgacgggtat gattaagatt     300
cacgagatga actccgagtt gtctgtcctg gcg                                  333
```

<210> SEQ ID NO 40
<211> LENGTH: 333
<212> TYPE: DNA
<213> ORGANISM: Artificial Sequence
<220> FEATURE:
<223> OTHER INFORMATION: Sequence of clone number 1044

<400> SEQUENCE: 40

```
gccccctca aaatccaagc gtacttcaac gaaactgcag acttaccgtg tcagtttgcc       60
aattcgcaga atctgaccct gagcgaactg gtggttttct ggcaggatca ggagaacctg     120
gttctgaacg aagtctatct gggcaaagag aaattcgaca gcgtgtctag caagtatatg     180
ggccgcacca gctttgatag cgacagctgg accctgcgtc tgcacaatct gcaaatcaaa     240
gataagggta tctaccagtg cattatccac cataagaagc cgacgggtat gattaagatt     300
cacgagatga gctccgagtt gtctgtcctg gcg                                  333
```

<210> SEQ ID NO 41
<211> LENGTH: 333
<212> TYPE: DNA
<213> ORGANISM: Artificial Sequence
<220> FEATURE:
<223> OTHER INFORMATION: Sequence of clone number 1045

<400> SEQUENCE: 41

```
gccccctca aaatccaagc gtacttcaac gaaactgcag acttaccgtg tcagtttgcc    60
aattcgcaga atctgaccct gagcgaactg gtggttttct ggcaggatca ggagaacctg   120
gttctgaacg aagtctatct gggcaaagag aaattcgaca gcgtggacag caagtatatg   180
ggccgcacca gctttgatag cgacagctgg accctgcgtc tgcacaatct gcaaatcaaa   240
gataagggtc tgtaccagtg cattatccac cataagaagc cgacgggtct ggtgaagatt   300
cacgagatga actccgagtt gtctgtcctg gcg                                333
```

<210> SEQ ID NO 42
<211> LENGTH: 333
<212> TYPE: DNA
<213> ORGANISM: Artificial Sequence
<220> FEATURE:
<223> OTHER INFORMATION: Sequence of clone number 1046

<400> SEQUENCE: 42

```
gccccctca aaatccaagc gtacttcaac gaaactgcag acttaccgtg tcagtttgcc    60
aattcgcaga atcaaagcct gagcgaactg gtggttttct ggcaggatca ggagaacctg   120
gttctgaacg aagtctatct gggcaaagag aaattcgaca gcgtggacag caagtatatg   180
ggccgcacca gctttgatag cgacagctgg accctgcgtc tgcacaatct gcaaatcgaa   240
gataaggta tctaccagtg cattatccac cataagaagc cgagcggtat ggtgaagatt   300
caccaaatgg actccgagtt gtctgtcctg gcg                                333
```

<210> SEQ ID NO 43
<211> LENGTH: 333
<212> TYPE: DNA
<213> ORGANISM: Artificial Sequence
<220> FEATURE:
<223> OTHER INFORMATION: Sequence of clone number 1047

<400> SEQUENCE: 43

```
gccccctca aaatccaagc gtacttcaac gaaactgcag acttaccgtg tcagtttgcc    60
aattcgcaga atctgagcct gagcgaactg gtggttttct ggcaggatca ggagaacctg   120
gttctgaacg aagtctatct gggcaaagag aaattcgaca gcgtggacag caagtatatg   180
ggccgcacca gctttgatag cgacagctgg accctgcgtc tgcacaatct gcaaatcaaa   240
gataaggta tctaccagtg cattatccac cataagaagc cgacgggtct ggtgaagatt   300
cacgagatga actccgagtt gtctgtcctg gcg                                333
```

<210> SEQ ID NO 44
<211> LENGTH: 329
<212> TYPE: PRT
<213> ORGANISM: Homo sapiens

<400> SEQUENCE: 44

```
Met Asp Pro Gln Cys Thr Met Gly Leu Ser Asn Ile Leu Phe Val Met
1               5                   10                  15
Ala Phe Leu Leu Ser Gly Ala Ala Pro Leu Lys Ile Gln Ala Tyr Phe
            20                  25                  30
Asn Glu Thr Ala Asp Leu Pro Cys Gln Phe Ala Asn Ser Gln Asn Gln
        35                  40                  45
Ser Leu Ser Glu Leu Val Val Phe Trp Gln Asp Gln Glu Asn Leu Val
    50                  55                  60
```

```
Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                 85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325

<210> SEQ ID NO 45
<211> LENGTH: 223
<212> TYPE: PRT
<213> ORGANISM: Mus musculus

<400> SEQUENCE: 45

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
                20                  25                  30

Val Phe Ser Glu Ala Ile Gln Val Thr Gln Pro Ser Val Val Leu Ala
            35                  40                  45

Ser Ser His Gly Val Ala Ser Phe Pro Cys Glu Tyr Ser Pro Ser His
        50                  55                  60

Asn Thr Asp Glu Val Arg Val Thr Val Leu Arg Gln Thr Asn Asp Gln
 65                 70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110
```

```
Asn Leu Thr Ile Gln Gly Leu Arg Ala Val Asp Thr Gly Leu Tyr Leu
        115                 120                 125

Cys Lys Val Glu Leu Met Tyr Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Val Ser Leu Gly Leu Phe Phe
                165                 170                 175

Tyr Ser Phe Leu Val Ser Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
    210                 215                 220

<210> SEQ ID NO 46
<211> LENGTH: 218
<212> TYPE: PRT
<213> ORGANISM: Mus musculus

<400> SEQUENCE: 46

Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
                20                  25                  30

Asp Ser Asn Glu Val Ser Leu Ser Cys Arg Tyr Ser Tyr Asn Leu Leu
            35                  40                  45

Ala Lys Glu Phe Arg Ala Ser Leu Tyr Lys Gly Val Asn Ser Asp Val
        50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
                100                 105                 110

Cys Lys Ile Glu Phe Met Tyr Pro Pro Pro Tyr Leu Asp Asn Glu Arg
                115                 120                 125

Ser Asn Gly Thr Ile Ile His Ile Lys Glu Lys His Leu Cys His Thr
            130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Val Thr Thr Met Asn Met
                180                 185                 190

Thr Pro Arg Arg Pro Gly Leu Thr Arg Lys Pro Tyr Gln Pro Tyr Ala
                195                 200                 205

Pro Ala Arg Asp Phe Ala Ala Tyr Arg Pro
    210                 215

<210> SEQ ID NO 47
<211> LENGTH: 11
<212> TYPE: PRT
<213> ORGANISM: Artificial Sequence
<220> FEATURE:
<223> OTHER INFORMATION: Linker sequence
```

<400> SEQUENCE: 47

Ser Gly Gly Gly Gly Ser Gly Gly Gly Ser
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Linker sequence

<400> SEQUENCE: 48

Ser Gly Gly Gly Gly Ser Gly Gly Gly Ser Ala Pro
1               5                   10

<210> SEQ ID NO 49
<211> LENGTH: 5
<212> TYPE: PRT
<213> ORGANISM: Artificial Sequence
<220> FEATURE:
<223> OTHER INFORMATION: Linker sequence

<400> SEQUENCE: 49

Asn Phe Ser Gln Pro
1               5

<210> SEQ ID NO 50
<211> LENGTH: 5
<212> TYPE: PRT
<213> ORGANISM: Artificial Sequence
<220> FEATURE:
<223> OTHER INFORMATION: Linker sequence

<400> SEQUENCE: 50

Lys Arg Thr Val Ala
1               5

<210> SEQ ID NO 51
<211> LENGTH: 277
<212> TYPE: PRT
<213> ORGANISM: Homo sapiens

<400> SEQUENCE: 51

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 52
<211> LENGTH: 8
<212> TYPE: PRT
<213> ORGANISM: Homo sapiens

<400> SEQUENCE: 52

Gly Phe Thr Phe Gly Gly Tyr Tyr
1               5

<210> SEQ ID NO 53
<211> LENGTH: 8
<212> TYPE: PRT
<213> ORGANISM: Homo sapiens

<400> SEQUENCE: 53

Gly Phe Thr Phe Tyr Gly Ser Ser
1               5

<210> SEQ ID NO 54
<211> LENGTH: 8
<212> TYPE: PRT
<213> ORGANISM: Homo sapiens

<400> SEQUENCE: 54

Gly Phe Thr Phe Ser Gly Ser Ser
1               5

<210> SEQ ID NO 55
<211> LENGTH: 8
<212> TYPE: PRT
<213> ORGANISM: Homo sapiens

<400> SEQUENCE: 55

Gly Phe Thr Phe Ser Ser Tyr Ala
1               5

<210> SEQ ID NO 56
<211> LENGTH: 8
<212> TYPE: PRT
<213> ORGANISM: Homo sapiens

<400> SEQUENCE: 56

```
Gly Phe Thr Phe Gly Tyr Tyr Tyr
1               5

<210> SEQ ID NO 57
<211> LENGTH: 8
<212> TYPE: PRT
<213> ORGANISM: Homo sapiens

<400> SEQUENCE: 57

Gly Phe Thr Phe Gly Ser Tyr Tyr
1               5

<210> SEQ ID NO 58
<211> LENGTH: 8
<212> TYPE: PRT
<213> ORGANISM: Homo sapiens

<400> SEQUENCE: 58

Gly Phe Thr Phe Ser Gly Tyr Ser
1               5

<210> SEQ ID NO 59
<211> LENGTH: 8
<212> TYPE: PRT
<213> ORGANISM: Homo sapiens

<400> SEQUENCE: 59

Gly Phe Thr Phe Gly Ser Ser Ser
1               5

<210> SEQ ID NO 60
<211> LENGTH: 8
<212> TYPE: PRT
<213> ORGANISM: Homo sapiens

<400> SEQUENCE: 60

Ile Ser Gly Ser Gly Gly Ser Thr
1               5

<210> SEQ ID NO 61
<211> LENGTH: 8
<212> TYPE: PRT
<213> ORGANISM: Homo sapiens

<400> SEQUENCE: 61

Ile Pro Gly Ser Gly Gly Ser Thr
1               5

<210> SEQ ID NO 62
<211> LENGTH: 8
<212> TYPE: PRT
<213> ORGANISM: Homo sapiens

<400> SEQUENCE: 62

Ile Tyr Ser Ser Gly Gly Tyr Thr
1               5

<210> SEQ ID NO 63
<211> LENGTH: 8
<212> TYPE: PRT
<213> ORGANISM: Homo sapiens

<400> SEQUENCE: 63

Ile Ser Tyr Tyr Gly Gly Tyr Thr
```

```
<210> SEQ ID NO 64
<211> LENGTH: 8
<212> TYPE: PRT
<213> ORGANISM: Homo sapiens

<400> SEQUENCE: 64

Ile Ser Tyr Tyr Ser Gly Tyr Thr
1               5

<210> SEQ ID NO 65
<211> LENGTH: 8
<212> TYPE: PRT
<213> ORGANISM: Homo sapiens

<400> SEQUENCE: 65

Ile Ser Ser Tyr Gly Ser Tyr Thr
1               5

<210> SEQ ID NO 66
<211> LENGTH: 8
<212> TYPE: PRT
<213> ORGANISM: Homo sapiens

<400> SEQUENCE: 66

Ile Gly Ser Tyr Tyr Gly Tyr Thr
1               5

<210> SEQ ID NO 67
<211> LENGTH: 8
<212> TYPE: PRT
<213> ORGANISM: Homo sapiens

<400> SEQUENCE: 67

Ile Gly Tyr Ser Gly Tyr Gly Thr
1               5

<210> SEQ ID NO 68
<211> LENGTH: 9
<212> TYPE: PRT
<213> ORGANISM: Homo sapiens

<400> SEQUENCE: 68

Ile Gly Tyr Tyr Ser Tyr Ser Thr Ser
1               5

<210> SEQ ID NO 69
<211> LENGTH: 10
<212> TYPE: PRT
<213> ORGANISM: Homo sapiens

<400> SEQUENCE: 69

Ala Arg Tyr Asp Tyr Ala Ser Met Asp Tyr
1               5                   10

<210> SEQ ID NO 70
<211> LENGTH: 10
<212> TYPE: PRT
<213> ORGANISM: Homo sapiens

<400> SEQUENCE: 70

Ala Arg Tyr Asp Tyr Tyr Trp Met Asp Tyr
1               5                   10
```

<210> SEQ ID NO 71
<211> LENGTH: 11
<212> TYPE: PRT
<213> ORGANISM: Homo sapiens

<400> SEQUENCE: 71

Ala Arg Gly Val Pro His Gly Tyr Phe Asp Tyr
1               5                   10

<210> SEQ ID NO 72
<211> LENGTH: 11
<212> TYPE: PRT
<213> ORGANISM: Homo sapiens

<400> SEQUENCE: 72

Ala Arg Tyr Phe Pro His Tyr Tyr Phe Asp Tyr
1               5                   10

<210> SEQ ID NO 73
<211> LENGTH: 9
<212> TYPE: PRT
<213> ORGANISM: Homo sapiens

<400> SEQUENCE: 73

Ala Arg Gly Tyr Gly Tyr Leu Asp Tyr
1               5

<210> SEQ ID NO 74
<211> LENGTH: 11
<212> TYPE: PRT
<213> ORGANISM: Homo sapiens

<400> SEQUENCE: 74

Ala Arg Tyr Tyr Pro His His Tyr Ile Asp Tyr
1               5                   10

<210> SEQ ID NO 75
<211> LENGTH: 14
<212> TYPE: PRT
<213> ORGANISM: Homo sapiens

<400> SEQUENCE: 75

Ala Arg Ser Gly Tyr Ser Asn Trp Ala Asn Ser Phe Asp Tyr
1               5                   10

<210> SEQ ID NO 76
<211> LENGTH: 17
<212> TYPE: PRT
<213> ORGANISM: Homo sapiens

<400> SEQUENCE: 76

Ala Arg Tyr Tyr Tyr Ser His Gly Tyr Tyr Val Tyr Gly Thr Leu Asp
1               5                   10                  15

Tyr

<210> SEQ ID NO 77
<211> LENGTH: 10
<212> TYPE: PRT
<213> ORGANISM: Homo sapiens

<400> SEQUENCE: 77

Ala Arg His Asp Tyr Gly Ala Leu Asp Tyr
1               5                   10

<210> SEQ ID NO 78
<211> LENGTH: 15
<212> TYPE: PRT
<213> ORGANISM: Homo sapiens

<400> SEQUENCE: 78

Ala Arg Tyr Tyr Phe His Asp Tyr Ala Ala Tyr Ser Leu Asp Tyr
1               5                   10                  15

<210> SEQ ID NO 79
<211> LENGTH: 11
<212> TYPE: PRT
<213> ORGANISM: Homo sapiens

<400> SEQUENCE: 79

Ala Arg Gly Tyr Pro His His Tyr Phe Asp Tyr
1               5                   10

<210> SEQ ID NO 80
<211> LENGTH: 6
<212> TYPE: PRT
<213> ORGANISM: Homo sapiens

<400> SEQUENCE: 80

Gln Ser Ile Ser Ser Tyr
1               5

<210> SEQ ID NO 81
<211> LENGTH: 3
<212> TYPE: PRT
<213> ORGANISM: Homo sapiens

<400> SEQUENCE: 81

Ala Ala Ser
1

<210> SEQ ID NO 82
<211> LENGTH: 10
<212> TYPE: PRT
<213> ORGANISM: Homo sapiens

<400> SEQUENCE: 82

Gln Gln Tyr Tyr Trp Tyr Gly Leu Ser Thr
1               5                   10

<210> SEQ ID NO 83
<211> LENGTH: 10
<212> TYPE: PRT
<213> ORGANISM: Homo sapiens

<400> SEQUENCE: 83

Gln Gln Gly His Gly Ser Tyr Pro His Thr
1               5                   10

<210> SEQ ID NO 84
<211> LENGTH: 9
<212> TYPE: PRT
<213> ORGANISM: Homo sapiens

<400> SEQUENCE: 84

Gln Gln Ser Tyr Ser Thr Pro Tyr Thr
1               5

<210> SEQ ID NO 85

<211> LENGTH: 8
<212> TYPE: PRT
<213> ORGANISM: Homo sapiens

<400> SEQUENCE: 85

Gln Gln Tyr Gly Ser Leu Leu Thr
1               5

<210> SEQ ID NO 86
<211> LENGTH: 9
<212> TYPE: PRT
<213> ORGANISM: Homo sapiens

<400> SEQUENCE: 86

Gln Gln Gly Asp Tyr Thr Leu Phe Thr
1               5

<210> SEQ ID NO 87
<211> LENGTH: 10
<212> TYPE: PRT
<213> ORGANISM: Homo sapiens

<400> SEQUENCE: 87

Gln Gln Tyr Gly Pro Ser Gly Leu Phe Thr
1               5                   10

<210> SEQ ID NO 88
<211> LENGTH: 10
<212> TYPE: PRT
<213> ORGANISM: Homo sapiens

<400> SEQUENCE: 88

Gln Gln Tyr Gly Ser Asp Ser Leu Leu Thr
1               5                   10

<210> SEQ ID NO 89
<211> LENGTH: 108
<212> TYPE: PRT
<213> ORGANISM: Homo sapiens

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Trp Tyr Gly Leu
                85                  90                  95

Ser Thr Phe Gly Gln Gly Thr Lys Leu Glu Ile Lys
            100                 105

<210> SEQ ID NO 90
<211> LENGTH: 324
<212> TYPE: DNA
<213> ORGANISM: Homo sapiens

<400> SEQUENCE: 90

```
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag tactactggt acggtctgtc cacttttggc   300
caggggacca agctggagat caaa                                          324
```

<210> SEQ ID NO 91
<211> LENGTH: 117
<212> TYPE: PRT
<213> ORGANISM: Homo sapiens

<400> SEQUENCE: 91

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asp Tyr Ala Ser Met Asp Tyr Trp Gly Gln Gly Thr Leu
            100                 105                 110

Val Thr Val Ser Ser
        115
```

<210> SEQ ID NO 92
<211> LENGTH: 351
<212> TYPE: DNA
<213> ORGANISM: Homo sapiens

<400> SEQUENCE: 92

```
gaggtgcagc tgttggagag cggggggaggc ttggtacagc ctgggggggtc cctgcgcctc    60 tcctgtgcag ccagcggatt cacctttggt ggttactaca tgtcttgggt ccgccaggct   120
ccagggaagg ggctggagtg ggtctcagct attagtggta gtggtggtag cacatactat   180
gcagactccg tgaagggccg gttcaccatc tcccgtgaca attccaagaa cacgctgtat   240
ctgcaaatga acagcctgcg tgccgaggac acggctgtat attattgtgc gcgctacgac   300
tacgcttcta tggactattg gggccaggga accctggtca ccgtctcctc a            351
```

<210> SEQ ID NO 93
<211> LENGTH: 108
<212> TYPE: PRT
<213> ORGANISM: Homo sapiens

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

```
                35                  40                  45
Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Gly Ser Tyr Pro
                 85                  90                  95

His Thr Phe Gly Gln Gly Thr Lys Leu Glu Ile Lys
            100                 105
```

<210> SEQ ID NO 94
<211> LENGTH: 324
<212> TYPE: DNA
<213> ORGANISM: Homo sapiens

<400> SEQUENCE: 94

```
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag ggtcatggtt cttacccgca cacttttggc     300
caggggacca agctggagat caaa                                            324
```

<210> SEQ ID NO 95
<211> LENGTH: 117
<212> TYPE: PRT
<213> ORGANISM: Homo sapiens

<400> SEQUENCE: 95

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Gly Tyr
             20                  25                  30

Tyr Met Ser Trp Val Arg Gln Ala Pro Gly Lys Gly Leu Glu Trp Val
         35                  40                  45

Ser Tyr Ile Pro Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Asp Tyr Tyr Trp Met Asp Tyr Trp Gly Gln Gly Thr Leu
            100                 105                 110

Val Thr Val Ser Ser
        115
```

<210> SEQ ID NO 96
<211> LENGTH: 351
<212> TYPE: DNA
<213> ORGANISM: Homo sapiens

<400> SEQUENCE: 96

```
gaggtgcagc tgttggagag cggggggaggc ttggtacagc ctggggggtc cctgcgcctc      60
tcctgtgcag ccagcggatt cacctttggt ggttactaca tgtcttgggt ccgccaggct     120
ccagggaagg ggctggagtg ggtctcatac attcctggtt ctggtggttc tacatactat     180
```

```
gcagactccg tgaagggccg gttcaccatc tcccgtgaca attccaagaa cacgctgtat    240
ctgcaaatga acagcctgcg tgccgaggac acggctgtat attattgtgc gcgctacgac    300
tactactgga tggactattg gggccaggga accctggtca ccgtctcctc a             351
```

<210> SEQ ID NO 97
<211> LENGTH: 107
<212> TYPE: PRT
<213> ORGANISM: Homo sapiens

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 98
<211> LENGTH: 321
<212> TYPE: DNA
<213> ORGANISM: Homo sapiens

<400> SEQUENCE: 98

```
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag agttacagta ccccttatac ttttggccag   300
gggaccaagc tggagatcaa a                                             321
```

<210> SEQ ID NO 99
<211> LENGTH: 118
<212> TYPE: PRT
<213> ORGANISM: Homo sapiens

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Gly Ser
                20                  25                  30

Ser Met Tyr Trp Val Arg Gln Ala Pro Gly Lys Gly Leu Glu Trp Val
            35                  40                  45

Ser Gly Ile Tyr Ser Ser Gly Gly Tyr Thr Tyr Ala Asp Ser Val
        50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                 85                  90                  95

Ala Arg Gly Val Pro His Gly Tyr Phe Asp Tyr Trp Gly Gln Gly Thr
            100                 105                 110

Leu Val Thr Val Ser Ser
        115

<210> SEQ ID NO 100
<211> LENGTH: 354
<212> TYPE: DNA
<213> ORGANISM: Homo sapiens

<400> SEQUENCE: 100
gaggtgcagc tgttggagag cggggggaggc ttggtacagc ctgggggggtc cctgcgcctc      60 tcctgtgcag ccagcggatt cacctttac ggttcttcta tgtactgggt ccgccaggct       120
ccagggaagg gctggagtg gtctcaggt atttactctt ctggtggtta cacatcttat        180
gcagactccg tgaagggccg gttcaccatc tcccgtgaca attccaagaa cacgctgtat      240
ctgcaaatga acagcctgcg tgccgaggac acggctgtat attattgtgc gcgcggtgtt     300
cctcatggtt actttgacta ttggggccag ggaaccctgg tcaccgtctc ctca           354

<210> SEQ ID NO 101
<211> LENGTH: 118
<212> TYPE: PRT
<213> ORGANISM: Homo sapiens

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45

Ser Ser Ile Ser Tyr Tyr Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Pro His Tyr Tyr Phe Asp Tyr Trp Gly Gln Gly Thr
            100                 105                 110

Leu Val Thr Val Ser Ser
        115

<210> SEQ ID NO 102
<211> LENGTH: 354
<212> TYPE: DNA
<213> ORGANISM: Homo sapiens

<400> SEQUENCE: 102
gaggtgcagc tgttggagag cggggggaggc ttggtacagc ctgggggggtc cctgcgcctc      60 tcctgtgcag ccagcggatt cacctttagt ggttcttcta tgtcttgggt ccgccaggct      120
ccagggaagg gctggagtg gtctcatct atttcttact acggtggtta cacatactat       180
gcagactccg tgaagggccg gttcaccatc tcccgtgaca attccaagaa cacgctgtat      240
ctgcaaatga acagcctgcg tgccgaggac acggctgtat attattgtgc gcgctacttc     300
```
ccgcattact actttgacta ttggggccag ggaaccctgg tcaccgtctc ctca             354

<210> SEQ ID NO 103
<211> LENGTH: 106
<212> TYPE: PRT
<213> ORGANISM: Homo sapiens

<400> SEQUENCE: 103

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Leu Leu Thr
                85                  90                  95

Phe Gly Gln Gly Thr Lys Leu Glu Ile Lys
            100                 105

<210> SEQ ID NO 104
<211> LENGTH: 318
<212> TYPE: DNA
<213> ORGANISM: Homo sapiens

<400> SEQUENCE: 104
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct    240
gaagattttg caacttatta ctgtcaacag tacggttctc tgctcacttt tggccagggg    300
accaagctgg agatcaaa                                                   318

<210> SEQ ID NO 105
<211> LENGTH: 116
<212> TYPE: PRT
<213> ORGANISM: Homo sapiens

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Tyr Tyr Ser Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Tyr Leu Asp Tyr Trp Gly Gln Gly Thr Leu Val
            100                 105                 110

Thr Val Ser Ser
       115

<210> SEQ ID NO 106
<211> LENGTH: 348
<212> TYPE: DNA
<213> ORGANISM: Homo sapiens

<400> SEQUENCE: 106
gaggtgcagc tgttggagag cggggggaggc ttggtacagc ctggggggtc cctgcgcctc       60
tcctgtgcag ccagcggatt cacctttagc agctatgcca tgagctgggt ccgccaggct      120
ccagggaagg ggctggagtg ggtctcatac atttcttact actctggtta cacatactat      180
gcagactccg tgaagggccg gttcaccatc tcccgtgaca attccaagaa cacgctgtat      240
ctgcaaatga acagcctgcg tgccgaggac acggctgtat attattgtgc gcgcggttac      300
ggttacttgg actattgggg ccagggaacc ctggtcaccg tctcctca               348

<210> SEQ ID NO 107
<211> LENGTH: 118
<212> TYPE: PRT
<213> ORGANISM: Homo sapiens

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Tyr Tyr Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Pro His His Tyr Ile Asp Tyr Trp Gly Gln Gly Thr
            100                 105                 110

Leu Val Thr Val Ser Ser
        115

<210> SEQ ID NO 108
<211> LENGTH: 354
<212> TYPE: DNA
<213> ORGANISM: Homo sapiens

<400> SEQUENCE: 108
gaggtgcagc tgttggagag cggggggaggc ttggtacagc ctggggggtc cctgcgcctc       60
tcctgtgcag ccagcggatt cacctttagc agctatgcca tgagctgggt ccgccaggct      120
ccagggaagg ggctggagtg ggtctcaggt atttcttact acgtggtta cacatactat       180 gcagactccg tgaagggccg gttcaccatc tcccgtgaca attccaagaa cacgctgtat      240
ctgcaaatga acagcctgcg tgccgaggac acggctgtat attattgtgc gcgctactac      300
ccgcatcatt acattgacta ttggggccag ggaaccctgg tcaccgtctc ctca           354

<210> SEQ ID NO 109
<211> LENGTH: 107

<212> TYPE: PRT
<213> ORGANISM: Homo sapiens

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Leu Thr Phe
                85                  90                  95

Thr Phe Gly Gln Gly Thr Lys Leu Glu Ile Lys
            100                 105
```

<210> SEQ ID NO 110
<211> LENGTH: 321
<212> TYPE: DNA
<213> ORGANISM: Homo sapiens

<400> SEQUENCE: 110

```
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag ggtgattaca ctctgttcac ttttggccag   300
gggaccaagc tggagatcaa a                                              321
```

<210> SEQ ID NO 111
<211> LENGTH: 121
<212> TYPE: PRT
<213> ORGANISM: Homo sapiens

<400> SEQUENCE: 111

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Tyr
            20                  25                  30

Tyr Met Ser Trp Val Arg Gln Ala Pro Gly Lys Gly Leu Glu Trp Val
        35                  40                  45

Ser Gly Ile Ser Ser Tyr Gly Ser Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Asn Trp Ala Asn Ser Phe Asp Tyr Trp Gly
            100                 105                 110

Gln Gly Thr Leu Val Thr Val Ser Ser
        115                 120
```

<210> SEQ ID NO 112
<211> LENGTH: 363
<212> TYPE: DNA
<213> ORGANISM: Homo sapiens

<400> SEQUENCE: 112

```
gaggtgcagc tgttggagag cggggggaggc ttggtacagc ctggggggtc cctgcgcctc      60
tcctgtgcag ccagcggatt cacctttggt tactactaca tgtcttgggt ccgccaggct     120
ccagggaagg ggctggagtg ggtctcaggt atttcttctt acggtagtta cacatactat     180
gcagactccg tgaagggccg gttcaccatc tcccgtgaca attccaagaa cacgctgtat     240
ctgcaaatga acagcctgcg tgccgaggac acggctgtat attattgtgc gcgctctggt     300
tactctaact gggctaactc ttttgactat tggggccagg gaaccctggt caccgtctcc     360
tca                                                                    363
```

<210> SEQ ID NO 113
<211> LENGTH: 124
<212> TYPE: PRT
<213> ORGANISM: Homo sapiens

<400> SEQUENCE: 113

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Ser His Gly Tyr Tyr Val Tyr Gly Thr Leu Asp
            100                 105                 110

Tyr Trp Gly Gln Gly Thr Leu Val Thr Val Ser Ser
        115                 120
```

<210> SEQ ID NO 114
<211> LENGTH: 372
<212> TYPE: DNA
<213> ORGANISM: Homo sapiens

<400> SEQUENCE: 114

```
gaggtgcagc tgttggagag cggggggaggc ttggtacagc ctggggggtc cctgcgcctc      60
tcctgtgcag ccagcggatt cacctttagc agctatgcca tgagctgggt ccgccaggct     120
ccagggaagg ggctggagtg ggtctcagct attagtggta gtggtggtag cacatactat     180
gcagactccg tgaagggccg gttcaccatc tcccgtgaca attccaagaa cacgctgtat     240
ctgcaaatga acagcctgcg tgccgaggac acggctgtat attattgtgc gcgctactac     300
tactctcatg gttactacgt ttacggtact ttggactatt ggggccaggg aaccctggtc     360
accgtctcct ca                                                          372
```

<210> SEQ ID NO 115
<211> LENGTH: 108
<212> TYPE: PRT

<213> ORGANISM: Homo sapiens

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Pro Ser Gly Leu
                85                  90                  95

Phe Thr Phe Gly Gln Gly Thr Lys Leu Glu Ile Lys
            100                 105

<210> SEQ ID NO 116
<211> LENGTH: 324
<212> TYPE: DNA
<213> ORGANISM: Homo sapiens

<400> SEQUENCE: 116
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag tacggtccgt ctggtctgtt cacttttggc     300
caggggacca agctggagat caaa                                            324

<210> SEQ ID NO 117
<211> LENGTH: 117
<212> TYPE: PRT
<213> ORGANISM: Homo sapiens

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Tyr Met Gly Trp Val Arg Gln Ala Pro Gly Lys Gly Leu Glu Trp Val
        35                  40                  45

Ser Ser Ile Gly Ser Tyr Tyr Gly Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Asp Tyr Gly Ala Leu Asp Tyr Trp Gly Gln Gly Thr Leu
            100                 105                 110

Val Thr Val Ser Ser
        115

<210> SEQ ID NO 118

```
<211> LENGTH: 351
<212> TYPE: DNA
<213> ORGANISM: Homo sapiens

<400> SEQUENCE: 118
gaggtgcagc tgttggagag cggggggaggc ttggtacagc ctgggggggtc cctgcgcctc    60 tcctgtgcag ccagcggatt cacctttggt tcttactaca tgggttgggt ccgccaggct   120
ccagggaagg ggctggagtg ggtctcatct attggttctt actacggtta cacatactat   180
gcagactccg tgaagggccg gttcaccatc tcccgtgaca attccaagaa cacgctgtat   240
ctgcaaatga acagcctgcg tgccgaggac acggctgtat attattgtgc gcgccatgac   300
tacggtgctt tggactattg gggccaggga accctggtca ccgtctcctc a            351

<210> SEQ ID NO 119
<211> LENGTH: 108
<212> TYPE: PRT
<213> ORGANISM: Homo sapiens

<400> SEQUENCE: 119
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Asp Ser Leu
                85                  90                  95

Leu Thr Phe Gly Gln Gly Thr Lys Leu Glu Ile Lys
            100                 105

```
<210> SEQ ID NO 120
<211> LENGTH: 324
<212> TYPE: DNA
<213> ORGANISM: Homo sapiens

<400> SEQUENCE: 120
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag tacggttctg attctctgct cacttttggc   300
caggggacca agctggagat caaa                                          324

<210> SEQ ID NO 121
<211> LENGTH: 122
<212> TYPE: PRT
<213> ORGANISM: Homo sapiens

<400> SEQUENCE: 121
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr

```
            20                  25                  30

Ser Met Tyr Trp Val Arg Gln Ala Pro Gly Lys Gly Leu Glu Trp Val
        35                  40                  45

Ser Gly Ile Gly Tyr Ser Gly Tyr Gly Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Phe His Asp Tyr Ala Ala Tyr Ser Leu Asp Tyr Trp
            100                 105                 110

Gly Gln Gly Thr Leu Val Thr Val Ser Ser
        115                 120

<210> SEQ ID NO 122
<211> LENGTH: 366
<212> TYPE: DNA
<213> ORGANISM: Homo sapiens

<400> SEQUENCE: 122
gaggtgcagc tgttggagag cgggggaggc ttggtacagc ctggggggtc cctgcgcctc      60
tcctgtgcag ccagcggatt cacctttttct ggttactcta tgtactgggt ccgccaggct    120
ccagggaagg gctggagtg gtctcaggt attggttact ctggttacgg tacatactat       180
gcagactccg tgaagggccg gttcaccatc tcccgtgaca attccaagaa cacgctgtat     240
ctgcaaatga acagcctgcg tgccgaggac acggctgtat attattgtgc gcgctactac    300
ttccatgact acgctgctta ctctttggac tattgggggcc agggaaccct ggtcaccgtc   360
tcctca                                                               366

<210> SEQ ID NO 123
<211> LENGTH: 118
<212> TYPE: PRT
<213> ORGANISM: Homo sapiens

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Ser
            20                  25                  30

Ser Met Tyr Trp Val Arg Gln Ala Pro Gly Lys Gly Leu Glu Trp Val
        35                  40                  45

Ser Gly Ile Gly Tyr Tyr Ser Tyr Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Pro His His Tyr Phe Asp Tyr Trp Gly Gln Gly Thr
            100                 105                 110

Leu Val Thr Val Ser Ser
        115

<210> SEQ ID NO 124
<211> LENGTH: 354
<212> TYPE: DNA
<213> ORGANISM: Homo sapiens
```

<400> SEQUENCE: 124

```
gaggtgcagc tgttggagag cgggggaggc ttggtacagc ctgggggtc cctgcgcctc      60
tcctgtgcag ccagcggatt cacctttggt tcttcttcta tgtactgggt ccgccaggct    120
ccagggaagg ggctggagtg ggtctcaggt attggttact actcttactc tacatcttat    180
gcagactccg tgaagggccg gttcaccatc tcccgtgaca attccaagaa cacgctgtat    240
ctgcaaatga acagcctgcg tgccgaggac acggctgtat attattgtgc gcgcggttac    300
ccgcatcatt actttgacta ttggggccag ggaaccctgg tcaccgtctc ctca          354
```

<210> SEQ ID NO 125
<211> LENGTH: 337
<212> TYPE: PRT
<213> ORGANISM: Homo sapiens

<400> SEQUENCE: 125

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Trp Tyr Gly Leu
                 85                  90                  95

Ser Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Ser Gly Gly Gly Ser Gly Gly Gly
    210                 215                 220

Gly Ser Ala Pro Leu Lys Ile Gln Ala Tyr Phe Asn Glu Thr Ala Asp
225                 230                 235                 240

Leu Pro Cys Gln Phe Ala Asn Ser Gln Asn Leu Ser Leu Ser Glu Leu
                245                 250                 255

Val Val Phe Trp Gln Asp Gln Glu Asn Leu Val Leu Asn Glu Val Tyr
            260                 265                 270

Leu Gly Lys Glu Arg Phe Asp Ser Val Asp Ser Lys Tyr Met Gly Arg
        275                 280                 285

Thr Ser Phe Asp Ser Asp Ser Trp Thr Leu Arg Leu His Asn Leu Gln
    290                 295                 300
```

```
Ile Lys Asp Lys Gly Arg Tyr Gln Cys Ile Ile His His Lys Lys Pro
305                 310                 315                 320

Thr Gly Met Ile Asn Ile His Gln Met Asn Ser Glu Leu Ser Val Leu
                325                 330                 335

Ala
```

<210> SEQ ID NO 126
<211> LENGTH: 1376
<212> TYPE: DNA
<213> ORGANISM: Homo sapiens

<400> SEQUENCE: 126

```
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag tactactggt acggtctgtc cacttttggc   300
caggggacca gctggagat caaacgtgag tcgtacgcta gcaagcttga tatcgaattc   360
taaactctga ggggtcgga tgacgtggcc attctttgcc taaagcattg agtttactgc   420
aaggtcagaa aagcatgcaa agccctcaga atggctgcaa agagctccaa caaaacaatt   480
tagaactttta ttaaggaata gggggaagct aggaagaaac tcaaaacatc aagatttaa   540
atacgcttct tggtctcctt gctataatta tctgggataa gcatgctgtt ttctgtctgt   600
ccctaacatg ccctgtgatt atccgcaaac aacacaccca agggcagaac tttgttactt   660
aaacaccatc ctgtttgctt ctttcctcag gaactgtggc tgcaccatct gtcttcatct   720
tcccgccatc tgatgagcag ttgaaatctg gaactgcctc tgttgtgtgc ctgctgaata   780
acttctatcc cagagaggcc aaagtacagt ggaaggtgga taacgccctc caatcgggta   840
actcccagga gagtgtcaca gagcaggaca gcaaggacag cacctacagc ctcagcagca   900
ccctgacgct gagcaaagca gactacgaga acacaaagt ctacgcctgc gaagtcaccc   960
atcagggcct gagctcgccc gtcacaaaga gcttcaacag gggagagtgt agcggaggag  1020
gaggaagcgg aggaggagga agcgcccccc tcaaaatcca agcgtacttc aacgaaactg  1080
cagacttacc gtgtcagttt gccaattcgc agaatctgag cctgagcgaa ctggtggttt  1140
tctggcagga tcaggagaac ctggttctga acgaagtcta tctgggcaaa gagcggttcg  1200
acagcgtgga cagcaagtat atgggccgca ccagctttga tagcgacagc tggacccctgc  1260
gtctgcacaa tctgcaaatc aaagataagg gtaggtacca gtgcattatc caccataaga  1320
agccgacggg tatgattaat attcaccaaa tgaactccga gttgtctgtc ctggcg      1376
```

<210> SEQ ID NO 127
<211> LENGTH: 337
<212> TYPE: PRT
<213> ORGANISM: Homo sapiens

<400> SEQUENCE: 127

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

Tyr Ala Ala Ser Ser Leu Gln Ser Gly Val Pro Ser Arg Phe Ser Gly
                50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly His Gly Ser Tyr Pro
                 85                  90                  95
His Thr Phe Gly Gln Gly Thr Lys Leu Glu Ile Lys Arg Thr Val Ala
                100                 105                 110
Ala Pro Ser Val Phe Ile Phe Pro Pro Ser Asp Glu Gln Leu Lys Ser
                115                 120                 125
Gly Thr Ala Ser Val Val Cys Leu Leu Asn Asn Phe Tyr Pro Arg Glu
            130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
Tyr Ala Cys Glu Val Thr His Gln Gly Leu Ser Ser Pro Val Thr Lys
                195                 200                 205
Ser Phe Asn Arg Gly Glu Cys Ser Gly Gly Gly Ser Gly Gly Gly
            210                 215                 220
Gly Ser Ala Pro Leu Lys Ile Gln Ala Tyr Phe Asn Glu Thr Ala Asp
225                 230                 235                 240
Leu Pro Cys Gln Phe Ala Asn Ser Gln Asn Leu Ser Leu Ser Glu Leu
                245                 250                 255
Val Val Phe Trp Gln Asp Gln Glu Asn Leu Val Leu Asn Glu Val Tyr
                260                 265                 270
Leu Gly Lys Glu Arg Phe Asp Ser Val Asp Ser Lys Tyr Met Gly Arg
            275                 280                 285
Thr Ser Phe Asp Ser Asp Ser Trp Thr Leu Arg Leu His Asn Leu Gln
290                 295                 300
Ile Lys Asp Lys Gly Arg Tyr Gln Cys Ile Ile His His Lys Lys Pro
305                 310                 315                 320
Thr Gly Met Ile Asn Ile His Gln Met Asn Ser Glu Leu Ser Val Leu
                325                 330                 335
Ala

<210> SEQ ID NO 128
<211> LENGTH: 1376
<212> TYPE: DNA
<213> ORGANISM: Homo sapiens

<400> SEQUENCE: 128
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag ggtcatggtt cttacccgca cacttttggc     300
caggggacca agctggagat caaacgtgag tcgtacgcta gcaagcttga tatcgaattc     360
taaactctga gggggtcgga tgacgtggcc attctttgcc taaagcattg agtttactgc     420

| | |
|---|---|
| aaggtcagaa aagcatgcaa agccctcaga atggctgcaa agagctccaa caaaacaatt | 480 |
| tagaacttta ttaaggaata gggggaagct aggaagaaac tcaaaacatc aagattttaa | 540 |
| atacgcttct tggtctcctt gctataatta tctgggataa gcatgctgtt ttctgtctgt | 600 |
| ccctaacatg ccctgtgatt atccgcaaac aacacaccca agggcagaac tttgttactt | 660 |
| aaacaccatc ctgtttgctt ctttcctcag gaactgtggc tgcaccatct gtcttcatct | 720 |
| tcccgccatc tgatgagcag ttgaaatctg gaactgcctc tgttgtgtgc ctgctgaata | 780 |
| acttctatcc cagagaggcc aaagtacagt ggaaggtgga taacgccctc caatcgggta | 840 |
| actcccagga gagtgtcaca gagcaggaca gcaaggacag cacctacagc ctcagcagca | 900 |
| ccctgacgct gagcaaagca gactacgaga acacaaagt ctacgcctgc gaagtcaccc | 960 |
| atcagggcct gagctcgccc gtcacaaaga gcttcaacag gggagagtgt agcggaggag | 1020 |
| gaggaagcgg aggaggagga agcgcccccc tcaaaatcca agcgtacttc aacgaaactg | 1080 |
| cagacttacc gtgtcagttt gccaattcgc agaatctgag cctgagcgaa ctggtggttt | 1140 |
| tctggcagga tcaggagaac ctggttctga acgaagtcta tctgggcaaa gagcggttcg | 1200 |
| acagcgtgga cagcaagtat atgggccgca ccagctttga tagcgacagc tggacccctg | 1260 |
| gtctgcacaa tctgcaaatc aaagataagg gtaggtacca gtgcattatc caccataaga | 1320 |
| agccgacggg tatgattaat attcaccaaa tgaactccga gttgtctgtc ctggcg | 1376 |

<210> SEQ ID NO 129
<211> LENGTH: 336
<212> TYPE: PRT
<213> ORGANISM: Homo sapiens

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

```
Phe Asn Arg Gly Glu Cys Ser Gly Gly Gly Ser Gly Gly Gly
210             215             220

Ser Ala Pro Leu Lys Ile Gln Ala Tyr Phe Asn Glu Thr Ala Asp Leu
225             230             235             240

Pro Cys Gln Phe Ala Asn Ser Gln Asn Leu Ser Leu Ser Glu Leu Val
            245             250             255

Val Phe Trp Gln Asp Gln Glu Asn Leu Val Leu Asn Glu Val Tyr Leu
        260             265             270

Gly Lys Glu Arg Phe Asp Ser Val Asp Ser Lys Tyr Met Gly Arg Thr
            275             280             285

Ser Phe Asp Ser Asp Ser Trp Thr Leu Arg Leu His Asn Leu Gln Ile
290             295             300

Lys Asp Lys Gly Arg Tyr Gln Cys Ile Ile His His Lys Lys Pro Thr
305             310             315             320

Gly Met Ile Asn Ile His Gln Met Asn Ser Glu Leu Ser Val Leu Ala
            325             330             335
```

<210> SEQ ID NO 130
<211> LENGTH: 1373
<212> TYPE: DNA
<213> ORGANISM: Homo sapiens

<400> SEQUENCE: 130

```
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag agttacagta cccttatac ttttggccag      300
gggaccaagc tggagatcaa acgtgagtcg tacgctagca agcttgatat cgaattctaa     360
actctgaggg ggtcggatga cgtggccatt ctttgcctaa agcattgagt ttactgcaag     420
gtcagaaaag catgcaaagc cctcagaatg gctgcaaaga gctccaacaa acaatttag     480
aactttatta aggaatagg ggaagctagg aagaaactca aaacatcaag atttaaata      540
cgcttcttgg tctccttgct ataattatct gggataagca tgctgttttc tgtctgtccc     600
taacatgccc tgtgattatc cgcaaacaac acacccaagg gcagaacttt gttacttaaa     660
caccatcctg tttgcttctt tcctcaggaa ctgtggctgc accatctgtc ttcatcttcc     720
cgccatctga tgagcagttg aaatctggaa ctgcctctgt tgtgtgcctg ctgaataact     780
tctatcccag agaggccaaa gtacagtgga aggtggataa cgccctccaa tcgggtaact     840
cccaggagag tgtcacagag caggacagca aggacagcac ctacagcctc agcagcaccc     900
tgacgctgag caaagcagac tacgagaaac acaaagtcta cgcctgcgaa gtcacccatc     960
agggcctgag ctcgcccgtc acaaagagct tcaacagggg agagtgtagc ggaggaggag    1020
gaagcggagg aggaggaagc gccccccctca aaatccaagc gtacttcaac gaaactgcag    1080
acttaccgtg tcagtttgcc aattcgcaga atctgagcct gagcgaactg gtggttttct    1140
ggcaggatca ggagaacctg gttctgaacg aagtctatct gggcaaagag cggttcgaca    1200
gcgtggacag caagtatatg ggccgcacca gctttgatag cgacagctgg accctgcgtc    1260
tgcacaatct gcaaatcaaa gataagggta ggtaccagtg cattatccac cataagaagc    1320
cgacgggtat gattaatatt caccaaatga actccgagtt gtctgtcctg gcg           1373
```

<210> SEQ ID NO 131
<211> LENGTH: 336
<212> TYPE: PRT
<213> ORGANISM: Homo sapiens

<400> SEQUENCE: 131

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Tyr Thr Leu Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Ser Gly Gly Gly Gly
    210                 215                 220

Ser Ala Pro Leu Lys Ile Gln Ala Tyr Phe Asn Glu Thr Ala Asp Leu
225                 230                 235                 240

Pro Cys Gln Phe Ala Asn Ser Gln Asn Leu Ser Leu Ser Glu Leu Val
                245                 250                 255

Val Phe Trp Gln Asp Gln Glu Asn Leu Val Leu Asn Glu Val Tyr Leu
            260                 265                 270

Gly Lys Glu Arg Phe Asp Ser Val Asp Ser Lys Tyr Met Gly Arg Thr
        275                 280                 285

Ser Phe Asp Ser Asp Ser Trp Thr Leu Arg Leu His Asn Leu Gln Ile
    290                 295                 300

Lys Asp Lys Gly Arg Tyr Gln Cys Ile Ile His His Lys Lys Pro Thr
305                 310                 315                 320

Gly Met Ile Asn Ile His Gln Met Asn Ser Glu Leu Ser Val Leu Ala
                325                 330                 335
```

<210> SEQ ID NO 132
<211> LENGTH: 1373
<212> TYPE: DNA
<213> ORGANISM: Homo sapiens

<400> SEQUENCE: 132

```
gacatccaga tgacccagtc tccatcctcc ctgagcgcat ctgtaggaga ccgcgtcacc       60
```

```
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag ggtgattaca ctctgttcac ttttggccag    300
gggaccaagc tggagatcaa acgtgagtcg tacgctagca agcttgatat cgaattctaa    360
actctgaggg gtcggatga cgtggccatt ctttgcctaa gcattgagt ttactgcaag      420 gtcagaaaag catgcaaagc cctcagaatg gctgcaaaga gctccaacaa aacaatttag    480
aactttatta aggaataggg ggaagctagg aagaaactca aaacatcaag attttaaata    540
cgcttcttgg tctccttgct ataattatct gggataagca tgctgttttc tgtctgtccc    600
taacatgccc tgtgattatc cgcaaacaac acacccaagg gcagaacttt gttacttaaa    660
caccatcctg tttgcttctt tcctcaggaa ctgtggctgc accatctgtc ttcatcttcc    720
cgccatctga tgagcagttg aaatctggaa ctgcctctgt tgtgtgcctg ctgaataact    780
tctatcccag agaggccaaa gtacagtgga aggtggataa cgccctccaa tcgggtaact    840
cccaggagag tgtcacagag caggacagca aggacagcac ctacagcctc agcagcaccc    900
tgacgctgag caaagcagac tacgagaaac acaaagtcta cgcctgcgaa gtcacccatc    960
agggcctgag ctcgcccgtc acaaagagct tcaacagggg agagtgtagc ggaggaggag   1020
gaagcggagg aggaggaagc gccccctca aatccaagc gtacttcaac gaaactgcag      1080
acttaccgtg tcagtttgcc aattcgcaga atctgagcct gagcgaactg gtggttttct   1140
ggcaggatca ggagaacctg ttctgaacg aagtctatct gggcaaagag cggttcgaca    1200
gcgtggacag caagtatatg ggccgcacca gctttgatag cgacagctgg accctgcgtc   1260
tgcacaatct gcaaatcaaa gataagggta ggtaccagtg cattatccac cataagaagc   1320
cgacgggtat gattaatatt caccaaatga actccgagtt gtctgtcctg gcg           1373
```

<210> SEQ ID NO 133
<211> LENGTH: 337
<212> TYPE: PRT
<213> ORGANISM: Homo sapiens

<400> SEQUENCE: 133

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Asp Ser Leu
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys Ser Gly Gly Gly Ser Gly Gly Gly
210                 215                 220

Gly Ser Ala Pro Leu Lys Ile Gln Ala Tyr Phe Asn Glu Thr Ala Asp
225                 230                 235                 240

Leu Pro Cys Gln Phe Ala Asn Ser Gln Asn Leu Ser Leu Ser Glu Leu
            245                 250                 255

Val Val Phe Trp Gln Asp Gln Glu Asn Leu Val Leu Asn Glu Val Tyr
        260                 265                 270

Leu Gly Lys Glu Arg Phe Asp Ser Val Asp Ser Lys Tyr Met Gly Arg
    275                 280                 285

Thr Ser Phe Asp Ser Asp Ser Trp Thr Leu Arg Leu His Asn Leu Gln
290                 295                 300

Ile Lys Asp Lys Gly Arg Tyr Gln Cys Ile Ile His His Lys Lys Pro
305                 310                 315                 320

Thr Gly Met Ile Asn Ile His Gln Met Asn Ser Glu Leu Ser Val Leu
            325                 330                 335

Ala

<210> SEQ ID NO 134
<211> LENGTH: 1376
<212> TYPE: DNA
<213> ORGANISM: Homo sapiens

<400> SEQUENCE: 134

```
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag tacggttctg attctctgct cacttttggc     300
caggggacca agctggagat caaacgtgag tcgtacgcta gcaagcttga tatcgaattc     360
taaactctga gggggtcgga tgacgtggcc attctttgcc taaagcattg agtttactgc     420
aaggtcagaa aagcatgcaa agccctcaga atggctgcaa agagctccaa caaacaatt      480
tagaacttta ttaaggaata gggggaagct aggaagaaac tcaaaacatc aagattttaa     540
atacgcttct tggtctcctt gctataatta tctgggataa gcatgctgtt ttctgtctgt     600
ccctaacatg ccctgtgatt atccgcaaac aacacaccca agggcagaac tttgttactt     660
aaacaccatc ctgtttgctt ctttcctcag gaactgtggc tgcaccatct gtcttcatct     720
tcccgccatc tgatgagcag ttgaaatctg gaactgcctc tgttgtgtgc ctgctgaata     780
acttctatcc cagagaggcc aaagtacagt ggaaggtgga taacgccctc caatcgggta     840
actcccagga gagtgtcaca gagcaggaca gcaaggacag cacctacagc ctcagcagca     900
ccctgacgct gagcaaagca gactacgaga aacacaaagt ctacgcctgc gaagtcaccc     960
```

```
atcagggcct gagctcgccc gtcacaaaga gcttcaacag gggagagtgt agcggaggag    1020
gaggaagcgg aggaggagga agcgcccccc tcaaaatcca agcgtacttc aacgaaactg    1080
cagacttacc gtgtcagttt gccaattcgc agaatctgag cctgagcgaa ctggtggttt    1140
tctggcagga tcaggagaac ctggttctga cgaagtcta tctgggcaaa gagcggttcg     1200
acagcgtgga cagcaagtat atgggccgca ccagctttga tagcgacagc tggaccctgc    1260
gtctgcacaa tctgcaaatc aaagataagg gtaggtacca gtgcattatc caccataaga    1320
agccgacggg tatgattaat attcaccaaa tgaactccga gttgtctgtc ctggcg        1376
```

<210> SEQ ID NO 135
<211> LENGTH: 330
<212> TYPE: PRT
<213> ORGANISM: Homo sapiens

<400> SEQUENCE: 135

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 136
<211> LENGTH: 107
<212> TYPE: PRT
<213> ORGANISM: Homo sapiens

<400> SEQUENCE: 136

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 137
<211> LENGTH: 327
<212> TYPE: PRT
<213> ORGANISM: Homo sapiens

<400> SEQUENCE: 137

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
145                 150                 155                 160

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn Arg Tyr Thr Gln Lys Ser
305                 310                 315                 320

Leu Ser Leu Ser Leu Gly Lys
                325

<210> SEQ ID NO 138
<211> LENGTH: 327
<212> TYPE: PRT
<213> ORGANISM: Homo sapiens

<400> SEQUENCE: 138

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 139
<211> LENGTH: 327
<212> TYPE: PRT
<213> ORGANISM: Homo sapiens

<400> SEQUENCE: 139

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
```

```
            275                 280                 285
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 140
<211> LENGTH: 981
<212> TYPE: DNA
<213> ORGANISM: Homo sapiens

<400> SEQUENCE: 140
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accttgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accgctacac acagaagagc     960
ctctccctgt ctctgggtaa a                                              981

<210> SEQ ID NO 141
<211> LENGTH: 2028
<212> TYPE: DNA
<213> ORGANISM: Homo sapiens

<400> SEQUENCE: 141
agctttctgg ggcaggccgg gcctgacttt ggctggggc agggaggggg ctaaggtgac       60
gcaggtggcg ccagccaggt gcacacccaa tgcccatgag cccagacact ggaccctgca     120
tggaccatcg cggatagaca agaaccgagg ggctctgcg ccctgggccc agctctgtcc      180
cacaccgcgg tcacatggca ccacctctct tgcagcttcc accaagggcc catccgtctt     240 cccccctggcg ccctgctcca ggagcacctc cgagagcaca gccgccctgg gctgcctggt    300
caaggactac ttccccgaac cggtgacggt gtcgtggaac tcaggcgccc tgaccagcgg     360
cgtgcacacc ttcccggctg tcctacagtc ctcaggactc tactccctca gcagcgtggt    420
gaccgtgccc tccagcagct tgggcacgaa gacctacacc tgcaacgtag atcacaagcc     480
cagcaacacc aaggtggaca gagagttgg tgagaggcca gcagggag ggagggtgtc        540
```

```
tgctggaagc caggctcagc cctcctgcct ggacgcaccc cggctgtgca gccccagccc      600
agggcagcaa ggcatgcccc atctgtctcc tcacccggag gcctctgacc accccactca      660
tgctcaggga gagggtcttc tggattttc caccaggctc ccggcaccac aggctggatg       720
cccctacccc aggccctgcg catacagggc aggtgctgcg ctcagacctg ccaagagcca      780
tatccgggag gaccctgccc ctgacctaag cccaccccaa aggccaaact ctccactccc      840
tcagctcaga caccttctct cctcccagat ctgagtaact cccaatcttc tctctgcaga      900
gtccaaatat ggtccccat gcccaccttg cccaggtaag ccaacccagg cctcgccctc       960
cagctcaagg cgggacaggt gccctagagt agcctgcatc cagggacagg ccccagccgg     1020
gtgctgacgc atccacctcc atctcttcct cagcacctga gttcctgggg ggaccatcag     1080
tcttcctgtt cccccaaaaa cccaaggaca ctctcatgat ctcccggacc cctgaggtca     1140
cgtgcgtggt ggtggacgtg agccaggaag acccgaggt ccagttcaac tggtacgtgg      1200
atggcgtgga ggtgcataat gccaagacaa agccgcggga ggagcagttc aacagcacgt     1260
accgtgtggt cagcgtcctc accgtcctgc accaggactg gctgaacggc aaggagtaca     1320
agtgcaaggt ctccaacaaa ggcctcccgt cctccatcga aaaaccatc tccaaagcca      1380
aaggtgggac ccacggggtg cgagggccac acggacagag gccagctcgg cccaccctct     1440
gccctgggag tgaccgctgt gccaacctct gtccctacag ggcagccccg agagccacag     1500
gtgtacaccc tgcccccatc ccaggaggag atgaccaaga accaggtcag cctgacctgc     1560
ctggtcaaag gcttctaccc cagcgacatc gccgtggagt gggagagcaa tgggcagccg     1620
gagaacaact acaagaccac gcctcccgtg ctggactccg acggctcctt cttcctctac     1680
agcaggctaa ccgtggacaa gagcaggtgg caggagggga atgtcttctc atgctccgtg     1740
atgcatgagg ctctgcacaa ccgctacaca cagaagagcc tctccctgtc tctgggtaaa     1800
tgagtgccag gccggcaag ccccgctcc ccgggctctc ggggtcgcgc gaggatgctt       1860
ggcacgtacc ccgtctacat acttcccagg cacccagcat ggaaataaag cacccaccac     1920
tgccctgggc cctgtgaga ctgtgatggt tctttccacg ggtcaggccg agtctgaggc      1980
ctgagtgaca tgagggaggc agagcgggtc ccactgtccc cacactgg                  2028
```

<210> SEQ ID NO 142
<211> LENGTH: 981
<212> TYPE: DNA
<213> ORGANISM: Homo sapiens

<400> SEQUENCE: 142

```
gcttccacca agggcccatc cgtcttcccc ctggcgccct gctccaggag cacctccgag       60
agcacagccg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacgaagacc      240
tacacctgca acgtagatca caagcccagc aacaccaagg tggacaagag agttgagtcc      300
aaatatggtc cccatgccc atcatgccca gcacctgagt tcctgggggg accatcagtc      360
ttcctgttcc cccaaaaacc caaggacact ctcatgatct cccggacccc tgaggtcacg      420
tgcgtggtgg tggacgtgag ccaggaagac cccgaggtcc agttcaactg gtacgtggat      480
ggcgtggagg tgcataatgc caagacaaag ccgcgggagg agcagttcaa cagcacgtac      540
cgtgtggtca gcgtcctcac cgtcctgcac caggactggc tgaacggcaa ggagtacaag      600
tgcaaggtct ccaacaaagg cctcccgtcc tccatcgaga aaaccatctc caaagccaaa      660
```

```
gggcagcccc gagagccaca ggtgtacacc ctgcccccat cccaggagga gatgaccaag      720
aaccaggtca gcctgacctg cctggtcaaa ggcttctacc ccagcgacat cgccgtggag      780
tgggagagca atgggcagcc ggagaacaac tacaagacca cgcctcccgt gctggactcc      840
gacggctcct tcttcctcta cagcaggcta accgtggaca agagcaggtg gcaggagggg      900
aatgtcttct catgctccgt gatgcatgag gctctgcaca accactacac acagaagagc      960 ctctcccctgt ctctgggtaa a                                               981
```

```
<210> SEQ ID NO 143
<211> LENGTH: 2028
<212> TYPE: DNA
<213> ORGANISM: Homo sapiens

<400> SEQUENCE: 143
```

```
agctttctgg ggcaggccgg gcctgacttt ggctgggggc agggagggg ctaaggtgac        60 gcaggtggcg ccagccaggt gcacacccaa tgcccatgag cccagacact ggaccctgca      120
tggaccatcg cggatagaca agaaccgagg ggcctctgcg ccctgggccc agctctgtcc      180
cacaccgcgc tcacatggca ccacctctct tgcagcttcc accaagggcc catccgtctt      240 cccctggcg ccctgctcca ggagcacctc cgagagcaca gccgccctgg gctgcctggt      300
caaggactac ttccccgaac cggtgacggt gtcgtggaac tcaggcgccc tgaccagcgg      360
cgtgcacacc ttcccggctg tcctacagtc ctcaggactc tactccctca gcagcgtggt      420
gaccgtgccc tccagcagct tgggcacgaa gacctacacc tgcaacgtag atcacaagcc      480
cagcaacacc aaggtggaca gagagttgg tgagaggcca gcacagggag ggagggtgtc      540
tgctggaagc caggctcagc cctcctgcct ggacgcaccc cggctgtgca gccccagccc      600
agggcagcaa ggcatgcccc atctgtctcc tcacccggag gcctctgacc ccccactca      660 tgctcaggga gagggtcttc tggatttttc caccaggctc ccggcaccac aggctggatg      720 ccctaccc aggccctgcg catacagggc aggtgctgcg ctcagacctg ccaagagcca      780
tatccgggag gaccctgccc ctgacctaag cccaccccaa aggccaaact ctccactccc      840
tcagctcaga caccttctct cctcccagat ctgagtaact cccaatcttc tctctgcaga      900
gtccaaatat ggtcccccat gcccatcatg cccaggtaag ccaacccagg cctcgccctc      960
cagctcaagg cgggacaggt gccctagagt agcctgcatc cagggacagg ccccagccgg     1020
gtgctgacgc atccacctcc atctcttcct cagcacctga gttcctgggg ggaccatcag     1080
tcttcctgtt ccccccaaaa cccaaggaca ctctcatgat ctcccggacc cctgaggtca     1140
cgtgcgtggt ggtggacgtg agccaggaag accccgaggt ccagttcaac tggtacgtgg     1200
atggcgtgga ggtgcataat gccaagacaa agccgcggga ggagcagttc aacagcacgt     1260
accgtgtggt cagcgtcctc accgtcctgc accaggactg gctgaacggc aaggagtaca     1320
agtgcaaggt ctccaacaaa ggcctcccgt cctccatcga aaaaccatc tccaaagcca     1380 aaggtgggac ccacggggtg cgagggccac acggacagag gccagctcgg cccaccctct     1440
gccctgggag tgaccgctgt gccaacctct gtcctacag gcagccccg agagccacag     1500 gtgtacaccc tgcccccatc ccaggaggag atgaccaaga accaggtcag cctgacctgc     1560
ctggtcaaag gcttctaccc cagcgacatc gccgtggagt gggagagcaa tgggcagccg     1620
gagaacaact acaagaccac gcctcccgtg ctggactccg acggctcctt cttcctctac     1680
agcaggctaa ccgtggacaa gagcaggtgg caggagggga atgtcttctc atgctccgtg     1740
```

| | |
|---|---|
| atgcatgagg ctctgcacaa ccactacaca cagaagagcc tctccctgtc tctgggtaaa | 1800 |
| tgagtgccag ggccggcaag cccccgctcc ccgggctctc ggggtcgcgc gaggatgctt | 1860 |
| ggcacgtacc ccgtctacat acttcccagg cacccagcat ggaaataaag cacccaccac | 1920 |
| tgccctgggc ccctgtgaga ctgtgatggt tctttccacg ggtcaggccg agtctgaggc | 1980 |
| ctgagtgaca tgagggaggc agagcgggtc ccactgtccc cacactgg | 2028 |

```
<210> SEQ ID NO 144
<211> LENGTH: 15
<212> TYPE: PRT
<213> ORGANISM: Artificial Sequence
<220> FEATURE:
<223> OTHER INFORMATION: Linker sequence

<400> SEQUENCE: 144

Gly Gly Gly Gly Ser Gly Gly Gly Gly Ser Gly Gly Gly Gly Ser
1               5                  10                  15

<210> SEQ ID NO 145
<211> LENGTH: 990
<212> TYPE: DNA
<213> ORGANISM: Homo sapiens

<400> SEQUENCE: 145
```

| | |
|---|---|
| gcctccacca agggcccatc ggtcttcccc ctggcaccct cctccaagag cacctctggg | 60 |
| ggcacagcgg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagaa agttgagccc | 300 |
| aaatcttgtg acaaaactca cacatgccca ccgtgcccag cacctgaact cctgggggga | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacaac | 540 |
| agcacgtacc gtgtggtcag cgtcctcacc gtcctgcacc aggactggct gaatggcaag | 600 |
| gagtacaagt gcaaggtctc caacaaagcc ctcccagccc ccatcgagaa aaccatctcc | 660 |
| aaagccaaag ggcagccccg agaaccacag gtgtacaccc tgcccccatc ccgggatgag | 720 |
| ctgaccaaga accaggtcag cctgacctgc ctggtcaaag gcttctatcc cagcgacatc | 780 |
| gccgtggagt gggagagcaa tgggcagccg gagaacaact acaagaccac gcctcccgtg | 840 |
| ctggactccg acggctcctt cttcctctac agcaagctca ccgtggacaa gagcaggtgg | 900 |
| cagcagggga acgtcttctc atgctccgtg atgcatgagg ctctgcacaa ccactacacg | 960 |
| cagaagagcc tctccctgtc tccgggtaaa | 990 |

```
<210> SEQ ID NO 146
<211> LENGTH: 1596
<212> TYPE: DNA
<213> ORGANISM: Homo sapiens

<400> SEQUENCE: 146
```

| | |
|---|---|
| gcctccacca agggcccatc ggtcttcccc ctggcaccct cctccaagag cacctctggg | 60 |
| ggcacagcgg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |

```
ggactctact ccctcagcag cgtggtgacc gtgccctcca gcagcttggg cacccagacc      240
tacatctgca acgtgaatca caagcccagc aacaccaagg tggacaagaa agttggtgag      300
aggccagcac agggagggag ggtgtctgct ggaagccagg ctcagcgctc ctgcctggac      360
gcatcccggc tatgcagccc cagtccaggc agcaaggca ggccccgtct gcctcttcac       420
ccggaggcct ctgcccgccc cactcatgct cagggagagg gtcttctggc ttttccccca     480
ggctctgggc aggcacaggc taggtgcccc taacccaggc cctgcacaca aaggggcagg     540
tgctgggctc agacctgcca agagccatat ccgggaggac cctgcccctg acctaagccc     600
accccaaagg ccaaactctc cactccctca gctcggacac cttctctcct cccagattcc     660
agtaactccc aatcttctct ctgcagagcc caaatcttgt gacaaaactc acacatgccc     720
accgtgccca gtaagccag cccaggcctc gccctccagc tcaaggcggg acaggtgccc      780
tagagtagcc tgcatccagg gacaggcccc agccgggtgc tgacacgtcc acctccatct     840
cttcctcagc acctgaactc ctgggggac cgtcagtctt cctcttcccc ccaaaaccca      900
aggacaccct catgatctcc cggacccctg aggtcacatg cgtggtggtg gacgtgagcc     960
acgaagaccc tgaggtcaag ttcaactggt acgtggacgg cgtggaggtg cataatgcca    1020
agacaaagcc gcgggaggag cagtacaaca gcacgtaccg tgtggtcagc gtcctcaccg    1080
tcctgcacca ggactggctg aatggcaagg agtacaagtg caaggtctcc aacaaagccc    1140
tcccagcccc catcgagaaa accatctcca aagccaaagg tgggacccgt ggggtgcgag    1200
ggccacatgg acagaggccg gctcggccca ccctctgccc tgagagtgac cgctgtacca    1260
acctctgtcc ctacagggca gccccgagaa ccacaggtgt acaccctgcc cccatcccgg    1320
gatgagctga ccaagaacca ggtcagcctg acctgcctgg tcaaaggctt ctatcccagc    1380
gacatcgccg tggagtggga gagcaatggg cagccggaga acaactacaa gaccacgcct    1440
cccgtgctgg actccgacgg ctccttcttc ctctacagca agctcaccgt ggacaagagc    1500
aggtggcagc aggggaacgt cttctcatgc tccgtgatgc atgaggctct gcacaaccac    1560
tacacgcaga agagcctctc cctgtctccg ggtaaa                              1596
```

<210> SEQ ID NO 147  
<211> LENGTH: 321  
<212> TYPE: DNA  
<213> ORGANISM: Homo sapiens

<400> SEQUENCE: 147

```
cgaactgtgg ctgcaccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg t                                                 321
```

<210> SEQ ID NO 148  
<211> LENGTH: 255  
<212> TYPE: PRT  
<213> ORGANISM: Homo sapiens

<400> SEQUENCE: 148

```
Met Gly Asn Ser Cys Tyr Asn Ile Val Ala Thr Leu Leu Leu Val Leu
 1               5                  10                  15
```

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
 50                  55                  60

Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 149
<211> LENGTH: 710
<212> TYPE: PRT
<213> ORGANISM: Homo sapiens

<400> SEQUENCE: 149

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Tyr Gly Ser
                20                  25                  30

Ser Met Tyr Trp Val Arg Gln Ala Pro Gly Lys Gly Leu Glu Trp Val
            35                  40                  45

Ser Gly Ile Tyr Ser Ser Gly Gly Tyr Thr Ser Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Val Pro His Gly Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

-continued

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Gly Ser Gly Gly Gly Gly Ser Glu
    450                 455                 460

Val Gln Leu Leu Glu Ser Gly Gly Gly Leu Val Gln Pro Gly Gly Ser
465                 470                 475                 480

Leu Arg Leu Ser Cys Ala Ala Ser Gly Phe Thr Phe Ser Ser Tyr Tyr
                485                 490                 495

Met Gly Trp Val Arg Gln Ala Pro Gly Lys Gly Leu Glu Trp Val Ser
            500                 505                 510

Gly Ile Gly Ser Tyr Tyr Gly Tyr Thr Gly Tyr Ala Asp Ser Val Lys
        515                 520                 525

Gly Arg Phe Thr Ile Ser Arg Asp Asn Ser Lys Asn Thr Leu Tyr Leu
    530                 535                 540

Gln Met Asn Ser Leu Arg Ala Glu Asp Thr Ala Val Tyr Tyr Cys Ala
545                 550                 555                 560
```

```
Arg Ala Tyr Tyr Asp Tyr Asn Tyr Tyr Tyr Ala Tyr Phe Asp Tyr Trp
            565                 570                 575

Gly Gln Gly Thr Leu Val Thr Val Ser Ser Gly Gly Gly Ser Gly
        580                 585                 590

Gly Gly Gly Ser Gly Gly Gly Ser Asp Ile Gln Met Thr Gln Ser
    595                 600                 605

Pro Ser Ser Leu Ser Ala Ser Val Gly Asp Arg Val Thr Ile Thr Cys
    610                 615                 620

Arg Ala Ser Gln Ser Ile Ser Ser Tyr Leu Asn Trp Tyr Gln Gln Lys
625                 630                 635                 640

Pro Gly Lys Ala Pro Lys Leu Leu Ile Tyr Ala Ala Ser Ser Leu Gln
                645                 650                 655

Ser Gly Val Pro Ser Arg Phe Ser Gly Ser Gly Ser Gly Thr Asp Phe
            660                 665                 670

Thr Leu Thr Ile Ser Ser Leu Gln Pro Glu Asp Phe Ala Thr Tyr Tyr
        675                 680                 685

Cys Gln Gln Ser Val Pro His Tyr Pro Phe Thr Phe Gly Gln Gly Thr
    690                 695                 700

Lys Leu Glu Ile Lys Arg
705                 710

<210> SEQ ID NO 150
<211> LENGTH: 2965
<212> TYPE: DNA
<213> ORGANISM: Homo sapiens

<400> SEQUENCE: 150
gaggtgcagc tgttggagag cgggggaggc ttggtacagc ctggggggtc cctgcgcctc      60
tcctgtgcag ccagcggatt caccttttac ggttcttcta tgtactgggt ccgccaggct     120
ccagggaagg ggctggagtg ggtctcaggt atttactctt ctggtggtta cacatcttat     180
gcagactccg tgaagggccg gttcaccatc tcccgtgaca attccaagaa cacgctgtat     240
ctgcaaatga acagcctgcg tgccgaggac acggctgtat attattgtgc gcgcggtgtt     300
cctcatggtt actttgacta ttggggccag ggaaccctgg tcaccgtctc ctcaggtgag     360
ttaacgtacg ctagcaagct ttctggggca ggccaggcct gaccttggct ttggggcagg     420
gagggggcta aggtgaggca ggtggcgcca gccaggtgca cacccaatgc ccatgagccc     480
agacactgga cgctgaacct cgcggacagt taagaaccca ggggcctctg cgccctgggc     540
ccagctctgt cccacaccgc ggtcacatgg caccacctct cttgcagcct ccaccaaggg     600
cccatcggtc ttccccctgg caccctcctc caagagcacc tctgggggca gcggccct      660 gggctgcctg gtcaaggact acttccccga accggtgacg gtgtcgtgga actcaggcgc     720
cctgaccagc ggcgtgcaca ccttcccggc tgtcctacag tcctcaggac tctactccct     780
cagcagcgtg gtgaccgtgc cctccagcag cttgggcacc cagacctaca tctgcaacgt     840
gaatcacaag cccagcaaca ccaaggtgga caagaaagtt ggtgagaggc cagcacaggg     900
agggagggtg tctgctggaa gccaggctca gcgctcctgc ctggacgcat cccggctatg     960
cagccccagt ccagggcagc aaggcaggcc ccgtctgcct cttcacccgg aggcctctgc    1020 ccgcccact catgctcagg gagagggtct tctggctttt ccccaggct ctgggcaggc      1080 acaggctagg tgcccctaac ccaggccctg cacacaaagg ggcaggtgct gggctcagac    1140
ctgccaagag ccatatccgg gaggaccctg ccctgacct aagcccaccc caaaggccaa     1200
actctccact ccctcagctc ggacaccttc tctcctccca gattccagta actcccaatc    1260
```

```
ttctctctgc agagcccaaa tcttgtgaca aaactcacac atgcccaccg tgcccaggta    1320
agccagccca ggcctcgccc tccagctcaa ggcgggacag gtgccctaga gtagcctgca    1380
tccagggaca ggccccagcc gggtgctgac acgtccacct ccatctcttc ctcagcacct    1440
gaactcctgg ggggaccgtc agtcttcctc ttccccccaa aacccaagga caccctcatg    1500
atctcccgga cccctgaggt cacatgcgtg gtggtggacg tgagccacga agaccctgag    1560
gtcaagttca actggtacgt ggacggcgtg gaggtgcata atgccaagac aaagccgcgg    1620
gaggagcagt acaacagcac gtaccgtgtg gtcagcgtcc tcaccgtcct gcaccaggac    1680
tggctgaatg gcaaggagta caagtgcaag gtctccaaca aagccctccc agcccccatc    1740
gagaaaacca tctccaaagc caaaggtggg acccgtgggg tgcgagggcc acatggacag    1800
aggccggctc ggcccaccct ctgccctgag agtgaccgct gtaccaacct ctgtccctac    1860
agggcagccc cgagaaccac aggtgtacac cctgccccca tcccgggatg agctgaccaa    1920
gaaccaggtc agcctgacct gcctggtcaa aggcttctat cccagcgaca tcgccgtgga    1980
gtgggagagc aatgggcagc cggagaacaa ctacaagacc acgcctcccg tgctggactc    2040
cgacggctcc ttcttcctct acagcaagct caccgtggac aagagcaggt ggcagcaggg    2100
gaacgtcttc tcatgctccg tgatgcatga ggctctgcac aaccactaca cgcagaagag    2160
cctctccctg tctccgggta aaggaggagg aggaagcgga ggaggaggaa gcggaggagg    2220
aggaagcgag gtgcagctgc tcgagagcgg gggaggcttg gtacagcctg gggggtccct    2280
gcgcctctcc tgtgcagcca gcggattcac ctttcttct tactacatgg gttgggtccg    2340
ccaggctcca gggaaggggc tggagtgggt ctcaggtatt ggttcttact acggttacac    2400
aggttatgca gactccgtga agggccggtt caccatctcc cgtgacaatt ccaagaacac    2460
gctgtatctg caaatgaaca gcctgcgtgc cgaggacacg gctgtatatt attgtgcgcg    2520
cgcttactac gactacaact actactacgc ttactttgac tattggggcc agggaaccct    2580
ggtcaccgtc tcctcaggtg gaggcggttc aggcggaggt ggatccggcg gtggcggatc    2640
ggacatccag atgacccagt ctccatcctc cctgagcgca tctgtaggag accgcgtcac    2700
catcacttgc cgggcaagtc agagcattag cagctattta aattggtatc agcagaaacc    2760
agggaaagcc cctaagctcc tgatctatgc tgcatccagt ttgcaaagtg ggtcccatc    2820 acgtttcagt ggcagtggaa gcgggacaga tttcactctc accatcagca gtctgcaacc    2880
tgaagatttt gcaacttatt actgtcaaca gtctgttccg cactacccgt tcacttttgg    2940
ccaggggacc aagctggaga tcaaa                                           2965
```

<210> SEQ ID NO 151
<211> LENGTH: 709
<212> TYPE: PRT
<213> ORGANISM: Homo sapiens

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Asp Tyr Ala Ser Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Glu Val
450                 455                 460

Gln Leu Leu Glu Ser Gly Gly Gly Leu Val Gln Pro Gly Gly Ser Leu
465                 470                 475                 480

Arg Leu Ser Cys Ala Ala Ser Gly Phe Thr Phe Ser Ser Tyr Tyr Met
```

```
                    485                 490                 495
Gly Trp Val Arg Gln Ala Pro Gly Lys Gly Leu Glu Trp Val Ser Gly
                500                 505                 510

Ile Gly Ser Tyr Tyr Gly Tyr Thr Gly Tyr Ala Asp Ser Val Lys Gly
            515                 520                 525

Arg Phe Thr Ile Ser Arg Asp Asn Ser Lys Asn Thr Leu Tyr Leu Gln
        530                 535                 540

Met Asn Ser Leu Arg Ala Glu Asp Thr Ala Val Tyr Tyr Cys Ala Arg
545                 550                 555                 560

Ala Tyr Tyr Asp Tyr Asn Tyr Tyr Ala Tyr Phe Asp Tyr Trp Gly
                565                 570                 575

Gln Gly Thr Leu Val Thr Val Ser Ser Gly Gly Gly Ser Gly Gly
                580                 585                 590

Gly Gly Ser Gly Gly Gly Gly Ser Asp Ile Gln Met Thr Gln Ser Pro
        595                 600                 605

Ser Ser Leu Ser Ala Ser Val Gly Asp Arg Val Thr Ile Thr Cys Arg
        610                 615                 620

Ala Ser Gln Ser Ile Ser Ser Tyr Leu Asn Trp Tyr Gln Gln Lys Pro
625                 630                 635                 640

Gly Lys Ala Pro Lys Leu Leu Ile Tyr Ala Ala Ser Ser Leu Gln Ser
                645                 650                 655

Gly Val Pro Ser Arg Phe Ser Gly Ser Gly Ser Gly Thr Asp Phe Thr
                660                 665                 670

Leu Thr Ile Ser Ser Leu Gln Pro Glu Asp Phe Ala Thr Tyr Tyr Cys
            675                 680                 685

Gln Gln Ser Val Pro His Tyr Pro Phe Thr Phe Gly Gln Gly Thr Lys
        690                 695                 700

Leu Glu Ile Lys Arg
705

<210> SEQ ID NO 152
<211> LENGTH: 2962
<212> TYPE: DNA
<213> ORGANISM: Homo sapiens

<400> SEQUENCE: 152
gaggtgcagc tgttggagag cgggggaggc ttggtacagc ctgggggtc cctgcgcctc      60 tcctgtgcag ccagcggatt caccttggt ggttactaca tgtcttgggt ccgccaggct    120
ccagggaagg ggctggagtg gtctcagct attagtggta gtggtggtag cacatactat    180
gcagactccg tgaagggccg gttcaccatc tcccgtgaca attccaagaa cacgctgtat    240
ctgcaaatga acagcctgcg tgccgaggac acggctgtat attattgtgc gcgctacgac    300
tacgcttcta tggactattg gggccaggga accctggtca ccgtctcctc aggtgagtta    360
acgtacgcta gcaagctttc tggggcaggc caggcctgac cttggctttg ggcagggag    420 ggggctaagg tgaggcaggt ggcgccagcc aggtgcacac ccaatgccca tgagcccaga    480
cactggacgc tgaacctcgc ggacagttaa gaacccaggg gcctctgcgc cctgggccca    540
gctctgtccc acaccgcggt cacatggcac cacctctctt gcagcctcca ccaagggccc    600
atcggtcttc cccctggcac cctcctccaa gagcacctct gggggcacag cggccctggg    660
ctgcctggtc aaggactact ccccgaacc ggtgacggtg tcgtggaact caggcgccct    720
gaccagcggc gtgcacacct tcccggctgt cctacagtcc tcaggactct actccctcag    780
cagcgtggtg accgtgccct ccagcagctt gggcacccag acctacatct gcaacgtgaa    840
```

```
tcacaagccc agcaacacca aggtggacaa gaaagttggt gagaggccag cacagggagg      900
gagggtgtct gctggaagcc aggctcagcg ctcctgcctg gacgcatccc ggctatgcag      960
ccccagtcca gggcagcaag gcaggccccg tctgcctctt cacccggagg cctctgcccg     1020
ccccactcat gctcagggag agggtcttct ggcttttcc ccaggctctg ggcaggcaca      1080
ggctaggtgc ccctaaccca ggccctgcac acaaggggc aggtgctggg ctcagacctg      1140
ccaagagcca tatccgggag gaccctgccc ctgacctaag cccaccccaa aggccaaact     1200
ctccactccc tcagctcgga caccttctct cctcccagat tccagtaact cccaatcttc     1260
tctctgcaga gcccaaatct tgtgacaaaa ctcacacatg cccaccgtgc ccaggtaagc     1320
cagcccaggc ctcgccctcc agctcaaggc gggacaggtg ccctagagta gcctgcatcc     1380
agggacaggc cccagccggg tgctgacacg tccacctcca tctcttcctc agcacctgaa     1440
ctcctggggg gaccgtcagt cttcctcttc cccccaaaac ccaaggacac cctcatgatc     1500
tcccggaccc ctgaggtcac atgcgtggtg gtggacgtga gccacgaaga ccctgaggtc     1560
aagttcaact ggtacgtgga cggcgtggag gtgcataatg ccaagacaaa gccgcgggag     1620
gagcagtaca acagcacgta ccgtgtggtc agcgtcctca ccgtcctgca ccaggactgg     1680
ctgaatggca aggagtacaa gtgcaaggtc tccaacaaag ccctcccagc ccccatcgag     1740
aaaaccatct ccaaagccaa aggtgggacc cgtggggtgc gagggccaca tggacagagg     1800
ccggctcggc ccaccctctg ccctgagagt gaccgctgta ccaacctctg tccctacagg     1860
gcagccccga gaaccacagg tgtacaccct gcccccatcc cgggatgagc tgaccaagaa     1920
ccaggtcagc ctgacctgcc tggtcaaagg cttctatccc agcgacatcg ccgtggagtg     1980
ggagagcaat gggcagccgg agaacaacta caagaccacg cctcccgtgc tggactccga     2040
cggctccttc ttcctctaca gcaagctcac cgtggacaag agcaggtggc agcaggggaa     2100
cgtcttctca tgctccgtga tgcatgaggc tctgcacaac cactacacgc agaagagcct     2160
ctccctgtct ccgggtaaag gaggaggagg aagcggagga ggaggaagcg gaggaggagg     2220
aagcgaggtg cagctgctcg agagcggggg aggcttggta cagcctgggg gtccctgcg     2280 cctctcctgt gcagccagcg gattcacctt ttcttcttac tacatgggtt gggtccgcca     2340
ggctccaggg aaggggctgg agtgggtctc aggtattggt tcttactacg gttacacagg     2400
ttatgcagac tccgtgaagg gccggttcac catctcccgt gacaattcca agaacacgct     2460
gtatctgcaa atgaacagcc tgcgtgccga ggacacggct gtatattatt gtgcgcgcgc     2520
ttactacgac tacaactact actacgctta ctttgactat ggggccagg gaaccctggt     2580 caccgtctcc tcaggtggag gcggttcagg cggaggtgga tccggcggtg gcggatcgga     2640
catccagatg acccagtctc catcctccct gagcgcatct gtaggagacc gcgtcaccat     2700
cacttgccgg gcaagtcaga gcattagcag ctatttaaat tggtatcagc agaaaccagg     2760
gaaagcccct aagctcctga tctatgctgc atccagtttg caaagtgggg tcccatcacg     2820
tttcagtggc agtggaagcg ggacagattt cactctcacc atcagcagtc tgcaacctga     2880
agattttgca acttattact gtcaacagtc tgttccgcac tacccgttca cttttggcca     2940
ggggaccaag ctggagatca aa                                             2962
```

<210> SEQ ID NO 153
<211> LENGTH: 710
<212> TYPE: PRT
<213> ORGANISM: Homo sapiens

<400> SEQUENCE: 153

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45

Ser Ser Ile Ser Tyr Tyr Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Tyr Phe Pro His Tyr Tyr Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415
```

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Gly Gly Gly Gly Ser Gly Gly Gly Ser Gly Gly Gly Ser Glu
            450                 455                 460

Val Gln Leu Leu Glu Ser Gly Gly Gly Leu Val Gln Pro Gly Gly Ser
465                 470                 475                 480

Leu Arg Leu Ser Cys Ala Ala Ser Gly Phe Thr Phe Ser Ser Tyr Tyr
                485                 490                 495

Met Gly Trp Val Arg Gln Ala Pro Gly Lys Gly Leu Glu Trp Val Ser
            500                 505                 510

Gly Ile Gly Ser Tyr Tyr Gly Tyr Thr Gly Tyr Ala Asp Ser Val Lys
            515                 520                 525

Gly Arg Phe Thr Ile Ser Arg Asp Asn Ser Lys Asn Thr Leu Tyr Leu
            530                 535                 540

Gln Met Asn Ser Leu Arg Ala Glu Asp Thr Ala Val Tyr Tyr Cys Ala
545                 550                 555                 560

Arg Ala Tyr Tyr Asp Tyr Asn Tyr Tyr Ala Tyr Phe Asp Tyr Trp
                565                 570                 575

Gly Gln Gly Thr Leu Val Thr Val Ser Ser Gly Gly Gly Ser Gly
            580                 585                 590

Gly Gly Ser Gly Gly Gly Ser Asp Ile Gln Met Thr Gln Ser
            595                 600                 605

Pro Ser Ser Leu Ser Ala Ser Val Gly Asp Arg Val Thr Ile Thr Cys
            610                 615                 620

Arg Ala Ser Gln Ser Ile Ser Ser Tyr Leu Asn Trp Tyr Gln Gln Lys
625                 630                 635                 640

Pro Gly Lys Ala Pro Lys Leu Leu Ile Tyr Ala Ala Ser Ser Leu Gln
                645                 650                 655

Ser Gly Val Pro Ser Arg Phe Ser Gly Ser Gly Ser Gly Thr Asp Phe
            660                 665                 670

Thr Leu Thr Ile Ser Ser Leu Gln Pro Glu Asp Phe Ala Thr Tyr Tyr
            675                 680                 685

Cys Gln Gln Ser Val Pro His Tyr Pro Phe Thr Phe Gly Gln Gly Thr
            690                 695                 700

Lys Leu Glu Ile Lys Arg
705                 710

<210> SEQ ID NO 154
<211> LENGTH: 2965
<212> TYPE: DNA
<213> ORGANISM: Homo sapiens

<400> SEQUENCE: 154
gaggtgcagc tgttggagag cggggggggc ttggtacagc ctgggggggtc cctgcgcctc        60 tcctgtgcag ccagcggatt cacctttagt ggttcttcta tgtcttgggt ccgccaggct       120
ccagggaagg ggctggagtg gtctcatct atttcttact acgtggttta cacatactat        180
gcagactccg tgaagggccg gttcaccatc tcccgtgaca attccaagaa cacgctgtat       240
ctgcaaatga acagcctgcg tgccgaggac acggctgtat attattgtgc gcgctacttc       300
ccgcattact actttgacta ttggggccag ggaaccctgg tcaccgtctc tcaggtgag        360 ttaacgtacg ctagcaagct ttctggggca ggccaggcct gaccttggct ttggggcagg       420

```
gagggggcta aggtgaggca ggtggcgcca gccaggtgca cacccaatgc ccatgagccc     480
agacactgga cgctgaacct cgcggacagt taagaaccca ggggcctctg cgccctgggc     540
ccagctctgt cccacaccgc ggtcacatgg caccacctct cttgcagcct ccaccaaggg     600
cccatcggtc ttcccctgg cacctcctc caagagcacc tctggggca cagcggccct        660
gggctgcctg gtcaaggact acttccccga accggtgacg gtgtcgtgga actcaggcgc     720
cctgaccagc ggcgtgcaca ccttcccggc tgtcctacag tcctcaggac tctactccct     780
cagcagcgtg gtgaccgtgc cctccagcag cttgggcacc cagacctaca tctgcaacgt     840
gaatcacaag cccagcaaca ccaaggtgga caagaaagtt ggtgagaggc cagcacaggg     900
agggagggtg tctgctggaa gccaggctca gcgctcctgc ctggacgcat cccggctatg     960
cagcccagt ccagggcagc aaggcaggcc cgtctgcct cttcacccgg aggcctctgc      1020
ccgccccact catgctcagg gagagggtct tctggctttt tccccaggct ctgggcaggc    1080
acaggctagg tgccctaac ccaggccctg cacacaaagg ggcaggtgct gggctcagac     1140
ctgccaagag ccatatccgg gaggaccctg cccctgacct aagcccaccc caaaggccaa    1200
actctccact ccctcagctc ggacaccttc tctcctccca gattccagta actcccaatc    1260
ttctctctgc agagcccaaa tcttgtgaca aaactcacac atgcccaccg tgcccaggta    1320
agccagccca ggcctcgccc tccagctcaa ggcgggacag gtgccctaga gtagcctgca    1380
tccagggaca ggccccagcc gggtgctgac acgtccacct ccatctcttc ctcagcacct    1440
gaactcctgg ggggaccgtc agtcttcctc ttccccccaa aacccaagga caccctcatg    1500
atctcccgga cccctgaggt cacatgcgtg gtggtggacg tgagccacga agaccctgag    1560
gtcaagttca actggtacgt ggacggcgtg gaggtgcata atgccaagac aaagccgcgg    1620
gaggagcagt acaacagcac gtaccgtgtg gtcagcgtcc tcaccgtcct gcaccaggac    1680
tggctgaatg gcaaggagta caagtgcaag gtctccaaca aagccctccc agcccccatc    1740
gagaaaacca tctccaaagc caaaggtggg acccgtgggg tgcgagggcc acatggacag    1800
aggccggctc ggcccaccct ctgccctgag agtgaccgct gtaccaacct ctgtccctac    1860
agggcagccc cgagaaccac aggtgtacac cctgccccca tcccgggatg agctgaccaa    1920
gaaccaggtc agcctgacct gcctggtcaa aggcttctat cccagcgaca tcgccgtgga    1980
gtgggagagc aatgggcagc cggagaacaa ctacaagacc acgcctcccg tgctggactc    2040
cgacggctcc ttcttcctct acagcaagct caccgtggac aagagcaggt ggcagcaggg    2100
gaacgtcttc tcatgctccg tgatgcatga ggctctgcac aaccactaca cgcagaagag    2160
cctctccctg tctccgggta aaggaggagg aggaagcgga ggaggaggaa gcggaggagg    2220
aggaagcgag gtgcagctgc tcgagagcgg gggaggcttg gtacagcctg ggggtccct    2280
gcgcctctcc tgtgcagcca gcggattcac cttttcttct tactacatgg gttgggtccg    2340
ccaggctcca gggaagggc tggagtgggt ctcaggtatt ggttcttact acggttacac    2400
aggttatgca gactccgtga agggccggtt caccatctcc cgtgacaatt ccaagaacac    2460
gctgtatctg caaatgaaca gcctgcgtgc cgaggacacg gctgtatatt attgtgcgcg    2520
cgcttactac gactacaact actactacgc ttactttgac tattgggggcc agggaaccct    2580
ggtcaccgtc tcctcaggtg gaggcggttc aggcggaggt ggatccggcg gtggcggatc    2640
ggacatccag atgacccagt ctccatcctc cctgagcgca tctgtaggag accgcgtcac    2700
catcacttgc cgggcaagtc agagcattag cagctattta aattggtatc agcagaaacc    2760
```

-continued

```
agggaaagcc cctaagctcc tgatctatgc tgcatccagt ttgcaaagtg gggtcccatc    2820
acgtttcagt ggcagtggaa gcgggacaga tttcactctc accatcagca gtctgcaacc    2880
tgaagatttt gcaacttatt actgtcaaca gtctgttccg cactaccgt tcacttttgg     2940 ccaggggacc aagctggaga tcaaa                                          2965
```

<210> SEQ ID NO 155
<211> LENGTH: 709
<212> TYPE: PRT
<213> ORGANISM: Homo sapiens

<400> SEQUENCE: 155

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Tyr
            20                  25                  30

Tyr Met Ser Trp Val Arg Gln Ala Pro Gly Lys Gly Leu Glu Trp Val
        35                  40                  45

Ser Tyr Ile Pro Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asp Tyr Tyr Trp Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Glu Val
    450                 455                 460

Gln Leu Leu Glu Ser Gly Gly Gly Leu Val Gln Pro Gly Gly Ser Leu
465                 470                 475                 480

Arg Leu Ser Cys Ala Ala Ser Gly Phe Thr Phe Ser Ser Tyr Tyr Met
                485                 490                 495

Gly Trp Val Arg Gln Ala Pro Gly Lys Gly Leu Glu Trp Val Ser Gly
            500                 505                 510

Ile Gly Ser Tyr Tyr Gly Tyr Thr Gly Tyr Ala Asp Ser Val Lys Gly
        515                 520                 525

Arg Phe Thr Ile Ser Arg Asp Asn Ser Lys Asn Thr Leu Tyr Leu Gln
    530                 535                 540

Met Asn Ser Leu Arg Ala Glu Asp Thr Ala Val Tyr Tyr Cys Ala Arg
545                 550                 555                 560

Ala Tyr Tyr Asp Tyr Asn Tyr Tyr Ala Tyr Phe Asp Tyr Trp Gly
                565                 570                 575

Gln Gly Thr Leu Val Thr Val Ser Ser Gly Gly Gly Ser Gly Gly
            580                 585                 590

Gly Gly Ser Gly Gly Gly Gly Ser Asp Ile Gln Met Thr Gln Ser Pro
        595                 600                 605

Ser Ser Leu Ser Ala Ser Val Gly Asp Arg Val Thr Ile Thr Cys Arg
610                 615                 620

Ala Ser Gln Ser Ile Ser Ser Tyr Leu Asn Trp Tyr Gln Gln Lys Pro
625                 630                 635                 640

Gly Lys Ala Pro Lys Leu Leu Ile Tyr Ala Ala Ser Ser Leu Gln Ser
                645                 650                 655

Gly Val Pro Ser Arg Phe Ser Gly Ser Gly Ser Gly Thr Asp Phe Thr
            660                 665                 670

Leu Thr Ile Ser Ser Leu Gln Pro Glu Asp Phe Ala Thr Tyr Tyr Cys
        675                 680                 685

Gln Gln Ser Val Pro His Tyr Pro Phe Thr Phe Gly Gln Gly Thr Lys
    690                 695                 700

Leu Glu Ile Lys Arg
705

<210> SEQ ID NO 156
<211> LENGTH: 2962
<212> TYPE: DNA
<213> ORGANISM: Homo sapiens

<400> SEQUENCE: 156
```

```
gaggtgcagc tgttggagag cgggggaggc ttggtacagc ctggggggtc cctgcgcctc    60
tcctgtgcag ccagcggatt cacctttggt ggttactaca tgtcttgggt ccgccaggct   120
ccagggaagg ggctggagtg ggtctcatac attcctggtt ctggtggttc tacatactat   180
gcagactccg tgaagggccg gttcaccatc tcccgtgaca attccaagaa cacgctgtat   240
ctgcaaatga acagcctgcg tgccgaggac acggctgtat attattgtgc gcgctacgac   300
tactactgga tggactattg gggccaggga accctggtca ccgtctcctc aggtgagtta   360
acgtacgcta gcaagctttc tggggcaggc caggcctgac cttggctttg ggcagggag   420
ggggctaagg tgaggcaggt ggcgccagcc aggtgcacac ccaatgccca tgagcccaga   480
cactggacgc tgaacctcgc ggacagttaa gaacccaggg gcctctgcgc cctgggccca   540
gctctgtccc acaccgcggt cacatggcac cacctctctt gcagcctcca ccaagggccc   600
atcggtcttc cccctggcac cctcctccaa gagcacctct gggggcacag cggccctggg   660
ctgcctggtc aaggactact tccccgaacc ggtgacggtg tcgtggaact caggcgccct   720
gaccagcggc gtgcacacct tcccggctgt cctacagtcc tcaggactct actccctcag   780
cagcgtggtg accgtgccct ccagcagctt gggcacccag acctacatct gcaacgtgaa   840
tcacaagccc agcaacacca aggtggacaa gaaagttggt gagaggccag cacagggagg   900
gagggtgtct gctggaagcc aggctcagcg ctcctgcctg gacgcatccc ggctatgcag   960
ccccagtcca gggcagcaag gcaggccccg tctgcctctt cacccggagg cctctgcccg  1020
ccccactcat gctcagggag agggtcttct ggcttttttcc ccaggctctg gcaggcaca  1080
ggctaggtgc ccctaaccca ggccctgcac acaaaggggc aggtgctggg ctcagacctg  1140
ccaagagcca tatccgggag gaccctgccc ctgacctaag cccacccaa aggccaaact  1200
ctccactccc tcagctcgga caccttctct cctcccagat tccagtaact cccaatcttc  1260
tctctgcaga gcccaaatct tgtgacaaaa ctcacacatg cccaccgtgc ccaggtaagc  1320
cagcccaggc ctcgccctcc agctcaaggc gggacaggtg cctagagta gcctgcatcc  1380
agggacaggc cccagccggg tgctgacacg tccacctcca tctcttcctc agcacctgaa  1440
ctcctggggg gaccgtcagt cttcctcttc ccccaaaac ccaaggacac cctcatgatc  1500
tcccggaccc ctgaggtcac atgcgtggtg gtggacgtga gccacgaaga ccctgaggtc  1560
aagttcaact ggtacgtgga cggcgtggag gtgcataatg ccaagacaaa gccgcgggag  1620
gagcagtaca acagcacgta ccgtgtggtc agcgtcctca ccgtcctgca ccaggactgg  1680
ctgaatggca aggagtacaa gtgcaaggtc tccaacaaag ccctcccagc ccccatcgag  1740
aaaaccatct ccaaagccaa aggtgggacc cgtggggtgc gagggccaca tggacagagg  1800
ccggctcggc ccaccctctg ccctgagagt gaccgctgta ccaacctctg tcctacagg  1860
gcagccccga gaaccacagg tgtacaccct gcccccatcc cgggatgagc tgaccaagaa  1920
ccaggtcagc ctgacctgcc tggtcaaagg cttctatccc agcgacatcg ccgtggagtg  1980
ggagagcaat gggcagccgg agaacaacta caagaccacg cctcccgtgc tggactccga  2040
cggctccttc ttcctctaca gcaagctcac cgtggacaag agcaggtggc agcaggggaa  2100
cgtcttctca tgctccgtga tgcatgaggc tctgcacaac cactacacgc agaagagcct  2160
ctccctgtct ccgggtaaag gaggaggagg aagcggagga ggaggaagcg gaggaggagg  2220
aagcgaggtg cagctgctcg agagcggggg aggcttggta cagcctgggg ggtccctgcg  2280
cctctcctgt gcagccagcg gattcacctt ttcttcttac tacatgggtt gggtccgcca  2340
```

-continued

```
ggctccaggg aagggqctgg agtgggtctc aggtattggt tcttactacg gttacacagg    2400
ttatgcagac tccgtgaagg gccggttcac catctcccgt gacaattcca agaacacgct    2460
gtatctgcaa atgaacagcc tgcgtgccga ggacacgggct gtatattatt gtgcgcgcgc   2520
ttactacgac tacaaactact actacgctta ctttgactat ggggccagg  gaaccctggt    2580 caccgtctcc tcaggtggag gcggttcagg cggaggtgga tccggcggtg gcggatcgga    2640
catccagatg acccagtctc catcctccct gagcgcatct gtaggagacc gcgtcaccat    2700
cacttgccgg gcaagtcaga gcattagcag ctatttaaat tggtatcagc agaaaccagg    2760
gaaagcccct aagctcctga tctatgctgc atccagtttg caaagtgggg tcccatcacg    2820
tttcagtggc agtggaagcg ggacagattt cactctcacc atcagcagtc tgcaacctga    2880
agattttgca acttattact gtcaacagtc tgttccgcac tacccgttca cttttggcca    2940
ggggaccaag ctggagatca aa                                             2962
```

<210> SEQ ID NO 157
<211> LENGTH: 708
<212> TYPE: PRT
<213> ORGANISM: Homo sapiens

<400> SEQUENCE: 157

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Tyr Tyr Ser Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Tyr Leu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Asp Glu Leu Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys Gly Gly
                435                 440                 445
Gly Gly Ser Gly Gly Gly Gly Ser Gly Gly Gly Gly Ser Glu Val Gln
        450                 455                 460
Leu Leu Glu Ser Gly Gly Gly Leu Val Gln Pro Gly Gly Ser Leu Arg
465                 470                 475                 480
Leu Ser Cys Ala Ala Ser Gly Phe Thr Phe Ser Ser Tyr Tyr Met Gly
                485                 490                 495
Trp Val Arg Gln Ala Pro Gly Lys Gly Leu Glu Trp Val Ser Gly Ile
                500                 505                 510
Gly Ser Tyr Tyr Gly Tyr Thr Gly Tyr Ala Asp Ser Val Lys Gly Arg
        515                 520                 525
Phe Thr Ile Ser Arg Asp Asn Ser Lys Asn Thr Leu Tyr Leu Gln Met
        530                 535                 540
Asn Ser Leu Arg Ala Glu Asp Thr Ala Val Tyr Tyr Cys Ala Arg Ala
545                 550                 555                 560
Tyr Tyr Asp Tyr Asn Tyr Tyr Ala Tyr Phe Asp Tyr Trp Gly Gln
                565                 570                 575
Gly Thr Leu Val Thr Val Ser Ser Gly Gly Gly Ser Gly Gly Gly
        580                 585                 590
Gly Ser Gly Gly Gly Gly Ser Asp Ile Gln Met Thr Gln Ser Pro Ser
                595                 600                 605
Ser Leu Ser Ala Ser Val Gly Asp Arg Val Thr Ile Thr Cys Arg Ala
                610                 615                 620
Ser Gln Ser Ile Ser Ser Tyr Leu Asn Trp Tyr Gln Gln Lys Pro Gly
625                 630                 635                 640
Lys Ala Pro Lys Leu Leu Ile Tyr Ala Ala Ser Ser Leu Gln Ser Gly
                645                 650                 655
Val Pro Ser Arg Phe Ser Gly Ser Gly Ser Gly Thr Asp Phe Thr Leu
                660                 665                 670
Thr Ile Ser Ser Leu Gln Pro Glu Asp Phe Ala Thr Tyr Tyr Cys Gln
                675                 680                 685
```

Gln Ser Val Pro His Tyr Pro Phe Thr Phe Gly Gln Gly Thr Lys Leu
    690                 695                 700

Glu Ile Lys Arg
705

<210> SEQ ID NO 158
<211> LENGTH: 2959
<212> TYPE: DNA
<213> ORGANISM: Homo sapiens

<400> SEQUENCE: 158

| | | | | | |
|---|---|---|---|---|---|
| gaggtgcagc | tgttggagag | cgggggaggc | ttggtacagc | ctgggggggtc | cctgcgcctc | 60 |
| tcctgtgcag | ccagcggatt | cacctttagc | agctatgcca | tgagctgggt | ccgccaggct | 120 |
| ccagggaagg | ggctggagtg | ggtctcatac | atttcttact | actctggtta | cacatactat | 180 |
| gcagactccg | tgaagggccg | gttcaccatc | tcccgtgaca | attccaagaa | cacgctgtat | 240 |
| ctgcaaatga | acagcctgcg | tgccgaggac | acggctgtat | attattgtgc | gcgcggttac | 300 |
| ggttacttgg | actattgggg | ccagggaacc | ctggtcaccg | tctcctcagg | tgagttaacg | 360 |
| tacgctagca | agctttctgg | ggcaggccag | gcctgacctt | ggctttgggg | cagggagggg | 420 |
| gctaaggtga | ggcaggtggc | gccagccagg | tgcacaccca | atgcccatga | gcccagacac | 480 |
| tggacgctga | acctcgcgga | cagttaagaa | cccaggggcc | tctgcgccct | gggcccagct | 540 |
| ctgtcccaca | ccgcggtcac | atggcaccac | ctctcttgca | gcctccacca | agggcccatc | 600 |
| ggtcttcccc | ctggcaccct | cctccaagag | cacctctggg | ggcacagcgg | ccctgggctg | 660 |
| cctggtcaag | gactacttcc | ccgaaccggt | gacggtgtcg | tggaactcag | gcgccctgac | 720 |
| cagcggcgtg | cacaccttcc | cggctgtcct | acagtcctca | ggactctact | ccctcagcag | 780 |
| cgtggtgacc | gtgccctcca | gcagcttggg | cacccagacc | tacatctgca | acgtgaatca | 840 |
| caagcccagc | aacaccaagg | tggacaagaa | agttggtgag | aggccagcac | agggagggag | 900 |
| ggtgtctgct | ggaagccagg | ctcagcgctc | ctgcctggac | gcatcccggc | tatgcagccc | 960 |
| cagtccaggg | cagcaaggca | ggccccgtct | gcctcttcac | ccggaggcct | ctgcccgccc | 1020 |
| cactcatgct | caggagagg | gtcttctggc | tttttcccca | ggctctgggc | aggcacaggc | 1080 |
| taggtgcccc | taacccaggc | cctgcacaca | aaggggcagg | tgctgggctc | agacctgcca | 1140 |
| agagccatat | ccgggaggac | cctgcccctg | acctaagccc | accccaaagg | ccaaactctc | 1200 |
| cactccctca | gctcggacac | cttctctcct | cccagattcc | agtaactccc | aatcttctct | 1260 |
| ctgcagagcc | caaatcttgt | gacaaaactc | acacatgccc | accgtgccca | ggtaagccag | 1320 |
| cccaggcctc | gccctccagc | tcaaggcggg | acaggtgccc | tagagtagcc | tgcatccagg | 1380 |
| gacaggcccc | agccgggtgc | tgacacgtcc | acctccatct | cttcctcagc | acctgaactc | 1440 |
| ctgggggggac | cgtcagtctt | cctcttcccc | ccaaaaccca | aggacaccct | catgatctcc | 1500 |
| cggacccctg | aggtcacatg | cgtggtggtg | gacgtgagcc | acgaagaccc | tgaggtcaag | 1560 |
| ttcaactggt | acgtggacgg | cgtggaggtg | cataatgcca | agacaaagcc | gcgggaggag | 1620 |
| cagtacaaca | gcacgtaccg | tgtggtcagc | gtcctcaccg | tcctgcacca | ggactggctg | 1680 |
| aatggcaagg | agtacaagtg | caaggtctcc | aacaaagccc | tcccagcccc | catcgagaaa | 1740 |
| accatctcca | aagccaaagg | tgggacccgt | ggggtgcgag | ggccacatgg | acagaggccg | 1800 |
| gctcggccca | ccctctgccc | tgagagtgac | cgctgtacca | acctctgtcc | ctacagggca | 1860 |
| gccccgagaa | ccacaggtgt | acaccctgcc | cccatcccgg | gatgagctga | ccaagaacca | 1920 |

-continued

```
ggtcagcctg acctgcctgg tcaaaggctt ctatcccagc gacatcgccg tggagtggga    1980
gagcaatggg cagccggaga acaactacaa gaccacgcct cccgtgctgg actccgacgg    2040
ctccttcttc ctctacagca agctcaccgt ggacaagagc aggtggcagc aggggaacgt    2100
cttctcatgc tccgtgatgc atgaggctct gcacaaccac tacacgcaga agagcctctc    2160
cctgtctccg ggtaaaggag gaggaggaag cggaggagga ggaagcggag gaggaggaag    2220
cgaggtgcag ctgctcgaga gcgggggagg cttggtacag cctggggggt ccctgcgcct    2280
ctcctgtgca gccagcggat tcacctttc ttcttactac atgggttggg tccgccaggc    2340
tccagggaag gggctggagt gggtctcagg tattggttct tactacggtt acacaggtta    2400
tgcagactcc gtgaagggcc ggttcaccat ctcccgtgac aattccaaga acacgctgta    2460
tctgcaaatg aacagcctgc gtgccgagga cacggctgta tattattgtg cgcgcgctta    2520
ctacgactac aactactact acgcttactt tgactattgg ggccagggaa ccctggtcac    2580
cgtctcctca ggtggaggcg gttcaggcgg aggtggatcc ggcggtggcg gatcggacat    2640
ccagatgacc cagtctccat cctccctgag cgcatctgta ggagaccgcg tcaccatcac    2700
ttgccgggca gtcagagca ttagcagcta tttaaattgg tatcagcaga accagggaa    2760 agcccctaag ctcctgatct atgctgcatc cagtttgcaa agtggggtcc catcacgttt    2820
cagtggcagt ggaagcggga cagatttcac tctcaccatc agcagtctgc aacctgaaga    2880
ttttgcaact tattactgtc aacagtctgt tccgcactac ccgttcactt ttggccaggg    2940
gaccaagctg gagatcaaa    2959
```

<210> SEQ ID NO 159
<211> LENGTH: 716
<212> TYPE: PRT
<213> ORGANISM: Homo sapiens

<400> SEQUENCE: 159

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Ser His Gly Tyr Tyr Val Tyr Gly Thr Leu Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

-continued

```
Val Thr Val Pro Ser Ser Leu Gly Thr Gln Thr Tyr Ile Cys Asn
        195                 200                 205
Val Asn His Lys Pro Ser Asn Thr Lys Val Asp Lys Lys Val Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                    245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
        290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                    325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Asp Glu Leu Thr Lys Asn
            355                 360                 365
Gln Val Ser Leu Thr Cys Leu Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                    405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
            435                 440                 445
Ser Leu Ser Pro Gly Lys Gly Gly Gly Ser Gly Gly Gly Gly Ser
        450                 455                 460
Gly Gly Gly Gly Ser Glu Val Gln Leu Leu Glu Ser Gly Gly Gly Leu
465                 470                 475                 480
Val Gln Pro Gly Gly Ser Leu Arg Leu Ser Cys Ala Ala Ser Gly Phe
                    485                 490                 495
Thr Phe Ser Ser Tyr Tyr Met Gly Trp Val Arg Gln Ala Pro Gly Lys
                500                 505                 510
Gly Leu Glu Trp Val Ser Gly Ile Gly Ser Tyr Tyr Gly Tyr Thr Gly
            515                 520                 525
Tyr Ala Asp Ser Val Lys Gly Arg Phe Thr Ile Ser Arg Asp Asn Ser
        530                 535                 540
Lys Asn Thr Leu Tyr Leu Gln Met Asn Ser Leu Arg Ala Glu Asp Thr
545                 550                 555                 560
Ala Val Tyr Tyr Cys Ala Arg Ala Tyr Tyr Asp Tyr Asn Tyr Tyr
                    565                 570                 575
Ala Tyr Phe Asp Tyr Trp Gly Gln Gly Thr Leu Val Thr Val Ser Ser
                580                 585                 590
Gly Gly Gly Gly Ser Gly Gly Gly Ser Gly Gly Gly Gly Ser Asp
            595                 600                 605
```

```
Ile Gln Met Thr Gln Ser Pro Ser Ser Leu Ser Ala Ser Val Gly Asp
    610                 615                 620
Arg Val Thr Ile Thr Cys Arg Ala Ser Gln Ser Ile Ser Ser Tyr Leu
625                 630                 635                 640
Asn Trp Tyr Gln Gln Lys Pro Gly Lys Ala Pro Lys Leu Leu Ile Tyr
                645                 650                 655
Ala Ala Ser Ser Leu Gln Ser Gly Val Pro Ser Arg Phe Ser Gly Ser
            660                 665                 670
Gly Ser Gly Thr Asp Phe Thr Leu Thr Ile Ser Ser Leu Gln Pro Glu
        675                 680                 685
Asp Phe Ala Thr Tyr Tyr Cys Gln Gln Ser Val Pro His Tyr Pro Phe
690                 695                 700
Thr Phe Gly Gln Gly Thr Lys Leu Glu Ile Lys Arg
705                 710                 715
```

<210> SEQ ID NO 160
<211> LENGTH: 2983
<212> TYPE: DNA
<213> ORGANISM: Homo sapiens

<400> SEQUENCE: 160

```
gaggtgcagc tgttggagag cggggggaggc ttggtacagc ctggggggtc cctgcgcctc      60
tcctgtgcag ccagcggatt cacctttagc agctatgcca tgagctgggt ccgccaggct     120
ccagggaagg ggctggagtg ggtctcagct attagtggta gtggtggtag cacatactat     180
gcagactccg tgaagggccg gttcaccatc tcccgtgaca attccaagaa cacgctgtat     240
ctgcaaatga acagcctgcg tgccgaggac acggctgtat attattgtgc gcgctactac     300
tactctcatg gttactacgt ttacggtact ttggactatt ggggccaggg aaccctggtc     360
accgtctcct caggtgagtt aacgtacgct agcaagcttt ctggggcagg ccaggcctga     420
ccttggcttt ggggcaggga gggggctaag gtgaggcagg tggcgccagc caggtgcaca     480
cccaatgccc atgagcccag acactggacg ctgaacctcg cggacagtta agaacccagg     540
ggcctctgcg ccctgggccc agctctgtcc cacaccgcgg tcacatggca ccacctctct     600
tgcagcctcc accaagggcc catcggtctt ccccctggca ccctcctcca agagcacctc     660
tggggggcaca gcggccctgg gctgcctggt caaggactac ttccccgaac cggtgacggt     720
gtcgtggaac tcaggcgccc tgaccagcgg cgtgcacacc ttcccggctg tcctacagtc     780
ctcaggactc tactccctca gcagcgtggt gaccgtgccc tccagcagct gggcaccca     840
gacctacatc tgcaacgtga atcacaagcc cagcaacacc aaggtggaca agaaagttgg     900
tgagaggcca gcacagggag ggagggtgtc tgctggaagc caggctcagc gctcctgcct     960
ggacgcatcc cggctatgca gccccagtcc agggcagcaa ggcaggcccc gtctgcctct    1020
tcacccggag gcctctgccc gccccactca tgctcaggga gagggtcttc tggcttttc    1080
cccaggctct gggcaggcac aggctaggtg cccctaaccc aggccctgca cacaaagggg    1140
caggtgctgg gctcagacct gccaagagcc atatccggga ggaccctgcc cctgacctaa    1200
gcccaccccca aaggccaaac tctccactcc ctcagctcgg acaccttctc tcctcccaga    1260
ttccagtaac tcccaatctt ctctctgcag agcccaaatc ttgtgacaaa actcacacat    1320
gcccaccgtg cccaggtaag ccagcccagg cctcgccctc cagctcaagg cgggacaggt    1380
gccctagagt agcctgcatc cagggacagg ccccagccgg tgctgacac gtccacctcc    1440
atctcttcct cagcacctga actcctgggg ggaccgtcag tcttcctctt ccccccaaaa    1500
```

-continued

```
cccaaggaca ccctcatgat ctcccggacc cctgaggtca catgcgtggt ggtggacgtg    1560
agccacgaag accctgaggt caagttcaac tggtacgtgg acggcgtgga ggtgcataat    1620
gccaagacaa agccgcggga ggagcagtac aacagcacgt accgtgtggt cagcgtcctc    1680
accgtcctgc accaggactg gctgaatggc aaggagtaca agtgcaaggt ctccaacaaa    1740
gccctcccag cccccatcga gaaaaccatc tccaaagcca aggtgggac ccgtggggtg     1800 cgagggccac atggacagag gccggctcgg cccaccctct gccctgagag tgaccgctgt    1860
accaacctct gtccctacag ggcagccccg agaaccacag gtgtacaccc tgcccccatc    1920
ccgggatgag ctgaccaaga accaggtcag cctgacctgc ctggtcaaag gcttctatcc    1980
cagcgacatc gccgtggagt gggagagcaa tgggcagccg gagaacaact acaagaccac    2040
gcctcccgtg ctggactccg acggctcctt cttcctctac agcaagctca ccgtggacaa    2100
gagcaggtgg cagcagggga acgtcttctc atgctccgtg atgcatgagg ctctgcacaa    2160
ccactacacg cagaagagcc tctccctgtc tccgggtaaa ggaggaggag gaagcggagg    2220
aggaggaagc ggaggaggag gaagcgaggt gcagctgctc gagagcgggg gaggcttggt    2280
acagcctggg gggtccctgc gcctctcctg tgcagccagc ggattcacct tttcttctta    2340
ctacatgggt tgggtccgcc aggctccagg gaagggctg gagtgggtct caggtattgg     2400
ttcttactac ggttacacag gttatgcaga ctccgtgaag gccggttca ccatctcccg      2460 tgacaattcc aagaacacgc tgtatctgca aatgaacagc ctgcgtgccg aggacacggc    2520
tgtatattat tgtgcgcgcg cttactacga ctacaactac tactacgctt actttgacta    2580
ttggggccag ggaaccctgg tcaccgtctc ctcaggtgga ggcggttcag gcggaggtgg    2640
atccggcggt ggcggatcgg acatccagat gacccagtct ccatcctccc tgagcgcatc    2700
tgtaggagac cgcgtcacca tcacttgccg ggcaagtcag agcattagca gctatttaaa    2760
ttggtatcag cagaaaccag ggaaagcccc taagctcctg atctatgctg catccagttt    2820
gcaaagtggg gtcccatcac gtttcagtgg cagtggaagc gggacagatt tcactctcac    2880
catcagcagt ctgcaacctg aagattttgc aacttattac tgtcaacagt ctgttccgca    2940
ctacccgttc acttttggcc aggggaccaa gctggagatc aaa                      2983
```

<210> SEQ ID NO 161
<211> LENGTH: 714
<212> TYPE: PRT
<213> ORGANISM: Homo sapiens

<400> SEQUENCE: 161

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ser Met Tyr Trp Val Arg Gln Ala Pro Gly Lys Gly Leu Glu Trp Val
        35                  40                  45

Ser Gly Ile Gly Tyr Ser Gly Tyr Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Phe His Asp Tyr Ala Ala Tyr Ser Leu Asp Tyr Trp
            100                 105                 110
```

```
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Lys Val Glu Pro Lys Ser
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
            290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
            355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly Lys Gly Gly Gly Ser Gly Gly Gly Ser Gly Gly Gly Gly
450                 455                 460
Gly Gly Ser Glu Val Gln Leu Leu Glu Ser Gly Gly Gly Leu Val Gln
465                 470                 475                 480
Pro Gly Gly Ser Leu Arg Leu Ser Cys Ala Ala Ser Gly Phe Thr Phe
                485                 490                 495
Ser Ser Tyr Tyr Met Gly Trp Val Arg Gln Ala Pro Gly Lys Gly Leu
            500                 505                 510
Glu Trp Val Ser Gly Ile Gly Ser Tyr Tyr Gly Tyr Thr Gly Tyr Ala
            515                 520                 525
Asp Ser Val Lys Gly Arg Phe Thr Ile Ser Arg Asp Asn Ser Lys Asn
```

```
                530                535                540
Thr Leu Tyr Leu Gln Met Asn Ser Leu Arg Ala Glu Asp Thr Ala Val
545                550                555                560

Tyr Tyr Cys Ala Arg Ala Tyr Asp Tyr Asn Tyr Tyr Ala Tyr
            565                570                575

Phe Asp Tyr Trp Gly Gln Gly Thr Leu Val Thr Val Ser Ser Gly Gly
            580                585                590

Gly Gly Ser Gly Gly Gly Gly Ser Gly Gly Gly Gly Ser Asp Ile Gln
            595                600                605

Met Thr Gln Ser Pro Ser Ser Leu Ser Ala Ser Val Gly Asp Arg Val
            610                615                620

Thr Ile Thr Cys Arg Ala Ser Gln Ser Ile Ser Ser Tyr Leu Asn Trp
625                630                635                640

Tyr Gln Gln Lys Pro Gly Lys Ala Pro Lys Leu Leu Ile Tyr Ala Ala
            645                650                655

Ser Ser Leu Gln Ser Gly Val Pro Ser Arg Phe Ser Gly Ser Gly Ser
            660                665                670

Gly Thr Asp Phe Thr Leu Thr Ile Ser Ser Leu Gln Pro Glu Asp Phe
            675                680                685

Ala Thr Tyr Tyr Cys Gln Gln Ser Val Pro His Tyr Pro Phe Thr Phe
            690                695                700

Gly Gln Gly Thr Lys Leu Glu Ile Lys Arg
705                710

<210> SEQ ID NO 162
<211> LENGTH: 2977
<212> TYPE: DNA
<213> ORGANISM: Homo sapiens

<400> SEQUENCE: 162
gaggtgcagc tgttggagag cggggggaggc ttggtacagc ctgggggggtc cctgcgcctc       60 tcctgtgcag ccagcggatt cacctttttct ggttactcta tgtactgggt ccgccaggct      120
ccagggaagg ggctggagtg ggtctcaggt attggttact ctggttacgg tacatactat      180
gcagactccg tgaagggccg gttcaccatc tcccgtgaca attccaagaa cacgctgtat      240
ctgcaaatga acagcctgcg tgccgaggac acggctgtat attattgtgc gcgctactac      300
ttccatgact acgctgctta ctctttggac tattggggcc agggaaccct ggtcaccgtc      360
tcctcaggtg agttaacgta cgctagcaag cttctggggg caggccaggc ctgaccttgg      420
ctttggggca gggagggggc taaggtgagg caggtggcgc cagccaggtg cacacccaat      480
gcccatgagc ccagacactg gacgctgaac ctcgcggaca gttaagaacc caggggcctc      540
tgcgccctgg gccagctct gtcccacacc gcggtcacat ggcaccacct ctcttgcagc      600
ctccaccaag ggcccatcgg tcttccccct ggcaccctcc tccaagagca cctctggggg      660
cacagcggcc ctgggctgcc tggtcaagga ctacttcccc gaaccggtga cggtgtcgtg      720
gaactcaggc gccctgacca gcggcgtgca caccttccg gctgtcctac agtcctcagg      780
actctactcc ctcagcagcg tggtgaccgt gccctccagc agcttgggca cccagaccta      840
catctgcaac gtgaatcaca agcccagcaa caccaaggtg gacaagaaag ttggtgagag      900
gccagcacag ggagggaggg tgtctgctgg aagccaggct cagcgctcct gcctggacgc      960
atcccggcta tgcagcccca gtccagggca gcaaggcagg cccgtctgc ctcttcaccc     1020 ggaggcctct gcccgcccca ctcatgctca gggagagggt cttctggctt tttccccagg     1080
```

```
ctctgggcag gcacaggcta ggtgcccta acccaggccc tgcacacaaa ggggcaggtg      1140
ctgggctcag acctgccaag agccatatcc gggaggaccc tgcccctgac ctaagcccac      1200
cccaaaggcc aaactctcca ctccctcagc tcggacacct tctctcctcc cagattccag      1260
taactcccaa tcttctctct gcagagccca atcttgtga caaaactcac acatgcccac       1320
cgtgcccagg taagccagcc caggcctcgc cctccagctc aaggcgggac aggtgcccta      1380
gagtagcctg catccaggga caggcccag ccgggtgctg acacgtccac ctccatctct       1440
tcctcagcac ctgaactcct gggggaccg tcagtcttcc tcttcccccc aaaacccaag       1500
gacaccctca tgatctcccg gacccctgag gtcacatgcg tggtggtgga cgtgagccac      1560
gaagaccctg aggtcaagtt caactggtac gtggacggcg tggaggtgca taatgccaag      1620
acaaagccgc gggaggagca gtacaacagc acgtaccgtg tggtcagcgt cctcaccgtc      1680
ctgcaccagg actggctgaa tggcaaggag tacaagtgca aggtctccaa caaagccctc      1740
ccagccccca tcgagaaaac catctccaaa gccaaaggtg ggacccgtgg ggtgcgaggg      1800
ccacatggac agaggccggc tcggcccacc ctctgccctg agagtgaccg ctgtaccaac      1860
ctctgtccct acagggcagc cccgagaacc acaggtgtac accctgcccc catcccggga      1920
tgagctgacc aagaaccagg tcagcctgac ctgcctggtc aaaggcttct atcccagcga      1980
catcgccgtg gagtgggaga gcaatgggca gccggagaac aactacaaga ccacgcctcc      2040
cgtgctggac tccgacggct ccttcttcct ctacagcaag ctcaccgtgg acaagagcag      2100
gtggcagcag gggaacgtct tctcatgctc cgtgatgcat gaggctctgc acaaccacta      2160
cacgcagaag agcctctccc tgtctccggg taaaggagga ggaggaagcg gaggaggagg      2220
aagcggagga ggaggaagcg aggtgcagct gctcgagagc gggggaggct tggtacagcc      2280 tgggggtcc ctgcgcctct cctgtgcagc cagcggattc accttttctt cttactacat       2340
gggttgggtc cgccaggctc cagggaaggg gctggagtgg gtctcaggta ttggttctta      2400
ctacggttac acaggttatg cagactccgt gaagggccgg ttcaccatct cccgtgacaa      2460
ttccaagaac acgctgtatc tgcaaatgaa cagcctgcgt gccgaggaca cggctgtata      2520
ttattgtgcg cgcgcttact acgactacaa ctactactac gcttactttg actattgggg      2580
ccagggaacc ctggtcaccg tctcctcagg tggaggcggt tcaggcggag gtggatccgg      2640
cggtggcgga tcggacatcc agatgaccca gtctccatcc tccctgagcg catctgtagg      2700
agaccgcgtc accatcactt gccgggcaag tcagagcatt agcagctatt taaattggta      2760
tcagcagaaa ccagggaaag cccctaagct cctgatctat gctgcatcca gtttgcaaag      2820
tggggtccca tcacgtttca gtggcagtgg aagcgggaca gatttcactc tcaccatcag      2880
cagtctgcaa cctgaagatt ttgcaactta ttactgtcaa cagtctgttc cgcactaccc      2940
gttcactttt ggccagggga ccaagctgga gatcaaa                              2977
```

<210> SEQ ID NO 163
<211> LENGTH: 710
<212> TYPE: PRT
<213> ORGANISM: Homo sapiens

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Ser
            20                  25                  30

Ser Met Tyr Trp Val Arg Gln Ala Pro Gly Lys Gly Leu Glu Trp Val

```
            35                  40                  45
Ser Gly Ile Gly Tyr Tyr Ser Tyr Ser Thr Ser Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Pro His His Tyr Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

Gly Gly Gly Gly Ser Gly Gly Gly Ser Gly Gly Gly Gly Ser Glu
                450                 455                 460
```

Val Gln Leu Leu Glu Ser Gly Gly Leu Val Gln Pro Gly Gly Ser
465                 470                 475                 480

Leu Arg Leu Ser Cys Ala Ala Ser Gly Phe Thr Phe Ser Ser Tyr Tyr
            485                 490                 495

Met Gly Trp Val Arg Gln Ala Pro Gly Lys Gly Leu Glu Trp Val Ser
        500                 505                 510

Gly Ile Gly Ser Tyr Tyr Gly Tyr Thr Gly Tyr Ala Asp Ser Val Lys
    515                 520                 525

Gly Arg Phe Thr Ile Ser Arg Asp Asn Ser Lys Asn Thr Leu Tyr Leu
530                 535                 540

Gln Met Asn Ser Leu Arg Ala Glu Asp Thr Ala Val Tyr Tyr Cys Ala
545                 550                 555                 560

Arg Ala Tyr Tyr Asp Tyr Asn Tyr Tyr Ala Tyr Phe Asp Tyr Trp
                565                 570                 575

Gly Gln Gly Thr Leu Val Thr Val Ser Ser Gly Gly Gly Ser Gly
            580                 585                 590

Gly Gly Ser Gly Gly Gly Ser Asp Ile Gln Met Thr Gln Ser
        595                 600                 605

Pro Ser Ser Leu Ser Ala Ser Val Gly Asp Arg Val Thr Ile Thr Cys
    610                 615                 620

Arg Ala Ser Gln Ser Ile Ser Ser Tyr Leu Asn Trp Tyr Gln Gln Lys
625                 630                 635                 640

Pro Gly Lys Ala Pro Lys Leu Leu Ile Tyr Ala Ala Ser Ser Leu Gln
                645                 650                 655

Ser Gly Val Pro Ser Arg Phe Ser Gly Ser Gly Ser Gly Thr Asp Phe
            660                 665                 670

Thr Leu Thr Ile Ser Ser Leu Gln Pro Glu Asp Phe Ala Thr Tyr Tyr
        675                 680                 685

Cys Gln Gln Ser Val Pro His Tyr Pro Phe Thr Phe Gly Gln Gly Thr
    690                 695                 700

Lys Leu Glu Ile Lys Arg
705                 710

<210> SEQ ID NO 164
<211> LENGTH: 2965
<212> TYPE: DNA
<213> ORGANISM: Homo sapiens

<400> SEQUENCE: 164
gaggtgcagc tgttggagag cggggggaggc ttggtacagc ctgggggggtc cctgcgcctc    60 tcctgtgcag ccagcggatt cacctttggt tcttcttcta tgtactgggt ccgccaggct   120
ccagggaagg ggctggagtg ggtctcaggt attggttact actcttactc tacatcttat   180
gcagactccg tgaagggccg gttcaccatc tcccgtgaca attccaagaa cacgctgtat   240
ctgcaaatga acagcctgcg tgccgaggac acggctgtat attattgtgc gcgcggttac   300
ccgcatcatt actttgacta ttggggccag ggaaccctgg tcaccgtctc ctcaggtgag   360
ttaacgtacg ctagcaagct ttctggggca ggccaggcct gaccttggct ttggggcagg   420
gagggggcta aggtgaggca ggtggcgcca gccaggtgca cacccaatgc ccatgagccc   480
agacactgga cgctgaacct cgcggacagt taagaaccca ggggcctctg cgccctgggc   540
ccagctctgt cccacaccgc ggtcacatgg caccacctct cttgcagcct ccaccaaggg   600
cccatcggtc ttccccctgg caccctcctc caagagcacc tctgggggca gcgcggccct   660

```
gggctgcctg gtcaaggact acttccccga accggtgacg gtgtcgtgga actcaggcgc    720
cctgaccagc ggcgtgcaca ccttcccggc tgtcctacag tcctcaggac tctactccct    780
cagcagcgtg gtgaccgtgc cctccagcag cttgggcacc cagacctaca tctgcaacgt    840
gaatcacaag cccagcaaca ccaaggtgga caagaaagtt ggtgagaggc cagcacaggg    900
agggagggtg tctgctggaa gccaggctca gcgctcctgc ctggacgcat cccggctatg    960
cagccccagt ccagggcagc aaggcaggcc cgtctgcct cttcacccgg aggcctctgc    1020
ccgccccact catgctcagg gagagggtct tctggctttt tccccaggct ctgggcaggc    1080
acaggctagg tgcccctaac ccaggccctg cacacaaagg ggcaggtgct gggctcagac    1140
ctgccaagag ccatatccgg gaggaccctg cccctgacct aagcccaccc caaaggccaa    1200
actctccact ccctcagctc ggacaccttc tctcctccca gattccagta actcccaatc    1260
ttctctctgc agagcccaaa tcttgtgaca aaactcacac atgcccaccg tgcccaggta    1320
agccagccca ggcctcgccc tccagctcaa ggcgggacag tgccctaga gtagcctgca    1380
tccagggaca ggccccagcc gggtgctgac acgtccacct ccatctcttc ctcagcacct    1440
gaactcctgg ggggaccgtc agtcttcctc ttccccccaa acccaaggac accctcatg    1500
atctcccgga cccctgaggt cacatgcgtg gtggtggacg tgagccacga agaccctgag    1560
gtcaagttca actggtacgt ggacggcgtg gaggtgcata atgccaagac aaagccgcgg    1620
gaggagcagt acaacagcac gtaccgtgtg gtcagcgtcc tcaccgtcct gcaccaggac    1680
tggctgaatg gcaaggagta caagtgcaag gtctccaaca aagccctccc agccccatc    1740
gagaaaacca tctccaaagc caaagtgggg acccgtgggg tgcgagggcc acatggacag    1800
aggccggctc ggcccaccct ctgccctgag agtgaccgct gtaccaacct ctgtccctac    1860
agggcagccc cgagaaccac aggtgtacac cctgccccca tcccgggatg agctgaccaa    1920
gaaccaggtc agcctgacct gcctggtcaa aggcttctat cccagcgaca tcgccgtgga    1980
gtgggagagc aatgggcagc cggagaacaa ctacaagacc acgcctcccg tgctggactc    2040
cgacggctcc ttcttcctct acagcaagct caccgtggac aagagcaggt ggcagcaggg    2100
gaacgtcttc tcatgctccg tgatgcatga ggctctgcac aaccactaca cgcagaagag    2160
cctctccctg tctccgggta aggaggagg aggaagcgga ggaggaggaa gcggaggagg    2220
aggaagcgag gtgcagctgc tcgagagcgg gggaggcttg gtacagcctg ggggtccct    2280
gcgcctctcc tgtgcagcca gcggattcac cttttcttct tactacatgg gttgggtccg    2340
ccaggctcca gggaagggc tggagtgggt ctcaggtatt ggttcttact acggttacac    2400
aggttatgca gactccgtga agggccggtt caccatctcc cgtgacaatt ccaagaacac    2460
gctgtatctg caaatgaaca gcctgcgtgc cgaggacacg gctgtatatt attgtgcgcg    2520
cgcttactac gactacaact actactacgc ttactttgac tattggggcc agggaaccct    2580
ggtcaccgtc tcctcaggtg gaggcggttc aggcggaggt ggatccggcg gtggcggatc    2640
ggacatccag atgacccagt ctccatcctc cctgagcgca tctgtaggag accgcgtcac    2700
catcacttgc cgggcaagtc agagcattag cagctattta aattggtatc agcagaaacc    2760
agggaaagcc cctaagctcc tgatctatgc tgcatccagt ttgcaaagtg ggtcccatc    2820
acgtttcagt ggcagtggaa gcgggacaga tttcactctc accatcagca gtctgcaacc    2880
tgaagatttt gcaacttatt actgtcaaca gtctgttccg cactaccgt tcacttttgg    2940
ccaggggacc aagctggaga tcaaa                                        2965
```

<210> SEQ ID NO 165
<211> LENGTH: 214
<212> TYPE: PRT
<213> ORGANISM: Homo sapiens

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 166
<211> LENGTH: 1007
<212> TYPE: DNA
<213> ORGANISM: Homo sapiens

<400> SEQUENCE: 166
gacatccaga tgacccagtc tccatcctcc ctgagcgcat ctgtaggaga ccgcgtcacc        60
atcacttgcc gggcaagtca gagcattagc agctatttaa attggtatca gcagaaacca       120
gggaaagccc ctaagctcct gatctatgct gcatccagtt tgcaaagtgg ggtcccatca       180
cgtttcagtg gcagtggaag cgggacagat ttcactctca ccatcagcag tctgcaacct       240
gaagattttg caacttatta ctgtcaacag agttacagta cccctatac ttttggccag        300 gggaccaagc tggagatcaa acgtgagtcg tacgctagca agcttgatat cgaattctaa       360
actctgaggg ggtcggatga cgtggccatt ctttgcctaa gcattgagt ttactgcaag        420 gtcagaaaag catgcaaagc cctcagaatg ctgcaaaga gctccaacaa acaatttag         480 aactttatta aggaataggg ggaagctagg aagaaactca aacatcaag atttaaata         540 cgcttcttgg tctccttgct ataattatct gggataagca tgctgttttc tgtctgtccc       600
taacatgccc tgtgattatc cgcaaacaac acacccaagg gcagaacttt gttacttaaa       660

```
caccatcctg tttgcttctt tcctcaggaa ctgtggctgc accatctgtc ttcatcttcc    720
cgccatctga tgagcagttg aaatctggaa ctgcctctgt tgtgtgcctg ctgaataact    780
tctatcccag agaggccaaa gtacagtgga aggtggataa cgccctccaa tcgggtaact    840
cccaggagag tgtcacagag caggacagca aggacagcac ctacagcctc agcagcaccc    900
tgacgctgag caaagcagac tacgagaaac acaaagtcta cgcctgcgaa gtcacccatc    960
agggcctgag ctcgcccgtc acaaagagct tcaacagggg agagtgt                1007
```

```
<210> SEQ ID NO 167
<211> LENGTH: 215
<212> TYPE: PRT
<213> ORGANISM: Homo sapiens

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Trp Tyr Gly Leu
                85                  90                  95

Ser Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 168
<211> LENGTH: 1010
<212> TYPE: DNA
<213> ORGANISM: Homo sapiens

<400> SEQUENCE: 168
gacatccaga tgacccagtc tccatcctcc ctgagcgcat ctgtaggaga ccgcgtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag tactactggt acggtctgtc cacttttggc    300
```

```
cagggggacca agctggagat caaacgtgag tcgtacgcta gcaagcttga tatcgaattc    360
taaactctga gggggtcgga tgacgtggcc attctttgcc taaagcattg agtttactgc    420
aaggtcagaa aagcatgcaa agccctcaga atggctgcaa agagctccaa caaaacaatt    480
tagaacttta ttaaggaata gggggaagct aggaagaaac tcaaaacatc aagattttaa    540
atacgcttct tggtctcctt gctataatta tctgggataa gcatgctgtt ttctgtctgt    600
ccctaacatg ccctgtgatt atccgcaaac aacacaccca agggcagaac tttgttactt    660
aaacaccatc ctgtttgctt ctttcctcag gaactgtggc tgcaccatct gtcttcatct    720
tcccgccatc tgatgagcag ttgaaatctg gaactgcctc tgttgtgtgc ctgctgaata    780
acttctatcc cagagaggcc aaagtacagt ggaaggtgga taacgccctc caatcgggta    840
actcccagga gagtgtcaca gagcaggaca gcaaggacag cacctacagc ctcagcagca    900
ccctgacgct gagcaaagca gactacgaga acacaaagt  ctacgcctgc gaagtcaccc    960
atcagggcct gagctcgccc gtcacaaaga gcttcaacag gggagagtgt                1010
```

<210> SEQ ID NO 169
<211> LENGTH: 215
<212> TYPE: PRT
<213> ORGANISM: Homo sapiens

<400> SEQUENCE: 169

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Gly Ser Tyr Pro
                85                  90                  95

His Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 170
<211> LENGTH: 1010
<212> TYPE: DNA

<213> ORGANISM: Homo sapiens

<400> SEQUENCE: 170

```
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag ggtcatggtt cttacccgca cacttttggc     300
caggggacca agctggagat caaacgtgag tcgtacgcta gcaagcttga tatcgaattc     360
taaactctga gggggtcgga tgacgtggcc attctttgcc taaagcattg agtttactgc     420
aaggtcagaa aagcatgcaa agccctcaga atggctgcaa agagctccaa caaaacaatt     480
tagaacttta ttaaggaata gggggaagct aggaagaaac tcaaacatca agattttaa      540
atacgcttct tggtctcctt gctataatta tctgggataa gcatgctgtt ttctgtctgt     600
ccctaacatg ccctgtgatt atccgcaaac aacacaccca agggcagaac tttgttactt     660
aaacaccatc ctgtttgctt ctttcctcag gaactgtggc tgcaccatct gtcttcatct     720
tcccgccatc tgatgagcag ttgaaatctg gaactgcctc tgttgtgtgc ctgctgaata     780
acttctatcc cagagaggcc aaagtacagt ggaaggtgga taacgccctc caatcgggta     840
actcccagga gagtgtcaca gagcaggaca gcaaggacag cacctacagc ctcagcagca     900
ccctgacgct gagcaaagca gactacgaga aacacaaagt ctacgcctgc gaagtcaccc     960
atcagggcct gagctcgccc gtcacaaaga gcttcaacag gggagagtgt                1010
```

<210> SEQ ID NO 171
<211> LENGTH: 213
<212> TYPE: PRT
<213> ORGANISM: Homo sapiens

<400> SEQUENCE: 171

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Leu Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 172
<211> LENGTH: 1004
<212> TYPE: DNA
<213> ORGANISM: Homo sapiens

<400> SEQUENCE: 172
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag tacggttctc tgctcacttt tggccagggg     300
accaagctgg agatcaaacg tgagtcgtac gctagcaagc ttgatatcga attctaaact     360
ctgaggggt cggatgacgt ggccattctt tgcctaaagc attgagttta ctgcaaggtc     420
agaaaagcat gcaaagccct cagaatggct gcaaagagct ccaacaaaac aatttagaac     480
tttattaagg aatagggga agctaggaag aaactcaaaa catcaagatt ttaaatacgc     540
ttcttggtct ccttgctata attatctggg ataagcatgc tgttttctgt ctgtccctaa     600
catgccctgt gattatccgc aaacaacaca cccaagggca gaactttgtt acttaaacac     660
catcctgttt gcttctttcc tcaggaactg tggctgcacc atctgtcttc atcttcccgc     720
catctgatga gcagttgaaa tctggaactg cctctgttgt gtgcctgctg aataacttct     780
atcccagaga ggccaaagta cagtggaagg tggataacgc cctccaatcg ggtaactccc     840
aggagagtgt cacagagcag gacagcaagg acagcaccta cagcctcagc agcaccctga     900
cgctgagcaa agcagactac gagaaacaca agtctacgc ctgcgaagtc acccatcagg     960
gcctgagctc gcccgtcaca aagagcttca cagggggaga gtgt                    1004

<210> SEQ ID NO 173
<211> LENGTH: 215
<212> TYPE: PRT
<213> ORGANISM: Homo sapiens

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Asp Ser Leu
                85                  90                  95

Leu Thr Phe Gly Gln Gly Thr Lys Leu Glu Ile Lys Arg Thr Val Ala
            100                 105                 110

```
Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 174
<211> LENGTH: 1010
<212> TYPE: DNA
<213> ORGANISM: Homo sapiens

<400> SEQUENCE: 174
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag tacggttctg attctctgct cacttttggc     300
caggggacca gctggagat caaacgtgag tcgtacgcta gcaagcttga tatcgaattc      360
taaactctga ggggtcgga tgacgtggcc attctttgcc taaagcattg agtttactgc      420
aaggtcagaa aagcatgcaa agccctcaga atggctgcaa agagctccaa caaaacaatt     480
tagaacttta ttaaggaata gggggaagct aggaagaaac tcaaaacatc aagattttaa     540
atacgcttct tggtctcctt gctataatta tctgggataa gcatgctgtt ttctgtctgt     600
ccctaacatg ccctgtgatt atccgcaaac aacacaccca agggcagaac tttgttactt     660
aaacaccatc ctgtttgctt cttttcctcag gaactgtggc tgcaccatct gtcttcatct     720
tcccgccatc tgatgagcag ttgaaatctg gaactgcctc tgttgtgtgc ctgctgaata     780
acttctatcc cagagaggcc aaagtacagt ggaaggtgga taacgccctc caatcgggta     840
actcccagga gagtgtcaca gagcaggaca gcaaggacag cacctacagc ctcagcagca     900
ccctgacgct gagcaaagca gactacgaga acacaaagt ctacgcctgc gaagtcaccc      960
atcagggcct gagctcgccc gtcacaaaga gcttcaacag gggagagtgt                1010

<210> SEQ ID NO 175
<211> LENGTH: 981
<212> TYPE: DNA
<213> ORGANISM: Homo sapiens

<400> SEQUENCE: 175
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
```

```
tacacctgca acgtagatca caagcccagc aacaccaagg tggacaagag agttgagtcc    300
aaatatggtc ccccatgccc accttgccca gcacctgagt tcctgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc aaagccaaa     660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggcta accgtggaca agagcaggtg gcaggagggg    900
aatgtcttct catgctccgt gatgcatgag gctctgcaca accactacac acagaagagc    960
ctctccctgt ctctgggtaa a                                              981

<210> SEQ ID NO 176
<211> LENGTH: 2028
<212> TYPE: DNA
<213> ORGANISM: Homo sapiens

<400> SEQUENCE: 176
agctttctgg ggcaggccgg gcctgacttt ggctggggc agggaggggg ctaaggtgac      60
gcaggtggcg ccagccaggt gcacacccaa tgcccatgag cccagacact ggaccctgca    120
tggaccatcg cggatagaca agaaccgagg ggcctctgcg ccctgggccc agctctgtcc    180
cacaccgcgg tcacatggca ccacctctct tgcagcttcc accaagggcc catccgtctt    240
cccctggcg ccctgctcca ggagcacctc cgagagcaca gccgccctgg gctgcctggt    300
caaggactac ttccccgaac cggtgacggt gtcgtggaac tcaggcgccc tgaccagcgg    360
cgtgcacacc ttcccggctg tcctacagtc ctcaggactc tactccctca gcagcgtggt    420
gaccgtgccc tccagcagct tgggcacgaa gacctacacc tgcaacgtag atcacaagcc    480
cagcaacacc aaggtggaca gagagagttg tgagaggcca gcacagggag ggagggtgtc    540
tgctggaagc caggctcagc cctcctgcct ggacgcaccc cggctgtgca gccccagccc    600
agggcagcaa ggcatgcccc atctgtctcc tcacccggag gcctctgacc accccactca    660
tgctcaggga gagggtcttc tggatttttc caccaggctc ccggcaccac aggctggatg    720
cccctacccc aggccctgcg catacagggc aggtgctgcg ctcagacctg ccaagagcca    780
tatccgggag gaccctgccc ctgacctaag cccacccaa aggccaaact ctccactccc    840
tcagctcaga caccttctct cctcccagat ctgagtaact cccaatcttc tctctgcaga    900
gtccaaatat ggtcccccat gcccaccttg cccaggtaag ccaacccagg cctcgccctc    960
cagctcaagg cgggacaggt gccctagagt agcctgcatc cagggacagg cccagccgg   1020
gtgctgacgc atccacctcc atctcttcct cagcacctga gttcctgggg gaccatcag   1080
tcttcctgtt cccccaaaaa cccaaggaca ctctcatgat ctcccggacc cctgaggtca   1140
cgtgcgtggt ggtggacgtg agccaggaag accccgaggt ccagttcaac tggtacgtgg   1200
atggcgtgga ggtgcataat gccaagacaa agccgcggga ggagcagttc aacagcacgt   1260
accgtgtggt cagcgtcctc accgtcctgc accaggactg gctgaacggc aaggagtaca   1320
```

```
agtgcaaggt ctccaacaaa ggcctcccgt cctccatcga gaaaaccatc tccaaagcca    1380
aaggtgggac ccacggggtg cgagggccac acggacagag gccagctcgg cccacccctct   1440 gccctgggag tgaccgctgt gccaacctct gtccctacag ggcagccccg agagccacag    1500
gtgtacaccc tgccccatc ccaggaggag atgaccaaga accaggtcag cctgacctgc     1560
ctggtcaaag gcttctaccc cagcgacatc gccgtggagt gggagagcaa tgggcagccg    1620
gagaacaact acaagaccac gcctcccgtg ctggactccg acggctcctt cttcctctac    1680
agcaggctaa ccgtggacaa gagcaggtgg caggagggga atgtcttctc atgctccgtg    1740
atgcatgagg ctctgcacaa ccactacaca cagaagagcc tctccctgtc tctgggtaaa    1800
tgagtgccag ggccggcaag ccccgctcc ccgggctctc ggggtcgcgc gaggatgctt     1860
ggcacgtacc ccgtctacat acttcccagg cacccagcat ggaaataaag cacccaccac    1920
tgccctgggc ccctgtgaga ctgtgatggt tctttccacg ggtcaggccg agtctgaggc    1980
ctgagtgaca tgagggaggc agagcgggtc ccactgtccc cacactgg                 2028
```

<210> SEQ ID NO 177
<211> LENGTH: 108
<212> TYPE: PRT
<213> ORGANISM: Homo sapiens
<220> FEATURE:
<223> OTHER INFORMATION: 1205, light chain VL

<400> SEQUENCE: 177

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Val Pro His Tyr Pro
                85                  90                  95
Phe Thr Phe Gly Gln Gly Thr Lys Leu Glu Ile Lys
            100                 105

<210> SEQ ID NO 178
<211> LENGTH: 324
<212> TYPE: DNA
<213> ORGANISM: Homo sapiens
<220> FEATURE:
<223> OTHER INFORMATION: 1205, light chain VL

<400> SEQUENCE: 178

```
gacatccaga tgacccagtc tccatcctcc ctgagcgcat ctgtaggaga ccgcgtcacc     60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag tctgttccgc actaccccgtt cacttttggc  300 caggggacca agctggagat caaa                                          324
```

<210> SEQ ID NO 179

<211> LENGTH: 123
<212> TYPE: PRT
<213> ORGANISM: Homo sapiens
<220> FEATURE:
<223> OTHER INFORMATION: 1204, heavy chain VH

<400> SEQUENCE: 179

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Tyr | Met | Gly | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Gly | Ile | Gly | Ser | Tyr | Tyr | Gly | Tyr | Thr | Gly | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Ala | Tyr | Tyr | Asp | Tyr | Asn | Tyr | Tyr | Ala | Tyr | Phe | Asp | Tyr |
|---|---|---|---|---|---|---|---|---|---|---|---|---|---|---|
| | | | | 100 | | | | | 105 | | | | | 110 |

| Trp | Gly | Gln | Gly | Thr | Leu | Val | Thr | Val | Ser | Ser |
|---|---|---|---|---|---|---|---|---|---|---|
| | | 115 | | | | | 120 | | | |

<210> SEQ ID NO 180
<211> LENGTH: 369
<212> TYPE: DNA
<213> ORGANISM: Homo sapiens
<220> FEATURE:
<223> OTHER INFORMATION: 1204, heavy chain VH

<400> SEQUENCE: 180

```
gaggtgcagc tgttggagag cggggggaggc ttggtacagc ctgggggggtc cctgcgcctc    60
tcctgtgcag ccagcggatt cacctttttct tcttactaca tgggttgggt ccgccaggct   120
ccagggaagg ggctggagtg gtctcaggt attggttctt actacggtta cacaggttat   180
gcagactccg tgaagggccg gttcaccatc tcccgtgaca attccaagaa cacgctgtat   240
ctgcaaatga acagcctgcg tgccgaggac acggctgtat attattgtgc gcgcgcttac   300
tacgactaca actactacta cgcttacttt gactattggg gccagggaac cctggtcacc   360
gtctcctca                                                           369
```

<210> SEQ ID NO 181
<211> LENGTH: 116
<212> TYPE: PRT
<213> ORGANISM: Homo sapiens
<220> FEATURE:
<223> OTHER INFORMATION: 1214 (VH)

<400> SEQUENCE: 181

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ser | Ile | Gly | Ser | Gly | Gly | Gly | Tyr | Thr | Gly | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |

```
            65                  70                  75                  80
Leu Gln Met Asn Ser Leu Arg Ala Glu Asp Thr Ala Val Tyr Tyr Cys
                    85                  90                  95

Ala Arg Val Gly His Pro Phe Asp Tyr Trp Gly Gln Gly Thr Leu Val
                100                 105                 110

Thr Val Ser Ser
        115

<210> SEQ ID NO 182
<211> LENGTH: 348
<212> TYPE: DNA
<213> ORGANISM: Homo sapiens
<220> FEATURE:
<223> OTHER INFORMATION: 1214 (VH)

<400> SEQUENCE: 182
gaggtgcagc tgttggagag cggggggaggc ttggtacagc ctgggggtc cctgcgcctc      60 tcctgtgcag ccagcggatt cacctttagc agctatgcca tgagctgggt ccgccaggct     120
ccagggaagg gctggagtg gtctcatct attggttctg gtggtggtta cacaggttat       180
gcagactccg tgaagggccg gttcaccatc tcccgtgaca attccaagaa cacgctgtat    240
ctgcaaatga acagcctgcg tgccgaggac acggctgtat attattgtgc gcgcgttggt    300
catccgtttg actattgggg ccagggaacc ctggtcaccg tctcctca                 348

<210> SEQ ID NO 183
<211> LENGTH: 106
<212> TYPE: PRT
<213> ORGANISM: Homo sapiens
<220> FEATURE:
<223> OTHER INFORMATION: 1215 (VL)

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ala Tyr Pro His Thr
                85                  90                  95

Phe Gly Gln Gly Thr Lys Leu Glu Ile Lys
            100                 105

<210> SEQ ID NO 184
<211> LENGTH: 318
<212> TYPE: DNA
<213> ORGANISM: Homo sapiens
<220> FEATURE:
<223> OTHER INFORMATION: 1215 (VL)

<400> SEQUENCE: 184
gacatccaga tgacccagtc tccatcctcc ctgagcgcat ctgtaggaga ccgcgtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
```

```
cgtttcagtg gcagtggaag cgggacagat ttcactctca ccatcagcag tctgcaacct    240
gaagattttg caacttatta ctgtcaacag gacgcttacc cgcacacttt tggccagggg    300
accaagctgg agatcaaa                                                   318
```

```
<210> SEQ ID NO 185
<211> LENGTH: 121
<212> TYPE: PRT
<213> ORGANISM: Homo sapiens
<220> FEATURE:
<223> OTHER INFORMATION: 1618 (VH)

<400> SEQUENCE: 185
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120
```

```
<210> SEQ ID NO 186
<211> LENGTH: 363
<212> TYPE: DNA
<213> ORGANISM: Homo sapiens
<220> FEATURE:
<223> OTHER INFORMATION: 1618 (VH)

<400> SEQUENCE: 186
```

```
gaggtgcagc tgttggagag cggggggaggc ttggtacagc ctgggggggtc cctgcgcctc     60 tcctgtgcag ccagcggatt cacctttct tacggttcta tgtactgggt ccgccaggct   120
ccagggaagg ggctggagtg ggtctcatct atttcttctg gttctggttc tacatactat   180
gcagactccg tgaagggccg gttcaccatc tcccgtgaca attccaagaa cacgctgtat   240
ctgcaaatga acagcctgcg tgccgaggac acggctgtat attattgtgc gcgctcttct   300
tactacggtt cttactactc tattgactat tggggccagg gaaccctggt caccgtctcc   360
tca                                                                  363
```

```
<210> SEQ ID NO 187
<211> LENGTH: 107
<212> TYPE: PRT
<213> ORGANISM: Homo sapiens
<220> FEATURE:
<223> OTHER INFORMATION: 1619 (VL)

<400> SEQUENCE: 187
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105

<210> SEQ ID NO 188
<211> LENGTH: 321
<212> TYPE: DNA
<213> ORGANISM: Homo sapiens
<220> FEATURE:
<223> OTHER INFORMATION: 1619 (VL)

<400> SEQUENCE: 188
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag tactacgaca acctgcccac ttttggccag     300
gggaccaagc tggagatcaa a                                                321

<210> SEQ ID NO 189
<211> LENGTH: 117
<212> TYPE: PRT
<213> ORGANISM: Homo sapiens
<220> FEATURE:
<223> OTHER INFORMATION: 1620 (VH)

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Tyr Met Tyr Trp Val Arg Gln Ala Pro Gly Lys Gly Leu Glu Trp Val
        35                  40                  45

Ser Gly Ile Ser Ser Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Val Gly Pro Tyr Phe Asp Tyr Trp Gly Gln Gly Thr Leu
            100                 105                 110

Val Thr Val Ser Ser
        115

<210> SEQ ID NO 190
<211> LENGTH: 351
<212> TYPE: DNA
<213> ORGANISM: Homo sapiens
<220> FEATURE:
```

<223> OTHER INFORMATION: 1620 (VH)

<400> SEQUENCE: 190

```
gaggtgcagc tgttggagag cggggggaggc ttggtacagc ctggggggtc cctgcgcctc    60
tcctgtgcag ccagcggatt caccttttct ggttactaca tgtactgggt ccgccaggct   120
ccagggaagg ggctggagtg ggtctcaggt atttcttctt ctggttctta cacatactat   180
gcagactccg tgaagggccg gttcaccatc tcccgtgaca attccaagaa cacgctgtat   240
ctgcaaatga acagcctgcg tgccgaggac acggctgtat attattgtgc gcgctctgtt   300
ggtccgtact ttgactattg gggccaggga accctggtca ccgtctcctc a           351
```

<210> SEQ ID NO 191
<211> LENGTH: 106
<212> TYPE: PRT
<213> ORGANISM: Homo sapiens
<220> FEATURE:
<223> OTHER INFORMATION: 1621 (VL)

<400> SEQUENCE: 191

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Val Gly Pro Tyr Thr
                85                  90                  95
Phe Gly Gln Gly Thr Lys Leu Glu Ile Lys
            100                 105

<210> SEQ ID NO 192
<211> LENGTH: 318
<212> TYPE: DNA
<213> ORGANISM: Homo sapiens
<220> FEATURE:
<223> OTHER INFORMATION: 1621 (VL)

<400> SEQUENCE: 192

```
gacatccaga tgacccagtc tccatcctcc ctgagcgcat ctgtaggaga ccgcgtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
cgtttcagtg gcagtggaag cgggacagat ttcactctca ccatcagcag tctgcaacct   240
gaagattttg caacttatta ctgtcaacag ggtgttggtc cgtacacttt tggccagggg   300
accaagctgg agatcaaa                                                 318
```

<210> SEQ ID NO 193
<211> LENGTH: 117
<212> TYPE: PRT
<213> ORGANISM: Homo sapiens
<220> FEATURE:
<223> OTHER INFORMATION: 1626 (VH)

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Tyr
            20                  25                  30

Ser Met Tyr Trp Val Arg Gln Ala Pro Gly Lys Gly Leu Glu Trp Val
        35                  40                  45

Ser Ser Ile Gly Gly Tyr Tyr Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Gly Ser Ile Asp Tyr Trp Gly Gln Gly Thr Leu
            100                 105                 110

Val Thr Val Ser Ser
            115

<210> SEQ ID NO 194
<211> LENGTH: 351
<212> TYPE: DNA
<213> ORGANISM: Homo sapiens
<220> FEATURE:
<223> OTHER INFORMATION: 1626 (VH)

<400> SEQUENCE: 194
gaggtgcagc tgttggagag cggggggaggc ttggtacagc ctggggggtc cctgcgcctc     60
tcctgtgcag ccagcggatt cacctttggt ggttactcta tgtactgggt ccgccaggct    120
ccagggaagg gcctggagtg gtctcatct attggtggtt actactactc tacatactat    180
gcagactccg tgaagggccg gttcaccatc tcccgtgaca attccaagaa cacgctgtat    240
ctgcaaatga acagcctgcg tgccgaggac acggctgtat attattgtgc gcgctcttac    300
tacggttcta ttgactattg gggccaggga accctggtca ccgtctcctc a             351

<210> SEQ ID NO 195
<211> LENGTH: 108
<212> TYPE: PRT
<213> ORGANISM: Homo sapiens
<220> FEATURE:
<223> OTHER INFORMATION: 1627 (VL)

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Thr Gly Tyr Gly Pro
                85                  90                  95

Leu Thr Phe Gly Gln Gly Thr Lys Leu Glu Ile Lys
            100                 105

<210> SEQ ID NO 196

```
<211> LENGTH: 324
<212> TYPE: DNA
<213> ORGANISM: Homo sapiens
<220> FEATURE:
<223> OTHER INFORMATION: 1627 (VL)

<400> SEQUENCE: 196
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag ggtactggtt acggtccgct cacttttggc     300
caggggacca agctggagat caaa                                            324

<210> SEQ ID NO 197
<211> LENGTH: 1376
<212> TYPE: DNA
<213> ORGANISM: Artificial Sequence
<220> FEATURE:
<223> OTHER INFORMATION: 1761 = 1205 Light chain VL, with constant kappa
      sequence, linker and CD86 mutant 1040 inclusive intron sequence

<400> SEQUENCE: 197
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag tctgttccgc actacccgtt cacttttggc     300
caggggacca agctggagat caaacgtgag tcgtacgcta gcaagcttga tatcgaattc     360
taaactctga gggggtcgga tgacgtggcc attctttgcc taaagcattg agtttactgc     420
aaggtcagaa aagcatgcaa agccctcaga atggctgcaa agagctccaa caaaacaatt     480
tagaacttta ttaaggaata ggggaagct aggaagaaac tcaaaacatc aagattttaa     540
atacgcttct tggtctcctt gctataatta tctgggataa gcatgctgtt ttctgtctgt     600
ccctaacatg ccctgtgatt atccgcaaac aacacaccca agggcagaac tttgttactt     660
aaacaccatc ctgtttgctt cttttcctcag gaactgtggc tgcaccatct gtcttcatct     720
tcccgccatc tgatgagcag ttgaaatctg gaactgcctc tgttgtgtgc ctgctgaata     780
acttctatcc cagagaggcc aaagtacagt ggaaggtgga taacgccctc caatcgggta     840
actcccagga gagtgtcaca gagcaggaca gcaaggacag cacctacagc ctcagcagca     900
ccctgacgct gagcaaagca gactacgaga aacacaaagt ctacgcctgc gaagtcaccc     960
atcagggcct gagctcgccc gtcacaaaga gcttcaacag gggagagtgt agcggaggag    1020
gaggaagcgg aggaggagga agcgcccccc tcaaaatcca agcgtacttc aacgaaactg    1080
cagacttacc gtgtcagttt gccaattcgc agaatctgag cctgagcgaa ctggtggttt    1140
tctggcagga tcaggagaac ctggttctga cgaagtcta tctgggcaaa gagcggttcg    1200
acagcgtgga cagcaagtat atgggccgca ccagctttga tagcgacagc tggacccttgc    1260
gtctgcacaa tctgcaaatc aaagataagg gtaggtacca gtgcattatc caccataaga    1320
agccgacggg tatgattaat attcaccaaa tgaactccga gttgtctgtc ctggcg        1376

<210> SEQ ID NO 198
```

<211> LENGTH: 337
<212> TYPE: PRT
<213> ORGANISM: Artificial Sequence
<220> FEATURE:
<223> OTHER INFORMATION: 1761 =1205 light chain VL, with constant kappa sequence, linker and CD86 mutant 1040

<400> SEQUENCE: 198

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Pro His Tyr Pro
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Ser Gly Gly Gly Ser Gly Gly Gly
210                 215                 220

Gly Ser Ala Pro Leu Lys Ile Gln Ala Tyr Phe Asn Glu Thr Ala Asp
225                 230                 235                 240

Leu Pro Cys Gln Phe Ala Asn Ser Gln Asn Leu Ser Leu Ser Glu Leu
                245                 250                 255

Val Val Phe Trp Gln Asp Gln Glu Asn Leu Val Leu Asn Glu Val Tyr
            260                 265                 270

Leu Gly Lys Glu Arg Phe Asp Ser Val Asp Ser Lys Tyr Met Gly Arg
        275                 280                 285

Thr Ser Phe Asp Ser Asp Ser Trp Thr Leu Arg Leu His Asn Leu Gln
290                 295                 300

Ile Lys Asp Lys Gly Arg Tyr Gln Cys Ile Ile His His Lys Lys Pro
305                 310                 315                 320

Thr Gly Met Ile Asn Ile His Gln Met Asn Ser Glu Leu Ser Val Leu
                325                 330                 335

Ala
```

<210> SEQ ID NO 199
<211> LENGTH: 1370
<212> TYPE: DNA
<213> ORGANISM: Artificial Sequence
<220> FEATURE:
<223> OTHER INFORMATION: 1763 = 1215 Light chain VL, with constant kappa
sequence, linker and CD86 mutant 1040

<400> SEQUENCE: 199

| | | | | |
|---|---|---|---|---|
| gacatccaga tgacccagtc tccatcctcc ctgagcgcat ctgtaggaga ccgcgtcacc | 60 |
| atcacttgcc gggcaagtca gagcattagc agctatttaa attggtatca gcagaaacca | 120 |
| gggaaagccc ctaagctcct gatctatgct gcatccagtt tgcaaagtgg ggtcccatca | 180 |
| cgtttcagtg gcagtggaag cgggacagat ttcactctca ccatcagcag tctgcaacct | 240 |
| gaagattttg caacttatta ctgtcaacag gacgcttacc cgcacacttt tggccagggg | 300 |
| accaagctgg agatcaaacg tgagtcgtac gctagcaagc ttgatatcga attctaaact | 360 |
| ctgaggggt cggatgacgt ggccattctt tgcctaaagc attgagttta ctgcaaggtc | 420 |
| agaaaagcat gcaaagccct cagaatggct gcaaagagct ccaacaaaac aatttagaac | 480 |
| tttattaagg aatagggga agctaggaag aaactcaaaa catcaagatt ttaaatacgc | 540 |
| ttcttggtct ccttgctata attatctggg ataagcatgc tgttttctgt ctgtccctaa | 600 |
| catgccctgt gattatccgc aaacaacaca cccaagggca gaactttgtt acttaaacac | 660 |
| catcctgttt gcttctttcc tcaggaactg tggctgcacc atctgtcttc atcttcccgc | 720 |
| catctgatga gcagttgaaa tctggaactg cctctgttgt gtgcctgctg aataacttct | 780 |
| atcccagaga ggccaaagta cagtggaagg tggataacgc cctccaatcg ggtaactccc | 840 |
| aggagagtgt cacagagcag gacagcaagg acagcaccta cagcctcagc agcaccctga | 900 |
| cgctgagcaa agcagactac gagaaacaca agtctacgc ctgcgaagtc acccatcagg | 960 |
| gcctgagctc gcccgtcaca aagagcttca cagggagag tgtagcgga ggaggaggaa | 1020 |
| gcggaggagg aggaagcgcc cccctcaaaa tccaagcgta cttcaacgaa actgcagact | 1080 |
| taccgtgtca gtttgccaat tcgcagaatc tgagcctgag cgaactggtg gttttctggc | 1140 |
| aggatcagga gaacctggtt ctgaacgaag tctatctggg caaagagcgg ttcgacagcg | 1200 |
| tggacagcaa gtatatgggc cgcaccagct ttgatagcga cagctggacc ctgcgtctgc | 1260 |
| acaatctgca aatcaaagat aagggtaggt accagtgcat tatccaccat aagaagccga | 1320 |
| cgggtatgat taatattcac caaatgaact ccgagttgtc tgtcctggcg | 1370 |

<210> SEQ ID NO 200
<211> LENGTH: 335
<212> TYPE: PRT
<213> ORGANISM: Artificial Sequence
<220> FEATURE:
<223> OTHER INFORMATION: 1763 = 1215 Light chain VL, with constant kappa
sequence, linker and CD86 mutant 1040

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ala Tyr Pro His Thr

```
                    85                  90                  95
Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys Ser Gly Gly Gly Ser Gly Gly Gly Gly Ser
210                 215                 220

Ala Pro Leu Lys Ile Gln Ala Tyr Phe Asn Glu Thr Ala Asp Leu Pro
225                 230                 235                 240

Cys Gln Phe Ala Asn Ser Gln Asn Leu Ser Leu Ser Glu Leu Val Val
                245                 250                 255

Phe Trp Gln Asp Gln Glu Asn Leu Val Leu Asn Glu Val Tyr Leu Gly
                260                 265                 270

Lys Glu Arg Phe Asp Ser Val Asp Ser Lys Tyr Met Gly Arg Thr Ser
                275                 280                 285

Phe Asp Ser Asp Ser Trp Thr Leu Arg Leu His Asn Leu Gln Ile Lys
                290                 295                 300

Asp Lys Gly Arg Tyr Gln Cys Ile Ile His His Lys Lys Pro Thr Gly
305                 310                 315                 320

Met Ile Asn Ile His Gln Met Asn Ser Glu Leu Ser Val Leu Ala
                325                 330                 335

<210> SEQ ID NO 201
<211> LENGTH: 1373
<212> TYPE: DNA
<213> ORGANISM: Artificial Sequence
<220> FEATURE:
<223> OTHER INFORMATION: 1765 = 1619 Light chain VL, with constant kappa
      sequence, linker and CD86 mutant 1040

<400> SEQUENCE: 201
gacatccaga tgacccagtc tccatcctcc ctgagcgcat ctgtaggaga ccgcgtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
cgtttcagtg gcagtggaag cgggacagat ttcactctca ccatcagcag tctgcaacct     240
gaagattttg caacttatta ctgtcaacag tactacgaca acctgcccac ttttggccag     300
gggaccaagc tggagatcaa acgtgagtcg tacgctagca agcttgatat cgaattctaa     360
actctgaggg gtcggatga cgtggccatt ctttgcctaa gcattgagt ttactgcaag      420 gtcagaaaag catgcaaagc cctcagaatg ctgcaaaga gctccaacaa acaatttag      480 aactttatta aggaataggg ggaagctagg aagaaactca aaacatcaag attttaaata    540
cgcttcttgg tctccttgct ataattatct gggataagca tgctgttttc tgtctgtccc    600
taacatgccc tgtgattatc cgcaaacaac acacccaagg gcagaacttt gttacttaaa    660
```

```
caccatcctg tttgcttctt tcctcaggaa ctgtggctgc accatctgtc ttcatcttcc      720
cgccatctga tgagcagttg aaatctggaa ctgcctctgt tgtgtgcctg ctgaataact      780
tctatcccag agaggccaaa gtacagtgga aggtggataa cgccctccaa tcgggtaact      840
cccaggagag tgtcacagag caggacagca aggacagcac ctacagcctc agcagcaccc      900
tgacgctgag caaagcagac tacgagaaac acaaagtcta cgcctgcgaa gtcacccatc      960
agggcctgag ctcgcccgtc acaaagagct tcaacagggg agagtgtagc ggaggaggag     1020
gaagcggagg aggaggaagc gcccccctca aaatccaagc gtacttcaac gaaactgcag     1080
acttaccgtg tcagtttgcc aattcgcaga atctgagcct gagcgaactg gtggttttct     1140
ggcaggatca ggagaacctg gttctgaacg aagtctatct gggcaaagag cggttcgaca     1200
gcgtggacag caagtatatg ggccgcacca gctttgatag cgcacgctgg accctgcgtc     1260
tgcacaatct gcaaatcaaa gataagggta ggtaccagtg cattatccac cataagaagc     1320
cgacgggtat gattaatatt caccaaatga actccgagtt gtctgtcctg gcg            1373
```

<210> SEQ ID NO 202
<211> LENGTH: 336
<212> TYPE: PRT
<213> ORGANISM: Artificial Sequence
<220> FEATURE:
<223> OTHER INFORMATION: 1765 = 1619 Light chain VL, with constant kappa sequence, linker and CD86 mutant 1040

<400> SEQUENCE: 202

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Ser Gly Gly Gly Gly
    210                 215                 220

Ser Ala Pro Leu Lys Ile Gln Ala Tyr Phe Asn Glu Thr Ala Asp Leu
```

```
                225                 230                 235                 240
        Pro Cys Gln Phe Ala Asn Ser Gln Asn Leu Ser Leu Ser Glu Leu Val
                        245                 250                 255

Val Phe Trp Gln Asp Gln Glu Asn Leu Val Leu Asn Glu Val Tyr Leu
                        260                 265                 270

Gly Lys Glu Arg Phe Asp Ser Val Asp Ser Lys Tyr Met Gly Arg Thr
                        275                 280                 285

Ser Phe Asp Ser Asp Ser Trp Thr Leu Arg Leu His Asn Leu Gln Ile
                        290                 295                 300

Lys Asp Lys Gly Arg Tyr Gln Cys Ile Ile His His Lys Lys Pro Thr
        305                 310                 315                 320

Gly Met Ile Asn Ile His Gln Met Asn Ser Glu Leu Ser Val Leu Ala
                        325                 330                 335

<210> SEQ ID NO 203
<211> LENGTH: 1370
<212> TYPE: DNA
<213> ORGANISM: Artificial Sequence
<220> FEATURE:
<223> OTHER INFORMATION: 1767 = 1621 Light chain VL, with constant kappa
      sequence, linker and CD86 mutant 1040

<400> SEQUENCE: 203
gacatccaga tgacccagtc tccatcctcc ctgagcgcat ctgtaggaga ccgcgtcacc        60
atcacttgcc gggcaagtca gagcattagc agctatttaa attggtatca gcagaaacca      120
gggaaagccc ctaagctcct gatctatgct gcatccagtt tgcaaagtgg ggtcccatca      180
cgtttcagtg gcagtggaag cgggacagat ttcactctca ccatcagcag tctgcaacct      240
gaagattttg caacttatta ctgtcaacag ggtgttggtc cgtacacttt tggccagggg      300
accaagctgg agatcaaacg tgagtcgtac gctagcaagc ttgatatcga attctaaact      360
ctgagggggt cggatgacgt ggccattctt tgcctaaagc attgagttta ctgcaaggtc      420
agaaaagcat gcaaagccct cagaatggct gcaaagagct ccaacaaaac aatttagaac      480
tttattaagg aatagggga agctaggaag aaactcaaaa catcaagatt ttaaatacgc      540
ttcttggtct ccttgctata attatctggg ataagcatgc tgttttctgt ctgtccctaa      600
catgccctgt gattatccgc aaacaacaca cccaagggca gaactttgtt acttaaacac      660
catcctgttt gcttctttcc tcaggaactg tggctgcacc atctgtcttc atcttcccgc      720
catctgatga gcagttgaaa tctggaactg cctctgttgt gtgcctgctg ataacttct      780 atcccagaga ggccaaagta cagtggaagg tggataacgc cctccaatcg ggtaactccc      840
aggagagtgt cacagagcag gacagcaagg acagcaccta cagcctcagc agcaccctga      900
cgctgagcaa agcagactac gagaaacaca agtctacgc ctgcgaagtc acccatcagg      960
gcctgagctc gcccgtcaca aagagcttca caggggaga gtgtagcgga ggaggaggaa     1020
gcggaggagg aggaagcgcc cccctcaaaa tccaagcgta cttcaacgaa actgcagact     1080
taccgtgtca gtttgccaat tcgcagaatc tgagcctgag cgaactggtg gttttctggc     1140
aggatcagga gaacctggtt ctgaacgaag tctatctggg caaagagcgg ttcgacagcg     1200
tggacagcaa gtatatgggc cgcaccagct tgatagcaca gctggacc ctgcgtctgc     1260 acaatctgca aatcaaagat aagggtaggt accagtgcat tatccaccat aagaagccga     1320
cgggtatgat taatattcac caaatgaact ccgagttgtc tgtcctggcg                1370

<210> SEQ ID NO 204
```

```
<211> LENGTH: 335
<212> TYPE: PRT
<213> ORGANISM: Artificial Sequence
<220> FEATURE:
<223> OTHER INFORMATION: 1767 = 1621 Light chain VL, with constant kappa
      sequence, linker and CD86 mutant 1040

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Gly Pro Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ser Gly Gly Gly Ser Gly Gly Gly Gly Ser
210                 215                 220

Ala Pro Leu Lys Ile Gln Ala Tyr Phe Asn Glu Thr Ala Asp Leu Pro
225                 230                 235                 240

Cys Gln Phe Ala Asn Ser Gln Asn Leu Ser Leu Ser Glu Leu Val Val
                245                 250                 255

Phe Trp Gln Asp Gln Glu Asn Leu Val Leu Asn Glu Val Tyr Leu Gly
            260                 265                 270

Lys Glu Arg Phe Asp Ser Val Asp Ser Lys Tyr Met Gly Arg Thr Ser
        275                 280                 285

Phe Asp Ser Asp Ser Trp Thr Leu Arg Leu His Asn Leu Gln Ile Lys
290                 295                 300

Asp Lys Gly Arg Tyr Gln Cys Ile Ile His His Lys Lys Pro Thr Gly
305                 310                 315                 320

Met Ile Asn Ile His Gln Met Asn Ser Glu Leu Ser Val Leu Ala
                325                 330                 335

<210> SEQ ID NO 205
<211> LENGTH: 1376
<212> TYPE: DNA
<213> ORGANISM: Artificial Sequence
<220> FEATURE:
<223> OTHER INFORMATION: 1769= 1627 Light chain VL, with constant kappa
``` sequence, linker and CD86 mutant 1040

<400> SEQUENCE: 205

```
gacatccaga tgacccagtc tccatcctcc ctgagcgcat ctgtaggaga ccgcgtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag ggtactggtt acggtccgct cacttttggc    300
caggggacca agctggagat caaacgtgag tcgtacgcta gcaagcttga tatcgaattc    360
taaactctga gggggtcgga tgacgtggcc attctttgcc taaagcattg agtttactgc    420
aaggtcagaa aagcatgcaa agccctcaga atggctgcaa agagctccaa caaaacaatt    480
tagaactttta ttaaggaata gggggaagct aggaagaaac tcaaaacatc aagattttaa    540
atacgcttct tggtctcctt gctataatta tctgggataa gcatgctgtt ttctgtctgt    600
ccctaacatg ccctgtgatt atccgcaaac aacacaccca agggcagaac tttgttactt    660
aaacaccatc ctgtttgctt ctttcctcag gaactgtggc tgcaccatct gtcttcatct    720
tcccgccatc tgatgagcag ttgaaatctg gaactgcctc tgttgtgtgc ctgctgaata    780
acttctatcc cagagaggcc aaagtacagt ggaaggtgga taacgccctc caatcgggta    840
actcccagga gagtgtcaca gagcaggaca gcaaggacag cacctacagc ctcagcagca    900
ccctgacgct gagcaaagca gactacgaga acacaaagt ctacgcctgc gaagtcaccc    960
atcagggcct gagctcgccc gtcacaaaga gcttcaacag gggagagtgt agcggaggag   1020
gaggaagcgg aggaggagga agcgccccc tcaaaatcca gcgtacttc aacgaaactg   1080
cagacttacc gtgtcagttt gccaattcgc agaatctgag cctgagcgaa ctggtggttt   1140
tctggcagga tcaggagaac ctggttctga cgaagtcta tctgggcaaa gagcggttcg   1200
acagcgtgga cagcaagtat atgggccgca ccagctttga tagcgacagc tggacccctg   1260
gtctgcacaa tctgcaaatc aaagataagg gtaggtacca gtgcattatc caccataaga   1320
agccgacggg tatgattaat attcaccaaa tgaactccga gttgtctgtc ctggcg        1376
```

<210> SEQ ID NO 206
<211> LENGTH: 337
<212> TYPE: PRT
<213> ORGANISM: Artificial Sequence
<220> FEATURE:
<223> OTHER INFORMATION: 1769 = 1627 Light chain VL, with constant kappa
    sequence, linker and CD86 mutant 1040

<400> SEQUENCE: 206

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Thr Gly Tyr Gly Pro
                85                  90                  95
```

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Ser Gly Gly Gly Ser Gly Gly Gly
    210                 215                 220

Gly Ser Ala Pro Leu Lys Ile Gln Ala Tyr Phe Asn Glu Thr Ala Asp
225                 230                 235                 240

Leu Pro Cys Gln Phe Ala Asn Ser Gln Asn Leu Ser Leu Ser Glu Leu
                245                 250                 255

Val Val Phe Trp Gln Asp Gln Glu Asn Leu Val Leu Asn Glu Val Tyr
            260                 265                 270

Leu Gly Lys Glu Arg Phe Asp Ser Val Asp Ser Lys Tyr Met Gly Arg
        275                 280                 285

Thr Ser Phe Asp Ser Asp Ser Trp Thr Leu Arg Leu His Asn Leu Gln
    290                 295                 300

Ile Lys Asp Lys Gly Arg Tyr Gln Cys Ile Ile His His Lys Lys Pro
305                 310                 315                 320

Thr Gly Met Ile Asn Ile His Gln Met Asn Ser Glu Leu Ser Val Leu
                325                 330                 335

Ala

<210> SEQ ID NO 207
<211> LENGTH: 8
<212> TYPE: PRT
<213> ORGANISM: Homo sapiens

<400> SEQUENCE: 207

Gly Phe Thr Phe Ser Ser Tyr Tyr
1               5

<210> SEQ ID NO 208
<211> LENGTH: 8
<212> TYPE: PRT
<213> ORGANISM: Homo sapiens

<400> SEQUENCE: 208

Gly Phe Thr Phe Ser Ser Tyr Ala
1               5

<210> SEQ ID NO 209
<211> LENGTH: 8
<212> TYPE: PRT
<213> ORGANISM: Homo sapiens

<400> SEQUENCE: 209

Gly Phe Thr Phe Ser Tyr Gly Ser
1               5

<210> SEQ ID NO 210
<211> LENGTH: 8
<212> TYPE: PRT
<213> ORGANISM: Homo sapiens

<400> SEQUENCE: 210

Gly Phe Thr Phe Ser Gly Tyr Tyr
1               5

<210> SEQ ID NO 211
<211> LENGTH: 8
<212> TYPE: PRT
<213> ORGANISM: Homo sapiens

<400> SEQUENCE: 211

Gly Phe Thr Phe Gly Gly Tyr Ser
1               5

<210> SEQ ID NO 212
<211> LENGTH: 8
<212> TYPE: PRT
<213> ORGANISM: Homo sapiens

<400> SEQUENCE: 212

Ile Gly Ser Tyr Tyr Gly Tyr Thr
1               5

<210> SEQ ID NO 213
<211> LENGTH: 8
<212> TYPE: PRT
<213> ORGANISM: Homo sapiens

<400> SEQUENCE: 213

Ile Gly Ser Gly Gly Gly Tyr Thr
1               5

<210> SEQ ID NO 214
<211> LENGTH: 8
<212> TYPE: PRT
<213> ORGANISM: Homo sapiens

<400> SEQUENCE: 214

Ile Ser Ser Gly Ser Gly Ser Thr
1               5

<210> SEQ ID NO 215
<211> LENGTH: 8
<212> TYPE: PRT
<213> ORGANISM: Homo sapiens

<400> SEQUENCE: 215

Ile Ser Ser Ser Gly Ser Tyr Thr
1               5

<210> SEQ ID NO 216
<211> LENGTH: 8
<212> TYPE: PRT
<213> ORGANISM: Homo sapiens

<400> SEQUENCE: 216

Ile Gly Gly Tyr Tyr Tyr Ser Thr
1               5

```
<210> SEQ ID NO 217
<211> LENGTH: 16
<212> TYPE: PRT
<213> ORGANISM: Homo sapiens

<400> SEQUENCE: 217

Ala Arg Ala Tyr Tyr Asp Tyr Asn Tyr Tyr Ala Tyr Phe Asp Tyr
1               5                   10                  15

<210> SEQ ID NO 218
<211> LENGTH: 9
<212> TYPE: PRT
<213> ORGANISM: Homo sapiens

<400> SEQUENCE: 218

Ala Arg Val Gly His Pro Phe Asp Tyr
1               5

<210> SEQ ID NO 219
<211> LENGTH: 14
<212> TYPE: PRT
<213> ORGANISM: Homo sapiens

<400> SEQUENCE: 219

Ala Arg Ser Ser Tyr Tyr Gly Ser Tyr Tyr Ser Ile Asp Tyr
1               5                   10

<210> SEQ ID NO 220
<211> LENGTH: 10
<212> TYPE: PRT
<213> ORGANISM: Homo sapiens

<400> SEQUENCE: 220

Ala Arg Ser Val Gly Pro Tyr Phe Asp Tyr
1               5                   10

<210> SEQ ID NO 221
<211> LENGTH: 10
<212> TYPE: PRT
<213> ORGANISM: Homo sapiens

<400> SEQUENCE: 221

Ala Arg Ser Tyr Tyr Gly Ser Ile Asp Tyr
1               5                   10

<210> SEQ ID NO 222
<211> LENGTH: 10
<212> TYPE: PRT
<213> ORGANISM: Homo sapiens

<400> SEQUENCE: 222

Gln Gln Ser Val Pro His Tyr Pro Phe Thr
1               5                   10

<210> SEQ ID NO 223
<211> LENGTH: 8
<212> TYPE: PRT
<213> ORGANISM: Homo sapiens

<400> SEQUENCE: 223

Gln Gln Asp Ala Tyr Pro His Thr
1               5

<210> SEQ ID NO 224
<211> LENGTH: 9
```

```
<212> TYPE: PRT
<213> ORGANISM: Homo sapiens

<400> SEQUENCE: 224

Gln Gln Tyr Tyr Asp Asn Leu Pro Thr
1               5

<210> SEQ ID NO 225
<211> LENGTH: 8
<212> TYPE: PRT
<213> ORGANISM: Homo sapiens

<400> SEQUENCE: 225

Gln Gln Gly Val Gly Pro Tyr Thr
1               5

<210> SEQ ID NO 226
<211> LENGTH: 10
<212> TYPE: PRT
<213> ORGANISM: Homo sapiens

<400> SEQUENCE: 226

Gln Gln Gly Thr Gly Tyr Gly Pro Leu Thr
1               5                   10
```

POLYPEPTIDES

This application is a continuation application of U.S. patent application Ser. No. 15/567,163, filed Oct. 17, 2017, which is a § 371 application of PCT/EP2016/061420, filed May 20, 2016, which claims priority to GB Application No. 1508729.9, filed May 21, 2015, GB Application No. 1514994.1, filed Aug. 24, 2015, and GB Application No. 1605450.4, filed Mar. 31, 2016. The entire disclosure of each of the foregoing applications is incorporated by reference herein.

Incorporated herein by reference in its entirety is the Sequence Listing being concurrently submitted via EFS-Web as a text file named SeqList.txt, created Apr. 12, 2021, and having a size of 274,067 bytes.

FIELD OF INVENTION

The present invention relates to bispecific polypeptides which specifically bind to two different T cell targets. Exemplary T cell targets include OX40, CTLA-4 and CD137, in particular human OX40, CTLA-4 and CD137.

BACKGROUND

Cancer is a leading cause of premature deaths in the developed world. Immunotherapy of cancer aims to mount an effective immune response against tumour cells. This may be achieved by, for example, breaking tolerance against tumour antigen, augmenting anti-tumor immune responses, and stimulating local cytokine responses at the tumor site. The key effector cell of a long lasting anti-tumor immune response is the activated tumor specific effector T cell. Potent expansion of activated effector T cells can redirect the immune response towards the tumor. In this context, regulatory T cells (Treg) play a role in inhibiting the anti-tumor immunity. Depleting, inhibiting, reverting or inactivating Tregs may therefore provide anti-tumor effects and revert the immune suppression in the tumor microenvironment. Further, incomplete activation of effector T cells by, for example, dendritic cells can cause T cell anergy, which results in an inefficient anti-tumor response, whereas adequate induction by dendritic cells can generate a potent expansion of activated effector T cells, redirecting the immune response towards the tumor. In addition, Natural killer (NK) cells play an important role in tumor immunology by attacking tumor cells with down-regulated human leukocyte antigen (HLA) expression and by inducing antibody dependent cellular cytotoxicity (ADCC). Stimulation of NK cells may thus also reduce tumor growth.

OX40 (otherwise known as CD134 or TNFRSF4) is a member of the TNFR family that is expressed mainly on activated T cells (mostly CD4+ effector T cells, but also CD8+ effector T-cells and regulatory T cells (Tregs)). In mice the expression is constitutive on Tregs, but not in humans. OX40 expression typically occurs within 24 hours of activation (T cell receptor engagement) and peaks after 48-72 hours. OX40 stimulation is important for the survival and proliferation of activated T cells. The only known ligand for OX40 is OX40L, which is mainly expressed on antigen presenting cells, such as dendritic cells and B cells, typically following their activation. The net result of OX40-mediated T cell activation is the induction of a TH1 effector T cell activation profile and a reduction in the activity and/or numbers of Treg cells e.g. via ADCC or ADCP. Overall these effects may contribute to anti-tumor immunity. OX40 is overexpressed on regulatory T cells in many solid tumors, such as melanoma, lung cancer and renal cancer.

OX40 agonist treatment of tumor models in mice has been shown to result in anti-tumor effects and cure of several different cancer forms, including melanoma, glioma, sarcoma, prostate, colon and renal cancers. The data is consistent with a tumor specific T-cell response, involving both CD4+ and CD8+ T cells, similar to the effect seen with CD40 agonist treatments. Addition of IL-12 and other cytokines, and combination with other immunomodulators and chemo/radiotherapy, has been shown to improve the therapeutic effect of OX40 agonist treatment. Evidence from pre-clinical models suggests that the effect of anti-OX40 antibodies is dependent upon activating FcγR. A clinical phase I study testing the mouse anti-human OX40 Clone 9B12 in late stage patients that had failed all other therapy has been conducted at the Providence Cancer Centre. The antibody was well-tolerated. Tumor shrinkage and an increase in CD4+ and CD8+ T cell proliferation were observed. The low toxicity may be caused by low half-life and anti-drug antibodies (the antibody was a mouse antibody), but also by the relatively low expression levels of OX40 on non-activated T cells. The anti-tumor effect with this antibody was modest.

CD137 (4-1BB, TNFRSF9) is also a member of the TNFR family. Activation of CD137 is dependent on receptor oligomerization. CD137 is expressed on activated CD4+ and CD8+ T cells, Treg, DC, monocytes, mast cells and eosinophils. CD137 activation plays an important role in CD8+ T cell activation and survival. It sustains and augments, rather than initiates effector functions and preferentially supports TH1 cytokine production. In CD4+ T cells, CD137 stimulation initially results in activation and later in activation-induced cell death, which may explain why CD137 agonistic antibodies have shown therapeutic effect in tumor immunity as well as in autoimmunity. CD137 also suppresses Treg function. CD137 is upregulated on NK cells activated by cytokines or CD16. Activation of CD137 on NK cells has been shown to increase ADCC activity of NK cells in both murine and human cells. Further, CD137 is expressed on antigen presenting cells, such as dendritic cells and macrophages, and stimulation of CD137 on these cell types may induce immune activation that can result in tumor directed immunity. CD137 agonistic antibody has also been shown to activate endothelial cells in the tumor environment, leading to upregulation of ICAM-1 and VCAM-1 and improved T cell recruitment. Several studies have demonstrated induction of tumor immunity by treatment with agonistic CD137 antibodies.

Two CD137 antibodies are in clinical development. Urelumab (BMS-66513) is a fully human IgG4 antibody developed by Bristol-Myers Squibb. Several phase I and II studies in various indications are currently ongoing. A Phase II study with Urelumab as a second line therapy in metastatic melanoma was terminated in 2009 due to fatal hepatoxicity. The other CD137 mAb in clinical development is PF-05082566, a fully human IgG2 antibody developed by Pfizer. It is currently in phase I development in lymphoma and various solid cancers and preliminary data suggest that it is well tolerated but with only modest anti-tumor effects.

Existing antibodies targeting CD137 or OX40 are in general dependent on cross linking via e.g. Fcgamma Receptors on other cells to induce strong signaling into cells expressing the respective receptor. Thus, they do not signal efficiently when no such cross linking is provided. In addition, prolonged and continuous activation through TNF receptor family members may lead to immune exhaustion.

The T cell receptor CTLA-4, serves as a negative regulator of T cell activation, and is upregulated on the T-cell surface following initial activation. The ligands of the CTLA-4 receptor, which are expressed by antigen presenting cells are the B7 proteins. The corresponding ligand receptor pair that is responsible for the upregulation of T cell activation is CD28-B7. Signalling via CD28 constitutes a costimulatory pathway, and follows upon the activation of T cells, through the T cell receptor recognizing antigenic peptide presented by the MHC complex. By blocking the CTLA-4 interaction to the B7-1 and, or B7-2 ligands, one of the normal check points of the immune response may be removed. The net result is enhanced activity of effector T cells which may contribute to anti-tumour immunity. As with OX40, this may be due to direct activation of the effector T cells but may also be due to a reduction in the activity and/or numbers of Treg cells, e.g. via ADCC or ADCP. Clinical studies have demonstrated that CTLA-4 blockade generates anti-tumor effects, but administration of anti-CTLA-4 antibodies has been associated with toxic side-effects. CTLA-4 is overexpressed on regulatory T cells in many solid tumors, such as melanoma lung cancer and renal cancer.

There is a need for an alternative to the existing monospecific drugs that target only one T cell target, such as OX40 or CD137 or CTLA-4.

SUMMARY OF INVENTION

A first aspect of the invention provides a bispecific polypeptide comprising a first binding domain, designated B1, which is capable of specifically binding to a first T cell target, and a second binding domain, designated B2, which is capable of specifically binding to a second T cell target, wherein the first and second T cell targets are different targets.

Bispecific antibodies targeting two different T cell targets, such as CTLA-4, CD137 and OX40, have the potential to specifically activate the immune system in locations were both targets are over expressed. For example, CTLA-4 and OX40 are overexpressed on regulatory T cells (Treg) in the tumor microenvironment, whereas their expression on effector T cells is lower. Thus, the bispecific antibodies of the invention have the potential to selectively target regulatory T cells in the tumor microenvironment.

Targeting Treg cells in the tumor microenvironment with a bispecific antibody of the invention also has the potential to deplete or reverse the immune suppressive function of the Tregs. This effect could be mediated by ADCC or ADCP induction via the Fc part of the bispecific antibody of the invention (for example, see Furness et al., 2014 *Trends Immunol* 35(7):290-8; the disclosures of which are incorporated herein by reference) or by signaling induced via OX40 and/or CTLA-4 and/or by blocking the CTLA-4 signaling pathway (for example, see Walker, 2014, *Nature Reviews* 11(12):852-63; the disclosures of which are incorporated herein by reference). On effector T cells, on the other hands, the bispecific antibodies of the invention have the potential to induce activation and increased function both via OX40 stimulation and through CTLA-4 checkpoint blockade.

The net effects of the bispecific antibodies targeting two T-cell receptors are thus:
1. A higher degree of immune activation compared to monospecific antibodies. The immune activation is higher than the combination of the monospecific antibodies.
2. A higher degree of induction of ADCC compared to the monospecific binders in combination.
3. A more directed/localized immune activation. The immune activation only occurs in environments that contains both high CTLA-4 expression and OX40 expression. The tumor microenvironment is such an environment. This has the potential to increase the effect and also to minimize toxic side effect. Thus the therapeutic window will be increased.

In exemplary embodiments, the bispecific polypeptide is capable of binding specifically to:
(a) OX40 and CTLA-4;
(b) OX40 and CD137; or
(c) CD137 and CTLA-4.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogs and peptidomimetics.

The term "bispecific" as used herein means the polypeptide is capable of specifically binding at least two target entities.

In one embodiment the first and/or second binding domains may be selected from the group consisting of: antibodies or antigen-binding fragments thereof.

For example, the bispecific polypeptide of the invention may comprise:
(i) a first binding domain which comprises or consists of an antibody variable domain or part thereof and a second binding domain which comprises or consists of an antibody variable domain or part thereof; or
(ii) a first binding domain which comprises or consists of an antibody variable domain or part thereof and a second binding domain which is not an antibody variable domain or part thereof.

Thus, in one embodiment the polypeptide is a bispecific antibody.

As used herein, the terms "antibody" or "antibodies" refer to molecules that contain an antigen binding site, e.g. immunoglobulin molecules and immunologically active fragments of immunoglobulin molecules that contain an antigen binding site. Immunoglobulin molecules can be of any type (e.g. IgG, IgE, IgM, IgD, IgA and IgY), class (e.g. IgG1, IgG2, IgG3, IgG4, IgA1 and IgA2) or a subclass of immunoglobulin molecule. Antibodies include, but are not limited to, synthetic antibodies, monoclonal antibodies, single domain antibodies, single chain antibodies, recombinantly produced antibodies, multi-specific antibodies (including bi-specific antibodies), human antibodies, humanized antibodies, chimeric antibodies, intrabodies, scFvs (e.g. including mono-specific and bi-specific, etc.), Fab fragments, F(ab') fragments, disulfide-linked Fvs (sdFv), anti-idiotypic (anti-Id) antibodies, and epitope-binding fragments of any of the above.

The terms antibody "directed to" or "directed against" are used interchangeably herein and refer to an antibody that is constructed to direct its binding specificity(ies) at a certain target/marker/epitope/antigen, i.e. an antibody that immunospecifically binds to a target/marker/epitope/antigen. Also, the expression antibodies "selective for" a certain target/marker/epitope may be used, having the same definition as "directed to" or "directed against". A bi-specific antibody directed to (selective for) two different targets/markers/epitopes/antigens binds immunospecifically to both targets/markers/epitopes/antigens. If an antibody is directed to a certain target antigen, such as CD137, it is thus assumed that said antibody could be directed to any suitable epitope present on said target antigen structure.

As used herein, the term "antibody fragment" is a portion of an antibody such as F(ab').sub.2, F(ab).sub.2, Fab', Fab, Fv, scFv and the like. Regardless of structure, an antibody fragment binds with the same antigen that is recognized by the intact antibody. For example, an anti-OX4 antibody fragment binds to OX40. The term "antibody fragment" also includes isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). As used herein, the term "antibody fragment" does not include portions of antibodies without antigen binding activity, such as Fc fragments or single amino acid residues.

ScFv are particularly preferred for inclusion in the bispecific antibodies of the invention.

Thus, in exemplary embodiments of the bispecific antibodies of the invention:
(a) binding domain B1 and/or binding domain B2 is an intact IgG antibody (or, together, form an intact IgG antibody);
(b) binding domain B1 and/or binding domain B2 is an Fv fragment (e.g. an scFv);
(c) binding domain B1 and/or binding domain B2 is a Fab fragment; and/or
(d) binding domain B1 and/or binding domain B2 is a single domain antibody (e.g.
domain antibodies and nanobodies).

It will be appreciated by persons skilled in the art that the bispecific polypeptides of the invention may be of several different structural formats (for example, see Chan & Carter, 2016, *Nature Reviews Immunology* 10, 301-316, the disclosures of which are incorporated herein by reference).

In exemplary embodiments, the bispecific antibody is selected from the groups consisting of:
(a) bivalent bispecific antibodies, such as IgG-scFv bispecific antibodies (for example, wherein B1 is an intact IgG and B2 is an scFv attached to B1 at the N-terminus of a light chain and/or at the C-terminus of a light chain and/or at the N-terminus of a heavy chain and/or at the C-terminus of a heavy chain of the IgG, or vice versa);
(b) monovalent bispecific antibodies, such as a DuoBody® (Genmab A S, Copenhagen, Denmark) or 'knob-in-hole' bispecific antibody (for example, an scFv-KIH, scFv-KIH', a BiTE-KIH or a BiTE-KIH' (see Xu et al., 2015, *mAbs* 7(1):231-242);
(c) scFv$_2$-Fc bispecific antibodies (such as ADAPTIR™ bispecific antibodies from Emergent Biosolutions Inc);
(d) BiTE/scFv$_2$ bispecific antibodies;
(e) DVD-Ig bispecific antibodies;
(f) DART-based bispecific antibodies (for example, DART$_2$-Fc, DART$_2$-Fc or DART);
(g) DNL-Fab$_3$ bispecific antibodies; and
(h) scFv-HSA-scFv bispecific antibodies.

For example, the bispecific antibody may be an IgG-scFv antibody. The IgG-scFv antibody may be in either VH-VL or VL-VH orientation. In one embodiment, the scFv may be stabilised by a S—S bridge between VH and VL.

In one embodiment, binding domain B1 and binding domain B2 are fused directly to each other.

In an alternative embodiment, binding domain B1 and binding domain B2 are joined via a polypeptide linker. For example, a polypeptide linker may be a short linker peptide between about 10 to about 25 amino acids. The linker is usually rich in glycine for flexibility, as well as serine or threonine for solubility, and can either connect the N-terminus of the VH with the C-terminus of the VL, or vice versa. Exemplary linkers include a peptide of amino acid sequence as shown in any one of SEQ ID NOs. 47 to 50, or 144. The peptide of sequence GGGGSGGGGSGGGGS (SEQ ID NO: 144) is particularly preferred. The same linkers may be used to join the anti-OX40 part of a bispecific antibody of the invention to the anti-CD137 part.

The bispecific polypeptides of the invention may be manufactured by any known suitable method used in the art. Methods of preparing bi-specific antibodies of the present invention include BiTE (Micromet), DART (MacroGenics), Fcab and Mab$^2$ (F-star), Fc-engineered IgGI (Xencor) or DuoBody (based on Fab arm exchange, Genmab). Examples of other platforms useful for preparing bi-specific antibodies include but are not limited to those described in WO 2008/119353 (Genmab), WO 2011/131746 (Genmab) and reported by van der Neut-Kolfschoten et al. (2007, *Science* 317(5844):1554-7). Traditional methods such as the hybrid hybridoma and chemical conjugation methods (Marvin and Zhu (2005) *Acta Pharmacol Sin* 26: 649) can also be used. Co-expression in a host cell of two antibodies, consisting of different heavy and light chains, leads to a mixture of possible antibody products in addition to the desired bi-specific antibody, which can then be isolated by, e.g. affinity chromatography or similar methods.

It will be appreciated by persons skilled in the art that the bispecific antibody may comprise a human Fc region, or a variant of a said region, where the region is an IgG1, IgG2, IgG3 or IgG4 region, preferably an IgG1 or IgG4 region.

The constant (Fc) regions of the antibodies may mediate the binding of the immunoglobulin to host tissues or factors, including various cells of the immune system (e.g., effector cells) and the first component (Clq) of the classical complement system. The Fc region is preferably a human Fc region, or a variant of a said region. The Fc region may be an IgG1, IgG2, IgG3 or IgG4 region, preferably an IgG1 or IgG4 region. A variant of an Fc region typically binds to Fc receptors, such as FcgammaR and/or neonatal Fc receptor (FcRn) with altered affinity providing for improved function and/or half-life of the polypeptide. The biological function and/or the half-life may be either increased or a decreased relative to the half-life of a polypeptide comprising a native Fc region. Examples of such biological functions which may be modulated by the presence of a variant Fc region include antibody dependent cell cytotoxicity (ADCC), antibody-dependent cellular phagocytosis (ADCP), complement-dependent cytotoxicity (CDC), and/or apoptosis.

An exemplary heavy chain constant region amino acid sequence which may be combined with any VH region sequence disclosed herein (to form a complete heavy chain) is the IgG1 heavy chain constant region sequence reproduced here:

```
                                         (SEQ ID NO: 135)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC
```

-continued

LVKGFYPSDIAVEWESNGQPENNYKTTPPVLDSDGSFFLYSKLTVDKSRW

QQGNVFSCSVMHEALHNHYTQKSLSLSPGK

Other heavy chain constant region sequences are known in the art and could also be combined with any VH region disclosed herein. For example, a preferred constant region is a modified IgG4 constant region such as that reproduced here:

(SEQ ID NO: 137)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNRYTQKSLSLSLGK

This modified IgG4 sequence exhibits reduced FcRn binding and hence results in a reduced serum half-life relative to wild type IgG4. In addition, it exhibits stabilization of the core hinge of IgG4 making the IgG4 more stable, preventing Fab arm exchange.

Another preferred constant region is a modified IgG4 constant region such as that reproduced here:

(SEQ ID NO: 139)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

This modified IgG4 sequence results in stabilization of the core hinge of IgG4 making the IgG4 more stable, preventing Fab arm exchange Also preferred is a wild type IgG4 constant region such as that reproduced here:

(SEQ ID NO: 138)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

An exemplary light chain constant region amino acid sequence which may be combined with any VL region sequence disclosed herein (to form a complete light chain) is the kappa chain constant region sequence reproduced here:

(SEQ ID NO: 136)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Other light chain constant region sequences are known in the art and could also be combined with any VL region disclosed herein.

The antibody, or antigen binding fragment thereof, has certain preferred binding characteristics and functional effects, which are explained in more detail below. Said antibody, or antigen binding fragment thereof, preferably retains these binding characteristics and functional effects when incorporated as part of a bispecific polypeptide of the invention.

In one embodiment the antigen-binding fragment may be selected from the group consisting of: an Fv fragment (such as a single chain Fv fragment, or a disulphide-bonded Fv fragment), a Fab-like fragment (such as a Fab fragment; a Fab' fragment or a F(ab)$_2$ fragment) and domain antibodies.

In one embodiment the bispecific polypeptide may be an IgG1 antibody with a non-immunoglobulin polypeptide (such as a CTLA-4 binding domain, e.g. CD86 or a mutated form thereof such as SEQ ID NO: 17; see below) fused to the C-terminal part of the kappa chain.

In one embodiment the bispecific polypeptide may be an IgG1 antibody with a scFv fragment fused to the C-terminal end of the heavy gamma 1 chain.

In one embodiment the bispecific polypeptide may contain 2-4 scFv binding to two different targets.

By "T cell target" we include polypeptide receptors located in the cell membrane of CD3+ T cells in an activated or inactive state. Such membrane-bound receptors may be exposed extracellularly in order that they accessed by the bispecific polypeptides of the invention following administration.

It will be appreciated by persons skilled in the art that the T cell targets may be localised on the surface of a cell. By "localised on the surface of a cell" it is meant that the T cell target is associated with the cell such that one or more region of the T cell target is present on the outer face of the cell surface. For example, the T cell target may be inserted into the cell plasma membrane (i.e. orientated as a transmembrane protein) with one or more regions presented on the extracellular surface. This may occur in the course of expression of the T cell target by the cell. Thus, in one embodiment, "localised on the surface of a cell" may mean "expressed on the surface of a cell." Alternatively, the T cell target may be outside the cell with covalent and/or ionic interactions localising it to a specific region or regions of the cell surface.

In one embodiment the first and/or second T cell target may be a checkpoint molecule. For example, in one embodiment the first and/or second T cell target is a co-stimulatory or co-inhibitory molecule.

By "co-stimulatory" we include co-signalling molecules which are capable of promoting T cell activation. By "co-inhibitory" we include co-signalling molecules which are capable of supressing T cell activation.

Accordingly, in one embodiment at least one of the T cell targets may be a stimulatory checkpoint molecule (such as CD137, GITR, CD27, CD28, ICOS and OX40). Advantageously, the bispecific polypeptide of the invention is an agonist at a stimulatory checkpoint molecule.

Alternatively or additionally, at least one of the T cell targets may be an inhibitory checkpoint molecule (such as CTLA-4, PD-1, Tim3, Lag3, Tigit or VISTA). Advantageously, the bispecific polypeptide of the invention is an antagonist at an inhibitory checkpoint molecule.

In one embodiment at least one of the T cell targets is a TNFR (tumor necrosis factor receptor) superfamily member. By TNFR superfamily member we include cytokine receptors characterised by the ability to bind tumor necrosis factors (TNFs) via an extracellular cysteine-rich domain. Examples of TNFRs include OX40 and CD137.

In one embodiment the first and/or second T cell target may be selected from the group consisting of: OX40, CTLA-4, CD137, CD40 and CD28. For example, the first and/or second T cell target may be selected from the group consisting of OX40, CTLA-4 and CD137.

It will be appreciated by persons skilled in the art that the bispecific antibodies of the invention may be capable of inducing antibody dependent cell cytotoxicity (ADCC), antibody-dependent cellular phagocytosis (ADCP), complement-dependent cytotoxicity (CDC), and/or apoptosis.

In a further embodiment the polypeptide is capable of inducing tumour immunity. This can be tested in vitro in T cell activation assays, e.g. by measuring. IL-2 and IFNγ production. Activation of effector T cells would imply that a tumor specific T cell response can be achieved in vivo. Further, an anti-tumor response in an in vivo model, such as a mouse model would imply that a successful immune response towards the tumor has been achieved.

The antibody may modulate the activity of a cell expressing the T cell target, wherein said modulation is an increase or decrease in the activity of said cell. The cell is typically a T cell. The antibody may increase the activity of a CD4+ or CD8+ effector cell, or may decrease the activity of a regulatory T cell (Treg). In either case, the net effect of the antibody will be an increase in the activity of effector T cells, particularly CD4+ effector T cells. Methods for determining a change in the activity of effector T cells are well known and include, for example, measuring for an increase in the level of T cell IL-2 production or an increase in T cell proliferation in the presence of the antibody relative to the level of T cell IL-2 production and/or T cell proliferation in the presence of a control. Assays for cell proliferation and/or IL-2 production are well known and are exemplified in the Examples.

Standard assays to evaluate the binding ability of ligands towards targets are well known in the art, including for example, ELISAs, Western blots, RIAs, and flow cytometry analysis. The binding kinetics (e.g., binding affinity) of the polypeptide also can be assessed by standard assays known in the art, such as by Surface Plasmon Resonance analysis (SPR).

The terms "binding activity" and "binding affinity" are intended to refer to the tendency of a polypeptide molecule to bind or not to bind to a target. Binding affinity may be quantified by determining the dissociation constant (Kd) for a polypeptide and its target. A lower Kd is indicative of a higher affinity for a target. Similarly, the specificity of binding of a polypeptide to its target may be defined in terms of the comparative dissociation constants (Kd) of the polypeptide for its target as compared to the dissociation constant with respect to the polypeptide and another, non-target molecule.

The value of this dissociation constant can be determined directly by well-known methods, and can be computed even for complex mixtures by methods such as those, for example, set forth in Caceci et al. (Byte 9:340-362, 1984; the disclosures of which are incorporated herein by reference). For example, the Kd may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art, including for example, ELISAs, Western blots, RIAs, and flow cytometry analysis. The binding kinetics (e.g., binding affinity) of the antibody also can be assessed by standard assays known in the art, such as by Biacore™ system analysis.

A competitive binding assay can be conducted in which the binding of the antibody to the target is compared to the binding of the target by another, known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

Alternative measures of binding affinity include EC50 or IC50. In this context EC50 indicates the concentration at which a polypeptide achieves 50% of its maximum binding to a fixed quantity of target. IC50 indicates the concentration at which a polypeptide inhibits 50% of the maximum binding of a fixed quantity of competitor to a fixed quantity of target. In both cases, a lower level of EC50 or IC50 indicates a higher affinity for a target. The EC50 and IC50 values of a ligand for its target can both be determined by well-known methods, for example ELISA. Suitable assays to assess the EC50 and IC50 of polypeptides are set out in the Examples.

A polypeptide of the invention is preferably capable of binding to its target with an affinity that is at least two-fold, 10-fold, 50-fold, 100-fold or greater than its affinity for binding to another non-target molecule.

The polypeptide of the invention may be produced by any suitable means. For example, all or part of the polypeptide may be expressed as a fusion protein by a cell comprising a nucleotide which encodes said polypeptide.

Alternatively parts B1 and B2 may be produced separately and then subsequently joined together. Joining may be achieved by any suitable means, for example using the chemical conjugation methods and linkers outlined above. Separate production of parts B1 and B2 may be achieved by any suitable means. For example by expression from separate nucleotides optionally in separate cells, as is explained in more detail below.

Variants

The bispecific polypeptides or constituent binding domains thereof (such as the OX40, CD137 and CTLA-4 binding domains) described herein may comprise a variant or a fragment of any of the specific amino acid sequences recited herein, provided that the polypeptide or binding domain retains binding to its target. In one embodiment the variant of an antibody or antigen binding fragment may retain the CDR sequences of the sequences recited herein. For example, the anti-OX40 or anti-CD137 antibody may comprise a variant or a fragment of any of the specific amino acid sequences recited in Tables B and H, provided that the antibody retains binding to its target. Such a variant or fragment may typically retain the CDR sequences of the said sequence of Table B or H. The CTLA-4 binding domain may comprise a variant of any of the sequences of Table C, providing that that the binding domain retains binding to its target.

A fragment of any one of the heavy or light chain amino acid sequences recited herein may comprise at least 7, at least 8, at least 9, at least 10, at least 12, at least 15, at least 18, at least 20, at least 25, at least 50, at least 60, at least 70, at least 80, at least 90 or at least 100 consecutive amino acids from the said amino acid sequence.

A variant of any one of the heavy or light chain amino acid sequences recited herein may be a substitution, deletion or addition variant of said sequence. A variant may comprise 1, 2, 3, 4, 5, up to 10, up to 20, up to 30 or more amino acid substitutions and/or deletions from the said sequence. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | |
|---|---|
| Ala, A | aliphatic, hydrophobic, neutral |
| Cys, C | polar, hydrophobic, neutral |
| Asp, D | polar, hydrophilic, charged (−) |
| Glu, E | polar, hydrophilic, charged (−) |
| Phe, F | aromatic, hydrophobic, neutral |
| Gly, G | aliphatic, neutral |
| His, H | aromatic, polar, hydrophilic, charged (+) |
| Ile, I | aliphatic, hydrophobic, neutral |
| Lys, K | polar, hydrophilic, charged(+) |
| Leu, L | aliphatic, hydrophobic, neutral |
| Met, M | hydrophobic, neutral |
| Asn, N | polar, hydrophilic, neutral |
| Pro, P | hydrophobic, neutral |
| Gln, Q | polar, hydrophilic, neutral |
| Arg, R | polar, hydrophilic, charged (+) |
| Ser, S | polar, hydrophilic, neutral |
| Thr, T | polar, hydrophilic, neutral |
| Val, V | aliphatic, hydrophobic, neutral |
| Trp, W | aromatic, hydrophobic, neutral |
| Tyr, Y | aromatic, polar, hydrophobic |

Amino acids herein may be referred to by full name, three letter code or single letter code.

Preferred "derivatives" or "variants" include those in which instead of the naturally occurring amino acid the amino acid which appears in the sequence is a structural analog thereof. Amino acids used in the sequences may also be derivatised or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably variants have an amino acid sequence which has more than 60%, or more than 70%, e.g. 75 or 80%, preferably more than 85%, e.g. more than 90 or 95% amino acid identity to a sequence as shown in the sequences disclosed herein. This level of amino acid identity may be seen across the full length of the relevant SEQ ID NO sequence or over a part of the sequence, such as across 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, *Nucleic Acids Res.* 22(22):4673-80; the disclosures of which are incorporated herein by reference) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatised.

Polynucleotides, Vectors and Cells

The invention also relates to polynucleotides that encode all or part of a polypeptide of the invention. Thus, a polynucleotide of the invention may encode any polypeptide as described herein, or all or part of B1 or all or part of B2. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Representative polynucleotides which encode examples of a heavy chain or light chain amino acid sequence of an antibody may comprise or consist of any one of the nucleotide sequences disclosed herein, for example the sequences set out in Table B or H. Representative polynucleotides which encode the polypeptides shown in Tables D, G or H may comprise or consist of the corresponding nucleotide sequences which are also shown in Tables D, G or H (intron sequences are shown in lower case). Representative polynucleotides which encode examples of CTLA-4 binding domains may comprise or consist of any one of SEQ ID NOS: 25 to 43 as shown in Table E.

A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of nucleic acid sequences disclosed herein, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al, 1984, *Nucleic Acids Research* 12:387-395; the disclosures of which are incorporated herein by reference).

The PILEUP and BLAST algorithms can also be used to calculate homology or line up sequences (typically on their default settings), for example as described in Altschul, 1993, *J Mol Evol* 36:290-300; Altschul et al, 1990, *J Mol Biol* 215:403-10, the disclosures of which are incorporated herein by reference).

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff & Henikoff, 1992, *Proc. Natl. Acad. Sci. USA* 89:10915-10919; the disclosures of which are incorporated herein by reference) alignments (B) of 50, expectation (E) of 10, M=5, N=4, and a comparison of both strands.

The BLAST algorithm performs a statistical analysis of the similarity between two sequences; see e.g. Karlin & Altschul, 1993, *Proc. Natl. Acad. Sci. USA* 90:5873-5787; the disclosures of which are incorporated herein by reference. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

A polypeptide of the invention may thus be produced from or delivered in the form of a polynucleotide which encodes and is capable of expressing it.

Polynucleotides of the invention can be synthesised according to methods well known in the art, as described by way of example in Green & Sambrook (2012, Molecular Cloning—a laboratory manual, $4^{th}$ edition; Cold Spring Harbor Press; the disclosures of which are incorporated herein by reference).

The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art (see Green & Sambrook, supra).

The invention also includes cells that have been modified to express a polypeptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for a polypeptide of the invention include mammalian HEK293T, CHO, HeLa, NS0 and COS cells. Preferably the cell line selected will be one which is not only stable, but also allows for mature glycosylation and cell surface expression of a polypeptide.

Such cell lines of the invention may be cultured using routine methods to produce a polypeptide of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

Pharmaceutical Formulations, Therapeutic Uses and Patient Groups

In another aspect, the present invention provides compositions comprising molecules of the invention, such as the antibodies, bispecific polypeptides, polynucleotides, vectors and cells described herein. For example, the invention provides a composition comprising one or more molecules of the invention, such as one or more antibodies and/or bispecific polypeptides of the invention, and at least one pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intramuscular or subcutaneous administration (e.g., by injection or infusion). Depending on the route of administration, the polypeptide may be coated in a material to protect the polypeptide from the action of acids and other natural conditions that may inactivate or denature the polypeptide.

Preferred pharmaceutically acceptable carriers comprise aqueous carriers or diluents. Examples of suitable aqueous carriers that may be employed in the compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. polypeptide) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Particularly preferred compositions are formulated for systemic administration or for local administration. Local administration may be at the site of a tumour or into a tumour draining lymph node. The composition may preferably be formulated for sustained release over a period of time. Thus the composition may be provided in or as part of a matrix facilitating sustained release. Preferred sustained release matrices may comprise a montanide or γ-polyglutamic acid (PGA) nanoparticles. Localised release of a polypeptide of the invention, optionally over a sustained period of time, may reduce potential autoimmune side-effects associated with administration of a CTLA-4 antagonist.

Compositions of the invention may comprise additional active ingredients as well as a polypeptide of the invention. As mentioned above, compositions of the invention may comprise one or more polypeptides of the invention. They may also comprise additional therapeutic or prophylactic agents.

Also within the scope of the present invention are kits comprising polypeptides or other compositions of the invention and instructions for use. The kit may further contain one or more additional reagents, such as an additional therapeutic or prophylactic agent as discussed above.

The polypeptides in accordance with the present invention maybe used in therapy or prophylaxis. In therapeutic applications, polypeptides or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". In prophylactic applications, polypeptides or compositions are administered to a subject not yet exhibiting symptoms of a disorder or condition, in an amount sufficient to prevent or delay the development of symptoms. Such an amount is defined as a "prophylactically effective amount". The subject may have been identified as being at risk of developing the disease or condition by any suitable means.

In particular, antibodies and bispecific polypeptides of the invention may be useful in the treatment or prevention of cancer. Accordingly, the invention provides an antibody or bispecific polypeptide of the invention for use in the treatment or prevention of cancer. The invention also provides a method of treating or preventing cancer comprising administering to an individual a polypeptide of the invention. The invention also provides an antibody or bispecific polypeptide of the invention for use in the manufacture of a medicament for the treatment or prevention of cancer.

The cancer may be prostate cancer, breast cancer, colorectal cancer, pancreatic cancer, ovarian cancer, lung cancer, cervical cancer, rhabdomyosarcoma, neuroblastoma, multiple myeloma, leukemia, acute lymphoblastic leukemia, melanoma, bladder cancer, gastric cancer, head and neck cancer, liver cancer, skin cancer, lymphoma or glioblastoma.

An antibody or bispecific polypeptide of the present invention, or a composition comprising said antibody or said polypeptide, may be administered via one or more routes of administration using one or more of a variety of methods known in the art. As will be appreciated by the skilled artisan, the route and/or mode of administration will vary depending upon the desired results. Systemic administration or local administration are preferred. Local administration may be at the site of a tumour or into a tumour draining lymph node. Preferred modes of administration for polypeptides or compositions of the invention include intravenous, intramuscular, intradermal, intraperitoneal, subcutaneous, spinal or other parenteral modes of administration, for example by injection or infusion. The phrase "parenteral administration" as used herein means modes of administration other than enteral and topical administration, usually by injection. Alternatively, a polypeptide or composition of the invention can be administered via a non-parenteral mode, such as a topical, epidermal or mucosal mode of administration.

A suitable dosage of an antibody or polypeptide of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular polypeptide employed, the route of administration, the time of administration, the rate of excretion of the polypeptide, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody or polypeptide of the invention may be, for example, in the range of from about 0.1 μg/kg to about 100 mg/kg body weight of the patient to be treated. For example, a suitable dosage may be from about 1 μg/kg to about 10 mg/kg body weight per day or from about 10 g/kg to about 5 mg/kg body weight per day.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Antibodies or polypeptides may be administered in a single dose or in multiple doses. The multiple doses may be administered via the same or different routes and to the same or different locations. Alternatively, antibodies or polypeptides can be administered as a sustained release formulation as described above, in which case less frequent administration is required. Dosage and frequency may vary depending on the half-life of the polypeptide in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Combined administration of two or more agents may be achieved in a number of different ways. In one embodiment, the antibody or polypeptide and the other agent may be administered together in a single composition. In another embodiment, the antibody or polypeptide and the other agent may be administered in separate compositions as part of a combined therapy. For example, the modulator may be administered before, after or concurrently with the other agent.

An antibody, polypeptide or composition of the invention may also be used in a method of increasing the activation of a population of cells expressing the first and second T cell target, the method comprising administering to said population of cells a polypeptide or composition of the invention under conditions suitable to permit interaction between said cell and a polypeptide of the invention. The population of cells typically comprises at least some cells which express the first T cell target, typically T cells, and at least some cells which express the second T cell target. The method is typically carried out ex vivo.

For example, an antibody, polypeptide or composition of the invention may also be used in a method of increasing the activation of a population of cells expressing human OX40 and human CTLA-4, the method as described above.

Alternatively an antibody, polypeptide or composition of the invention may also be used in a method of increasing the activation of a population of cells expressing human OX40 and human CD137, the method as described above.

Alternatively an antibody, polypeptide or composition of the invention may also be used in a method of increasing the activation of a population of cells expressing human CTLA-4 and human CD137, the method as described above.

Binding Domains for CD137

The bispecific polypeptides of the invention may comprise a binding domain which is specific for CD137.

The antibody, or antigen binding fragment thereof, that binds specifically to CD137 has certain preferred binding characteristics and functional effects, which are explained in more detail below. Said antibody, or antigen binding fragment thereof, preferably retains these binding characteristics and functional effects when incorporated as part of a bispecific antibody of the invention. The invention also provides said antibody as an antibody or antigen-binding fragment thereof in isolated form, i.e. independently of a bispecific antibody of the invention.

The anti-CD137 antibody preferably specifically binds to CD137, i.e. it binds to CD137 but does not bind, or binds at a lower affinity, to other molecules. The term CD137 as used herein typically refers to human CD137. The sequence of human CD137 is set out in SEQ ID NO: 148 (corresponding to GenBank: AAH06196.1). The antibody may have some binding affinity for CD137 from other mammals, such as CD137 from a non-human primate, for example *Macaca fascicularis* (cynomolgus monkey). The antibody preferably does not bind to murine CD137 and/or does not bind to other human TNFR superfamily members, for example human OX40 or CD40.

The antibody has the ability to bind to CD137 in its native state and in particular to CD137 localised on the surface of a cell. Preferably, the antibody will bind specifically to CD137. That is, an antibody of the invention will preferably bind to CD137 with greater binding affinity than that at which it binds to another molecule.

"Localised on the surface of a cell" is as defined previously.

The antibody may modulate the activity of a cell expressing CD137, wherein said modulation is an increase or decrease in the activity of said cell. The cell is typically a T cell. The antibody may increase the activity of a CD4+ or CD8+ effector cell, or may decrease the activity of, or deplete, a regulatory T cell (T reg). In either case, the net effect of the antibody will be an increase in the activity of effector T cells, particularly CD4+, CD8+ or NK effector T cells. Methods for determining a change in the activity of effector T cells are well known and are as described earlier.

The antibody preferably causes an increase in activity in a CD8+ T cell in vitro, optionally wherein said increase in activity is an increase in proliferation, IFN-γ production and/or IL-2 production by the T cell. The increase is preferably at least 2-fold, more preferably at least 10-fold and even more preferably at least 25-fold higher than the change in activity caused by an isotype control antibody measured in the same assay.

The antibody preferably binds to human CD137 with a Kd value which is less than $10 \times 10^{-9}$M or less than $7 \times 10^{-9}$M, more preferably less than 4, or $2 \times 10^{-9}$M, most preferably less than $1.2 \times 10^{-9}$M.

For example, the antibody preferably does not bind to murine CD137 or any other TNFR superfamily member, such as OX40 or CD40. Therefore, typically, the Kd for the antibody with respect to human CD137 will be 2-fold, preferably 5-fold, more preferably 10-fold less than Kd with respect to the other, non-target molecule, such as murine CD137, other TNFR superfamily members, or any other unrelated material or accompanying material in the environment. More preferably, the Kd will be 50-fold less, even more preferably 100-fold less, and yet more preferably 200-fold less.

The value of this dissociation constant can be determined directly by well-known methods, as described earlier. A competitive binding assay can also be conducted, as described earlier.

An antibody of the invention is preferably capable of binding to its target with an affinity that is at least two-fold, 10-fold, 50-fold, 100-fold or greater than its affinity for binding to another non-target molecule.

In summary therefore, the anti-CD137 antibody preferably exhibits at least one of the following functional characteristics:

I. binding to human CD137 with a $K_D$ value which is less than $10 \times 10^{-9}$M, more preferably less than $1.2 \times 10^{-9}$M; and II. is capable of causing an increase in activity in a CD8+ T cell in vitro, optionally wherein said increase in activity is an increase in proliferation, IFN-γ production and/or IL-2 production by the T cell. The increase is preferably at least 2-fold, more preferably at least 10-fold and even more preferably at least 25-fold higher than the change in activity caused by an isotype control antibody measured in the same assay.

The antibody is specific for CD137, typically human CD137 and may comprise any one, two, three, four, five or all six of the exemplary CDR sequences of any corresponding pair of rows in Tables I(1) and I(2).

For example, the antibody may comprise any one, two, three, four, five or all six of the exemplary CDR sequences of the first rows of Table I(1) and Table I(2) (SEQ ID NOs: 207, 212, 217, 80, 81, 222)

Alternatively the antibody may comprise any one, two, three, four, five or all six of the exemplary CDR sequences of the second, third, fourth or fifth rows of Tables I(1) and I(2).

Preferred anti-CD137 antibodies may comprise at least a heavy chain CDR3 as defined in any individual row of Table I(1) and/or a light chain CDR3 as defined in in any individual row of Table I(2). The antibody may comprise all three heavy chain CDR sequences shown in an individual row of Table I(1) (that is, all three heavy chain CDRs of a given "VH number") and/or all three light chain CDR sequences shown in an individual row of Table I(2) (that is, all three light chain CDRs of a given "VL number").

Examples of complete heavy and light chain variable region amino acid sequences of anti-CD137 antibodies are shown in Table H. Exemplary nucleic acid sequences encoding each amino acid sequence are also shown. SEQ ID NOs 177 to 196 refer to the relevant amino acid and nucleotide sequences of anti-CD137 antibodies. The numbering of said VH and VL regions in Table H corresponds to the numbering system used as in Table I(1) and (2). Thus, for example, the amino acid sequence for "1205 light chain VL" is an example of a complete VL region sequence comprising all three CDRs of VL number 1205 shown in Table I(2) and the amino acid sequence for "1204, heavy chain VH" is an example of a complete VH region sequence comprising all three CDRs of VH number 1204 shown in Table I(1).

Preferred anti-CD137 antibodies of the invention include a VH region which comprises all three CDRs of a particular VH number and a VL region which comprises all three CDRs of a particular VL number. For example: an antibody may comprise all three CDRs of VH number 1204 and all three CDRs of VL number 1205. Such an antibody may be referred to as 1204/1205. Such an antibody may preferably comprise the corresponding complete VH and VL sequences of 1204 and 1205 as shown in Table H (SEQ ID NOs: 179 and 177).

An antibody may alternatively comprise all three CDRs of VH number 1214 and all three CDRs of VL number 1215. Such an antibody may be referred to as 1214/1215. Such an antibody may preferably comprise the corresponding complete VH and VL sequences of 1214 and 1215 as shown in Table H (SEQ ID NOs: 181 and 183).

An antibody may alternatively comprise all three CDRs of VH number 1618 and all three CDRs of VL number 1619. Such an antibody may be referred to as 1618/1619. Such an antibody may preferably comprise the corresponding complete VH and VL sequences of 1618 and 1619 as shown in Table H (SEQ ID NOs: 185 and 187).

An antibody may alternatively comprise all three CDRs of VH number 1620 and all three CDRs of VL number 1621. Such an antibody may be referred to as 1620/1621. Such an antibody may preferably comprise the corresponding complete VH and VL sequences of 1620 and 1621 as shown in Table H (SEQ ID NOs: 189 and 191)

An antibody may alternatively comprise all three CDRs of VH number 1626 and all three CDRs of VL number 1627. Such an antibody may be referred to as 1626/1627. Such an antibody may preferably comprise the corresponding complete VH and VL sequences of 1626 and 1627 as shown in Table H (SEQ ID NOs: 193 and 195)

The anti-CD137 antibody may bind to the same epitope as any of the specific anti-CD137 antibodies described herein. Preferably it binds to the same epitope as any one of the antibodies designated 1204/1205, 1214/1215, 1618/1619, 1620/1621, and 1626/1627.

Binding Domains for CTLA-4

The bispecific polypeptides of the invention may comprise a binding domain specific for CTLA-4.

CD86 and CD80 may be referred to herein as B7 proteins (B7-2 and B7-1 respectively). These proteins are expressed on the surface of antigen presenting cells and interact with the T cell receptors CD28 and CTLA-4. The binding of the B7 molecules to CD28 promotes T cell activation while binding of B7 molecules to CTLA-4 switches off the activation of the T cell. The interaction between the B7 proteins with CD28 and/or CTLA-4 constitutes a costimulatory signalling pathway which plays an important role in immune activation and regulation. Thus, the B7 molecules are part of a pathway, amenable to manipulation in order to uncouple immune inhibition, thereby enhancing immunity in patients.

The CD86 protein is a monomer and consists of two extracellular immunoglobulin superfamily domains. The receptor binding domain of CD86 has a typical IgV-set structure, whereas the membrane proximal domain has a C1-set like structure. The structures of CD80 and CD86 have been determined on their own or in complex with CTLA-4. The contact residues on the CD80 and CD86 molecules are in the soluble extracellular domain, and mostly located in the beta-sheets and not in the (CDR-like) loops.

SEQ ID NO: 3 is the amino acid sequence of the monomeric soluble extracellular domain of human wild-type CD86. This wild type sequence may optionally lack Alanine and Proline at the N terminus, i.e. positions 24 and 25. These amino acids may be referred to herein as A24 and P25 respectively.

A bispecific polypeptide of the invention may incorporate as a polypeptide binding domain a domain which is specific for CTLA-4, a "CTLA-4 binding domain". Suitable examples of such binding domains are disclosed in WO 2014/207063, the contents of which are incorporated by reference. The binding domain specific for CTLA-4 may also bind to CD28. The term CTLA-4 as used herein typically refers to human CTLA-4 and the term CD28 as used herein typically refers to human CD28. The sequences of human CTLA-4 and human CD28 are set out in SEQ ID NOs: 1 and 2 respectively. The CTLA-4 binding domain of the polypeptide of the present invention may have some binding affinity for CTLA-4 or CD28 from other mammals, for example primate or murine CTLA-4 or CD28.

The CTLA-4 binding domain has the ability to bind to CTLA-4 in its native state and in particular to CTLA-4 localised on the surface of a cell.

"Localised on the surface of a cell" is as defined above.

The CTLA-4 binding domain part of the polypeptide of the invention may comprise or consist of:
 (i) the amino acid sequence of SEQ ID NO: 3; or
 (ii) an amino acid sequence in which at least one amino acid is changed when compared to the amino acid sequence of SEQ ID NO: 3 provided that said binding domain binds to human CTLA-4 with higher affinity than wild-type human CD86.

In other words, the CTLA-4 binding domain is a polypeptide binding domain specific for human CTLA-4 which comprises or consists of (i) the monomeric soluble extracellular domain of human wild-type CD86, or (ii) a polypeptide variant of said soluble extracellular domain, provided that said polypeptide variant binds to human CTLA-4 with higher affinity than wild-type human CD86.

Accordingly, the CTLA-4 binding domain of the polypeptide of the invention may have the same target binding properties as human wild-type CD86, or may have different target binding properties compared to the target binding properties of human wild-type CD86. For the purposes of comparing such properties, "human wild-type CD86" typically refers to the monomeric soluble extracellular domain of human wild-type CD86 as described in the preceding section.

Human wild-type CD86 specifically binds to two targets, CTLA-4 and CD28. Accordingly, the binding properties of the CTLA-4 binding domain of the polypeptide of the invention may be expressed as an individual measure of the ability of the polypeptide to bind to each of these targets. For example, a polypeptide variant of the monomeric extracellular domain of human wild-type CD86 preferably binds to CTLA-4 with a higher binding affinity than that of wild-type human CD86 for CTLA-4. Such a polypeptide may optionally also bind to CD28 with a lower binding affinity than that of wild-type human CD86 for CD28.

The CTLA-4 binding domain of the polypeptide of the invention is a polypeptide binding domain specific for CTLA-4. This means that it binds to CTLA-4 preferably with a greater binding affinity than that at which it binds to another molecule. The CTLA-4 binding domain preferably binds to CTLA-4 with the same or with a higher affinity than that of wild-type human CD86 for CTLA-4.

Preferably, the Kd of the CTLA-4 binding domain of the polypeptide of the invention for human CTLA-4 will be at least 2-fold, at least 2.5-fold, at least 3-fold, at least 3.5-fold, at least 4-fold, at least 4.5-fold, at least 5-fold, at least 5.5-fold, at least 8-fold or at least 10-fold less than the Kd of wild-type human CD86 for human CTLA-4. Most preferably, the Kd of the CTLA-4 binding domain for human CTLA-4 will be at least 5-fold or at least 10-fold less than the Kd of wild-type human CD86 for human CTLA-4. A preferred method for determining the Kd of a polypeptide for CTLA-4 is SPR analysis, e.g. with a Biacore™ system. Suitable protocols for the SPR analysis of polypeptides are set out in the Examples.

Preferably, the EC50 of the CTLA-4 binding domain of the polypeptide of the invention for human CTLA-4 will be at least 1.5-fold, at least 2-fold, at least 3-fold, at least 5-fold, at least 10-fold, at least 12-fold, at least 14-fold, at least 15-fold, at least 17-fold, at least 20-fold, at least 25-fold or at least 50-fold less than the EC50 of wild-type human CD86 for human CTLA-4 under the same conditions. Most preferably, the EC50 of the CTLA-4 binding domain for human CTLA-4 will be at least 10-fold or at least 25-fold less than the EC50 of wild-type human CD86 for human CTLA-4 under the same conditions. A preferred method for determining the EC50 of a polypeptide for CTLA-4 is via ELISA. Suitable ELISA assays for use in the assessment of the EC50 of polypeptides are set out in the Examples.

Preferably, the IC50 of the CTLA-4 binding domain of the polypeptide of the invention when competing with wild-type human CD86 for binding to human CTLA-4 will be at least 2-fold, at least 3-fold, at least 4-fold, at least 5-fold, at least 10-fold, at least 13-fold, at least 15-fold, at least 50-fold, at least 100-fold, or at least 300-fold less than the IC50 of wild-type human CD86 under the same conditions. Most preferably, the IC50 of the CTLA-4 binding domain will be at least 10-fold or at least 300-fold less than the IC50 of wild-type human CD86 under the same conditions. A preferred method for determining the IC50 of a polypeptide of the invention is via ELISA. Suitable ELISA assays for use in the assessment of the IC50 of polypeptides of the invention are set out in the Examples.

The CTLA-4 binding domain of the polypeptide of the invention may also bind specifically to CD28. That is, the CTLA-4 binding domain may bind to CD28 with greater binding affinity than that at which it binds to another molecule, with the exception of CTLA-4. The CTLA-4 binding domain may bind to human CD28 with a lower affinity than that of wild-type human CD86 for human CD28. Preferably, the Kd of the CTLA-4 binding domain for human CD28 will be at least 2-fold, preferably at least 5-fold, more preferably at least 10-fold higher than the Kd of wild-type human CD86 for human CD28.

The binding properties of the CTLA-4 binding domain of the polypeptide of the invention may also be expressed as a relative measure of the ability of a polypeptide to bind to the two targets, CTLA-4 and CD28. That is, the binding properties of the CTLA-4 binding domain may be expressed as a relative measure of the ability of the polypeptide to bind to CTLA-4 versus its ability to bind to CD28. Preferably the CTLA-4 binding domain has an increased relative ability to bind to CTLA-4 versus CD28, when compared to the corresponding relative ability of human wild-type CD86 to bind to CTLA-4 versus CD28.

When the binding affinity of a polypeptide for both CTLA-4 and CD28 is assessed using the same parameter (e.g. Kd, EC50), then the relative binding ability of the polypeptide for each target may be expressed as a simple ratio of the values of the parameter for each target. This ratio may be referred to as the binding ratio or binding strength ratio of a polypeptide. For many parameters used to assess binding affinity (e.g. Kd, EC50), a lower value indicates a higher affinity. When this is the case, the ratio of binding affinities for CTLA-4 versus CD28 is preferably expressed as a single numerical value calculated according to the following formula:

Binding ratio=[binding affinity for CD28]÷[binding affinity for CTLA-4]

Alternatively, if binding affinity is assessed using a parameter for which a higher value indicates a higher affinity, the inverse of the above formula is preferred. In either context, the CTLA-4 binding domain of the polypeptide of the invention preferably has a higher binding ratio than human wild-type CD86. It will be appreciated that direct comparison of the binding ratio for a given polypeptide to the binding ratio for another polypeptide typically requires that the same parameters be used to assess the binding affinities and calculate the binding ratios for both polypeptides.

Preferably, the binding ratio for a polypeptide is calculated by determining the Kd of the polypeptide for each target and then calculating the ratio in accordance with the formula [Kd for CD28]÷[Kd for CTLA-4]. This ratio may be referred to as the Kd binding ratio of a polypeptide. A preferred method for determining the Kd of a polypeptide for a target is SPR analysis, e.g. with a Biacore™ system. Suitable protocols for the SPR analysis of polypeptides of the invention are set out in the Examples. The binding ratio of the CTLA-4 binding domain of the polypeptide of the invention calculated according to this method is preferably at least 2-fold or at least 4-fold higher than the binding ratio of wild-type human CD86 calculated according to the same method.

Alternatively, the binding ratio for a polypeptide may be calculated by determining the EC50 of the polypeptide for each target and then calculating the ratio in accordance with the formula [EC50 for CD28]+[EC50 for CTLA-4]. This ratio may be referred to as the EC50 binding ratio of a polypeptide. A preferred method for determining the EC50 of a polypeptide for a target is via ELISA. Suitable ELISA assays for use in the assessment of the EC50 of polypeptides of the invention are set out in the Examples. The binding ratio of the CTLA-4 binding domain of the polypeptide of the invention calculated according to this method is at least 2-fold, at least 3-fold, at least 4-fold, at least 5-fold, at least 6-fold, at least 7-fold, at least 8-fold, at least 9-fold or at least 10-fold higher than the binding ratio of wild-type human CD86 calculated according to the same method.

The CTLA-4 binding domain of the polypeptide of the invention may have the ability to cross-compete with another polypeptide for binding to CTLA-4. For example, the CTLA-4 binding domain may cross-compete with a polypeptide having the amino acid sequence of any one of SEQ ID NOs: 6 to 24 for binding to CTLA-4. Such cross-competing polypeptides may be identified in standard binding assays. For example, SPR analysis (e.g. with a Biacore™ system), ELISA assays or flow cytometry may be used to demonstrate cross-competition.

In addition to the above functional characteristics, the CTLA-4 binding domain of the polypeptide of the invention has certain preferred structural characteristics. The CTLA-4 binding domain either comprises or consists of (i) the monomeric soluble extracellular domain of human wild-type CD86, or (ii) a polypeptide variant of said soluble extracellular domain, provided that said polypeptide variant binds to human CTLA-4 with higher affinity than wild-type human CD86.

A polypeptide variant of the monomeric soluble extracellular domain of human wild-type CD86 comprises or consists of an amino acid sequence which is derived from that of human wild-type CD86, specifically the amino acid sequence of the soluble extracellular domain of human wild-type CD86 (SEQ ID NO: 3), optionally lacking A24 and P25. In particular, a variant comprises an amino acid sequence in which at least one amino acid is changed when compared to the amino acid sequence of SEQ ID NO: 3 (or said sequence lacking A24 and P25). By "changed" it is meant that at least one amino acids is deleted, inserted, or substituted compared to the amino acid sequence of SEQ ID NO: 3 (or said sequence lacking A24 and P25). By "deleted" it is meant that the at least one amino acid present in the amino acid sequence of SEQ ID NO: 3 (or said sequence lacking A24 and P25) is removed, such that the amino acid sequence is shortened by one amino acid. By "inserted" it is meant that the at least one additional amino acid is introduced into the amino acid sequence of SEQ ID NO: 3 (or said sequence lacking A24 and P25), such that the amino acid sequence is lengthened by one amino acid. By "substituted" it is meant that the at least one amino acid in the amino acid sequence of SEQ ID NO: 3 (or said sequence lacking A24 and P25) is replaced with an alternative amino acid.

Typically, at least 1, 2, 3, 4, 5, 6, 7, 8 or 9 amino acids are changed when compared to the amino acid sequence of SEQ ID NO: 3 (or said sequence lacking A24 and P25). Typically, no more than 10, 9, 8, 7, 6, 5, 4, 2 or 1 amino acids are changed when compared to the amino acid sequence of SEQ ID NO: 3 (or said sequence lacking A24 and P25). It will be appreciated that any of these lower limits may be combined with any of these upper limits to define a range for the permitted number of changes compared to the amino acid sequence of SEQ ID NO: 3 (or said sequence lacking A24 and P25). Thus, for example, a polypeptide of the invention may comprise an amino acid sequence in which the permitted number of amino acid changes compared to the amino acid sequence of SEQ ID NO: 3 (or said sequence lacking A24 and P25) is in the range 2 to 3, 2 to 4, 2 to 5, 2 to 6, 2 to 7, 2 to 8, 2 to 9, 2 to 10, 3 to 4, 3 to 5, 3 to 6, and so on.

It is particularly preferred that at least 2 amino acids are changed when compared to the amino acid sequence of SEQ ID NO: 3 (or said sequence lacking A24 and P25). Preferably, the permitted number of amino acid changes compared to the amino acid sequence of SEQ ID NO: 3 (or said sequence lacking A24 and P25) is in the range 2 to 9, 2 to 8 or 2 to 7.

The numbers and ranges set out above may be achieved with any combination of deletions, insertions or substitutions compared to the amino acid sequence of SEQ ID NO: 3 (or said sequence lacking A24 and P25). For example, there may be only deletions, only insertions, or only substitutions compared to the amino acid sequence of SEQ ID NO: 3 (or said sequence lacking A24 and P25), or any mixture of deletions, insertions or substitutions. Preferably the variant comprises an amino acid sequence in which all of the changes compared to the amino acid sequence of SEQ ID NO: 3 (or said sequence lacking A24 and P25) are substitutions. That is, a sequence in which no amino acids are deleted or inserted compared to the sequence of SEQ ID NO: 3 (or said sequence lacking A24 and P25). In the amino acid sequence of a preferred variant, 1, 2, 3, 4, 5, 6, 7, or 8 amino acids are substituted when compared to the amino acid sequence of SEQ ID NO: 3 (or said sequence lacking A24 and P25) and no amino acids are deleted or inserted compared to the sequence of SEQ ID NO: 3 (or said sequence lacking A24 and P25).

Preferably the changes compared to the sequence of SEQ ID NO: 3 (or said sequence lacking A24 and P25) are in the FG loop region (positions 114 to 121) and/or the beta sheet region of SEQ ID NO: 3. The strands of the beta sheet region have the following positions in SEQ ID NO: 3: A:27-31, B:36-37, C:54-58, C':64-69, C":72-74, D:86-88, E:95-97, F:107-113, G:122-133.

Most preferably, the changes compared to the sequence of SEQ ID NO: 3 (or said sequence lacking A24 and P25) are in one or more of the positions selected from 32, 48, 49, 54, 74, 77, 79, 103, 107, 111, 118, 120, 121, 122, 125, 127 or 134. All numbering of amino acid positions herein is based on counting the amino acids in SEQ ID NO: 4 starting from the N terminus. Thus, the first position at the N terminus of SEQ ID NO: 3 is numbered 24 (see schematic diagram in FIG. 4).

Particularly preferred insertions include a single additional amino acid inserted between positions 116 and 117 and/or a single additional amino acid inserted between positions 118 and 119. The inserted amino acid is preferably Tyrosine (Y), Serine (S), Glycine (G), Leucine (L) or Aspartic Acid (D).

A particularly preferred substitution is at position 122, which is Arginine (R). The polypeptide of the invention preferably includes an amino acid sequence in which at least position 122 is substituted compared to the amino acid sequence of SEQ ID NO: 3 (or said sequence lacking A24 and P25). The most preferred substitution at position 122 is to replace Arginine (R) with Lysine (K) or Asparagine (N), ranked in order of preference. This substitution may be referred to as R122K/N.

Other preferred substitutions are at positions 107, 121, and 125, which are Leucine (L), Isoleucine (I) and Glutamic acid (Q), respectively. In addition to the substitution at position 122, the polypeptide of the invention preferably includes an amino acid sequence in which at least one of the amino acids at positions 107, 121 and 125 is also substituted compared to the amino acid sequence of SEQ ID NO: 3 (or said sequence lacking A24 and P25). The amino acid sequence of the polypeptide of the invention may also be substituted at one or more of positions 32, 48, 49, 54, 64, 74, 77, 79, 103, 111, 118, 120, 127 and 134.

The most preferred substitution at position 107 is to replace Leucine (L) with Isoleucine (I), Phenylalanine (F) or Arginine (R), ranked in order of preference. This substitution may be referred to as L1071/F/R. Similar notation is used for other substitutions described herein. The most preferred substitution at position 121 is to replace Isoleucine (I) with Valine (V). This substitution may be referred to as I121V.

The most preferred substitution at position 125 is to replace Glutamine (Q) with Glutamic acid (E). This substitution may be referred to as Q125E.

Other substitutions which may be preferred in the amino acid sequence of the polypeptide of the invention include: F321, Q48L, S49T, V541, V641, K741/R, S77A, H79D/S/A, K103E, I111V, T118S, M120L, N127S/D and A134T.

Particularly preferred variants of said soluble extracellular domain of human wild-type CD86 comprise or consist of any one of the amino acid sequences of SEQ ID NOs: 6 to 24, as shown in Table C.

The amino acid sequences shown in SEQ ID NOs: 6 to 14 may optionally include the additional residues AP at the N-terminus. The amino acid sequences shown in SEQ ID NOs: 15 to 24 may optionally lack the residues AP at the N-terminus. In either case, these residues correspond to A24 and P25 of SEQ ID NO: 3.

The CTLA-4 binding domain of the polypeptide of the invention may comprise or consist of any of the above-described variants of said soluble extracellular domain of human wild-type CD86. That is, the CTLA-4 binding domain of the polypeptide of the invention may comprise or consist of the amino acid sequence of any one of SEQ ID NOs: 6 to 24, as shown in Table C.

The binding domain may modulate signalling from CTLA-4, for example when administered to a cell expressing CTLA-4, such as a T cell. Preferably the binding domain reduces, i.e. inhibits or blocks, said signalling and thereby increases the activation of said cell. Changes in CTLA-4 signalling and cell activation as a result of administration of a test agent (such as the binding domain) may be determined by any suitable method. Suitable methods include assaying for the ability of membrane-bound CD86 (e.g. on Raji cells) to bind and signal through CTLA-4 expressed on the surface of T cells, when in the presence of a test agent or in the presence of a suitable control. An increased level of T cell IL-2 production or an increase in T cell proliferation in the presence of the test agent relative to the level of T cell IL-2 production and/or T cell proliferation in the presence of the control is indicative of reduced signalling through CTLA-4 and increased cell activation. A typical assay of this type is disclosed in Example 9 of US20080233122.

Binding Domains for OX40

The bispecific binding molecules of the invention may incorporate as a binding domain (for example, as B1) any OX40 binding domain, for example an anti-OX40 antibody.

The antibody, or antigen binding fragment thereof, that binds specifically to OX40 has certain preferred binding characteristics and functional effects, which are explained in more detail below. Said antibody, or antigen binding fragment thereof, preferably retains these binding characteristics and functional effects when incorporated as part of a bispecific antibody of the invention. This binding domain may also be provided independently of the bispecific molecules of the invention.

The antibody preferably specifically binds to OX40, i.e. it binds to OX40 but does not bind, or binds at a lower affinity, to other molecules. The term OX40 as used herein typically refers to human OX40. The sequence of human OX40 is set out in SEQ ID NO:51 (corresponding to GenBank: NP_003318.1). The antibody may have some binding affinity for OX40 from other mammals, such as OX40 from a non-human primate (for example *Macaca fascicularis* (cynomolgus monkey), *Macaca mulatta*). The antibody preferably does not bind to murine OX40 and/or does not bind to other human TNFR superfamily members, for example human CD137 or CD40.

The antibody has the ability to bind to OX40 in its native state and in particular to OX40 localised on the surface of a cell. Preferably, the antibody will bind specifically to OX40. That is, an antibody of the invention will preferably bind to OX40 with greater binding affinity than that at which it binds to another molecule.

"Localised on the surface of a cell" is as defined above.

The antibody may modulate the activity of a cell expressing OX40, wherein said modulation is an increase or decrease in the activity of said cell, as defined above. The cell is typically a T cell. The antibody may increase the activity of a CD4+ or CD8+ effector cell, or may decrease the activity of a regulatory T cell (T reg), as described above.

In either case, the net effect of the antibody will be an increase in the activity of effector T cells, particularly CD4+ effector T cells. Methods for determining a change in the activity of effector T cells are well known and are described above.

The antibody preferably binds to human OX40 with a Kd value which is less than $50 \times 10^{-10}$M or less than $25 \times 10^{-10}$M, more preferably less than 10, 9, 8, 7, or $6 \times 10^{-10}$M, most preferably less than $5 \times 10^{-10}$M.

For example, the antibody preferably does not bind to murine OX40 or any other TNFR superfamily member, such as CD137 or CD40. Therefore, typically, the Kd for the antibody with respect to human OX40 will be 2-fold, preferably 5-fold, more preferably 10-fold less than Kd with respect to the other, non-target molecule, such as murine OX40, other TNFR superfamily members, or any other unrelated material or accompanying material in the environment. More preferably, the Kd will be 50-fold less, even more preferably 100-fold less, and yet more preferably 200-fold less.

The value of this dissociation constant can be determined directly by well-known methods, as described above.

An antibody of the invention is preferably capable of binding to its target with an affinity that is at least two-fold, 10-fold, 50-fold, 100-fold or greater than its affinity for binding to another non-target molecule.

In summary therefore, the antibody preferably exhibits at least one of the following functional characteristics:
I. binding to human OX40 with a $K_D$ value which is less than $10 \times 10{-10}$M;
II. does not bind to murine OX40;
III. does not bind to other human TNFR superfamily members, for example human CD137 or CD40.

The antibody is specific for OX40, typically human OX40 and may comprise any one, two, three, four, five or all six of the following:

(a) a heavy chain CDR1 sequence which is 8 amino acids in length and comprises the consensus sequence: "G, F, T, F, G/Y/S, G/Y/S, Y/S, Y/S/A";
(b) a heavy chain CDR2 sequence which is 8 amino acids in length and comprises the consensus sequence: "I, G/Y/S/T, G/S/Y, S/Y, G/S/Y, G/S/Y, G/S/Y, T";
(c) a heavy chain CDR3 sequence which is 9 to 17 amino acids in length and which comprises the consensus sequence of: "A, R, G/Y/S/H, G/Y/F/V/D, G/Y/P/F, -/H/S, -/N/D/H, -/Y/G, -/Y, -/Y, -/W/A/V, -/A/Y, -/D/A/Y/G/H/N, Y/S/V/V/A/T, L/M/I/F, D, Y". Preferred heavy chain CDR3 sequences within this definition include a CDR3 sequence of 10 amino acids in length which comprises the consensus sequence "A, R, Y/H, D, Y, A/Y/G, S/W/A, M/L, D, Y" or a CDR3 sequence of 11 amino acids in length which comprises the consensus sequence "A, R, G/Y, V/F/Y, P, H, G/Y/H, Y, F/I, D, Y";
(d) a light chain CDR1 sequence which consists of the sequence: "Q, S, I, S, S, Y";
(e) a light chain CDR2 sequence which consists of the sequence: "A, A, S";
(f) a light chain CDR3 sequence which is 8 to 10 amino acids in length and comprises the consensus sequence: "Q,Q, S/Y/G, -/Y/H/G, -/S/Y/G/D, S/Y/G/D , S/Y/G/T, P/L, Y/S/H/L/F, T". A preferred example a light chain CDR3 sequence within this definition consists of the sequence "Q, Q, S, Y, S, T, P, Y, T"

The antibody may comprise at least a heavy chain CDR3 as defined in (c) and/or a light chain CDR3 as defined in (f). The antibody may comprise all three heavy chain CDR sequences of (a), (b) and (c) and/or all three light chain CDR sequences of (d), (e) and (f).

Exemplary CDR sequences are recited in tables A(1) and A(2), SEQ ID NOs: 52 to 88.

Preferred anti-OX40 antibodies may comprise at least a heavy chain CDR3 as defined in any individual row of Table A(1) and/or a light chain CDR3 as defined in in any individual row of Table A(2). The antibody may comprise all three heavy chain CDR sequences shown in an individual row of Table A(1) (that is, all three heavy chain CDRs of a given "VH number") and/or all three light chain CDR sequences shown in an individual row of Table A(2) (that is, all three light chain CDRs of a given "VL number").

Examples of complete heavy and light chain variable region amino acid sequences are shown in Table B. Exemplary nucleic acid sequences encoding each amino acid sequence are also shown. The numbering of said VH and VL regions in Table B corresponds to the numbering system used as in Table A(1) and (2). Thus, for example, the amino acid sequence for "1167, light chain VL" is an example of a complete VL region sequence comprising all three CDRs of VL number 1167 shown in Table A(2) and the amino acid sequence for "1166, heavy chain VH" is an example of a complete VH region sequence comprising all three CDRs of VH number 1166 shown in Table A(1).

Preferred anti-OX40 antibodies of the invention include a VH region which comprises all three CDRs of a particular VH number and a VL region which comprises all three CDRs of a particular VL number. For example:

an antibody may comprise all three CDRs of VH number 1166 and all three CDRs of VL number 1167. Such an antibody may be referred to as 1166/1167. Such an antibody may preferably comprise the corresponding complete VH and VL sequences of 1166 and 1167 as shown in Table B (SEQ ID NOs: 91 and 89).

an antibody may comprise all three CDRs of VH number 1170 and all three CDRs of VL number 1171. Such an antibody may be referred to as 1170/1171. Such an antibody may preferably comprise the corresponding complete VH and VL sequences of 1170 and 1171 as shown in Table B (SEQ ID NOs: 95 and 93).

an antibody may comprise all three CDRs of VH number 1164 and all three CDRs of VL number 1135. Such an antibody may be referred to as 1164/1135. Such an antibody may preferably comprise the corresponding complete VH and VL sequences of 1164 and 1135 as shown in Table B (SEQ ID NOs: 99 and 97)

an antibody may comprise all three CDRs of VH number 1168 and all three CDRs of VL number 1135. Such an antibody may be referred to as 1168/1135. Such an antibody may preferably comprise the corresponding complete VH and VL sequences of 1168 and 1135 as shown in Table B (SEQ ID NOs: 101 and 97)

an antibody may comprise all three CDRs of VH number 1482 and all three CDRs of VL number 1483. Such an antibody may be referred to as 1482/1483 Such an antibody may preferably comprise the corresponding complete VH and VL sequences of 1482 and 1483 as shown in Table B (SEQ ID NOs: 105 and 103).

an antibody may comprise all three CDRs of VH number 1490 and all three CDRs of VL number 1135. Such an antibody may be referred to as 1490/1135. Such an antibody may preferably comprise the corresponding complete VH and VL sequences of 1490 and 1135 as shown in Table B (SEQ ID NOs: 107 and 97).

an antibody may comprise all three CDRs of VH number 1514 and all three CDRs of VL number 1515. Such an antibody may be referred to as 1514/1515. Such an antibody may preferably comprise the corresponding complete VH and VL sequences of 1514 and 1515 as shown in Table B (SEQ ID NOs: 111 and 109).

an antibody may comprise all three CDRs of VH number 1520 and all three CDRs of VL number 1135. Such an antibody may be referred to as 1520/1135. Such an antibody may preferably comprise the corresponding complete VH and VL sequences of 1520 and 1135 as shown in Table B (SEQ ID NOs: 113 and 97).

an antibody may comprise all three CDRs of VH number 1524 and all three CDRs of VL number 1525. Such an antibody may be referred to as 1524/1525. Such an antibody may preferably comprise the corresponding complete VH and VL sequences of 1524 and 1525 as shown in Table B (SEQ ID NOs: 117 and 115).

an antibody may comprise all three CDRs of VH number 1526 and all three CDRs of VL number 1527. Such an antibody may be referred to as 1526/1527. Such an antibody may preferably comprise the corresponding complete VH and VL sequences of 1526 and 1527 as shown in Table B (SEQ ID NOs: 121 and 119).

an antibody may comprise all three CDRs of VH number 1542 and all three CDRs of VL number 1135. Such an antibody may be referred to as 1542/1135. Such an antibody may preferably comprise the corresponding complete VH and VL sequences of 1542 and 1135 as shown in Table B (SEQ ID NOs: 123 and 97).

The antibody may comprise a variant or a fragment of any of the specific amino acid sequences recited in Table B, provided that the antibody binds to human OX40 and exhibits at least one of functional characteristics I to III. Such a variant or fragment may typically retain the CDR sequences of the said sequence of Table B.

A fragment of any one of the heavy or light chain amino acid sequences shown in Table B may comprise at least 7, at least 8, at least 9, at least 10, at least 12, at least 15, at least 18, at least 20, least 25, at least 50, at least 60, at least 70, at least 80, at least 90 or at least 100 consecutive amino acids from the said amino acid sequence.

A variant of any one of the heavy or light chain amino acid sequences shown in Table B may be a substitution, deletion or addition variant of said sequence, as defined above.

The antibody may bind to the same epitope as any of the specific antibodies described herein. Preferably it binds to the same epitope as any one of the antibodies designated 1166/1167, 1170/1171, 1164/1135, 1168/1135, 1482/1483, 1490/1135, 1514/1515, 1520/1135, 1524/1525, 1526/1527 and 1542/1135.

Exemplary heavy chain constant region amino acid sequences which may be combined with any VH region sequence disclosed herein (to form a complete heavy chain), such as the IgG1 heavy chain constant region sequence, are described above.

Exemplary light chain constant region amino acid sequences which may be combined with any VL region sequence disclosed herein (to form a complete light chain), such as the kappa chain constant region sequence, are described above.

Embodiment of the Invention: Bispecific Polypeptide Specific for CTLA-4 and CD137

In an embodiment of the first aspect of the invention, the bispecific polypeptide has binding domains which are specific for CD137 and CTLA-4, for example B1 is specific for CD137 and B2 is specific for CTLA-4.

These binding domains are as defined above.

The bispecific polypeptide of the embodiment part B1—binding domain specific for CD137

The binding domain specific for CD137 is as defined above.

The bispecific polypeptide of the embodiment part B2—binding domain specific for CTLA-4

The binding domain specific for CTLA-4 is as defined above.

The Bispecific Polypeptide of the Embodiment

The bispecific polypeptide of the invention is capable of specifically binding to both human CD137 and human CTLA-4. By "capable of specifically binding to both CD137 and CTLA-4", it is meant that the anti-CTLA-4 part specifically binds to CTLA-4 and the anti-CD137 part specifically binds to CD137, in accordance with the definitions provided for each part above. The bispecific polypeptide may comprise any CD137 binding domain as described herein linked to any CTLA-4 binding domain as described herein. Preferably the binding characteristics of the different parts for their respective targets are unchanged or substantially unchanged when they are present as part of a bispecific antibody of the invention, when compared to said characteristics for the individual parts when present as separate entities.

Typically this means that the bispecific molecule will have a Kd for CTLA-4 which is preferably substantially the same as the Kd value for CTLA-4 of the CTLA-4 binding domain when present alone. Alternatively, if the bispecific molecule has a Kd for CTLA-4 which is increased relative to the Kd for CTLA-4 of the CTLA-4 binding domain when present alone, then the increase is by no more than 10 fold, preferably no more than 9 fold, 8 fold, 7 fold, 6 fold, 5 fold, 4 fold, 3 fold or 2 fold. In addition, the bispecific molecule will independently have a Kd for CD137 which is preferably substantially the same as the Kd value for C137 of the CD137 binding domain when present alone. Alternatively, if the bispecific molecule has a Kd for CD137 which is increased relative to the Kd for CD137 of the anti-CD137 antibody when present alone, then the increase is by no more than 10 fold, preferably no more than 9 fold, 8 fold, 7 fold, 6 fold, 5 fold, 4 fold, 3 fold or 2 fold. Preferred Kd values for the individual binding domains are as described above.

It will be appreciated that any of the fold changes in CTLA-4 binding may be independently combined with any of the recited fold changes in CD137 binding to describe the binding characteristics of a given bispecific molecule.

The binding characteristics for CD137 or CTLA-4 of any bispecific polypeptide of the invention may be assessed by any suitable assay. In particular, the assays set out above for each separate part may also be applied to a bispecific antibody or a combined assay to assess simultaneous binding to both targets may be used. Suitable assays for assessing the binding characteristics of bispecific polypeptides of the invention are also set out in the Examples.

The bispecific polypeptide of the embodiment is capable of modulating the activity of cells of the immune system to a greater extent than an individual agonist of CD137 or CTLA-4 alone, or than a combination of such individual agonists. In particular, administration of the bispecific polypeptide produces a higher level of T cell activity, in particular effector T cell activity, for example CD4+ effector T cell activity. The increase in effector T cell activity is also more localised than that which results from administration of an individual CD137 or CTLA-4 agonist alone (or a combination thereof), because the bispecific polypeptide exerts the greatest effect only in a microenvironment in which CTLA-4 and CD137 are both highly expressed. Tumours are such a microenvironment. CD137 is expressed in high levels on CD8 T cells and may thus activate them in particular. CD8 T cells are one of the main effector component of an effective tumor response.

The increase in effector T cell activity may result directly from stimulation of the effector T cells via activation of the CD137 pathway or via blockade of the CTLA-4 inhibition pathway, or may result indirectly from depletion or down-regulation of Tregs, thereby reducing their immunosuppressive effect. Depletion/down-regulation of Tregs may be mediated by antibody dependent cellular phagocytosis (ADCP) or antibody dependent cellular cytotoxicity (ADCC) mechanisms. Overall, the result will be a very powerful, localised immune activation for the immediate generation of tumoricidal activity.

The cell surface expression pattern of CTLA-4 and CD137 is partly overlapping, thus, the bispecific antibodies of the invention may bind to both targets both in cis and in trans. This may result in stimulation through CD137 and CTLA-4 in a FcγR-cross-linking independent manner, either by increasing the level of receptor clustering in cis on the same cell, or by creating an artificial immunological synapse between two cells in trans, which in turn may lead to enhanced receptor clustering and increased signalling in both cells. Overall, the result will be a very powerful, tumor directed immune activation for the generation of tumoricidal activity.

Measurement of the effect of a bispecific polypeptide of the invention on cells of the immune system may be achieved with any suitable assay. For example, increased activity of effector T cells may be measured by assays as described above in respect of individual components B1 and B2 of the bispecific polypeptide, and include measurement of proliferation or IL-2 production by CD4+ and/or CD8+%0 T cells in the presence of the bispecific polypeptide relative to a control. An increase of proliferation or IL-2 production relative to control is indicative of increased cell activation. A typical assay of this type is disclosed in Example 9 of US20080233122. Assays for cell proliferation and/or IL-2 production are well known and are also exemplified in the Examples. When assessed in the same assay, the bispecific molecule will typically induce an increase in the activity of an effector T cell which is at least 1.5 fold higher or at least 2 fold higher, more preferably 3 fold higher, most preferably 5 fold higher than the increase in activity of an effector T cell induced by a combination of monospecific agents binding to the same targets.

The bispecific molecule potently activates the immune system when in a microenvironment in which both CD137 and CTLA-4 are highly expressed. Typically, the bispecific molecule will increase the activity of a CD4+ or CD8+%0 effector cell, or may decrease the activity of a regulatory T cell (T reg). In either case, the net effect of the antibody will be an increase in the activity of effector T cells, particularly CD4+ effector T cells. When assessed in the same assay, the bispecific molecule will typically induce an increase in the activity of an effector T cell which is at least 1.5 fold higher or at least 1.7 fold higher, more preferably 4.5 fold higher, most preferably 7 fold higher than the increase in activity of an effector T cell induced by a combination of monospecific agents binding to the same targets.

Methods for determining a change in the activity of effector T cells are well known and are as described earlier. Assays for cell proliferation and/or IL-2 production are well known and are exemplified in the Examples.

For example, the polypeptide may be capable of specifically binding to both CTLA-4 and CD137, and B1 may be an antibody, or antigen binding fragment thereof, specific for CD137; and B2 may be a polypeptide binding domain specific for CTLA-4, which comprises or consists of:
  i) the amino acid sequence of SEQ ID NO: 3; or
  ii) an amino acid sequence in which at least one amino acid is changed when compared to the amino acid sequence of SEQ ID NO: 3 provided that said binding domain binds to human CTLA-4 with higher affinity than wild-type human CD86.

The CTLA-4 specifically bound by the polypeptide may be primate or murine, preferably human, CTLA-4, and/or the CD137 specifically bound by the polypeptide may be primate, preferably human, CD137.

Part B1 of the polypeptide of the invention is an antibody, or antigen-binding fragment thereof, which typically comprises at least one heavy chain (H) and/or at least one light chain (L). Part B2 of the polypeptide of the invention may be attached to any part of B1, but may typically be attached to said at least one heavy chain (H) or at least one light chain (L), preferably at either the N or the C terminus. Part B2 of the polypeptide of the invention may be so attached either directly or indirectly via any suitable linking molecule (a linker).

Part B1 preferably comprises at least one heavy chain (H) and at least one light chain (L) and part B2 is preferably attached to the N or the C terminus of either said heavy chain (H) or said light chain (L). An exemplary antibody of B1 consists of two identical heavy chains (H) and two identical light chains (L). Such an antibody is typically arranged as two arms, each of which has one H and one L joined as a heterodimer, and the two arms are joined by disulfide bonds between the H chains. Thus, the antibody is effectively a homodimer formed of two H-L heterodimers. Part B2 of the polypeptide of the invention may be attached to both H chains or both L chains of such an antibody, or to just one H chain, or just one L chain.

The polypeptide of the invention may therefore alternatively be described as an anti-CD137 antibody, or an antigen binding fragment thereof, to which is attached at least one polypeptide binding domain specific for CTLA-4, which comprises or consists of the monomeric soluble extracellular domain of human wild-type CD86 or a variant thereof. The binding domains of B1 and B2 may be the only binding domains in the polypeptide of the invention.

The polypeptide of the invention may comprise a polypeptide arranged according to any one of the following formulae, written in the direction N-C:
  (A) L-(X)n-B2;
  (B) B2-(X)n-L;
  (C) B2-(X)n-H; %p1 (D) H-(X)n-B%b 2;
wherein H is the heavy chain of an antibody (i.e. of B1), L is the light chain of an antibody (i.e. of B1), X is a linker and n is 0 or 1. Where the linker (X) is a peptide, it typically has the amino acid sequence SGGGGSGGGGS (SEQ ID NO: 47), SGGGGSGGGGSAP (SEQ ID NO: 48), NFSQP (SEQ ID NO:49), KRTVA (SEQ ID NO: 50) or (SG)m, where m=1 to 7. Schematic representations of formulae (A) to (D) are shown in FIG. 1.

The present invention also provides a polypeptide which consists of a polypeptide arranged according to any of formulae (A) to (D). Said polypeptide may be provided as a monomer or may be present as a component of a multimeric protein, such as an antibody. Said polypeptide may be isolated. Examples of amino acid sequences of such polypeptides are shown in Table H. Exemplary nucleic acid sequences encoding each amino acid sequence are also shown. Exemplary amino acid and nucleotide sequences are recited in SEQ ID NOs 197-206.

Part B2 may be attached to any part of a polypeptide of the invention, or to a linker, by any suitable means. For example, the various parts of the polypeptide may be joined by chemical conjugation, such as with a peptide bond. Thus the polypeptide of the invention may comprise or consist of a fusion protein comprising B1 (or a component part thereof) and B2, optionally joined by a peptide linker. In such a fusion protein, the CD137-binding domain or domains of B1 and the CTLA-4-binding domain or domains of B2 may be the only binding domains.

Other methods for conjugating molecules to polypeptides are known in the art. For example, carbodiimide conjugation (see Bauminger & Wilchek, 1980, *Methods Enzymol.* 70:151-159; the disclosures of which are incorporated herein by reference) may be used to conjugate a variety of agents, including doxorubicin, to antibodies or peptides. The water-soluble carbodiimide, 1-ethyl-3-(3-dimethylaminopropyl) carbodiimide (EDC) is particularly useful for conjugating a functional moiety to a binding moiety. As a further example, conjugation may be achieved by sodium periodate oxidation followed by reductive alkylation of appropriate reactants, or by glutaraldehyde cross-linking. However, it is recognised that, regardless of which method is selected, a determination should preferably be made that parts B1 and B2 retain or substantially retain their target binding properties when present as parts of the polypeptide of the invention.

The same techniques may be used to link the polypeptide of the invention (directly or indirectly) to another molecule. The other molecule may be a therapeutic agent or a detectable label. Suitable therapeutic agents include a cytotoxic moiety or a drug.

A polypeptide of the invention may be provided in isolated or substantially isolated form. By substantially isolated, it is meant that there may be substantial, but not total, isolation of the polypeptide from any surrounding medium. The polypeptides may be mixed with carriers or diluents which will not interfere with their intended use and still be regarded as substantially isolated.

Exemplary polypeptides of the invention may comprise or consist of any one of the amino acid sequences shown in Table H.

Representative polynucleotides which encode examples of a heavy chain or light chain amino acid sequence of an antibody may comprise or consist of any one of the nucleotide sequences set out in Table H as SEQ ID NOs 178, 180, 182, 184, 186, 188, 190, 192, 194 or 196. Representative polynucleotides which encode the polypeptides shown in Table H may comprise or consist of the corresponding nucleotide sequences which are also shown in Table H (intron sequences are shown in lower case) (For example, SEQ ID NOs 197, 199, 201, 203 and 205). Representative polynucleotides which encode examples of part B2 may comprise or consist of any one of SEQ ID NOS: 25 to 43 as shown in Table E.

Embodiment of the Invention: Bispecific Polypeptide Specific for OX40 and CTLA-4

In an alternative embodiment of the first aspect of the invention the polypeptide has binding domains which are specific for OX40 and CTLA-4, for example B1 is specific for OX40 and B2 is specific for CTLA-4.

These binding domains are as defined above.

The bispecific polypeptide of the embodiment part B1—antibody specific for OX40

The binding domain specific for OX40 is as defined above.

The bispecific polypeptide of the embodiment part B2—binding domain specific for CTLA-4

Part B2 of the polypeptide of the invention is a polypeptide binding domain specific for CTLA-4, as described above.

The Bispecific Polypeptide of the Embodiment

The bispecific polypeptide of the embodiment is capable of modulating the activity of cells of the immune system to a greater extent than an individual agonist of OX40 or CTLA-4 alone, or than a combination of such individual agonists. In particular, administration of the bispecific polypeptide produces a higher level of effector T cell activity, particular CD4+ effector T cell activity. The increase in effector T cell activity is also more localised than that which results from administration of an individual OX40 or CTLA-4 agonist alone (or a combination thereof), because the bispecific polypeptide exerts the greatest effect only in a microenvironment in which CTLA-4 and OX40 are both highly expressed. Tumours are such a microenvironment. Tumor infiltrating regulatory T cells (Tregs) express high levels of CTLA-4 and OX40, and higher than effector T cells (both CD4 and CD8).

The increase in effector T cell activity may result directly from stimulation of the effector T cells via activation of the OX40 pathway or via blockade of the CTLA-4 inhibition pathway, or may result indirectly from depletion or down-regulation of Tregs, thereby reducing their immunosuppressive effect. Depletion/down-regulation of Tregs may be mediated by antibody dependent cellular phagocytosis (ADCP) or antibody dependent cellular cytotoxicity (ADCC) mechanisms. The high expression of both CTLA-4 and OX40 on Tregs, compared to effector T cells, may induce a significantly higher killing of Tregs compared to the monospecific antibodies. Effector T cells, having lower expression of CTLA-4 and OX40 will not be depleted by this mechanism. Overall, the result will be a very powerful, localised immune activation for the immediate generation of tumoricidal activity.

Measurement of the effect of a bispecific polypeptide of the invention on cells of the immune system may be achieved with any suitable assay. For example, increased activity of effector T cells may be measured by assays as described above in respect of individual components B1 and B2 of the bispecific polypeptide, and include measurement of proliferation or IL-2 production by CD4+ and/or CD8+ T cells in the presence of the bispecific polypeptide relative to a control.

The bispecific polypeptide of the invention is capable of specifically binding to both human CTLA-4 and human OX40, and comprises B1 and B2 as defined above.

By "capable of specifically binding to both CTLA-4 and OX40", it is meant that part B1 specifically binds to OX40 and part B2 specifically binds to CTLA-4, in accordance with the definitions provided for each part above. Preferably the binding characteristics of parts B1 and B2 for their respective targets are unchanged or substantially unchanged when they are present as part of a polypeptide of the invention, when compared to said characteristics for parts B1 and B2 when present as separate entities.

Typically this means that the bispecific molecule will have a Kd for OX40 which is preferably substantially the same as the Kd value for OX40 of B1 when present alone. Alternatively, if the bispecific molecule has a Kd for OX40 which is increased relative to the Kd for OX40 of B1 when present alone, then the increase is by no more than 10 fold, preferably no more than 9 fold, 8 fold, 7 fold, 6 fold, 5 fold, 4 fold, 3 fold or 2 fold. The bispecific molecule preferably binds to human OX40 with a Kd value which is less than $50 \times 10^{-10}$M, more preferably less than $25 \times 10^{-10}$M, most preferably less than $20 \times 10^{-10}$M. In addition, the bispecific molecule will independently have a Kd for CTLA-4 which is preferably substantially the same as the Kd value for CTLA4 of B2 when present alone. Alternatively, if the bispecific molecule has a Kd for CTLA-4 which is increased relative to the Kd for CTLA-4 of B2 when present alone, then the increase is by no more than 3 fold, preferably no more than 2 fold. The bispecific molecule preferably binds to human CTLA-4 with a Kd value which is less than $60 \times 10^{-9}$M, more preferably less than $25 \times 10^{-9}$M, most preferably less than $10 \times 10^{-9}$M.

In other words, the bispecific molecule may have a Kd for OX40 which is less than $50 \times 10^{-10}$M, $25 \times 10^{-10}$M, or $20 \times 10^{-10}$M and independent have a Kd for CTLA-4 which is less than $60 \times 10^{-9}$M, $25 \times 10^{-9}$M, or $10 \times 10^{-9}$M. It will be appreciated that any of the Kd values recited for OX40 may be independently combined with any of the Kd values recited for CTLA-4 to describe the binding characteristics of a given bispecific molecule. Similarly, any of the recited fold changes in OX40 binding may be independently combined with any of the recited fold changes in CTLA-4 binding to describe the binding characteristics of a given bispecific molecule.

The binding characteristics of parts B1 and B2 when present as part a polypeptide of the invention may be assessed by any suitable assay. In particular, the assays set out above for each separate part may also be applied to B1 and B2 when they are present as part of a polypeptide of the invention. Suitable assays for assessing the binding characteristics of bispecific polypeptides of the invention are also set out in the Examples.

The bispecific molecule potently activates the immune system when in a microenvironment in which both OX40 and CTLA-4 are highly expressed. Typically, the bispecific molecule will increase the activity of a CD4+ or CD8+ effector cell, or may decrease the activity of a regulatory T cell (T reg). In either case, the net effect of the antibody will be an increase in the activity of effector T cells, particularly CD4+ effector T cells. When assessed in the same assay, the bispecific molecule will typically induce an increase in the activity of an effector T cell which is at least 1.5 fold higher or at least 1.7 fold higher, more preferably 4.5 fold higher, most preferably 7 fold higher than the increase in activity of an effector T cell induced by a combination of monospecific agents binding to the same targets.

Methods for determining a change in the activity of effector T cells are well known and are as described earlier. Assays for cell proliferation and/or IL-2 production are well known and are exemplified in the Examples.

For example, the polypeptide may be capable of specifically binding to both CTLA-4 and OX40, and B1 may be an antibody, or antigen binding fragment thereof, specific for OX40; and B2 may be a polypeptide binding domain specific for CTLA-4, which comprises or consists of:
  i) the amino acid sequence of SEQ ID NO: 3; or
  ii) an amino acid sequence in which at least one amino acid is changed when compared to the amino acid sequence of SEQ ID NO: 3 provided that said binding domain binds to human CTLA-4 with higher affinity than wild-type human CD86.

The CTLA-4 specifically bound by the polypeptide may be primate or murine, preferably human, CTLA-4, and/or the OX40 specifically bound by the polypeptide may be primate, preferably human, OX40.

Part B1 of the polypeptide of the invention is an antibody, or antigen-binding fragment thereof, which typically comprises at least one heavy chain (H) and/or at least one light chain (L). Part B2 of the polypeptide of the invention may be attached to any part of B1, but may typically be attached to said at least one heavy chain (H) or at least one light chain (L), preferably at either the N or the C terminus. Part B2 of the polypeptide of the invention may be so attached either directly or indirectly via any suitable linking molecule (a linker).

Part B1 preferably comprises at least one heavy chain (H) and at least one light chain (L) and part B2 is preferably attached to the N or the C terminus of either said heavy chain (H) or said light chain (L). An exemplary antibody of B1 consists of two identical heavy chains (H) and two identical light chains (L). Such an antibody is typically arranged as two arms, each of which has one H and one L joined as a heterodimer, and the two arms are joined by disulfide bonds between the H chains. Thus, the antibody is effectively a homodimer formed of two H-L heterodimers. Part B2 of the polypeptide of the invention may be attached to both H chains or both L chains of such an antibody, or to just one H chain, or just one L chain.

The polypeptide of the invention may therefore alternatively be described as an anti-OX40 antibody, or an antigen binding fragment thereof, to which is attached at least one polypeptide binding domain specific for CTLA-4, which comprises or consists of the monomeric soluble extracellular domain of human wild-type CD86 or a variant thereof. The binding domains of B1 and B2 may be the only binding domains in the polypeptide of the invention.

The polypeptide of the invention may comprise a polypeptide arranged according to any one of the following formulae, written in the direction N-C:

(A) L-(X)n-B2;
(B) B2-(X)n-L;
(C) B2-(X)n-H; and
(D) H-(X)n-B2;

wherein H is the heavy chain of an antibody (i.e. of B1), L is the light chain of an antibody (i.e. of B1), X is a linker and n is 0 or 1. Where the linker (X) is a peptide, it typically has the amino acid sequence SGGGGSGGGGS (SEQ ID NO: 47), SGGGGSGGGGSAP (SEQ ID NO: 48), NFSQP (SEQ ID NO:49), KRTVA (SEQ ID NO: 50) or (SG)m, where m=1 to 7. Schematic representations of formulae (A) to (D) are shown in FIG. 1.

The present invention also provides a polypeptide which consists of a polypeptide arranged according to any of formulae (A) to (D). Said polypeptide may be provided as a monomer or may be present as a component of a multimeric protein, such as an antibody. Said polypeptide may be isolated. Examples of amino acid sequences of such polypeptides are shown in Table D. Exemplary nucleic acid sequences encoding each amino acid sequence are also shown.

Part B2 may be attached to any part of a polypeptide of the invention, or to a linker, by any suitable means. For example, the various parts of the polypeptide may be joined by chemical conjugation, such as with a peptide bond. Thus the polypeptide of the invention may comprise or consist of a fusion protein comprising B1 (or a component part thereof) and B2, optionally joined by a peptide linker. In such a fusion protein, the OX40-binding domain or domains of B1 and the CTLA-4-binding domain or domains of B2 may be the only binding domains.

Other methods for conjugating molecules to polypeptides are known in the art. For example, carbodiimide conjugation (see Bauminger & Wilchek, 1980, *Methods Enzymol.* 70:151-159; the disclosures of which are incorporated herein by reference) may be used to conjugate a variety of agents, including doxorubicin, to antibodies or peptides. The water-soluble carbodiimide, 1-ethyl-3-(3-dimethylaminopropyl) carbodiimide (EDC) is particularly useful for conjugating a functional moiety to a binding moiety. As a further example, conjugation may be achieved by sodium periodate oxidation followed by reductive alkylation of appropriate reactants, or by glutaraldehyde cross-linking. However, it is recognised that, regardless of which method is selected, a determination should preferably be made that parts B1 and B2 retain or substantially retain their target binding properties when present as parts of the polypeptide of the invention.

The same techniques may be used to link the polypeptide of the invention (directly or indirectly) to another molecule. The other molecule may be a therapeutic agent or a detectable label. Suitable therapeutic agents include a cytotoxic moiety or a drug.

A polypeptide of the invention may be provided in isolated or substantially isolated form. By substantially isolated, it is meant that there may be substantial, but not total, isolation of the polypeptide from any surrounding medium. The polypeptides may be mixed with carriers or diluents which will not interfere with their intended use and still be regarded as substantially isolated.

Exemplary polypeptides of the invention may comprise or consist of any one of the amino acid sequences shown in Table D. In one embodiment the polypeptide comprises or consists of the amino acid sequence selected of from within the group SEQ ID NOs 125 to 134, optionally wherein said polypeptide is a provided as a component part of an antibody.

Representative polynucleotides which encode examples of a heavy chain or light chain amino acid sequence of an antibody may comprise or consist of any one of the nucleotide sequences set out in Table B. Representative polynucleotides which encode the polypeptides shown in Table D may comprise or consist of the corresponding nucleotide sequences which are also shown in Table D (intron sequences are shown in lower case). Representative polynucleotides which encode examples of part B2 may comprise or consist of any one of SEQ ID NOS: 25 to 43 as shown in Table E.

Embodiment of the Invention: Bispecific Polypeptide for OX40 and CD137

In an alternative embodiment of the first aspect of the invention the polypeptide has binding domains which are specific for OX40 and CD137.

These binding domains are as described above.

The bispecific polypeptide of the embodiment—binding domain specific for OX40

The binding domain specific for OX40 is as defined above.

The bispecific polypeptide of the embodiment—binding domain specific for CD137

The binding domain specific for CD137 is as defined above, with the previously described functional and structural characteristics.

Preferably the antibody is 1204/1205, as previously defined, with reference to the sequences of Tables H and I. The anti-CD137 antibody may bind to the same epitope as any of the specific anti-CD137 antibodies described herein. Preferably it binds to the same epitope as the antibody designated 1204/1205.

The Bispecific Polypeptide of the Embodiment

The bispecific polypeptide of the invention is capable of specifically binding to both human CD137 and human OX40. By "capable of specifically binding to both CD137 and OX40", it is meant that the anti-OX40 part specifically binds to OX40 and the anti-CD137 part specifically binds to CD137, in accordance with the definitions provided for each part above. The bispecific antibody may comprise any anti-CD137 antibody as described herein linked to any anti-OX40 antibody as described herein. Preferably the binding characteristics of the different parts for their respective targets are unchanged or substantially unchanged when they are present as part of a bispecific antibody of the invention, when compared to said characteristics for the individual parts when present as separate entities.

Typically this means that the bispecific molecule will have a Kd for OX40 which is preferably substantially the same as the Kd value for OX40 of the anti-OX40 antibody when present alone. Alternatively, if the bispecific molecule has a Kd for OX40 which is increased relative to the Kd for OX40 of the anti-OX40 antibody when present alone, then the increase is by no more than 10 fold, preferably no more than 9 fold, 8 fold, 7 fold, 6 fold, 5 fold, 4 fold, 3 fold or 2 fold. In addition, the bispecific molecule will independently have a Kd for CD137 which is preferably substantially the same as the Kd value for C137 of the anti-CD137 antibody when present alone. Alternatively, if the bispecific molecule has a Kd for CD137 which is increased relative to the Kd for CD137 of the anti-CD137 antibody when present alone, then the increase is by no more than 10 fold, preferably no more than 9 fold, 8 fold, 7 fold, 6 fold, 5 fold, 4 fold, 3 fold or 2 fold.

It will be appreciated that any of the fold changes in OX40 binding may be independently combined with any of the recited fold changes in CD137 binding to describe the binding characteristics of a given bispecific molecule.

The binding characteristics for CD137 or OX40 of any bispecific antibody of the invention may be assessed by any suitable assay. In particular, the assays set out above for each separate part may also be applied to a bispecific antibody or a combined assay to assess simultaneous binding to both targets may be used. Suitable assays for assessing the binding characteristics of bispecific polypeptides of the invention are also set out in the Examples.

The bispecific antibody of the invention is capable of modulating the activity of cells of the immune system to a greater extent than an individual agonist of OX40 or CD137 alone, or than a combination of such individual agonists. In particular, administration of the bispecific antibody produces a higher level of T cell activity. The increase in effector T cell activity is also more localised than that which results from administration of an individual OX40 or CD137 agonist alone (or a combination thereof), because the bispecific polypeptide exerts the greatest effect only in a microenvironment in which CD137 and OX40 are both highly expressed. Tumours are such a microenvironment.

The cell surface expression pattern of OX40 and CD137 is partly overlapping, thus, the bispecific antibodies of the invention may bind to both targets both in cis and in trans. This may result in stimulation through CD137 and OX40 in a FcγR-cross-linking independent manner, either by increasing the level of receptor clustering in cis on the same cell, or by creating an artificial immunological synapse between two cells in trans, which in turn may lead to enhanced receptor clustering and increased signalling in both cells. Overall, the result will be a very powerful, tumor directed immune activation for the generation of tumoricidal activity.

Measurement of the effect of a bispecific antibody of the invention on cells of the immune system may be achieved with any suitable assay. For example, increased activity of effector T cells may be measured by assays as described above in respect of the monospecific components of the bispecific antibody, and include measurement of proliferation or IL-2 production by CD4+ and/or CD8+ T cells in the presence of the bispecific antibody relative to a control. An increase of proliferation or IL-2 production relative to control is indicative of increased cell activation. A typical assay of this type is disclosed in Example 9 of US20080233122. Assays for cell proliferation and/or IL-2 production are well known and are also exemplified in the Examples. When assessed in the same assay, the bispecific molecule will typically induce an increase in the activity of an effector T cell which is at least 1.5 fold higher or at least 2 fold higher, more preferably 3 fold higher, most preferably 5 fold higher than the increase in activity of an effector T cell induced by a combination of monospecific agents binding to the same targets.

The invention provides a bispecific antibody comprising an antibody which specifically binds to OX40 (an anti-OX40 antibody) and an antibody which specifically binds to CD137 (an anti-CD137 antibody), joined to each other directly or indirectly. By "joined indirectly" it is meant that another moiety (a linker) links the anti-OX40 antibody to the anti-CD137 antibody. Exemplary linkers include a peptide of amino acid sequence as shown in any one of SEQ ID NOs. 47 to 50, or 144. The peptide of sequence GGGGSGGGGSGGGGS (SEQ ID NO: 144) is particularly preferred.

The anti-OX40 antibody may be attached to any part of the anti-CD137 antibody, or to a linker, by any suitable means. For example, the various parts of the polypeptide may be joined by chemical conjugation, such as with a peptide bond. Thus the polypeptide of the invention may comprise or consist of a fusion protein comprising an anti-OX40 antibody (or antigen binding fragment thereof) and an anti-CD137 antibody (or antigen binding fragment thereof), optionally joined by a peptide linker. In such a fusion protein, the CD137-binding domain or domains and the OX40-binding domain or domains may be the only binding domains present.

Other methods for conjugating molecules to polypeptides are known in the art. For example, carbodiimide conjugation (see Bauminger & Wilchek, 1980, *Methods Enzymol.* 70:151-159; the disclosures of which are incorporated herein by reference) may be used to conjugate a variety of agents, including doxorubicin, to antibodies or peptides. The water-soluble carbodiimide, 1-ethyl-3-(3-dimethylaminopropyl) carbodiimide (EDC) is particularly useful for conjugating a functional moiety to a binding moiety. As a further example, conjugation may be achieved by sodium periodate oxidation followed by reductive alkylation of appropriate reactants, or by glutaraldehyde cross-linking. However, it is recognised that, regardless of which method is selected, a determination should preferably be made that the anti-OX40 and anti-CD137 parts of the bispecific antibody retain or substantially retain their target binding properties when present as parts of the bispecific antibody of the invention.

The same techniques may be used to link any antibody of the invention (directly or indirectly) to another molecule. The other molecule may be a therapeutic agent or a detectable label. Suitable therapeutic agents include a cytotoxic moiety or a drug.

The bispecific antibody of the invention may comprise the anti-OX40 antibody (or antigen binding fragment thereof) and the anti-CD137 antibody (or antigen binding fragment thereof) arranged together in any suitable format. It will be appreciated that in any given bispecific format, the anti-OX40 antibody and the anti-CD137 antibody may each independently be a whole antibody or an antigen binding portion thereof. Irrespective of the particular bispecific format used, bispecific antibodies described herein may typically be referred to by a numbering scheme based on the composition of the OX40 binding domain (which may be referred to as binding domain 1) and the composition of the CD137 binding domain (which may be referred to as binding domain 2). The numbering scheme is therefore typically in the form VH1/VL1 for the OX40 binding domain (binding domain 1) and VH2/VL2 for the CD137 binding domain (binding domain 2), written together as VH1/VL1-VH2/VL2. Thus, for example, a bispecific antibody referred to as 1164/1135-1204/1205 comprises at least one OX40 binding domain which consists of the VH sequence 1164 and the VL sequence 1135 (i.e. 1164/1135=VH1/VL1), and at least one CD137 binding domain which consists of the VH sequence 1204 and the VL sequence 1205 (i.e. 1204/1205=VH2/VL2). It will be appreciated that this numbering scheme does not reflect the total number of binding domains present in the bispecific antibody nor the presence or absence of any constant regions in the bispecific antibody, both of which are determined by the particular format of bispecific antibody that is used. The total number of binding domains and the presence or absence of constant regions may be in accordance with any suitable bispecific antibody format known in the art.

Many suitable formats of bispecific antibody are known in the art and the bispecific antibody of the invention may be in any of these formats. Suitable formats include those described in FIGS. 1 and 19 (see also Kontermann & Brinkmann, 2015, *Drug Discov Today.* 838-847; the disclosures of which are incorporated herein by reference).

In FIG. 19, constant regions are shown as filled light grey; variable heavy chain region VH1 is shown as checkered black and white; variable light chain region VL1 is shown as filled white; variable heavy chain region VH2 is shown as filled black; and variable light chain region VL2 is shown as white with diagonal lines. Thus, OX40 binding domains (referred to as binding domain 1) are typically represented as a pair of a checkered black and white domain with a filled white domain; CD137 binding domains (referred to as binding domain 2) are typically represented as a pair of a filled black domain and a white domain with diagonal lines. However, in all of the formats shown, it will be appreciated that binding domains 1 and 2 may be switched. That is, an OX40 binding domain may occur in any position shown in FIG. 19 for a CD137 domain, and vice versa.

A preferred format for the bispecific antibody is a kih or "knob-in-hole" arrangement, which is the first shown in the second row of FIG. 19. In this arrangement, the CH3 domain of the heavy chain of each antibody is mutated to allow heterodimerisation between a heavy chain from the anti-OX40 antibody and a heavy chain from the anti-CD137 antibody. Each heavy chain associates with its corresponding light chain to form one complete OX40 binding domain and one complete CD137 binding domain. Modifications may be made to the heavy chain CH1 regions to promote association with the correct light chain. Kih format bispecific antibodies are well-known in the art. See for example Ridgway et al 1996; *Protein Eng* 9:617-621, the disclosures of which are incorporated herein by reference.

Another preferred format for the bispecific antibody of the invention is scFv$_2$-Fc format, which is the second shown in the second row of FIG. 19. In this arrangement, one scFv specific for each target is fused to constant immunoglobulin domains. The single chains may be fused to the Fc region of the heavy chain, with one specificity fused to the N-terminal end and the other specificity fused to the C-terminal end of the Fc region (Park et al., 2000, *Mol Immunol* 37(18):1123-30; the disclosures of which are incorporated herein by reference).

Another preferred format for the bispecific antibody of the invention is the BITE/scFv$_2$ format which is the third format shown in the second row of FIG. 19. In this arrangement two scFv, one specific for OX40 and the other specific for CD137, are fused together with a linker (Brischwein et al., 2007, *J Immunother* 30(8):798-807; the disclosures of which are incorporated herein by reference). The linker may optionally include a protein that increases solubility and serum half-life, such as human serum albumin (HSA), creating scFv-HSA-scFv bispecific antibodies, as shown in the fourth row of FIG. 19.

Another preferred format for the bispecific antibody of the invention is double variable domain (DVD) immunoglobulins, which is the fourth format shown in the second row of FIG. 19. In this arrangement the second variable domain (VL2) is fused to the first variable light chain (VL1), and the second variable heavy chain (VH2) is fused to the first variable heavy chain (VH1) of an IgG molecule. VH1 and VL1 form binding site 1 and VH2 and VL2 form binding site 2, thus creating a bispecific antibody (Wu, 2007, *Nat Biotechnol* 25(11):1290-7; the disclosures of which are incorporated herein by reference).

Another preferred format for the bispecific antibody of the invention is the Dual affinity retargeting (DART) format in which the VH1 is fused to VL2 and VH2 fused to VL1 with a short peptide linker forcing them to form VH1/VL1 and VH2/VL2 binding sites. This construct may be stabilized by formation of a disulphide bridge between the binding sites. The DART format may be fused to IgG Fc domains, creating monovalent bispecific antibodies (DART-Fc) or bivalent bispecific antibodies (DART$_2$-Fc) (Moore et al., 2011, Blood 117(17):4542-51). The DART, DART-Fc and DART$_2$-Fc formats are shown in the third row of FIG. 19.

Another preferred format for the bispecific antibody of the invention is bispecific antibodies generated by the dock and lock technology (DNL). cAMP dependent protein kinase A and A kinase anchoring protein can be fused to antibodies, Fab fragments or scFv for each target, thereby generating multivalent bispecific antibodies, e.g. DNL-Fab$_2$ (Chang et al., 2007, *Clin Cancer Res* 13(18 Pt 2):5586s-5591s, as shown in the fourth row of FIG. 19; the disclosures of which are incorporated herein by reference).

A particularly preferred format for the bispecific antibody of the invention is the scFv-IgG format. Four different possible arrangements of this format are shown in the top row of FIG. 19. As shown in FIG. 19, in scFv-IgG format the anti-OX40 antibody is a whole IgG molecule and the anti-CD137 antibody is an scFv antibody connected to the anti-OX40 antibody at any one of four general locations (heavy chain constant region; light chain constant region; heavy chain variable region; light chain variable region). In each case, the reverse arrangement is also envisaged. That is, with the anti-CD137 antibody as a whole IgG and the anti-OX40 antibody as an scFv connected to the anti-CD137 antibody at any one of the four general locations. In the scFv-IgG format, the whole IgG molecule may be joined directly to the scFv or may be joined indirectly via a linker. Exemplary linkers include a peptide of amino acid sequence as shown in any one of SEQ ID NOs. 47 to 50, or 144, with the peptide of sequence GGGGSGGGGSGGGGS (SEQ ID NO: 144) particularly preferred.

In the first scFv-IgG arrangement shown in FIG. 19 (top left of the Figure) the bispecific antibodies comprise two copies of a polypeptide chain which comprises the heavy chain variable sequence VH1 (checkered black and white), linked to a heavy chain constant sequence (Hc; filled grey), linked (optionally via a linker) to an scFv sequence consisting of the heavy chain variable sequence VH2 (filled black) and the light chain variable sequence VL2 (white with diagonal lines). This chain may be referred to as VH1-Hc-VH2/VL2 (ordered N terminus-C terminus). The bispecific antibody also comprises two copies of a smaller chain which comprises the light chain variable sequence VL1 (filled white) linked to a light chain constant sequence (Lc; filled grey), which may be referred to as VL1-Lc (ordered N terminus-C terminus). The alternative scFv-IgG arrangements shown in FIG. 19 also comprise two copies each of two different chains, which may be described in similar fashion. Thus, reading from left to right in the top row of FIG. 22, the second arrangement comprises two VH1-Hc chains and two VL1-Lc-VH2/VL2 chains. The third arrangement comprises two VH1/VH2-VH1-Hc chains and two VL1-Lc chains. The fourth arrangement comprises two VH1-Hc and two VH1/VH2-VL1-Lc chains.

The most preferred scFv-IgG format for bispecific antibodies of the invention is the first scFv-IgG arrangement shown in FIG. 19 (top left of the Figure). Exemplary amino acid sequences for polypeptide chains of the type VH1-Hc-VH2/VL2 from this scFv-IgG arrangement are shown in Table F and are used in the bispecific molecules of the Examples. In each case, for the amino acid sequences the underlined/bold sequence is VH1, the italic sequence is the heavy chain constant sequence Hc (typically an IgG1 constant domain in the sequences shown, but this may be replaced with any suitable IgG constant domain such as those disclosed herein), the underlined sequence is an optional linker, the bold sequence is VH2 and the bold italic sequence is VL2. Corresponding exemplary nucleotide sequences encoding the polypeptide chains are also shown in Table F. The nucleotide sequences include introns. Exemplary amino acid sequences for polypeptide chains of the type VL1-Lc from this scFv-IgG arrangement are shown in Table G and are used in the bispecific molecules of the Examples. In each case, for the amino acid sequences the underlined/bold sequence is VL1 and the italic sequence is the light chain constant sequence Lc (typically kappa, but may be replaced with any suitable light chain constant region). Corresponding exemplary nucleotide sequences encoding the polypeptide chains are also shown in Table G.

The present invention provides a polypeptide comprising or consisting of any of the amino acid sequences set out in Tables F and G, either alone or, preferably as part of a monospecific or bispecific antibody. In all of the sequences shown in Tables F and G, the sequences corresponding to heavy or light chain constant regions are exemplary and may be replaced with any other suitable heavy or light chain constant region sequence. Preferred heavy and light chain constant region sequences are those of SEQ ID NOs: 135, 136, 137, 138 and 139.

A bispecific or monospecific antibody of the invention may be provided in isolated or substantially isolated form. By substantially isolated, it is meant that there may be substantial, but not total, isolation of the polypeptide from any surrounding medium. The polypeptides may be mixed with carriers or diluents which will not interfere with their intended use and still be regarded as substantially isolated.

An antibody of the invention may be produced by any suitable means. For example, all or part of the antibody may be expressed as a fusion protein by a cell comprising a nucleotide which encodes said polypeptide.

Alternatively the individual parts may be produced separately and then subsequently joined together. Joining may be achieved by any suitable means, for example using the chemical conjugation methods and linkers outlined above. Separate production of individual parts may be achieved by any suitable means. For example by expression from separate nucleotides optionally in separate cells, as is explained in more detail below.

Representative polynucleotides which encode all or part of an antibody of the invention may comprise or consist of any one of the nucleotide sequences set out in Tables B, F, G and H. A suitable polynucleotide may alternatively be a variant of any of these sequences, as defined above.

Further Aspects of the Invention

A second aspect of the invention comprises a bispecific polypeptide according to the first aspect of the invention for use in a method for treating or preventing a disease or condition in an individual, as described above.

A third aspect of the invention is a method of treating or preventing a disease or condition in an individual, the method comprising administering to an individual a bispecific polypeptide according to the first or second aspects of the invention, as described above.

One embodiment of the invention is a bispecific polypeptide according to the second aspect of the invention or a method according to third aspect of the invention wherein the disease or condition is cancer and optionally wherein the individual is human.

In a further embodiment, the method comprises administering the bispecific antibody systemically or locally, such as at the site of a tumour or into a tumour draining lymph node, as described above.

The cancer may be prostate cancer, breast cancer, colorectal cancer, pancreatic cancer, ovarian cancer, lung cancer, cervical cancer, rhabdomyosarcoma, neuroblastoma, multiple myeloma, leukemia, acute lymphoblastic leukemia, melanoma, bladder cancer, gastric cancer, head and neck cancer, liver cancer, skin cancer, lymphoma or glioblastoma.

A fourth aspect of the invention is a polynucleotide encoding at least one polypeptide chain of a bispecific polypeptide according to the first or second aspects of the invention, as described above.

A fifth aspect of the invention is a composition comprising a bispecific polypeptide according to the first or second aspects of the invention and at least one pharmaceutically acceptable diluent or carrier.

In one embodiment of the invention a polypeptide according to either the first or second aspect of the embodiment is conjugated to an additional therapeutic moiety.

A sixth aspect of the invention is an antibody specific for CD137 which is as defined earlier.

Embodiments of the Invention

Embodiments of the invention are described in the following paragraphs:

1. A polypeptide capable of specifically binding to both CTLA-4 and OX40, said polypeptide comprising B1 and B2, wherein:

B1 is an antibody, or antigen binding fragment thereof, specific for OX40; and

B2 is a polypeptide binding domain specific for CTLA-4, which comprises or consists of:

i) the amino acid sequence of SEQ ID NO: 3; or ii) an amino acid sequence in which at least one amino acid is changed when compared to the amino acid sequence of SEQ ID NO: 3 provided that said binding domain binds to human CTLA-4 with higher affinity than wild-type human CD86.

2. A polypeptide according to paragraph 1 in which the CTLA-4 specifically bound by the polypeptide is primate or murine, preferably human, CTLA-4, and/or wherein the OX40 specifically bound by the polypeptide is primate, preferably human, OX40.

3. A polypeptide according to paragraph 1 or 2 in which B1 comprises at least one heavy chain (H) and/or at least one light chain (L) and B2 is attached to said at least one heavy chain (H) or least one light chain (L).

4. A polypeptide according to paragraph 3 in which B1 comprises:

at least one heavy chain (H) and at least one light chain (L) and B2 is attached to either the heavy chain or the light chain; or two identical heavy chains (H) and two identical light chains (L) and B2 is attached to both heavy chains or to both light chains.

5. A polypeptide according to any one of the preceding paragraphs which comprises or consists of a polypeptide chain arranged according to any one of the following formulae, written in the direction N-C:

(A) L-(X)n-B2;
(B) B2-(X)n-L;
(C) B2-(X)n-H;
(D) H-(X)n-B2;
wherein X is a linker and n is 0 or 1.

6. A polypeptide according to paragraph 5, wherein X is a peptide with the amino acid sequence SGGGGSGGGGS (SEQ ID NO: 47), SGGGGSGGGGSAP (SEQ ID NO: 48), NFSQP (SEQ ID NO:49), KRTVA (SEQ ID NO: 50) or (SG)m, where m=1 to 7.

7. A polypeptide according to any one of the preceding paragraphs, which binds to human OX40 with a Kd of less than $50\times10^{-10}$M, $25\times10^{-10}$M, or $20\times10^{-10}$M and/or which binds to human CTLA-4 with a Kd value which is less than $60\times10^{-9}$M, $25\times10^{-9}$M, or $10\times10^{-9}$M.

8. A polypeptide according to any one of the preceding paragraphs, which induces an increase in the activity of an effector T cell, preferably a CD4+ effector T cell, optionally wherein said increase is at least 1.5 fold, 4.5 fold or 7 fold higher than the increase in activity of an effector T cell induced by a combination of B1 and B2 administered to the T cell as separate molecules.

9. A polypeptide according to paragraph 8, wherein said increase in T cell activity is an increase in proliferation and/or IL-2 production by the T cell.

10. A polypeptide according to any one of the preceding paragraphs, wherein 1, 2, 3, 4, 5, 6, 7, 8, 9 or 10 amino acids in said amino acid sequence of B2 (ii) are substituted when compared to the amino acid sequence of SEQ ID NO: 3; optionally wherein there are no insertions or deletions compared to the amino acid sequence of SEQ ID NO: 3.

11. A polypeptide according to paragraph 10, wherein at least one of said amino acid substitutions in said amino acid sequence of said first binding domain is at position 122, and optionally wherein said amino acid sequence is also substituted in at least one of positions 107, 121 and 125.

12. A polypeptide according to any one of the preceding paragraphs wherein said amino acid sequence of B2 comprises or consists of an amino acid sequence selected from any one of SEQ ID NOs 8, 6, 7 and 9 to 24.

13. A polypeptide according to any one of the preceding paragraphs, wherein B1 exhibits at least one of the following functional characteristics when present independently of B2:
  I. binding to human OX40 with a $K_D$ value which is less than $10\times10^{-10}$M, more preferably less than $5\times10^{-10}$M;
  II. does not bind to murine OX40; and
  III. does not bind to other human TNFR superfamily members, for example human CD137 or CD40

14. A polypeptide according to any one of the preceding paragraphs, wherein B1 comprises any one, two, three, four, five or all six features independently selected from the following:
  (a) a heavy chain CDR1 sequence which is 8 amino acids in length and comprises the consensus sequence: "G, F, T, F, G/Y/S, G/Y/S, Y/S, Y/S/A";
  (b) a heavy chain CDR2 sequence which is 8 amino acids in length and comprises the consensus sequence: "I, G/Y/S/T, G/S/Y, S/Y, G/S/Y, G/S/Y, G/S/Y, T";
  (c) a heavy chain CDR3 sequence which is 9 to 17 amino acids in length and which comprises the consensus sequence of: "A, R, G/Y/S/H, G/Y/F/V/D, G/Y/P/F, -/H/S, -/N/D/H, -/Y/G, -/Y, -/Y, -/W/A/V, -/A/Y, -/D/A/Y/G/H/N, Y/S/W/A/T, UM/I/F, D, Y"
  (d) a light chain CDR1 sequence which consists of the sequence: "Q, S, I, S, S, Y";
  (e) a light chain CDR2 sequence which consists of the sequence: "A, A, S";
  (f) a light chain CDR3 sequence which is 8 to 10 amino acids in length and comprises the consensus sequence: "Q,Q, S/Y/G, -/Y/H/G, -/S/Y/G/D, S/Y/G/D , S/Y/G/T, P/L, Y/S/H/L/F, T";

wherein the heavy chain CDR3 sequence of (c) is preferably a sequence of 10 amino acids in length which comprises the consensus sequence "A, R, Y/H, D, Y, A/Y/G, S/W/A, M/L, D, Y" or a CDR3 sequence of 11 amino acids in length which comprises the consensus sequence "A, R, G/Y, V/F/Y, P, H, G/Y/H, Y, F/I, D, Y"; and
the light chain CDR3 sequence of (f) preferably consists of the sequence "Q, Q, S, Y, S, T, P, Y, T".

15. A polypeptide according to any one of the preceding paragraphs, wherein B1 comprises all three heavy chain CDR sequences of a VH sequence as shown in Table A(1) and/or all three light chain CDR sequences of a VL sequence as shown in Table A(2), or wherein B1 comprises a heavy chain VH sequence and/or a light chain VL sequence as shown in Table B.

16. A polypeptide according to any one of the preceding paragraphs, wherein B1 comprises a heavy chain CDR3 sequence of 11 amino acids in length which comprises the consensus sequence "A, R, G/Y, V/F/Y, P, H, G/Y/H, Y, F/I, D, Y"; and the light chain VL sequence of SEQ ID NO: 97 (1135 as shown in Table B), optionally wherein the light chain VL sequence of SEQ ID NO: 97 is present as part of the longer sequence of SEQ ID NO: 129 (1141 as shown in Table D).

17. A polypeptide according to any one of the preceding paragraphs, wherein B1 comprises an human Fc region or a variant of a said region, where the region is an IgG1, IgG2, IgG3 or IgG4 region, preferably an IgG1 or IgG4 region.

18. A polypeptide according to any one of the preceding paragraphs, which comprises or consists of the amino acid sequence of any one of SEQ ID NOs 125 to 134, optionally wherein said polypeptide is a provided as a component part of an antibody.

19. A polypeptide according to any one of the preceding paragraphs for use in a method for treating or preventing a disease or condition in an individual.

20. A method of treating or preventing a disease or condition in an individual, the method comprising administering to an individual a polypeptide according to any one of the preceding paragraphs.

21. A polypeptide according to paragraph 19 or a method according to paragraph 20, wherein the disease or condition is cancer and optionally wherein the individual is human.

22. A polypeptide or method according to paragraph 21, wherein the method comprises administering the polypeptide systemically or locally, such as at the site of a tumour or into a tumour draining lymph node.

23. A polypeptide or method according to paragraph 21 or 22 wherein the cancer is prostate cancer, breast cancer, colorectal cancer, pancreatic cancer, ovarian cancer, lung cancer, cervical cancer, rhabdomyosarcoma, neuroblastoma, multiple myeloma, leukemia, acute lymphoblastic leukemia, melanoma, bladder cancer, gastric cancer, head and neck cancer, liver cancer, skin cancer, lymphoma or glioblastoma.

24. A polynucleotide encoding a polypeptide according to any one of paragraphs 1 to 18.

25. A polypeptide according to any one of paragraphs 1 to 18 conjugated to an additional therapeutic moiety.

26. A composition comprising a polypeptide according to any one of paragraphs 1 to 18 and at least one pharmaceutically acceptable diluent or carrier.

Further distinct embodiments are described in the following paragraphs:

1. A bispecific antibody comprising an antibody which specifically binds to OX40 (an anti-OX40 antibody) and an antibody which specifically binds to CD137 (an anti-CD137 antibody), joined to each other directly or indirectly.

2. A bispecific antibody according to paragraph 1 in which the CD137 that is specifically bound is primate or murine, preferably human CD137, and/or wherein the OX40 that is specifically bound is primate, preferably human, OX40.

3. A bispecific antibody according to any one of the preceding paragraphs, which binds to human OX40 with a Kd of less than $50\times10^{-10}$M, $25\times10^{-10}$M, or $20\times10^{-10}$M and/or which binds to human CD137 with a Kd value which is less than $10\times10^{-9}$M, $4\times10^{-9}$M, or $1.2\times10^{-9}$M 4. A bispecific antibody according to any one of the preceding paragraphs, which induces an increase in the activity of an effector T cell, optionally wherein said increase is at least 1.5 fold, 2 fold, 3 fold or 5 fold higher than the increase in activity of an effector T cell induced by a combination of the corresponding monospecific antibodies administered to the T cell as separate molecules.

5. A bispecific antibody according to paragraph 4, wherein said increase in T cell activity is an increase in proliferation and/or IL-2 production and/or IFN-γ production by the T cell, optionally wherein the T cell is a CD4+ or CD8+ T cell.

6. A bispecific antibody according to any one of the preceding paragraphs, wherein the anti-OX40 antibody and the anti-CD137 antibody are joined to each other indirectly via a linker which is a peptide of the amino acid sequence GGGGSGGGGSGGGGS (SEQ ID NO: 144), SGGGGSGGGGS (SEQ ID NO: 47), SGGGGSGGGGSAP (SEQ ID NO: 48), NFSQP (SEQ ID NO:49), KRTVA (SEQ ID NO: 50) or (SG)m, where m=1 to 7.

7. A bispecific antibody according to any one of the preceding paragraphs which is an scFv-IgG format bispecific antibody.

8. A bispecific antibody according to any one of the preceding paragraphs, wherein the anti-OX40 antibody exhibits at least one of the following functional characteristics when present independently of the anti-CD137 antibody:
   I. binding to human OX40 with a $K_D$ value which is less than $10\times10^{-10}$M, more preferably less than $5\times10^{-10}$M;
   II. does not bind to murine OX40; and
   III. does not bind to other human TNFR superfamily members, for example human CD137 or CD40

9. A bispecific antibody according to any one of the preceding paragraphs, wherein the anti-OX40 antibody comprises any one, two, three, four, five or all six features independently selected from the following:
   (a) a heavy chain CDR1 sequence which is 8 amino acids in length and comprises the consensus sequence: "G, F, T, F, G/Y/S, G/Y/S, Y/S, Y/S/A";
   (b) a heavy chain CDR2 sequence which is 8 amino acids in length and comprises the consensus sequence: "I, G/Y/S/T, G/S/Y, S/Y, G/S/Y, G/S/Y, G/S/Y, T";
   (c) a heavy chain CDR3 sequence which is 9 to 17 amino acids in length and which comprises the consensus sequence of: "A, R, G/Y/S/H, G/Y/F/V/D, G/Y/P/F, -/H/S, -/N/D/H, -/Y/G, -/Y, -/Y, -/W/A/V, -/A/Y, -/D/A/Y/G/H/N, Y/S/W/A/T, UM/I/F, D, Y"
   (d) a light chain CDR1 sequence which consists of the sequence: "Q, S, I, S, S, Y";
   (e) a light chain CDR2 sequence which consists of the sequence: "A, A, S";
   (f) a light chain CDR3 sequence which is 8 to 10 amino acids in length and comprises the consensus sequence: "Q,Q, S/Y/G, -/Y/H/G, -/S/Y/G/D, S/Y/G/D , S/Y/G/T, P/L, Y/S/H/L/F, T";
   wherein the heavy chain CDR3 sequence of (c) is preferably a sequence of 10 amino acids in length which comprises the consensus sequence "A, R, Y/H, D, Y, A/Y/G, S/W/A, M/L, D, Y" or a CDR3 sequence of 11 amino acids in length which comprises the consensus sequence "A, R, G/Y, V/F/Y, P, H, G/Y/H, Y, F/I, D, Y"; and
   the light chain CDR3 sequence of (f) preferably consists of the sequence "Q, Q, S, Y, S, T, P, Y, T".

10. A bispecific antibody according to any one of the preceding paragraphs, wherein the anti-OX40 antibody comprises all three heavy chain CDR sequences of a VH sequence as shown in Table A(1) and/or all three light chain CDR sequences of a VL sequence as shown in Table A(2), or wherein the anti-OX40 antibody comprises a heavy chain VH sequence and/or a light chain VL sequence as shown in Table B.

11. A bispecific antibody according to any one of the preceding paragraphs, wherein the anti-OX40 antibody comprises a heavy chain CDR3 sequence of 11 amino acids in length which comprises the consensus sequence "A, R, G/Y, V/F/Y, P, H, G/Y/H, Y, F/I, D, Y"; and the light chain VL sequence of SEQ ID NO: 97 (1135 as shown in Table B), optionally wherein the light chain VL sequence of SEQ ID NO: 97 is present as part of the longer sequence of SEQ ID NO: 129 (1141 as shown in Table D).

12. A bispecific antibody according to any one of the preceding paragraphs, wherein the anti-OX40 antibody when present independently of the anti-CD137 antibody competes for binding to OX40 with an anti-OX40 antibody as defined in any one of paragraphs 8 to 11.

13. A bispecific antibody according to any one of the preceding paragraphs, wherein the anti-CD137 antibody exhibits at least one of the following functional characteristics when present independently of the anti-OX40 antibody:
   I. binding to human CD137 with a $K_D$ value which is less than $2\times10^{-9}$M, more preferably less than $1.2\times10^{-9}$M; and
   II. ability to cause an increase in activity in a CD8+ T cell in vitro, optionally wherein said increase in activity is an increase in proliferation and/or IL-2 production and/or IFN-γ production by the T cell 14. A bispecific antibody according to any one of the preceding paragraphs, wherein the anti-CD137 antibody comprises all three heavy chain CDR sequences of a VH sequence as shown in the first row of Table I(1) and/or all three light chain CDR sequences of a VL sequence as shown in the first row of Table I(2), or wherein the anti-CD137 antibody comprises a heavy chain VH sequence and/or a light chain VL sequence as shown in Table H, SEQ ID NOs 177-180.

15. A bispecific antibody according to any one of the preceding paragraphs, wherein the anti-CD137 antibody when present independently of the anti-OX40 antibody competes for binding to CD137 with an anti-CD137 antibody as defined in paragraph 14.

16. A bispecific antibody according to any one of the preceding paragraphs, wherein the anti-OX40 and/or the anti-CD137 antibody comprises an human Fc region or a variant of a said region, where the region is an IgG1, IgG2, IgG3 or IgG4 region, preferably an IgG1 or IgG4 region.

17. A bispecific antibody according to any one of the preceding paragraphs, which comprises the amino acid sequence of any one of SEQ ID NOs 149, 151, 153, 155, 157, 159, 161 or 163.

18. A bispecific antibody according to any one of the preceding paragraphs which comprises the amino acid sequence of any one of SEQ ID Nos 165, 167, 169, 171 or 173.

19. A bispecific antibody according to any one of the preceding paragraphs which comprises the amino acid sequences of:
SEQ ID NO: 165 and any one of SEQ ID NOs: 149, 153, 159 and 163; or
SEQ ID NO: 167 and SEQ ID NO 151; or
SEQ ID NO: 169 and SEQ ID NO: 155; or
SEQ ID NO: 171 and SEQ ID NO: 157; or
SEQ ID NO: 173 and SEQ ID NO: 161.

20. A bispecific antibody according to any one of the preceding paragraphs for use in a method for treating or preventing a disease or condition in an individual.

21. A method of treating or preventing a disease or condition in an individual, the method comprising administering to an individual a bispecific antibody according to any one of the preceding paragraphs.

22. A bispecific antibody according to paragraph 20 or a method according to paragraph 21 wherein the disease or condition is cancer and optionally wherein the individual is human.

23. A bispecific antibody or method according to paragraph 22, wherein the method comprises administering the bispecific antibody systemically or locally, such as at the site of a tumour or into a tumour draining lymph node.

24. A bispecific antibody or method according to paragraph 22 or 23 wherein the cancer is prostate cancer, breast cancer, colorectal cancer, pancreatic cancer, ovarian cancer, lung cancer, cervical cancer, rhabdomyosarcoma, neuroblastoma, multiple myeloma, leukemia, acute lymphoblastic leukemia, melanoma, bladder cancer, gastric cancer, head and neck cancer, liver cancer, skin cancer, lymphoma or glioblastoma.

25. A polynucleotide encoding at least one polypeptide chain of a bispecific antibody according to any one of paragraphs 1 to 20.

26. A composition comprising a bispecific antibody according to any one of paragraphs 1 to 20 and at least one pharmaceutically acceptable diluent or carrier.

27. An antibody specific for CD137 which is as defined in any one of paragraphs 13 to 15.

BRIEF DESCRIPTION OF THE FIGURES

Preferred, non-limiting examples which embody certain aspects of the invention will now be described, with reference to the following figures:

FIG. 1 shows a schematic representation of the structure of exemplary arrangements for the bispecific polypeptides of the invention. Anti-OX40 antibody variable domains are filled in black; constant domains in white. CTLA-A binding domains are shaded with diagonal lines.

FIG. 2 shows the CTLA-4 binding properties of CTLA-4 binding domains of polypeptides the invention as determined by an ELISA binding assay.

FIG. 3 shows the CTLA-4 binding properties of CTLA-4 binding domains of polypeptides of the invention as determined by an ELISA inhibition assay.

FIG. 4 provides a schematic representation of human wild-type CD86 amino acid sequences disclosed herein. (A) is the amino acid sequence of the monomeric soluble extracellular domain of human CD86 without N-terminal signal sequence (SEQ ID NO: 3); (B) is the amino acid sequence of the monomeric extracellular and transmembrane domains of human wildtype CD86, including N-terminal signal sequence (SEQ ID NO: 4); (C) is the full length amino acid sequence of human CD86 (Genbank ABK41931.1; SEQ ID NO: 44). The sequence in A may optionally lack Alanine and Proline at the N terminus, i.e. positions 24 and 25, shown in bold. Signal sequences in B and C are underlined. Numbering of amino acid positions is based on SEQ ID NOs: 4 and 44, starting from the N terminus.

FIG. 11 shows results of an ELISA assay showing binding of exemplary bispecific molecules to both OX40 and CTLA-4 simultaneously.

FIG. 21 shows an overview of human/mouse CD137 chimeras (mouse sequence=black lines, human sequence=white lines).

FIG. 24 shows the results from a dual ELISA. CD137 was coated to an ELISA well and the bispecific antibody was added at different concentrations. Binding was detected using biotinylated CTLA-4.

DESCRIPTION OF THE SEQUENCES

Figure 5:
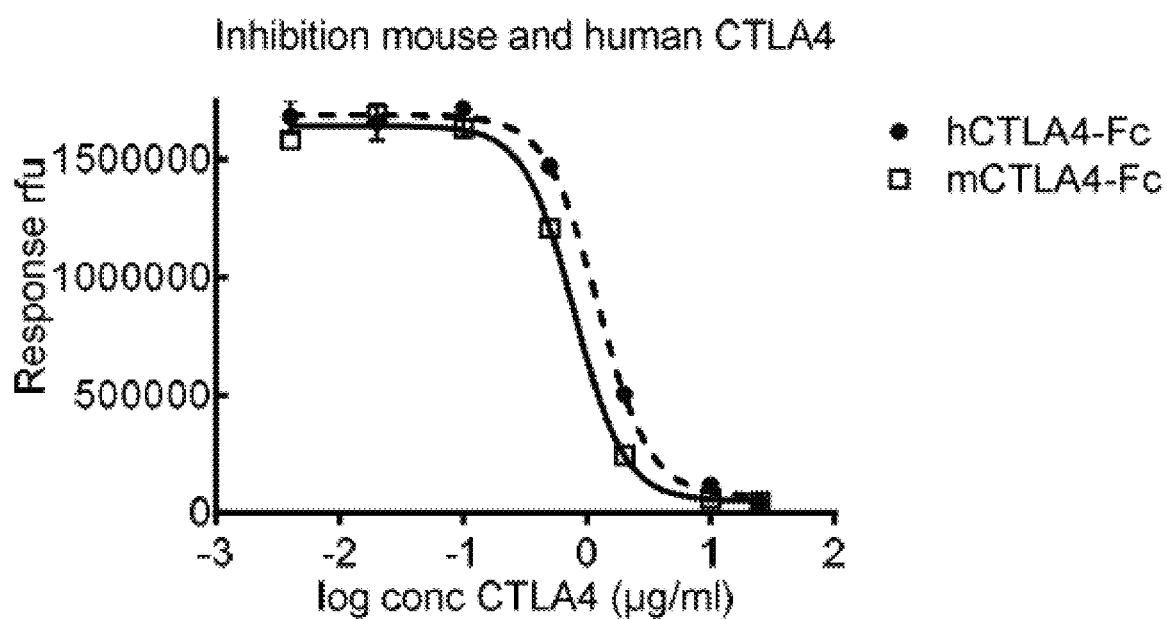
FIG. 5 shows the results of an inhibition ELISA demonstrating that a CTLA-4 binding domains of polypeptides of the invention has binding affinity of a similar magnitude for both human and murine CTLA-4.

SEQ ID NO: 1 is the amino acid sequence of human CTLA-4 (corresponding to GenBank: AAD00698.1)

SEQ ID NO: 2 is the amino acid sequence of human CD28 (corresponding to GenBank: AAA51944.1)

SEQ ID NO: 3 is the amino acid sequence of the monomeric extracellular domain of human wildtype CD86, excluding a 23 amino acid signal sequence from the N terminus.

SEQ ID NO: 4 is the amino acid sequence of the monomeric extracellular and transmembrane domains of human wildtype CD86, including N-terminal signal sequence (see FIG. 4). All numbering of amino acid positions herein is based on the positions in SEQ ID NO: 4 starting from the N terminus. Thus, the Alanine at the N terminus of SEQ ID NO: 3 is numbered 24.

SEQ ID NO: 5 is the amino acid sequence of a mutant form of the extracellular domain of human CD86 disclosed in Peach et al (Journal of Biological Chemistry 1995, vol 270(36), 21181-21187). H at position 79 of the wild type sequence is substituted with A in the corresponding position for the sequence of SEQ ID NO: 5. This change is referred to herein as H79A. Equivalent nomenclature is used throughout for other amino acid substitutions referred to herein. Numbering of positions is based on SEQ ID NO: 4 as outlined above.

SEQ ID NOs: 6 to 24 are the amino acid sequences of specific proteins of the invention.

SEQ ID NOs: 25 to 43 are nucleotide sequences encoding the amino acid sequences of each of SEQ ID NOs 6 to 24, respectively SEQ ID NO: 44 is the full length amino acid sequence of human CD86 (corresponding to GenBank: ABK41931.1)

SEQ ID NO: 45 is the amino acid sequence of murine CTLA-4 (corresponding to UniProtKB/Swiss-Prot: P09793.1).

SEQ ID NO: 46 is the amino acid sequence of murine CD28 (corresponding to GenBank: AAA37395.1).

SEQ ID NOs: 47 to 50 are various linkers which may be used in the bispecific polypeptides of the invention.

SEQ ID NO: 51 is the amino acid sequence of human OX40 (corresponding to GenBank: NP_003318.1)

SEQ ID NOs: 52 to 88 are exemplary CDR sequences of anti-OX40 antibodies disclosed herein.

SEQ ID NOs: 89 to 124 are exemplary amino acid and nucleotide sequences of the heavy and light chain variable regions of antibodies disclosed herein.

SEQ ID NOs: 125 to 134 are exemplary amino acid and nucleotide sequences of bispecific polypeptides disclosed herein.

SEQ ID NO: 135 is an exemplary heavy chain constant region amino acid sequence.

SEQ ID NO: 136 is an exemplary light chain constant region amino acid sequence.

SEQ ID NO: 137 is an exemplary modified human heavy chain IgG4 constant region sequence with a mutation from Ser to Pro in the hinge region (position 108) and from His to Arg in the CH3 region (position 315). Mutations result in reduced serum half-life and stabilization of the core hinge of IgG4 making the IgG4 more stable, preventing Fab arm exchange.

SEQ ID NO: 138 is an exemplary wild type human heavy chain IgG4 constant region sequence. That is a sequence lacking the mutations of SEQ ID NO: 137.

SEQ ID NO: 139 is an exemplary modified human heavy chain IgG4 constant region sequence with a single mutation from Ser to Pro in the hinge region (position 108). Mutation results in stabilization of the core hinge of IgG4 making the IgG4 more stable, preventing Fab arm exchange.

SEQ ID NO: 140 is an exemplary cDNA sequence (i.e. lacking introns) encoding the IgG4 constant region of SEQ ID NO: 137.

SEQ ID NO: 141 is an exemplary genomic DNA sequence (i.e. including introns) encoding the IgG4 constant region of SEQ ID NO: 137

SEQ ID NO: 142 is an exemplary cDNA sequence (i.e. lacking introns) encoding the IgG4 constant region of SEQ ID NO: 138.

SEQ ID NO: 143 is an exemplary genomic DNA sequence (i.e. including introns) encoding the IgG4 constant region of SEQ ID NO: 138.

SEQ ID NO 144 is a linker which may be used in the bispecific polypeptides of the invention.

SEQ ID NOs: 145 and 146 are exemplary cDNA and genomic DNA sequences, respectively, encoding the IgG1 constant region of SEQ ID NO: 135.

SEQ ID NOs: 147 is an exemplary DNA sequence encoding the light chain kappa region of SEQ ID NO: 136.

SEQ ID NO: 148 is the amino acid sequence of human CD137 (corresponding to GenBank: AAH06196.1)

SEQ ID NOs: 149 to 174 are amino acid and nucleotide sequences of exemplary bispecific antibodies disclosed herein.

SEQ ID NO: 175 is an exemplary cDNA sequence (i.e. lacking introns) encoding the IgG4 region of SEQ ID NO: 139.

SEQ ID NO: 176 is an exemplary genomic DNA sequence (i.e. including introns) encoding the IgG4 region of SEQ ID NO: 139.

SEQ ID NOs: 177 to 196 are exemplary amino acid and nucleotide sequences of the heavy and light chain variable regions of anti-CD137 antibodies disclosed herein.

SEQ ID NOs: 197 to 206 are exemplary bispecific polypeptides of the invention.

SEQ ID NOs 207 to 226 correspond to exemplary CDR sequences for CD137 binding domains (as do SEQ ID NOs 80 and 81)

TABLES (SEQUENCES)

TABLE A(1)

Exemplary heavy chain CDR sequences ) (OX40 antibody

| VH number | SEQ | H CDR1 | SEQ | H CDR2 | SEQ | H CDR3 |
|---|---|---|---|---|---|---|
| 1166 | 52 | GFTFGGYY | 60 | ISGSGGST | 69 | ARYDYASMDY |
| 1170 |  | As 1166 | 61 | IPGSGGST | 70 | ARYDYYWMDY |
| 1164 | 53 | GFTFYGSS | 62 | IYSSGGYT | 71 | ARGVPHGYFDY |
| 1168 | 54 | GFTFSGSS | 63 | ISYYGGYT | 72 | ARYFPHYYFDY |
| 1482 | 55 | GFTFSSYA | 64 | ISYYSGYT | 73 | ARGYGYLDY |
| 1490 |  | As 1482 |  | As 1168 | 74 | ARYYPHHYIDY |
| 1514 | 56 | GFTFGYYY | 65 | ISSYGSYT | 75 | ARSGYSNWANSFDY |
| 1520 |  | As 1482 |  | As 1166 | 76 | ARYYYSHGYYVYGTLDY |

TABLE A(1)-continued

Exemplary heavy chain CDR sequences (OX40 antibody)

| VH number | SEQ | H CDR1 | SEQ | H CDR2 | SEQ | H CDR3 |
|---|---|---|---|---|---|---|
| 1524 | 57 | GFTFGSYY | 66 | IGSYYGYT | 77 | ARHDYGALDY |
| 1526 | 58 | GFTFSGYS | 67 | IGYSGYGT | 78 | ARYYFHDYAAYSLDY |
| 1542 | 59 | GFTFGSSS | 68 | IGYYSYSTS | 79 | ARGYPHHYFDY |

TABLE A(2)

Exemplary light chain CDR sequences (OX40 antibody)

| VL number | SEQ | L CDR1 | SEQ | L CDR2 | SEQ | L CDR3 |
|---|---|---|---|---|---|---|
| 1167 | 80 | QSISSY | 81 | AAS | 82 | QQYYWYGLST |
| 1171 | | As 1167 | | As 1167 | 83 | QQGHGSYPHT |
| 1135 | | As 1167 | | As 1167 | 84 | QQSYSTPYT |
| 1483 | | As 1167 | | As 1167 | 85 | QQYGSLLT |
| 1515 | | As 1167 | | As 1167 | 86 | QQGDYTLFT |
| 1525 | | As 1167 | | As 1167 | 87 | QQYGPSGLFT |
| 1527 | | As 1167 | | As 1167 | 88 | QQYGSDSLLT |

TABLE B

Exemplary sequences (OX40 antibody)

| SEQ ID NO. | CHAIN NO. | TYPE | SEQUENCE |
|---|---|---|---|
| 89 | 1167, light chain VL | aa | DIQMTQSPSSLSASVGDRVTITCRASQSISSYLN WYQQKPGKAPKLLIYAASSLQSGVPSRFSGSG SGTDFTLTISSLQPEDFATYYCQQYYWYGLSTF GQGTKLEIK |
| 90 | 1167, light chain VL | nt | GACATCCAGATGACCCAGTCTCCATCCTCCC TGAGCGCATCTGTAGGAGACCGCGTCACCAT CACTTGCCGGGCAAGTCAGAGCATTAGCAGC TATTTAAATTGGTATCAGCAGAAACCAGGGAA AGCCCCTAAGCTCCTGATCTATGCTGCATCC AGTTTGCAAAGTGGGGTCCCATCACGTTTCA GTGGCAGTGGAAGCGGGACAGATTTCACTCT CACCATCAGCAGTCTGCAACCTGAAGATTTTG CAACTTATTACTGTCAACAGTACTACTGGTAC GGTCTGTCCACTTTTGGCCAGGGGACCAAGC TGGAGATCAAA |
| 91 | 1166, heavy chain VH | aa | EVQLLESGGGLVQPGGSLRLSCAASGFTFGGY YMSWVRQAPGKGLEWVSAISGSGGSTYYADS VKGRFTISRDNSKNTLYLQMNSLRAEDTAVYYC ARYDYASMDYWGQGTLVTVSS |
| 92 | 1166, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTGGTGG TTACTACATGTCTTGGGTCCGCCAGGCTCCA GGGAAGGGGCTGGAGTGGGTCTCAGCTATTA GTGGTAGTGGTGGTAGCACATACTATGCAGA CTCCGTGAAGGGCCGGTTCACCATCTCCCGT GACAATTCCAAGAACACGCTGTATCTGCAAAT GAACAGCCTGCGTGCCGAGGACACGGCTGT ATATTATTGTGCGCGCTACGACTACGCTTCTA TGGACTATTGGGGCCAGGGAACCCTGGTCAC CGTCTCCTCA |
| 93 | 1171, light chain VL | aa | DIQMTQSPSSLSASVGDRVTITCRASQSISSYLN WYQQKPGKAPKLLIYAASSLQSGVPSRFSGSG SGTDFTLTISSLQPEDFATYYCQQGHGSYPHTF GQGTKLEIK |
| 94 | 1171, light chain VL | nt | GACATCCAGATGACCCAGTCTCCATCCTCCC TGAGCGCATCTGTAGGAGACCGCGTCACCAT CACTTGCCGGGCAAGTCAGAGCATTAGCAGC |

TABLE B-continued

Exemplary sequences (OX40 antibody)

| SEQ ID NO. | CHAIN NO. | TYPE | SEQUENCE |
|---|---|---|---|
| | | | TATTTAAATTGGTATCAGCAGAAACCAGGGAA AGCCCCTAAGCTCCTGATCTATGCTGCATCC AGTTTGCAAAGTGGGGTCCCATCACGTTTCA GTGGCAGTGGAAGCGGGACAGATTTCACTCT CACCATCAGCAGTCTGCAACCTGAAGATTTTG CAACTTATTACTGTCAACAGGGTCATGGTTCT TACCCGCACACTTTTGGCCAGGGGACCAAGC TGGAGATCAAA |
| 95 | 1170, heavy chain VH | aa | EVQLLESGGGLVQPGGSLRLSCAASGFTFGGY YMSVWRQAPGKGLEWWSYIPGSGGSTYYADS VKGRFTISRDNSKNTLYLQMNSLRAEDTAVYYC ARYDYYWMDYWGQGTLVTVSS |
| 96 | 1170, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTGGTGG TTACTACATGTCTTGGGTCCGCCAGGCTCCA GGGAAGGGGCTGGAGTGGGTCTCATACATTC CTGGTTCTGGTGGTTCTACATACTATGCAGAC TCCGTGAAGGGCCGGTTCACCATCTCCCGTG ACAATTCCAAGAACACGCTGTATCTGCAAATG AACAGCCTGCGTGCCGAGGACACGGCTGTAT ATTATTGTGCGCGCTACGACTACTACTGGATG GACTATTGGGGCCAGGGAACCCTGGTCACC GTCTCCTCA |
| 97 | 1135, light chain VL | aa | DIQMTQSPSSLSASVGDRVTITCRASQSISSYLN WYQQKPGKAPKLLIYAASSLQSGVPSRFSGSG SGTDFTLTISSLQPEDFATYYCQQSYSTPYTFG QGTKLEIK |
| 98 | 1135, light chain VL | nt | GACATCCAGATGACCCAGTCTCCATCCTCCC TGAGCGCATCTGTAGGAGACCGCGTCACCAT CACTTGCCGGGCAAGTCAGAGCATTAGCAGC TATTTAAATTGGTATCAGCAGAAACCAGGGAA AGCCCCTAAGCTCCTGATCTATGCTGCATCC AGTTTGCAAAGTGGGGTCCCATCACGTTTCA GTGGCAGTGGAAGCGGGACAGATTTCACTCT CACCATCAGCAGTCTGCAACCTGAAGATTTTG CAACTTATTACTGTCAACAGAGTTACAGTACC CCTTATACTTTTGGCCAGGGGACCAAGCTGG AGATCAAA |
| 99 | 1164, heavy chain VH | aa | EVQLLESGGGLVQPGGSLRLSCAASGFTFYGS SMYWVRQAPGKGLEWVSGIYSSGGYTSYADS VKGRFTISRDNSKNTLYLQMNSLRAEDTAVYYC ARGVPHGYFDYWGQGTLVTVSS |
| 100 | 1164, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTTACGG TTCTTCTATGTACTGGGTCCGCCAGGCTCCA GGGAAGGGGCTGGAGTGGGTCTCAGGTATTT ACTCTTCTGGTGGTTACACATCTTATGCAGAC TCCGTGAAGGGCCGGTTCACCATCTCCCGTG ACAATTCCAAGAACACGCTGTATCTGCAAATG AACAGCCTGCGTGCCGAGGACACGGCTGTAT ATTATTGTGCGCGCGGTGTTCCTCATGGTTAC TTTGACTATTGGGGCCAGGGAACCCTGGTCA CCGTCTCCTCA |
| 101 | 1168, heavy chain VH | aa | EVQLLESGGGLVQPGGSLRLSCAASGFTFSGS SMSWVRQAPGKGLEWVSSISYYGGYTYYADS VKGRFTISRDNSKNTLYLQMNSLRAEDTAVYYC ARYFPHYYFDYWGQGTLVTVSS |
| 102 | 1168, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTAGTGG TTCTTCTATGTCTTGGGTCCGCCAGGCTCCA GGGAAGGGGCTGGAGTGGGTCTCATCTATTT CTTACTACGGTGGTTACACATACTATGCAGAC TCCGTGAAGGGCCGGTTCACCATCTCCCGTG |

TABLE B-continued

Exemplary sequences (OX40 antibody)

| SEQ ID NO. | CHAIN NO. | TYPE | SEQUENCE |
|---|---|---|---|
| | | | ACAATTCCAAGAACACGCTGTATCTGCAAATG AACAGCCTGCGTGCCGAGGACACGGCTGTAT ATTATTGTGCGCGCTACTTCCCGCATTACTAC TTTGACTATTGGGGCCAGGGAACCCTGGTCA CCGTCTCCTCA |
| 103 | 1483, light chain VL | aa | DIQMTQSPSSLSASVGDRVTITCRASQSISSYLN WYQQKPGKAPKLLIYAASSLQSGVPSRFSGSG SGTDFTLTISSLQPEDFATYYCQQYGSLLTFGQ GTKLEIK |
| 104 | 1483, light chain VL | nt | GACATCCAGATGACCCAGTCTCCATCCTCCC TGAGCGCATCTGTAGGAGACCGCGTCACCAT CACTTGCCGGGCAAGTCAGAGCATTAGCAGC TATTTAAATTGGTATCAGCAGAAACCAGGGAA AGCCCCTAAGCTCCTGATCTATGCTGCATCC AGTTTGCAAAGTGGGGTCCCATCACGTTTCA GTGGCAGTGGAAGCGGGACAGATTTCACTCT CACCATCAGCAGTCTGCAACCTGAAGATTTTG CAACTTATTACTGTCAACAGTACGGTTCTCTG CTCACTTTTGGCCAGGGGACCAAGCTGGAGA TCAAA |
| 105 | 1482, heavy chain VH | aa | EVQLLESGGGLVQPGGSLRLSCAASGFTFSSY AMSWVRQAPGKGLEWVSYISYYSGYTYYADSV KGRFTISRDNSKNTLYLQMNSLRAEDTAVYYCA RGYGYLDYWGQGTLVTVSS |
| 106 | 1482, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTAGCAG CTATGCCATGAGCTGGGTCCGCCAGGCTCCA GGGAAGGGGCTGGAGTGGGTCTCATACATTT CTTACTACTCTGGTTACACATACTATGCAGAC TCCGTGAAGGGCCGGTTCACCATCTCCCGTG ACAATTCCAAGAACACGCTGTATCTGCAAATG AACAGCCTGCGTGCCGAGGACACGGCTGTAT ATTATTGTGCGCGCGGTTACGGTTACTTGGA CTATTGGGGCCAGGGAACCCTGGTCACCGTC TCCTCA |
| 107 | 1490, heavy chain VH | aa | EVQLLESGGGLVQPGGSLRLSCAASGFTFSSY AMSWVRQAPGKGLEWVSGISYYGGYTYYADS VKGRFTISRDNSKNTLYLQMNSLRAEDTAVYYC ARYYPHHYIDYWGQGTLVTVSS |
| 108 | 1490, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTAGCAG CTATGCCATGAGCTGGGTCCGCCAGGCTCCA GGGAAGGGGCTGGAGTGGGTCTCAGGTATTT CTTACTACGGTGGTTACACATACTATGCAGAC TCCGTGAAGGGCCGGTTCACCATCTCCCGTG ACAATTCCAAGAACACGCTGTATCTGCAAATG AACAGCCTGCGTGCCGAGGACACGGCTGTAT ATTATTGTGCGCGCTACTACCCGCATCATTAC ATTGACTATTGGGGCCAGGGAACCCTGGTCA CCGTCTCCTCA |
| 109 | 1515, light chain VL | aa | DIQMTQSPSSLSASVGDRVTITCRASQSISSYLN WYQQKPGKAPKLLIYAASSLQSGVPSRFSGSG SGTDFTLTISSLQPEDFATYYCQQGDYTLFTFG QGTKLEIK |
| 110 | 1515, light chain VL | nt | GACATCCAGATGACCCAGTCTCCATCCTCCC TGAGCGCATCTGTAGGAGACCGCGTCACCAT CACTTGCCGGGCAAGTCAGAGCATTAGCAGC TATTTAAATTGGTATCAGCAGAAACCAGGGAA AGCCCCTAAGCTCCTGATCTATGCTGCATCC AGTTTGCAAAGTGGGGTCCCATCACGTTTCA |

TABLE B-continued

Exemplary sequences (OX40 antibody)

| SEQ ID NO. | CHAIN NO. | TYPE | SEQUENCE |
|---|---|---|---|
| | | | GTGGCAGTGGAAGCGGGACAGATTTCACTCT CACCATCAGCAGTCTGCAACCTGAAGATTTTG CAACTTATTACTGTCAACAGGGTGATTACACT CTGTTCACTTTTGGCCAGGGGACCAAGCTGG AGATCAAA |
| 111 | 1514, heavy chain VH | aa | EVQLLESGGGLVQPGGSLRLSCAASGFTFGYY YMSWVRQAPGKGLEWVSGISSYGSYTYYADS VKGRFTISRDNSKNTLYLQMNSLRAEDTAVYYC ARSGYSNWANSFDYWGQGTLVTVSS |
| 112 | 1514, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTGGTTA CTACTACATGTCTTGGGTCCGCCAGGCTCCA GGGAAGGGGCTGGAGTGGGTCTCAGGTATTT CTTCTTACGGTAGTTACACATACTATGCAGAC TCCGTGAAGGGCCGGTTCACCATCTCCCGTG ACAATTCCAAGAACACGCTGTATCTGCAAATG AACAGCCTGCGTGCCGAGGACACGGCTGTAT ATTATTGTGCGCGCTCTGGTTACTCTAACTGG GCTAACTCTTTTGACTATTGGGGCCAGGGAA CCCTGGTCACCGTCTCCTCA |
| 113 | 1520, heavy chain VH | aa | EVQLLESGGGLVQPGGSLRLSCAASGFTFSSY AMSWVRQAPGKGLEWVSAISGSGGSTYYADS VKGRFTISRDNSKNTLYLQMNSLRAEDTAVYYC ARYYYSHGYYVYGTLDYWGQGTLVTVSS |
| 114 | 1520, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTAGCAG CTATGCCATGAGCTGGGTCCGCCAGGCTCCA GGGAAGGGGCTGGAGTGGGTCTCAGCTATTA GTGGTAGTGGTGGTAGCACATACTATGCAGA CTCCGTGAAGGGCCGGTTCACCATCTCCCGT GACAATTCCAAGAACACGCTGTATCTGCAAAT GAACAGCCTGCGTGCCGAGGACACGGCTGT ATATTATTGTGCGCGCTACTACTACTCTCATG GTTACTACGTTTACGGTACTTTGGACTATTGG GGCCAGGGAACCCTGGTCACCGTCTCCTCA |
| 115 | 1525, light chain VL | aa | DIQMTQSPSSLSASVGDRVTITCRASQSISSYLN WYQQKPGKAPKLLIYAASSLQSGVPSRFSGSG SGTDFTLTISSLQPEDFATYYCQQYGPSGLFTF GQGTKLEIK |
| 116 | 1525, light chain VL | nt | GACATCCAGATGACCCAGTCTCCATCCTCCC TGAGCGCATCTGTAGGAGACCGCGTCACCAT CACTTGCCGGGCAAGTCAGAGCATTAGCAGC TATTTAAATTGGTATCAGCAGAAACCAGGGAA AGCCCCTAAGCTCCTGATCTATGCTGCATCC AGTTTGCAAAGTGGGGTCCCATCACGTTTCA GTGGCAGTGGAAGCGGGACAGATTTCACTCT CACCATCAGCAGTCTGCAACCTGAAGATTTTG CAACTTATTACTGTCAACAGTACGGTCCGTCT GGTCTGTTCACTTTTGGCCAGGGGACCAAGC TGGAGATCAAA |
| 117 | 1524, heavy chain VH | aa | EVQLLESGGGLVQPGGSLRLSCAASGFTFGSY YMGWVRQAPGKGLEWVSSIGSYYGYTYYADS VKGRFTISRDNSKNTLYLQMNSLRAEDTAVYYC ARHDYGALDYWGQGTLVTVSS |
| 118 | 1524, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTGGTTC TTACTACATGGGTTGGGTCCGCCAGGCTCCA GGGAAGGGGCTGGAGTGGGTCTCATCTATTG GTTCTTACTACGGTTACACATACTATGCAGAC TCCGTGAAGGGCCGGTTCACCATCTCCCGTG ACAATTCCAAGAACACGCTGTATCTGCAAATG AACAGCCTGCGTGCCGAGGACACGGCTGTAT ATTATTGTGCGCGCCATGACTACGGTGCTTT |

TABLE B-continued

Exemplary sequences (OX40 antibody)

| SEQ ID NO. | CHAIN NO. | TYPE | SEQUENCE |
|---|---|---|---|
| | | | GGACTATTGGGGCCAGGGAACCCTGGTCAC CGTCTCCTCA |
| 119 | 1527, light chain VL | aa | DIQMTQSPSSLSASVGDRVTITCRASQSISSYLN WYQQKPGKAPKLLIYAASSLQSGVPSRFSGSG SGTDFTLTISSLQPEDFATYYCQQYGSDSLLTF GQGTKLEIK |
| 120 | 1527, light chain VL | nt | GACATCCAGATGACCCAGTCTCCATCCTCCC TGAGCGCATCTGTAGGAGACCGCGTCACCAT CACTTGCCGGGCAAGTCAGAGCATTAGCAGC TATTTAAATTGGTATCAGCAGAAACCAGGGAA AGCCCCTAAGCTCCTGATCTATGCTGCATCC AGTTTGCAAAGTGGGGTCCCATCACGTTTCA GTGGCAGTGGAAGCGGGACAGATTTCACTCT CACCATCAGCAGTCTGCAACCTGAAGATTTTG CAACTTATTACTGTCAACAGTACGGTTCTGAT TCTCTGCTCACTTTTGGCCAGGGGACCAAGC TGGAGATCAAA |
| 121 | 1526, heavy chain VH | aa | EVQLLESGGGLVQPGGSLRLSCAASGFTFSGY SMYWVRQAPGKGLEWVSGIGYSGYGTYYADS VKGRFTISRDNSKNTLYLQMNSLRAEDTAVYYC ARYYFHDYAAYSLDYWGQGTLVTVSS |
| 122 | 1526, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTTCTGG TTACTCTATGTACTGGGTCCGCCAGGCTCCA GGGAAGGGGCTGGAGTGGGTCTCAGGTATT GGTTACTCTGGTTACGGTACATACTATGCAGA CTCCGTGAAGGGCCGGTTCACCATCTCCCGT GACAATTCCAAGAACACGCTGTATCTGCAAAT GAACAGCCTGCGTGCCGAGGACACGGCTGT ATATTATTGTGCGCGCTACTACTTCCATGACT ACGCTGCTTACTCTTTGGACTATTGGGGCCA GGGAACCCTGGTCACCGTCTCCTCA |
| 123 | 1542, heavy chain VH | aa | EVQLLESGGGLVQPGGSLRLSCAASGFTFGSS SMYWVRQAPGKGLEWVSGIGYYSYSTSYADS VKGRFTISRDNSKNTLYLQMNSLRAEDTAVYYC ARGYPHHYFDYWGQGTLVTVSS |
| 124 | 1542, heavy chain VH | nt | GAGGTGCAGCTGTTGGAGAGCGGGGGAGGC TTGGTACAGCCTGGGGGGTCCCTGCGCCTCT CCTGTGCAGCCAGCGGATTCACCTTTGGTTC TTCTTCTATGTACTGGGTCCGCCAGGCTCCA GGGAAGGGGCTGGAGTGGGTCTCAGGTATT GGTTACTACTCTTACTCTACATCTTATGCAGA CTCCGTGAAGGGCCGGTTCACCATCTCCCGT GACAATTCCAAGAACACGCTGTATCTGCAAAT GAACAGCCTGCGTGCCGAGGACACGGCTGT ATATTATTGTGCGCGCGGTTACCCGCATCATT ACTTTGACTATTGGGGCCAGGGAACCCTGGT CACCGTCTCCTCA |

TABLE C

Exemplary variants of domain of human CD86

| SEQ ID NO. | DESIGNA-TION | SEQUENCE |
|---|---|---|
| 6 | 900 | LKIQAYFNETADLPCQFANSQNQSLSELVVFWQDQENLVLNEVYL GKEKFDSVDSKYMGRTSFDSDSWTLRLHNLQIKDKGIYQCVIHHK KPSGLVKIHEMNSELSVLA |
| 7 | 901 | LKIQAYFNETADLPCQFANSQNLTLSELVVFWQDQENLVLNEVYLG KEKFDSVHSKYMGRTSFDSDSWTLRLHNLQIKDKGIYQCVIHHKKP TGMIKIHEMNSELSVLT |

TABLE C-continued

Exemplary variants of domain of human CD86

| SEQ ID NO. | DESIGNATION | SEQUENCE |
|---|---|---|
| 8 | 904 | LKIQAYFNETADLPCQFANSQNQSLSELIVFWQDQENLVLNEVYLG KERFDAVDSKYMGRTSFDSDSWTLRLHNLQIKDKGIYQCIIHHKKP SGMVKIHQMDSELSVLA |
| 9 | 906 | LKIQAYINETADLPCQFANSQNLSLSELVVFWQDQENLVLNEVYLG KERFDSVDSKYMGRTSFDSDSWTLRLHNLQIKDKGFYQCIIHHKKP TGLVKIHEMNSELSVLA |
| 10 | 907 | LKIQAYFNETADLPCQFANSQNQSLSELVVFWQDQENLVLNEVYL GKEKFDSVHSKYMGRTSFDSDSWTLRLHNLQIKDKGLYQCIIHHKK PTGMIKIHEMNSELSVLA |
| 11 | 908 | LKIQAYFNETADLPCQFANSQNQSLSELVVFWQDQENLVLNEVYL GKEKFDSVHSKYMGRTSFDSDSWTLRLHNLQIKDKGIYQCIIHHKK PTGMVKIHEMNSELSVLA |
| 12 | 910 | LKIQAYFNETADLPCQFANSQNQSLSELVVFWQDQENLVLNEVYL GKEKFDSVDSKYMGRTSFDSDSWTLRLHNLQIKDKGIYQCIIHHKK PTGMVKIHEMNSELSVLA |
| 13 | 915 | LKIQAYFNETADLPCQFANSQNQSLSELVVFWQDQENLILNEVYLG KEKFDSVDSKYMGRTSFDSDSWTLRLHNLQIKDKGFYQCIIHHKKP SGLIKIHQMDSELSVLA |
| 14 | 938 | LKIQAYFNETADLPCQFANSQNQSLSELVVFWQDQENLILNEVYLG KEKFDSVHSKYMGRTSFDSDSWTLRLHNLQIKDKGIYQCIIHHKKP TGMVKIHQMNSELSVLA |
| 15 | 1038 | APLKIQAYFNETADLPCQFANSQNLSLSELVVFWQDQENLVLNEVY LGKEKFDSVDSKYMGRTSFDSDSWTLRLHNLQIKDKGIYQCIIHHK KPTGMVKI HEM NSELSVLA |
| 16 | 1039 | APLKIQAYFNETADLPCQFANSQNLSLSELVVFWQDQENLVLNEVY LGKEKFDSVSSKYMGRTSFDSDSWTLRLHNLQIKDKGIYQCIIHHK KPSGMVKIHQMDSELSVLA |
| 17 | 1040 | APLKIQAYFNETADLPCQFANSQNLSLSELVVFWQDQENLVLNEVY LGKERFDSVDSKYMGRTSFDSDSWTLRLHNLQIKDKGRYQCIIHH KKPTGMINIHQMNSELSVLA |
| 18 | 1041 | APLKIQAYLNETADLPCQFANSQNLSLSELVVFWQDQENLVLNEVY LGKEKFDSVDSKYMGRTSFDSDSWTLRLHNLQIKDKGIYQCIIHHK KPTGLVKIHEMNSELSVLA |
| 19 | 1042 | APLKIQAYFNETADLPCQFANSQNLSLSELVVFWQDQENLVLNEVY LGKEIFDSVSSKYMGRTSFDSDSWTLRLHNLQIKDKGIYQCIIHHKK PSGMVKIHQMDSELSVLA |
| 20 | 1043 | APLKIQAYFNETADLPCQFANSQNLSLSELVVFWQDQENLVLNEVY LGKEKFDSVDSKYMGRTSFDSDSWTLRLHNLQIKDKGIYQCIIHHK KPTGMIKIHEMNSELSVLA |
| 21 | 1044 | APLKIQAYFNETADLPCQFANSQNLTLSELVVFWQDQENLVLNEVY LGKEKFDSVSSKYMGRTSFDSDSWTLRLHNLQIKDKGIYQCIIHHK KPTGMIKIHEMSSELSVLA |
| 22 | 1045 | APLKIQAYFNETADLPCQFANSQNLTLSELVVFWQDQENLVLNEVY LGKEKFDSVDSKYMGRTSFDSDSWTLRLHNLQIKDKGLYQCIIHHK KPTGLVKIHEMNSELSVLA |
| 23 | 1046 | APLKIQAYFNETADLPCQFANSQNQSLSELVVFWQDQENLVLNEV YLGKEKFDSVDSKYMGRTSFDSDSWTLRLHNLQIEDKGIYQCIIHH KKPSGMVKIHQMDSELSVLA |
| 24 | 1047 | APLKIQAYFNETADLPCQFANSQNLSLSELVVFWQDQENLVLNEVY LGKEKFDSVDSKYMGRTSFDSDSWTLRLHNLQIKDKGIYQCIIHHK KPTGLVKIHEMNSELSVLA |

TABLE D

Exemplary polypeptides for OX40 and CTLA-4

| SEQ ID NO. | DESIGNATION | TYPE | SEQUENCE |
|---|---|---|---|
| 125 | 1261 = 1167 light chain VL, with constant kappa sequence, linker (underlined) and CD86 mutant 1040 | aa | DIQMTQSPSSLSASVGDRVTITCRASQSISSYLN WYQQKPGKAPKLLIYAASSLQSGVPSRFSGSG SGTDFTLTISSLQPEDFATYYCQQYYWYGLSTF GQGTKLEIKRTVAAPSVFIFPPSDEQLKSGTASV VCLLNNFYPREAKVQWKVDNALQSGNSQESVT EQDSKDSTYSLSSTLTLSKADYEKHKVYACEVT HQGLSSPVTKSFNRGECSGGGGSGGGGSAPL KIQAYFNETADLPCQFANSQNLSLSELVVFWQD QENLVLNEVYLGKERFDSVDSKYMGRTSFDSD SWTLRLHNLQIKDKGRYQCIIHHKKPTGMINIHQ MNSELSVLA<br>LIGHT CHAIN PREFERABLY ASSEMBLES WITH A HEAVY CHAIN COMPRISING THE 1166 VH SEQUENCE<br>THUS, COMPLETE MOLECULE MAY BE DESIGNATED 1166/1261 |
| 126 | 1261 = 1267 light chain VL, with constant kappa sequence, linker and CD86 mutant 1040 | nt | GACATCCAGATGACCCAGTCTCCATCCTCCC TGAGCGCATCTGTAGGAGACCGCGTCACCAT CACTTGCCGGGCAAGTCAGAGCATTAGCAGC TATTTAAATTGGTATCAGCAGAAACCAGGGAA AGCCCCTAAGCTCCTGATCTATGCTGCATCC AGTTTGCAAAGTGGGGTCCCATCACGTTTCA GTGGCAGTGGAAGCGGGACAGATTTCACTCT CACCATCAGCAGTCTGCAACCTGAAGATTTTG CAACTTATTACTGTCAACAGTACTACTGGTAC GGTCTGTCCACTTTTGGCCAGGGGACCAAGC TGGAGATCAAACgtgagtcgtacgctagcaagcttgatatc gaattctaaactctgaggggggtcggatgacgtggccattctttgcct aaagcattgagtttactgcaaggtcagaaaagcatgcaaagccct cagaatggctgcaaagagctccaacaaaacaatttagaactttatt aaggaataggggggaagctaggaagaaactcaaaacatcaaga ttttaaatacgcttcttggtctccttgctataattatctgggataagcatg ctgtttttctgtctgtccctaacatgccctgtgattatccgcaaacaaca cacccaagggcagaactttgttacttaaacaccatcctgtttgcttctt tcctcagGAACTGTGGCTGCACCATCTGTCTTCA TCTTCCCGCCATCTGATGAGCAGTTGAAATCT GGAACTGCCTCTGTTGTGTGCCTGCTGAATA ACTTCTATCCCAGAGAGGCCAAAGTACAGTG GAAGGTGGATAACGCCCTCCAATCGGGTAAC TCCCAGGAGAGTGTCACAGAGCAGGACAGCA AGGACAGCACCTACAGCCTCAGCAGCACCCT GACGCTGAGCAAAGCAGACTACGAGAAACAC AAAGTCTACGCCTGCGAAGTCACCCATCAGG GCCTGAGCTCGCCCGTCACAAAGAGCTTCAA CAGGGGAGAGTGTAGCGGAGGAGGAGGAAG CGGAGGAGGAGGAAGCGCCCCCCTCAAAAT CCAAGCGTACTTCAACGAAACTGCAGACTTA CCGTGTCAGTTTGCCAATTCGCAGAATCTGA GCCTGAGCGAACTGGTGGTTTTCTGGCAGGA TCAGGAGAACCTGGTTCTGAACGAAGTCTAT CTGGGCAAAGAGCGGTTCGACAGCGTGGAC AGCAAGTATATGGGCCGCACCAGCTTTGATA GCGACAGCTGGACCCTGCGTCTGCACAATCT GCAAATCAAAGATAAGGGTAGGTACCAGTGC ATTATCCACCATAAGAAGCCGACGGGTATGA TTAATATTCACCAAATGAACTCCGAGTTGTCT GTCCTGGCG |
| 127 | 1263 = 1171 light chain VL, with constant kappa sequence, linker (underlined) and CD86 mutant 1040 | aa | DIQMTQSPSSLSASVGDRVTITCRASQSISSYLN WYQQKPGKAPKLLIYAASSLQSGVPSRFSGSG SGTDFTLTISSLQPEDFATYYCQQHGSYPHTF GQGTKLEIKRTVAAPSVFIFPPSDEQLKSGTASV VCLLNNFYPREAKVQWKVDNALQSGNSQESVT EQDSKDSTYSLSSTLTLSKADYEKHKVYACEVT HQGLSSPVTKSFNRGECSGGGGSGGGGSAPL KIQAYFNETADLPCQFANSQNLSLSELVVFWQD QENLVLNEVYLGKERFDSVDSKYMGRTSFDSD SWTLRLHNLQIKDKGRYQCIIHHKKPTGMINIHQ MNSELSVLA |

TABLE D-continued

Exemplary polypeptides for OX40 and CTLA-4

| SEQ ID NO. | DESIGNATION | TYPE | SEQUENCE |
|---|---|---|---|
| | | | LIGHT CHAIN PREFERABLY ASSEMBLES WITH A HEAVY CHAIN COMPRISING THE 1170 VH SEQUENCE<br>THUS, COMPLETE MOLECULE MAY BE DESIGNATED 1170/1263 |
| 128 | 1263 = 1171 light chain VL, with constant kappa sequence, linker and CD86 mutant 1040 | nt | GACATCCAGATGACCCAGTCTCCATCCTCCC<br>TGAGCGCATCTGTAGGAGACCGCGTCACCAT<br>CACTTGCCGGGCAAGTCAGAGCATTAGCAGC<br>TATTTAAATTGGTATCAGCAGAAACCAGGGAA<br>AGCCCCTAAGCTCCTGATCTATGCTGCATCC<br>AGTTTGCAAAGTGGGGTCCCATCACGTTTCA<br>GTGGCAGTGGAAGCGGGACAGATTTCACTCT<br>CACCATCAGCAGTCTGCAACCTGAAGATTTTG<br>CAACTTATTACTGTCAACAGGGTCATGGTTCT<br>TACCCGCACACTTTTGGCCAGGGGACCAAGC<br>TGGAGATCAAAGgtgagtcgtacgctagcaagcttgatatc<br>gaattctaaactctgagggggtcggatgacgtggccattctttgcct<br>aaagcattgagtttactgcaaggtcagaaaagcatgcaaagccct<br>cagaatggctgcaaagagctccaacaaaacaatttagaactttatt<br>aaggaatagggggaagctaggaagaaactcaaaacatcaaga<br>ttttaaatacgcttcttggtctccttgctataattatctgggataagcatg<br>ctgttttctgtctgtccctaacatgcccgtgattatccgcaaacaaca<br>cacccaagggcagaacttttgttacttaaacaccatcctgtttgcttctt<br>tcctcagGAACTGTGGCTGCACCATCTGTCTTCA<br>TCTTCCCGCCATCTGATGAGCAGTTGAAATCT<br>GGAACTGCCTCTGTTGTGTGCCTGCTGAATA<br>ACTTCTATCCCAGAGAGGCCAAAGTACAGTG<br>GAAGGTGGATAACGCCCTCCAATCGGGTAAC<br>TCCCAGGAGAGTGTCACAGAGCAGGACAGCA<br>AGGACAGCACCTACAGCCTCAGCAGCACCCT<br>GACGCTGAGCAAAGCAGACTACGAGAAACAC<br>AAAGTCTACGCCTGCGAAGTCACCCATCAGG<br>GCCTGAGCTCGCCCGTCACAAAGAGCTTCAA<br>CAGGGGAGAGTGTAGCGGAGGAGGAGGAAG<br>CGGAGGAGGAGGAAGCGCCCCCCTCAAAAT<br>CCAAGCGTACTTCAACGAAACTGCAGACTTA<br>CCGTGTCAGTTTGCCAATTCGCAGAATCTGA<br>GCCTGAGCGAACTGGTGGTTTTCTGGCAGGA<br>TCAGGAGAACCTGGTTCTGAACGAAGTCTAT<br>CTGGGCAAAGAGCGGTTCGACAGCGTGGAC<br>AGCAAGTATATGGGCCGCACCAGCTTTGATA<br>GCGACAGCTGGACCCTGCGTCTGCACAATCT<br>GCAAATCAAAGATAAGGGTAGGTACCAGTGC<br>ATTATCCACCATAAGAAGCCGACGGGTATGA<br>TTAATATTCACCAAATGAACTCCGAGTTGTCT<br>GTCCTGGCG |
| 129 | 1141 = 1135 light chain VL, with constant kappa sequence, linker (underlined) and CD86 mutant 1040 | aa | DIQMTQSPSSLSASVGDRVTITCRASQSISSYLN<br>WYQQKPGKAPKLLIYAASSLQSGVPSRFSGSG<br>SGTDFTLTISSLQPEDFATYYCQQSYSTPYTFG<br>QGTKLEIKRTVAAPSVFIFPPSDEQLKSGTASVV<br>CLLNNFYPREAKVQWKVDNALQSGNSQESVTE<br>QDSKDSTYSLSSTLTLSKADYEKHKVYACEVTH<br>QGLSSPVTKSFNRGEC<u>SGGGGSGGGGSA</u>PLKI<br>QAYFNETADLPCQFANSQNLSLSELVVFWQDQ<br>ENLVLNEVYLGKERFDSVDSKYMGRTSFDSDS<br>WTLRLH N LQIKDKGRYQCIIH H KKPTGMINIHQM<br>NSELSVLA<br>LIGHT CHAIN PREFERABLY ASSEMBLES WITH A HEAVY CHAIN COMPRISING ANY ONE OF THE 1164, 1168, 1520, OR 1542 VH SEQUENCES<br>THUS, COMPLETE MOLECULES MAY BE DESIGNATED 1164/1141, 1168/1141, 1520/1141 OR 1542/1141 |

TABLE D-continued

Exemplary polypeptides for OX40 and CTLA-4

| SEQ ID NO. | DESIGNATION | TYPE | SEQUENCE |
|---|---|---|---|
| 130 | 1141 = 1135 light chain VL, with constant kappa sequence, linker and CD86 mutant 1040 | nt | GACATCCAGATGACCCAGTCTCCATCCTCCC<br>TGAGCGCATCTGTAGGAGACCGCGTCACCAT<br>CACTTGCCGGGCAAGTCAGAGCATTAGCAGC<br>TATTTAAATTGGTATCAGCAGAAACCAGGGAA<br>AGCCCCTAAGCTCCTGATCTATGCTGCATCC<br>AGTTTGCAAAGTGGGGTCCCATCACGTTTCA<br>GTGGCAGTGGAAGCGGGACAGATTTCACTCT<br>CACCATCAGCAGTCTGCAACCTGAAGATTTTG<br>CAACTTATTACTGTCAACAGAGTTACAGTACC<br>CCTTATACTTTTGGCCAGGGGACCAAGCTGG<br>AGATCAAAcgtgagtcgtacgctagcaagcttgatatcgaatt<br>ctaaactctgaggggtcggatgacgtggccattctttgcctaaag<br>cattgagtttactgcaaggtcagaaaagcatgcaaagccctcaga<br>atggctgcaaagagctccaacaaaacaatttagaactttattaagg<br>aataggggaagctaggaagaaactcaaaacatcaagattttaa<br>atacgcttcttggtctccttgctataattatctgggataagcatgctgttt<br>tctgtctgtccctaacatgccctgtgattatccgcaaacaacacacc<br>caagggcagaactttgttacttaaacaccatcctgtttgcttctttcctc<br>agGAACTGTGGCTGCACCATCTGTCTTCATCT<br>TCCCGCCATCTGATGAGCAGTTGAAATCTGG<br>AACTGCCTCTGTTGTGTGCCTGCTGAATAACT<br>TCTATCCCAGAGAGGCCAAAGTACAGTGGAA<br>GGTGGATAACGCCCTCCAATCGGGTAACTCC<br>CAGGAGAGTGTCACAGAGCAGGACAGCAAG<br>GACAGCACCTACAGCCTCAGCAGCACCCTGA<br>CGCTGAGCAAAGCAGACTACGAGAAACACAA<br>AGTCTACGCCTGCGAAGTCACCCATCAGGGC<br>CTGAGCTCGCCCGTCACAAAGAGCTTCAACA<br>GGGGAGAGTGTAGCGGAGGAGGAGGAAGCG<br>GAGGAGGAGGAAGCGCCCCCCCTCAAAATCC<br>AAGCGTACTTCAACGAAACTGCAGACTTACC<br>GTGTCAGTTTGCCAATTCGCAGAATCTGAGC<br>CTGAGCGAACTGGTGGTTTTCTGGCAGGATC<br>AGGAGAACCTGGTTCTGAACGAAGTCTATCT<br>GGGCAAAGAGCGGTTCGACAGCGTGGACAG<br>CAAGTATATGGGCCGCACCAGCTTTGATAGC<br>GACAGCTGGACCCTGCGTCTGCACAATCTGC<br>AAAATCAAAGATAAGGGTAGGTACCAGTGCATT<br>ATCCACCATAAGAAGCCGACGGGTATGATTA<br>ATATTCACCAAATGAACTCCGAGTTGTCTGTC<br>CTGGCG |
| 131 | 1581 = 1515 light chain VL, with constant kappa sequence, linker (underlined) and CD86 mutant 1040 | aa | DIQMTQSPSSLSASVGDRVTITCRASQSISSYLN<br>WYQQKPGKAPKLLIYAASSLQSGVPSRFSGSG<br>SGTDFTLTISSLQPEDFATYYCQQGDYTLFTFG<br>QGTKLEIKRTVAAPSVFIFPPSDEQLKSGTASVV<br>CLLNNFYPREAKVQWKVDNALQSGNSQESVTE<br>QDSKDSTYSLSSTLTLSKADYEKHKVYACEVTH<br>QGLSSPVTKSFNRGECSGGGGSGGGGSAPLKI<br>QAYFNETADLPCQFANSQNLSLSELVVFWQDQ<br>ENLVLNEVYLGKERFDSVDSKYMGRTSFDSDS<br>WTLRLRHNLQIKDKGRYQCIIHHKKPTGMINIHQM<br>NSELSVLA<br>LIGHT CHAIN PREFERABLY ASSEMBLES<br>WITH A HEAVY CHAIN COMPRISING THE 1514<br>VH SEQUENCE<br>THUS, COMPLETE MOLECULE MAY BE<br>DESIGNATED 1514/1581 |
| 132 | 1581 = 1515 light chain VL, with constant kappa sequence, linker and CD86 mutant 1040 | nt | GACATCCAGATGACCCAGTCTCCATCCTCCC<br>TGAGCGCATCTGTAGGAGACCGCGTCACCAT<br>CACTTGCCGGGCAAGTCAGAGCATTAGCAGC<br>TATTTAAATTGGTATCAGCAGAAACCAGGGAA<br>AGCCCCTAAGCTCCTGATCTATGCTGCATCC<br>AGTTTGCAAAGTGGGGTCCCATCACGTTTCA<br>GTGGCAGTGGAAGCGGGACAGATTTCACTCT<br>CACCATCAGCAGTCTGCAACCTGAAGATTTTG<br>CAACTTATTACTGTCAACAGGGTGATTACACT<br>CTGTTCACTTTTGGCCAGGGGACCAAGCTGG<br>AGATCAAAcgtgagtcgtacgctagcaagcttgatatcgaatt<br>ctaaactctgaggggtcggatgacgtggccattctttgcctaaag<br>cattgagtttactgcaaggtcagaaaagcatgcaaagccctcaga<br>atggctgcaaagagctccaacaaaacaatttagaactttattaagg |

TABLE D-continued

Exemplary polypeptides for OX40 and CTLA-4

| SEQ ID NO. | DESIGNATION | TYPE | SEQUENCE |
|---|---|---|---|
| | | | aatagggggaagctaggaagaaactcaaaacatcaagattttaa<br>atacgcttcttggtctccttgctataattatctgggataagcatgctgttt<br>tctgtctgtccctaacatgccctgtgattatccgcaaacaacacacc<br>caagggcagaactttgttacttaaacaccatcctgtttgcttctttcctc<br>agGAACTGTGGCTGCACCATCTGTCTTCATCT<br>TCCCGCCATCTGATGAGCAGTTGAAATCTGG<br>AACTGCCTCTGTTGTGTGCCTGCTGAATAACT<br>TCTATCCCAGAGAGGCCAAAGTACAGTGGAA<br>GGTGGATAACGCCCTCCAATCGGGTAACTCC<br>CAGGAGAGTGTCACAGAGCAGGACAGCAAG<br>GACAGCACCTACAGCCTCAGCAGCACCCTGA<br>CGCTGAGCAAAGCAGACTACGAGAAACACAA<br>AGTCTACGCCTGCGAAGTCACCCATCAGGGC<br>CTGAGCTCGCCCGTCACAAAGAGCTTCAACA<br>GGGGAGAGTGTAGCGGAGGAGGAGGAAGCG<br>GAGGAGGAGGAAGCGCCCCCCTCAAAATCC<br>AAGCGTACTTCAACGAAACTGCAGACTTACC<br>GTGTCAGTTTGCCAATTCGCAGAATCTGAGC<br>CTGAGCGAACTGGTGG IIIICTGGCAGGATC<br>AGGAGAACCTGGTTCTGAACGAAGTCTATCT<br>GGGCAAAGAGCGGTTCGACAGCGTGGACAG<br>CAAGTATATGGGCCGCACCAGCTTTGATAGC<br>GACAGCTGGACCCTGCGTCTGCACAATCTGC<br>AAATCAAAGATAAGGGTAGGTACCAGTGCATT<br>ATCCACCATAAGAAGCCGACGGGTATGATTA<br>ATATTCACCAAATGAACTCCGAGTTGTCTGTC<br>CTGGCG |
| 133 | 1585 = 1527 light chain VL, with constant kappa sequence, linker (underlined) and CD86 mutant 1040 | aa | DIQMTQSPSSLSASVGDRVTITCRASQSISSYLN<br>WYQQKPGKAPKLLIYAASSLQSGVPSRFSGSG<br>SGTDFTLTISSLQPEDFATYYCQQYGSDSLLTF<br>GQGTKLEIKRTVAAPSVFIFPPSDEQLKSGTASV<br>VCLLNNFYPREAKVQWKVDNALQSGNSQESVT<br>EQDSKDSTYSLSSTLTLSKADYEKHKVYACEVT<br>HQGLSSPVTKSFNRGEC<u>SGGGGSGGGGSAPL</u>KIQAYFNETADLPCQFANSQNLSLSELVVFWQD<br>QENLVLNEVYLGKERFDSVDSKYMGRTSFDSD<br>SWTLRLHNLQIKDKGRYQCIIHHKKPTGMINIHQ<br>MNSELSVLA<br>LIGHT CHAIN PREFERABLY ASSEMBLES<br>WITH A HEAVY CHAIN COMPRISING THE 1526<br>VH SEQUENCE<br>THUS, COMPLETE MOLECULE MAY BE<br>DESIGNATED 1526/1585 |
| 134 | 1585 = 1527 light chain VL, with constant kappa sequence, linker and CD86 mutant 1040 | nt | GACATCCAGATGACCCAGTCTCCATCCTCCC<br>TGAGCGCATCTGTAGGAGACCGCGTCACCAT<br>CACTTGCCGGGCAAGTCAGAGCATTAGCAGC<br>TATTTAAATTGGTATCAGCAGAAACCAGGGAA<br>AGCCCCTAAGCTCCTGATCTATGCTGCATCC<br>AGTTTGCAAAGTGGGGTCCCATCACGTTTCA<br>GTGGCAGTGGAAGCGGGACAGATTTCACTCT<br>CACCATCAGCAGTCTGCAACCTGAAGAI I I IG<br>CAACTTATTACTGTCAACAGTACGGTTCTGAT<br>TCTCTGCTCACIIIIGGCCAGGGGACCAAGC<br>TGGAGATCAAACgtgagtcgtacgctagcaagcttgatatc<br>gaattctaaactctgagggggtcggatgacgtggccattctttgcct<br>aaagcattgagtttactgcaaggtcagaaaagcatgcaaagccct<br>cagaatggctgcaaagagctccaacaaaacaatttagaactttatt<br>aaggaataggggggaagctaggaagaaactcaaaacatcaaga<br>ttttaaatacgcttcttggtctccttgctataattatctgggataagcatg<br>ctgttttctgtctgtccctaacatgccctgtgattatccgcaaacaaca<br>cacccaagggcagaactttgttacttaaacaccatcctgtttgcttctt<br>tcctcagGAACTGTGGCTGCACCATCTGTCTTCA<br>TCTTCCCGCCATCTGATGAGCAGTTGAAATCT<br>GGAACTGCCTCTGTTGTGTGCCTGCTGAATA<br>ACTTCTATCCCAGAGAGGCCAAAGTACAGTG<br>GAAGGTGGATAACGCCCTCCAATCGGGTAAC<br>TCCCAGGAGAGTGTCACAGAGCAGGACAGCA<br>AGGACAGCACCTACAGCCTCAGCAGCACCCT<br>GACGCTGAGCAAAGCAGACTACGAGAAACAC<br>AAAGTCTACGCCTGCGAAGTCACCCATCAGG<br>GCCTGAGCTCGCCCGTCACAAAGAGCTTCAA<br>CAGGGGAGAGTGTAGCGGAGGAGGAGGAAG |

TABLE D-continued

Exemplary polypeptides for OX40 and CTLA-4

| SEQ ID NO. | DESIGNATION | TYPE | SEQUENCE |
|---|---|---|---|
| | | | CGGAGGAGGAGGAAGCGCCCCCCTCAAAAT CCAAGCGTACTTCAACGAAACTGCAGACTTA CCGTGTCAGTTTGCCAATTCGCAGAATCTGA GCCTGAGCGAACTGGTGGTTTTCTGGCAGGA TCAGGAGAACCTGGTTCTGAACGAAGTCTAT CTGGGCAAAGAGCGGTTCGACAGCGTGGAC AGCAAGTATATGGGCCGCACCAGCTTTGATA GCGACAGCTGGACCCTGCGTCTGCACAATCT GCAAATCAAAGATAAGGGTAGGTACCAGTGC ATTATCCACCATAAGAAGCCGACGGGTATGA TTAATATTCACCAAATGAACTCCGAGTTGTCT GTCCTGGCG |

TABLE E

Exemplary polynucleotides encoding B2 - CTLA-4

| SEQ ID | | |
|---|---|---|
| 25 | 900 | CTCAAAATCCAAGCGTACTTCAACGAAACTGCAGACTTACCGTG TCAGTTTGCCAATTCGCAGAATCAAAGCCTGAGCGAACTGGTG GTTTTCTGGCAGGATCAGGAGAACCTGGTTCTGAACGAAGTCTA TCTGGGCAAAGAGAAATTCGACAGCGTGGACAGCAAGTATATG GGCCGCACCAGCTTTGATAGCGACAGCTGGACCCTGCGTCTGC ACAATCTGCAAATCAAAGATAAGGGTATCTACCAGTGCGTGATC CACCATAAGAAGCCGAGCGGTCTGGTGAAGATTCACGAGATGA ACTCCGAGTTGTCTGTCCTGGCG |
| 26 | 901 | CTCAAAATCCAAGCGTACTTCAACGAAACTGCAGACTTACCGTG TCAGTTTGCCAATTCGCAGAATCTGACCCTGAGCGAACTGGTG GTTTTCTGGCAGGATCAGGAGAACCTGGTTCTGAACGAAGTCTA TCTGGGCAAAGAGAAATTCGACAGCGTGCATAGCAAGTATATG GGCCGCACCAGCTTTGATAGCGACAGCTGGACCCTGCGTCTGC ACAATCTGCAAATCAAAGATAAGGGTATCTACCAGTGCGTGATC CACCATAAGAAGCCGACGGGTATGATTAAGATTCACGAGATGAA CTCCGAGTTGTCTGTCCTGACC |
| 27 | 904 | CTCAAAATCCAAGCGTACTTCAACGAAACTGCAGACTTACCGTG TCAGTTTGCCAATTCGCAGAATCAAAGCCTGAGCGAACTGATCG llli CTGGCAGGATCAGGAGAACCTGGTTCTGAACGAAGTCTAT CTGGGCAAAGAGCGGTTCGACGCCGTGGACAGCAAGTATATGG GCCGCACCAGCTTTGATAGCGACAGCTGGACCCTGCGTCTGCA CAATCTGCAAATCAAAGATAAGGGTATCTACCAGTGCATTATCC ACCATAAGAAGCCGAGCGGTATGGTGAAGATTCACCAAATGGA CTCCGAGTTGTCTGTCCTGGCG |
| 28 | 906 | CTCAAAATCCAAGCGTACATCAACGAAACTGCAGACTTACCGTG TCAGTTTGCCAATTCGCAGAATCTGAGCCTGAGCGAACTGGTG GTTTTCTGGCAGGATCAGGAGAACCTGGTTCTGAACGAAGTCTA TCTGGGCAAAGAGCGGTTCGACAGCGTGGACAGCAAGTATATG GGCCGCACCAGCTTTGATAGCGACAGCTGGACCCTGCGTCTGC ACAATCTGCAAATCAAAGATAAGGGTTTCTACCAGTGCATTATC CACCATAAGAAGCCGACGGGTCTGGTGAAGATTCACGAGATGA ACTCCGAGTTGTCTGTCCTGGCG |
| 29 | 907 | CTCAAAATCCAAGCGTACTTCAACGAAACTGCAGACTTACCGTG TCAGTTTGCCAATTCGCAGAATCAAAGCCTGAGCGAACTGGTG GTTTTCTGGCAGGATCAGGAGAACCTGGTTCTGAACGAAGTCTA TCTGGGCAAAGAGAAATTCGACAGCGTGCATAGCAAGTATATG GGCCGCACCAGCTTTGATAGCGACAGCTGGACCCTGCGTCTGC ACAATCTGCAAATCAAAGATAAGGGTCTGTACCAGTGCATTATC CACCATAAGAAGCCGACGGGTATGATTAAGATTCACGAGATGAA CTCCGAGTTGTCTGTCCTGGCG |
| 30 | 908 | CTCAAAATCCAAGCGTACTTCAACGAAACTGCAGACTTACCGTG TCAGTTTGCCAATTCGCAGAATCAAAGCCTGAGCGAACTGGTG GTTTTCTGGCAGGATCAGGAGAACCTGGTTCTGAACGAAGTCTA TCTGGGCAAAGAGAAATTCGACAGCGTGCATAGCAAGTATATG GGCCGCACCAGCTTTGATAGCGACAGCTGGACCCTGCGTCTGC ACAATCTGCAAATCAAAGATAAGGGTATCTACCAGTGCATTATC |

TABLE E-continued

Exemplary polynucleotides encoding B2 - CTLA-4

| SEQ ID | | |
|---|---|---|
| | | CACCATAAGAAGCCGACGGGTATGGTGAAGATTCACGAGATGA<br>ACTCCGAGTTGTCTGTCCTGGCG |
| 31 | 910 | CTCAAAATCCAAGCGTACTTCAACGAAACTGCAGACTTACCGTG<br>TCAGTTTGCCAATTCGCAGAATCAAAGCCTGAGCGAACTGGTG<br>GTTTTCTGGCAGGATCAGGAGAACCTGGTTCTGAACGAAGTCTA<br>TCTGGGCAAAGAGAAATTCGACAGCGTGGACAGCAAGTATATG<br>GGCCGCACCAGCTTTGATAGCGACAGCTGGACCCTGCGTCTGC<br>ACAATCTGCAAATCAAAGATAAGGGTATCTACCAGTGCATTATC<br>CACCATAAGAAGCCGACGGGTATGGTGAAGATTCACGAGATGA<br>ACTCCGAGTTGTCTGTCCTGGCG |
| 32 | 915 | CTCAAAATCCAAGCGTACTTCAACGAAACTGCAGACTTACCGTG<br>TCAGTTTGCCAATTCGCAGAATCAAAGCCTGAGCGAACTGGTG<br>GTTTTCTGGCAGGATCAGGAGAACCTGATCCTGAACGAAGTCTA<br>TCTGGGCAAAGAGAAATTCGACAGCGTGGACAGCAAGTATATG<br>GGCCGCACCAGCTTTGATAGCGACAGCTGGACCCTGCGTCTGC<br>ACAATCTGCAAATCAAAGATAAGGGTTTCTACCAGTGCATTATC<br>CACCATAAGAAGCCGAGCGGTCTGATTAAGATTCACCAAATGGA<br>CTCCGAGTTGTCTGTCCTGGCG |
| 33 | 938 | CTCAAAATCCAAGCGTACTTCAACGAAACTGCAGACTTACCGTG<br>TCAGTTTGCCAATTCGCAGAATCTGAGCCTGAGCGAACTGGTG<br>GTTTTCTGGCAGGATCAGGAGAACCTGATCCTGAACGAAGTCTA<br>TCTGGGCAAAGAGCGGTTCGACAGCGTGCATAGCAAGTATATG<br>GGCCGCACCAGCTTTGATAGCGACAGCTGGACCCTGCGTCTGC<br>ACAATCTGCAAATCAAAGATAAGGGTCTGTACCAGTGCATTATC<br>CACCATAAGAAGCCGAGCGGTATGGTGAAGATTCACGAGATGA<br>ACTCCGAGTTGTCTGTCCTGGCG |
| 34 | 1038 | GCCCCCCTCAAAATCCAAGCGTACTTCAACGAAACTGCAGACTT<br>ACCGTGTCAGTTTGCCAATTCGCAGAATCTGAGCCTGAGCGAA<br>CTGGTGGTTTTCTGGCAGGATCAGGAGAACCTGGTTCTGAACG<br>AAGTCTATCTGGGCAAAGAGAAATTCGACAGCGTGGACAGCAA<br>GTATATGGGCCGCACCAGCTTTGATAGCGACAGCTGGACCCTG<br>CGTCTGCACAATCTGCAAATCAAAGATAAGGGTATCTACCAGTG<br>CATTATCCACCATAAGAAGCCGACGGGTATGGTGAAGATTCAC<br>GAGATGAACTCCGAGTTGTCTGTCCTGGCG |
| 35 | 1039 | GCCCCCCTCAAAATCCAAGCGTACTTCAACGAAACTGCAGACTT<br>ACCGTGTCAGTTTGCCAATTCGCAGAATCTGAGCCTGAGCGAA<br>CTGGTGGTTTTCTGGCAGGATCAGGAGAACCTGGTTCTGAACG<br>AAGTCTATCTGGGCAAAGAGAAATTCGACAGCGTGAGTAGCAA<br>GTATATGGGCCGCACCAGCTTTGATAGCGACAGCTGGACCCTG<br>CGTCTGCACAATCTGCAAATCAAAGATAAGGGTATCTACCAGTG<br>CATTATCCACCATAAGAAGCCGAGCGGTATGGTGAAGATTCACC<br>AAATGGACTCCGAGTTGTCTGTCCTGGCG |
| 36 | 1040 | GCCCCCCTCAAAATCCAAGCGTACTTCAACGAAACTGCAGACTT<br>ACCGTGTCAGTTTGCCAATTCGCAGAATCTGAGCCTGAGCGAA<br>CTGGTGGTTTTCTGGCAGGATCAGGAGAACCTGGTTCTGAACG<br>AAGTCTATCTGGGCAAAGAGCGGTTCGACAGCGTGGACAGCAA<br>GTATATGGGCCGCACCAGCTTTGATAGCGACAGCTGGACCCTG<br>CGTCTGCACAATCTGCAAATCAAAGATAAGGGTAGGTACCAGTG<br>CATTATCCACCATAAGAAGCCGACGGGTATGATTAATATTCACC<br>AAATGAACTCCGAGTTGTCTGTCCTGGCG |
| 37 | 1041 | GCCCCCCTCAAAATCCAAGCGTACCTCAACGAAACTGCAGACTT<br>ACCGTGTCAGTTTGCCAATTCGCAGAATCTGAGCCTGAGCGAA<br>CTGGTGGTTTTCTGGCAGGATCAGGAGAACCTGGTTCTGAACG<br>AAGTCTATCTGGGCAAAGAGAAATTCGACAGCGTGGACAGCAA<br>GTATATGGGCCGCACCAGCTTTGATAGCGACAGCTGGACCCTG<br>CGTCTGCACAATCTGCAAATCAAAGATAAGGGTATCTACCAGTG<br>CATTATCCACCATAAGAAGCCGACGGGTCTGGTGAAGATTCAC<br>GAGATGAACTCCGAGTTGTCTGTCCTGGCG |
| 38 | 1042 | GCCCCCCTCAAAATCCAAGCGTACTTCAACGAAACTGCAGACTT<br>ACCGTGTCAGTTTGCCAATTCGCAGAATCTGAGCCTGAGCGAA<br>CTGGTGGTTTTCTGGCAGGATCAGGAGAACCTGGTTCTGAACG<br>AAGTCTATCTGGGCAAAGAGATTTTCGACAGCGTGAGTAGCAA<br>GTATATGGGCCGCACCAGCTTTGATAGTGACAGCTGGACCCTG<br>CGTCTGCACAATCTGCAAATCAAAGATAAGGGTATCTACCAGTG<br>CATTATCCACCATAAGAAGCCGAGCGGTATGGTGAAGATTCACC<br>AAATGGACTCCGAGTTGTCTGTCCTGGCG |

TABLE E-continued

Exemplary polynucleotides encoding B2 - CTLA-4

| SEQ ID | | |
|---|---|---|
| 39 | 1043 | GCCCCCCTCAAAATCCAAGCGTACTTCAACGAAACTGCAGACTT<br>ACCGTGTCAGTTTGCCAATTCGCAGAATCTGAGCCTGAGCGAA<br>CTGGTGGTTTTCTGGCAGGATCAGGAGAACCTGGTTCTGAACG<br>AAGTCTATCTGGGCAAAGAGAAATTCGACAGCGTGGATAGCAA<br>GTATATGGGCCGCACCAGCTTTGATAGCGACAGCTGGACCCTG<br>CGTCTGCACAATCTGCAAATCAAAGATAAGGGTATCTACCAGTG<br>CATTATCCACCATAAGAAGCCGACGGGTATGATTAAGATTCACG<br>AGATGAACTCCGAGTTGTCTGTCCTGGCG |
| 40 | 1044 | GCCCCCCTCAAAATCCAAGCGTACTTCAACGAAACTGCAGACTT<br>ACCGTGTCAGTTTGCCAATTCGCAGAATCTGACCCTGAGCGAA<br>CTGGTGGTTTTCTGGCAGGATCAGGAGAACCTGGTTCTGAACG<br>AAGTCTATCTGGGCAAAGAGAAATTCGACAGCGTGTCTAGCAA<br>GTATATGGGCCGCACCAGCTTTGATAGCGACAGCTGGACCCTG<br>CGTCTGCACAATCTGCAAATCAAAGATAAGGGTATCTACCAGTG<br>CATTATCCACCATAAGAAGCCGACGGGTATGATTAAGATTCACG<br>AGATGAGCTCCGAGTTGTCTGTCCTGGCG |
| 41 | 1045 | GCCCCCCTCAAAATCCAAGCGTACTTCAACGAAACTGCAGACTT<br>ACCGTGTCAGTTTGCCAATTCGCAGAATCTGACCCTGAGCGAA<br>CTGGTGGTTTTCTGGCAGGATCAGGAGAACCTGGTTCTGAACG<br>AAGTCTATCTGGGCAAAGAGAAATTCGACAGCGTGGACAGCAA<br>GTATATGGGCCGCACCAGCTTTGATAGCGACAGCTGGACCCTG<br>CGTCTGCACAATCTGCAAATCAAAGATAAGGGTCTGTACCAGTG<br>CATTATCCACCATAAGAAGCCGACGGGTCTGGTGAAGATTCAC<br>GAGATGAACTCCGAGTTGTCTGTCCTGGCG |
| 42 | 1046 | GCCCCCCTCAAAATCCAAGCGTACTTCAACGAAACTGCAGACTT<br>ACCGTGTCAGTTTGCCAATTCGCAGAATCAAAGCCTGAGCGAA<br>CTGGTGGTTTTCTGGCAGGATCAGGAGAACCTGGTTCTGAACG<br>AAGTCTATCTGGGCAAAGAGAAATTCGACAGCGTGGACAGCAA<br>GTATATGGGCCGCACCAGCTTTGATAGCGACAGCTGGACCCTG<br>CGTCTGCACAATCTGCAAATCGAAGATAAGGGTATCTACCAGTG<br>CATTATCCACCATAAGAAGCCGAGCGGTATGGTGAAGATTCACC<br>AAATGGACTCCGAGTTGTCTGTCCTGGCG |
| 43 | 1047 | GCCCCCCTCAAAATCCAAGCGTACTTCAACGAAACTGCAGACTT<br>ACCGTGTCAGTTTGCCAATTCGCAGAATCTGAGCCTGAGCGAA<br>CTGGTGGTTTTCTGGCAGGATCAGGAGAACCTGGTTCTGAACG<br>AAGTCTATCTGGGCAAAGAGAAATTCGACAGCGTGGACAGCAA<br>GTATATGGGCCGCACCAGCTTTGATAGCGACAGCTGGACCCTG<br>CGTCTGCACAATCTGCAAATCAAAGATAAGGGTATCTACCAGTG<br>CATTATCCACCATAAGAAGCCGACGGGTCTGGTGAAGATTCAC<br>GAGATGAACTCCGAGTTGTCTGTCCTGGCG |

TABLE F

Exemplary sequences

| SEQ ID NO. | DESIGNATION | SEQUENCE |
|---|---|---|
| 149 | Fusion of:<br>VH1: 1164 (bold underlined)<br>IgG1 constant domains (italics)<br>Linker (underlined)<br>VH2: 1204 (bold)<br>VL2: 1205 (bold, italics) | EVQLLESGGGLVQPGGSLRLSCAASGFTFYGSSMW<br>VRQAPGKGLEEVSGIYSSGGYTSYADSVKGRFTISRD<br>NSKNTLYLQMNSLRAEDTAVYYCARGVPHGYFDYWG<br>QGTLVTVSS*ASTKGPSVFPLAPSSKSTSGGTAALGCLV*<br>*KDYFPEPVTVSWNSGALTSGVHTFPAVLQSSGLYSLS*<br>*SVVTVPSSSLGTQTYICNVNHKPSNTKVDKKVEPKSCD*<br>*KTHTCPPCPAPELLGGPSVFLFPPKPKDTLMISRTPEV*<br>*TCVVVDVSHEDPEVKFNWYVDGVEVHNAKTKPREEQ*<br>*YNSTYRVVSVLTVLHQDWLNGKEYKCKVSNKALPAPIE*<br>*KTISKAKGQPREPQVYTLPPSRDELTKNQVSLTCLVKG*<br>*FYPSDIAVEWESNGQPENNYKTTPPVLDSDGSFFLYSK*<br>*LTVDKSRWQQGNVFSCSVMHEALHNHYTQKSLSLSP*<br>*GK*<u>GGGGSGGGGSGGGGS</u>EVQLLESGGGLVQPGGSL<br>RLSCAASGFTFSSYYMGWVRQAPGKGLEWVSGIGSY<br>YGYTGYADSVKGRFTISRDNSKNTLYLQMNSLRAEDT<br>AVYYCARAYYDYNYYYAYFDYWGQGTLVTVSS<u>GGGG</u> |

TABLE F-continued

Exemplary sequences

| SEQ ID NO. | DESIGNATION | SEQUENCE |
|---|---|---|
| | | SGGGGSGGGG*DIQMTQSPSSLSASVGDRVTITCRA SQSISSYLNWYQQKPGKAPKLLIYAASSLQSGVPSRF SGSGSGTDFTLTISSLQPEDFATYYCQQSVPHYPFTFG QGTKLEIKR* This sequence typically expressed together with a light chain sequence comprising VL1 1135 (SEQ ID NO: 97) fused to kappa sequence (SEQ ID NO: 136) to assemble a 1164/1135-1204/1205 bispecific antibody. |
| 150 | Nucleotide sequence encoding SEQ ID NO: 149 | GAGGTGCAGCTGTTGGAGAGCGGGGGAGGCTTGGT ACAGCCTGGGGGGTCCCTGCGCCTCTCCTGTGCAG CCAGCGGATTCACCTTTTACGGTTCTTCTATGTACTG GGTCCGCCAGGCTCCAGGGAAGGGGCTGGAGTGG GTCTCAGGTATTTACTCTTCTGGTGGTTACACATCTT ATGCAGACTCCGTGAAGGGCCGGTTCACCATCTCCC GTGACAATTCCAAGAACACGCTGTATCTGCAAATGA ACAGCCTGCGTGCCGAGGACACGGCTGTATATTATT GTGCGCGCGGTGTTCCTCATGGTTACTTTGACTATT GGGGCCAGGGAACCCTGGTCACCGTCTCCTCAGGT GAGTTaaCgtacgctagcaagctttctggggcaggccaggcctgaccttggctttggggcagggaggggctaaggtgaggcaggtggcgccagccaggtgcacaccaatgcccatgagcccagacactggacgctgaacctcgcggacagttaagaacccaggggcctctgcgccctgggcccagctctgtcccacaccgcggtcacatggcaccacctctcttgcagCCTCCACCAAGGGC CCATCGGTCTTCCCCCTGGCACCCTCCTCCAAGAGC ACCTCTGGGGGCACAGCGGCCCTGGGCTGCCTGGT CAAGGACTACTTCCCCGAACCGGTGACGGTGTCGT GGAACTCAGGCGCCCTGACCAGCGGCGTGCACACC TTCCCGGCTGTCCTACAGTCCTCAGGACTCTACTCC CTCAGCAGCGTGGTGACCGTGCCCTCCAGCAGCTT GGGCACCCAGACCTACATCTGCAACGTGAATCACAA GCCCAGCAACACCAAGGTGGACAAGAAAGTTGgtgagaggccagcacagggagggagggtgtctgctggaagccaggctcagcgctcctgcctggacgcatcccggctatgcagcccagtccagggcagcaaggcaggcccgtctgcctcttcacccggaggcctctgcccgccccactcatgctcagggagagggtcttctggctttttcccaggctctgggcaggcacaggctaggtgccctaacccaggccctgcacacaaaggggcaggtgctgggctcagacctgccaagagccatatccgggaggaccctgccctgacctaagcccaccccaaaggccaaactctccactccctcagctcggacaccttctctcctcccagattccagtaactcccaatcttctctctgcagAGCCCAAATCTTGTGACAA AACTCACACATGCCCACCGTGCCCAGgtaagccagcccaggcctcgccctccagctcaaggcgggacaggtgccctagagtagcctgcatccagggacaggccccagccgggtgctgacacgtccacctccatctcttcctcagCACCTGAACTCCTGGGGGGACCGTCAGTCTTCCT CTTCCCCCCAAAACCCAAGGACACCCTCATGATCTC CCGGACCCCTGAGGTCACATGCGTGGTGGTGGACG TGAGCCACGAAGACCCTGAGGTCAAGTTCAACTGGT ACGTGGACGGCGTGGAGGTGCATAATGCCAAGACA AAGCCGCGGGAGGAGCAGTACAACAGCACGTACCG TGTGGTCAGCGTCCTCACCGTCCTGCACCAGGACTG GCTGAATGGCAAGGAGTACAAGTGCAAGGTCTCCAA CAAAGCCCTCCCAGCCCCCATCGAGAAAACCATCTC CAAAGCCAAAGgtgggacccgtggggtgcgagggccacatggacagaggccggctcggcccaccctctgccctgagagtgaccgctgtaccaacctctgtccctacagGGCAGCCCCGAGAACCACAGGTGTACA CCCTGCCCCCATCCCGGGATGAGCTGACCAAGAAC CAGGTCAGCCTGACCTGCCTGGTCAAAGGCTTCTAT CCCAGCGACATCGCCGTGGAGTGGGAGAGCAATGG GCAGCCGGAGAACAACTACAAGACCACGCCTCCCG TGCTGGACTCCGACGGCTCCTTCTTCCTCTACAGCA AGCTCACCGTGGACAAGAGCAGGTGGCAGCAGGGG AACGTCTTCTCATGCTCCGTGATGCATGAGGCTCTG CACAACCACTACACGCAGAAGAGCCTCTCCCTGTCT CCGGGTAAAGGAGGAGGAGGAAGCGGAGGAGGAG GAAGCGGAGGAGGAGGAAGCGAGGTGCAGCTGCTC GAGAGCGGGGAGGCTTGGTACAGCCTGGGGGGT CCCTGCGCCTCTCCTGTGCAGCCAGCGGATTCACCT TTTCTTCTTACTACATGGGTTGGGTCCGCCAGGCTC CAGGGAAGGGGCTGGAGTGGGTCTCAGGTATTGGT TCTTACTACGGTTACACAGGTTATGCAGACTCCGTG AAGGGCCGGTTCACCATCTCCCGTGACAATTCCAAG AACACGCTGTATCTGCAAATGAACAGCCTGCGTGCC |

TABLE F-continued

Exemplary sequences

| SEQ ID NO. | DESIGNATION | SEQUENCE |
|---|---|---|
| | | GAGGACACGGCTGTATATTATTGTGCGCGCGCTTAC<br>TACGACTACAACTACTACTACGCTTACTTTGACTATT<br>GGGGCCAGGGAACCCTGGTCACCGTCTCCTCAGGT<br>GGAGGCGGTTCAGGCGGAGGTGGATCCGGCGGTG<br>GCGGATCGGACATCCAGATGACCCAGTCTCCATCCT<br>CCCTGAGCGCATCTGTAGGAGACCGCGTCACCATCA<br>CTTGCCGGGCAAGTCAGAGCATTAGCAGCTATTTAA<br>ATTGGTATCAGCAGAAACCAGGGAAAGCCCCTAAGC<br>TCCTGATCTATGCTGCATCCAGTTTGCAAAGTGGGG<br>TCCCATCACGTTTCAGTGGCAGTGGAAGCGGGACA<br>GATTTCACTCTCACCATCAGCAGTCTGCAACCTGAA<br>GATTTTGCAACTTATTACTGTCAACAGTCTGTTCCGC<br>ACTACCCGTTCACTTTTGGCCAGGGGACCAAGCTGG<br>AGATCAAACGC |
| 151 | Fusion of:<br>VH1: 1166 (bold underlined)<br>IgG1 constant domains (italics)<br>Linker (underlined)<br>VH2: 1204 (bold)<br>VL2: 1205 (bold, italics) | EVQLLESGGGLVQPGGSLRLSCAASGFTFGGYYMSW<br>VRQAPGKGLEWVSAISGSGGSTYYADSVKGRFTISRD<br>NSKNTLYLQMNSLRAEDTAVYYCARYDYASMDYWG<br>QGTLVTVSSASTKGPSVFPLAPSSKSTSGGTAALGCLV<br>KDYFPEPVTVSWNSGALTSGVHTFPAVLQSSGLYSLS<br>SVVTVPSSSLGTQTYICNVNHKPSNTKVDKKVEPKSCD<br>KTHTCPPCPAPELLGGPSVFLFPPKPKDTLMISRTPEV<br>TCVVVDVSHEDPEVKFNWYVDGVEVHNAKTKPREEQ<br>YNSTYRVVSVLTVLHQDWLNGKEYKCKVSNKALPAPIE<br>KTISKAKGQPREPQVYTLPPSRDELTKNQVSLTCLVKG<br>FYPSDIAVEWESNGQPENNYKTTPPVLDSDGSFFLYSK<br>LTVDKSRWQQGNVFSCSVMHEALHNHYTQKSLSLSP<br>G<u>KGGGGSGGGGSGGGGS</u>EVQLLESGGGLVQPGGSL<br>RLSCAASGFTFSSYYMGWVRQAPGKGLEWVSGIGSY<br>YGYTGYADSVKGRFTISRDNSKNTLYLQMNSLRAEDT<br>AVYYCARAYYDYNYYYAYFDYWGQGTLVTVSS<u>GGGG</u><br><u>SGGGGSGGGGS</u>*DIQMTQSPSSLSASVGDRVTITCRA*<br>*SQSISSYLNWYQQKPGKAPKLLIYAASSLQSGVPSRF*<br>*SGSGSGTDFTLTISSLQPEDFATYYCQQSVPHYPFTFG*<br>*QGTKLEIKR*<br>This sequence typically expressed together with a light chain sequence comprising VL1 1167 (SEQ ID NO: 89) fused to kappa sequence (SEQ ID NO: 136) to assemble a 1166/1167-1204/1205 bispecific antibody. |
| 152 | Nucleotide sequence encoding SEQ ID NO: 151 | GAGGTGCAGCTGTTGGAGAGCGGGGGAGGCTTGGT<br>ACAGCCTGGGGGTCCCTGCGCCTCTCCTGTGCAG<br>CCAGCGGATTCACCTTTGGTGGTTACTACATGTCTT<br>GGGTCCGCCAGGCTCCAGGGAAGGGGCTGGAGTG<br>GGTCTCAGCTATTAGTGGTAGTGGTGGTAGCACATA<br>CTATGCAGACTCCGTGAAGGGCCGGTTCACCATCTC<br>CCGTGACAATTCCAAGAACACGCTGTATCTGCAAAT<br>GAACAGCCTGCGTGCCGAGGACACGGCTGTATATTA<br>TTGTGCGCGCTACGACTACGCTTCTATGGACTATTG<br>GGGCCAGGGAACCCTGGTCACCGTCTCCTCAGGTG<br>AGTTaaCgtacgctagcaagctttctggggcaggccaggcctgaccttgg<br>ctttgggggcagggaggggggctaaggtgaggcaggtggcgcgcagccaggtg<br>cacacccaatgcccatgagcccagacactggacgctgaacctcgcggaca<br>gttaagaacccaggggcctctgcgccctgggcccagctctgtcccacaccg<br>cggtcacatggcaccacctctcttgcagCCTCCACCAAGGGCCCA<br>TCGGTCTTCCCCCTGGCACCCTCCTCCAAGAGCACC<br>TCTGGGGGCACAGCGGCCCTGGGCTGCCTGGTCAA<br>GGACTACTTCCCCGAACCGGTGACGGTGTCGTGGA<br>ACTCAGGCGCCCTGACCAGCGGCGTGCACACCTTC<br>CCGGCTGTCCTACAGTCCTCAGGACTCTACTCCCTC<br>AGCAGCGTGGTGACCGTGCCCTCCAGCAGCTTGGG<br>CACCCAGACCTACATCTGCAACGTGAATCACAAGCC<br>CAGCAACACCAAGGTGGACAAGAAAGTTGgtgagaggc<br>cagcacagggagggagggtgtctgctggaagccaggctcagcgctcctgc<br>ctggacgcatcccggctatgcagcccagtccagggcagcaaggcaggcc<br>ccgtctgcctcttcacccggaggcctctgcccgccccactcatgctcagggag<br>agggtcttctggcttttttccccaggctctgggcaggcacaggtaggtgcccct<br>aaccaggccctgcacacaaaggggcaggtgctgggctcagacctgcca<br>agagccatatccgggaggaccctgccctgacctaagcccaccccaaagg<br>ccaaactctccactccctcagctcggacaccttctctcctcccagattccagta<br>actcccaatcttctctctgcagAGCCCAAATCTTGTGACAAAAC<br>TCACACATGCCCACCGTGCCCAGgtaagccagcccaggcct |

TABLE F-continued

Exemplary sequences

| SEQ ID NO. | DESIGNATION | SEQUENCE |
|---|---|---|
| | | cgccctccagctcaaggcgggacaggtgccctagagtagcctgcatccagg gacaggccccagccgggtgctgacacgtccacctccatctcttcctcagCA CCTGAACTCCTGGGGGACCGTCAGTCTTCCTCTTC CCCCCAAAACCCAAGGACACCCTCATGATCTCCCGG ACCCCTGAGGTCACATGCGTGGTGGTGGACGTGAG CCACGAAGACCCTGAGGTCAAGTTCAACTGGTACGT GGACGGCGTGGAGGTGCATAATGCCAAGACAAAGC CGCGGGAGGAGCAGTACAACAGCACGTACCGTGTG GTCAGCGTCCTCACCGTCCTGCACCAGGACTGGCT GAATGGCAAGGAGTACAAGTGCAAGGTCTCCAACAA AGCCCTCCCAGCCCCCATCGAGAAAACCATCTCCAA AGCCAAAGgtgggacccgtggggtgcgagggccacatggacagagg ccggctcggcccaccctctgccctgagagtgaccgctgtaccaacctctgtcc ctacagGGCAGCCCCGAGAACCACAGGTGTACACCCT GCCCCCATCCCGGGATGAGCTGACCAAGAACCAGG TCAGCCTGACCTGCCTGGTCAAAGGCTTCTATCCCA GCGACATCGCCGTGGAGTGGGAGAGCAATGGGCAG CCGGAGAACAACTACAAGACCACGCCTCCCGTGCT GGACTCCGACGGCTCCTTCTTCCTCTACAGCAAGCT CACCGTGGACAAGAGCAGGTGGCAGCAGGGGAACG TCTTCTCATGCTCCGTGATGCATGAGGCTCTGCACA ACCACTACACGCAGAAGAGCCTCTCCCTGTCTCCGG GTAAAGGAGGAGGAGGAAGCGGAGGAGGAGGAAG CGGAGGAGGAGGAAGCGAGGTGCAGCTGCTCGAGA GCGGGGGAGGCTTGGTACAGCCTGGGGGGTCCCT GCGCCTCTCCTGTGCAGCCAGCGGATTCACCTTTTC TTCTTACTACATGGGTTGGGTCCGCCAGGCTCCAGG GAAGGGGCTGGAGTGGGTCTCAGGTATTGGTTCTTA CTACGGTTACACAGGTTATGCAGACTCCGTGAAGGG CCGGTTCACCATCTCCCGTGACAATTCCAAGAACAC GCTGTATCTGCAAATGAACAGCCTGCGTGCCGAGGA CACGGCTGTATATTATTGTGCGCGCTTACTACGA CTACAACTACTACTACGCTTACTTTGACTATTGGGGC CAGGGAACCCTGGTCACCGTCTCCTCAGGTGGAGG CGGTTCAGGCGGAGGTGGATCCGGCGGTGGCGGAT CGGACATCCAGATGACCCAGTCTCCATCCTCCCTGA GCGCATCTGTAGGAGACCGCGTCACCATCACTTGCC GGGCAAGTCAGAGCATTAGCAGCTATTTAAATTGGT ATCAGCAGAAACCAGGGAAAGCCCCTAAGCTCCTGA TCTATGCTGCATCCAGTTTGCAAAGTGGGGTCCCAT CACGTTTCAGTGGCAGTGGAAGCGGGACAGATTTCA CTCTCACCATCAGCAGTCTGCAACCTGAAGATTTTG CAACTTATTACTGTCAACAGTCTGTTCCGCACTACCC GTTCACTTTTGGCCAGGGGACCAAGCTGGAGATCAA ACGC |
| 153 | Fusion of: VH1: 1168 (bold underlined) IgG1 constant domains (italics) Linker (underlined) VH2: 1204 (bold) | EVQLLESGGGLVQPGGSLRLSCAASGFTFSGSSMSW VRQAPGKGLEWVSSISYYGGYTYYADSVKGRFTISRD NSKNTLYLQMNSLRAEDTAVYYCARYFPHYYFDYWG QGTLVTVSS_ASTKGPSVFPLAPSSKSTSGGTAALGCLV KDYFPEPVTVSWNSGALTSGVHTFPAVLQSSGLYSLS SVVTVPSSSLGTQTYICNVNHKPSNTKVDKKVEPKSCD KTHTCPPCPAPELLGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALPAPIE KTISKAKGQPREPQVYTLPPSRDELTKNQVSLTCLVKG FYPSDIAVEWESNGQPENNYKTTPPVLDSDGSFFLYSK LTVDKSRWQQGNVFSCSVMHEALHNHYTQKSLSLSP GK_GGGGSGGGGSGGGGSEVQLLESGGGLVQPGGSL RLSCAASGFTFSSYYMGWVRQAPGKGLEWVSGIGSY YGYTGYADSVKGRFTISRDNSKNTLYLQMNSLRAEDT AVYYCARAYYDYNYYYAYFDYWGQGTLVTVSSGGGG SGGGGSGGGGS_DIQMTQSPSSLSASVGDRVTITCRA SQSISSYLNWYQQKPGKAPKLLIYAASSLQSGVPSRF SGSGSGTDFTLTISSLQPEDFATYYCQQSVPHYPFTFG QGTKLEIKR_ This sequence typically expressed together with a light chain sequence comprising VL1 1135 (SEQ ID NO: 97) fused to kappa sequence (SEQ ID NO: 136) to assemble a 1168/1135-1204/ 1205 bispecific antibody. |

TABLE F-continued

Exemplary sequences

| SEQ ID NO. | DESIGNATION | SEQUENCE |
|---|---|---|
| 154 | Nucleotide sequence encoding SEQ ID NO: 153 | GAGGTGCAGCTGTTGGAGAGCGGGGGAGGCTTGGT<br>ACAGCCTGGGGGGTCCCTGCGCCTCTCCTGTGCAG<br>CCAGCGGATTCACCTTTAGTGGTTCTTCTATGTCTTG<br>GGTCCGCCAGGCTCCAGGGAAGGGGCTGGAGTGG<br>GTCTCATCTATTTCTTACTACGGTGGTTACACATACT<br>ATGCAGACTCCGTGAAGGGCCGGTTCACCATCTCCC<br>GTGACAATTCCAAGAACACGCTGTATCTGCAAATGA<br>ACAGCCTGCGTGCCGAGGACACGGCTGTATATTATT<br>GTGCGCGCTACTTCCCGCATTACTACTTTGACTATTG<br>GGGCCAGGGAACCCTGGTCACCGTCTCCTCAGGTG<br>AGTTaaCgtacgctagcaagctttctggggcaggccaggcctgaccttgg<br>ctttggggcagggaggggctaaggtgaggcaggtggcgccagccaggtg<br>cacacccaatgcccatgagcccagacactggacgctgaacctcgcggaca<br>gttaagaacccaggggcctctgcgccctgggcccagctctgtcccacaccg<br>cggtcacatggcaccacctctcttgcagCCTCCACCAAGGGCCCA<br>TCGGTCTTCCCCCTGGCACCCTCCTCCAAGAGCACC<br>TCTGGGGGCACAGCGGCCCTGGGCTGCCTGGTCAA<br>GGACTACTTCCCCGAACCGGTGACGGTGTCGTGGA<br>ACTCAGGCGCCCTGACCAGCGGCGTGCACACCTTC<br>CCGGCTGTCCTACAGTCCTCAGGACTCTACTCCCTC<br>AGCAGCGTGGTGACCGTGCCCTCCAGCAGCTTGGG<br>CACCCAGACCTACATCTGCAACGTGAATCACAAGCC<br>CAGCAACACCAAGGTGGACAAGAAAGTTGgtgagaggc<br>cagcacagggagggagggtgtctgctggaagccaggctcagcgctcctgc<br>ctggacgcatcccggctatgcagccccagtccagggcagcaaggcaggcc<br>ccgtctgcctcttcacccggaggcctctgcccgccccactcatgctcagggag<br>agggtcttctggcttttccccaggctctgggcaggcacaggctaggtgcccct<br>aacccaggccctgcacacaaaggggcaggtgctgggctcagacctgcca<br>agagccatatccgggaggaccctgcccctgacctaagcccaccccaaagg<br>ccaaactctccactccctcagctcggacaccttctctcctcccagattccagta<br>actcccaatcttctctctgcagAGCCCAAATCTTGTGACAAAAC<br>TCACACATGCCCACCGTGCCCAGgtaagccagcccaggcct<br>cgccctccagctcaaggcgggacaggtgccctagagtagcctgcatccagg<br>gacaggcccagccgggtgctgacacgtccacctccatctcttcctcagCA<br>CCTGAACTCCTGGGGGGACCGTCAGTCTTCCTCTTC<br>CCCCCAAAACCCAAGGACACCCTCATGATCTCCCGG<br>ACCCCTGAGGTCACATGCGTGGTGGTGGACGTGAG<br>CCACGAAGACCCTGAGGTCAAGTTCAACTGGTACGT<br>GGACGGCGTGGAGGTGCATAATGCCAAGACAAAGC<br>CGCGGGAGGAGCAGTACAACAGCACGTACCGTGTG<br>GTCAGCGTCCTCACCGTCCTGCACCAGGACTGGCT<br>GAATGGCAAGGAGTACAAGTGCAAGGTCTCCAACAA<br>AGCCCTCCCAGCCCCCATCGAGAAAACCATCTCCAA<br>AGCCAAAGgtgggacccgtggggtgcgagggccacatggacagagg<br>ccggctcggcccaccctctgccctgagagtgaccgctgtaccaacctctgtcc<br>ctacagGGCAGCCCCGAGAACCACAGGTGTACACCCT<br>GCCCCCATCCCGGGATGAGCTGACCAAGAACCAGG<br>TCAGCCTGACCTGCCTGGTCAAAGGCTTCTATCCCA<br>GCGACATCGCCGTGGAGTGGGAGAGCAATGGGCAG<br>CCGGAGAACAACTACAAGACCACGCCTCCCGTGCT<br>GGACTCCGACGGCTCCTTCTTCCTCTACAGCAAGCT<br>CACCGTGGACAAGAGCAGGTGGCAGCAGGGGAACG<br>TCTTCTCATGCTCCGTGATGCATGAGGCTCTGCACA<br>ACCACTACACGCAGAAGAGCCTCTCCCTGTCTCCGG<br>GTAAAGGAGGAGGAGGAAGCGGAGGAGGAGGAAG<br>CGGAGGAGGAGGAAGCGAGGTGCAGCTGCTCGAGA<br>GCGGGGGAGGCTTGGTACAGCCTGGGGGGTCCCT<br>GCGCCTCTCCTGTGCAGCCAGCGGATTCACCTTTTC<br>TTCTTACTACATGGGTTGGGTCCGCCAGGCTCCAGG<br>GAAGGGCTGGAGTGGGTCTCAGGTATTGGTTCTTA<br>CTACGGTTACACAGGTTATGCAGACTCCGTGAAGGG<br>CCGGTTCACCATCTCCCGTGACAATTCCAAGAACAC<br>GCTGTATCTGCAAATGAACAGCCTGCGTGCCGAGGA<br>CACGGCTGTATATTATTGTGCGCGCGCTTACTACGA<br>CTACAACTACTACTACGCTTACTTTGACTATTGGGGC<br>CAGGGAACCCTGGTCACCGTCTCCTCAGGTGGAGG<br>CGGTTCAGGCGGAGGTGGATCCGGCGGTGGCGGAT<br>CGGACATCCAGATGACCCAGTCTCCATCCTCCCTGA<br>GCGCATCTGTAGGAGACCGCGTCACCATCACTTGCC<br>GGGCAAGTCAGAGCATTAGCAGCTATTTAAATTGGT<br>ATCAGCAGAAACCAGGGAAAGCCCCTAAGCTCCTGA<br>TCTATGCTGCATCCAGTTTGCAAAGTGGGGTCCCAT<br>CACGTTTCAGTGGCAGTGGAAGCGGGACAGATTTCA |

TABLE F-continued

Exemplary sequences

| SEQ ID NO. | DESIGNATION | SEQUENCE |
|---|---|---|
| | | CTCTCACCATCAGCAGTCTGCAACCTGAAGATTTTG<br>CAACTTATTACTGTCAACAGTCTGTTCCGCACTACCC<br>GTTCACTTTTGGCCAGGGGACCAAGCTGGAGATCAA<br>ACGC |
| 155 | Fusion of:<br>VH1: 1170 (bold underlined)<br>IgG1 constant domains (italics)<br>Linker (underlined)<br>VH2: 1204 (bold)<br>VL2: 1205 (bold, italics) | <u>EVQLLESGGGLVQPGGSLRLSCAASGFTFGGYYMSW</u><br><u>VRQAPGKGLEWVSYIPGSGGSTYYADSVKGRFTISRD</u><br><u>NSKNTLYLQMNSLRAEDTAVYYCARYDYYWMDYWG</u><br><u>QGTLVTVSS</u>*ASTKGPSVFPLAPSSKSTSGGTAALGCLV*<br>*KDYFPEPVTVSWNSGALTSGVHTFPAVLQSSGLYSLS*<br>*SVVTVPSSSLGTQTYICNVNHKPSNTKVDKKVEPKSCD*<br>*KTHTCPPCPAPELLGGPSVFLFPPKPKDTLMISRTPEV*<br>*TCVVVDVSHEDPEVKFNWYVDGVEVHNAKTKPREEQ*<br>*YNSTYRVVSVLTVLHQDWLNGKEYKCKVSNKALPAPIE*<br>*KTISKAKGQPREPQVYTLPPSRDELTKNQVSLTCLVKG*<br>*FYPSDIAVEWESNGQPENNYKTTPPVLDSDGSFFLYSK*<br>*LTVDKSRWQQGNVFSCSVMHEALHNHYTQKSLSLSP*<br>*GK*<u>GGGGSGGGGSGGGGS</u>EVQLLESGGGLVQPGGSL<br>RLSCAASGFTFSSYYMGWVRQAPGKGLEWVSGIGSY<br>YGYTGYADSVKGRFTISRDNSKNTLYLQMNSLRAEDT<br>AVYYCARAYYDYNYYYAYFDYWGQGTLVTVSS<u>GGGG</u><br><u>SGGGGSGGGGS</u>*DIQMTQSPSSLSASVGDRVTITCRA*<br>*SQSISSYLNWYQQKPGKAPKLLIYAASSLQSGVPSRF*<br>*SGSGSGTDFTLTISSLQPEDFATYYCQQSVPHYPFTFG*<br>*QGTKLEIKR*<br>This sequence typically expressed together with a light chain sequence comprising VL1 1171 (SEQ ID NO: 93) fused to kappa sequence (SEQ ID NO: 136) to assemble a 1170/1171-1204/1205 bispecific antibody. |
| 156 | Nucleotide sequence encoding SEQ ID NO: 155 | GAGGTGCAGCTGTTGGAGAGCGGGGGAGGCTTGGT<br>ACAGCCTGGGGGGTCCCTGCGCCTCTCCTGTGCAG<br>CCAGCGGATTCACCTTTGGTGGTTACTACATGTCTT<br>GGGTCCGCCAGGCTCCAGGGAAGGGGCTGGAGTG<br>GGTCTCATACATTCCTGGTTCTGGTGGTTCTACATAC<br>TATGCAGACTCCGTGAAGGGCCGGTTCACCATCTCC<br>CGTGACAATTCCAAGAACACGCTGTATCTGCAAATG<br>AACAGCCTGCGTGCCGAGGACACGGCTGTATATTAT<br>TGTGCGCGCTACGACTACTACTGGATGGACTATTGG<br>GGCCAGGGAACCCTGGTCACCGTCTCCTCAGGTGA<br>GTTaaCgtacgctagcaagctttctggggcaggccaggcctgaccttggct<br>ttggggcagggaggggggctaaggtgaggcaggtggcgccagccaggtgc<br>acacccaatgcccatgagcccagacactggacgctgaacctcgcggacag<br>ttaagaacccaggggcctctgcgccctgggcccagctctgtcccacaccgc<br>ggtcacatggcaccacctctcttgcagCCTCCACCAAGGGCCCA<br>TCGGTCTTCCCCCTGGCACCCTCCTCCAAGAGCACC<br>TCTGGGGGCACAGCGGCCCTGGGCTGCCTGGTCAA<br>GGACTACTTCCCCGAACCGGTGACGGTGTCGTGGA<br>ACTCAGGCGCCCTGACCAGCGGCGTGCACACCTTC<br>CCGGCTGTCCTACAGTCCTCAGGACTCTACTCCCTC<br>AGCAGCGTGGTGACCGTGCCCTCCAGCAGCTTGGG<br>CACCCAGACCTACATCTGCAACGTGAATCACAAGCC<br>CAGCAACACCAAGGTGGACAAGAAAGTTGgtgagaggc<br>cagcacagggagggagggtgtctgctggaagccaggctcagcgctcctgc<br>ctggacgcatcccgcgtatgcagccccagtccagggcagcaaggcaggcc<br>ccgtctgcctcttcacccggaggcctctgcccgccccactcatgctcagggag<br>agggtcttctggcttttttccccaggctctgggcaggcacaggctaggtgcccct<br>aacccaggccctgcacacaaaggggcaggtgctgggctcagacctgcca<br>agagccatatccgggaggaccctgcccctgacctaagcccacccccaaagg<br>ccaaactctccactccctcagctcggacaccttctctcctcccagattccagta<br>actcccaatcttctctctgcagAGCCCAAATCTTGTGACAAAAC<br>TCACACATGCCCACCGTGCCCAGgtaagccagcccaggcct<br>cgccctccagctcaaggcgggacaggtgccctagagtagcctgcatccagg<br>gacaggccccagccgggtgctgacacgtccacctccatctcttcctcagCA<br>CCTGAACTCCTGGGGGGACCGTCAGTCTTCCTCTTC<br>CCCCCAAAACCCAAGGACACCCTCATGATCTCCCGG<br>ACCCCTGAGGTCACATGCGTGGTGGTGGACGTGAG<br>CCACGAAGACCCTGAGGTCAAGTTCAACTGGTACGT<br>GGACGGCGTGGAGGTGCATAATGCCAAGACAAAGC<br>CGCGGGAGGAGCAGTACAACAGCACGTACCGTGTG<br>GTCAGCGTCCTCACCGTCCTGCACCAGGACTGGCT<br>GAATGGCAAGGAGTACAAGTGCAAGGTCTCCAACAA |

TABLE F-continued

Exemplary sequences

| SEQ ID NO. | DESIGNATION | SEQUENCE |
|---|---|---|
| | | AGCCCTCCCAGCCCCCATCGAGAAAACCATCTCCAA<br>AGCCAAAGgtgggacccgtggggtgcgagggccacatggacagagg<br>ccggctcggcccacccctctgccctgagagtgaccgctgtaccaacctctgtcc<br>ctacagGGCAGCCCCGAGAACCACAGGTGTACACCCT<br>GCCCCCATCCCGGGATGAGCTGACCAAGAACCAGG<br>TCAGCCTGACCTGCCTGGTCAAAGGCTTCTATCCCA<br>GCGACATCGCCGTGGAGTGGGAGAGCAATGGGCAG<br>CCGGAGAACAACTACAAGACCACGCCTCCCGTGCT<br>GGACTCCGACGGCTCCTTCTTCCTCTACAGCAAGCT<br>CACCGTGGACAAGAGCAGGTGGCAGCAGGGGAACG<br>TCTTCTCATGCTCCGTGATGCATGAGGCTCTGCACA<br>ACCACTACACGCAGAAGAGCCTCTCCCTGTCTCCGG<br>GTAAAGGAGGAGGAGGAAGCGGAGGAGGAGGAAG<br>CGGAGGAGGAGGAAGCGAGGTGCAGCTGCTCGAGA<br>GCGGGGGAGGCTTGGTACAGCCTGGGGGGTCCCT<br>GCGCCTCTCCTGTGCAGCCAGCGGATTCACCTTTTC<br>TTCTTACTACATGGGTTGGGTCCGCCAGGCTCCAGG<br>GAAGGGGCTGGAGTGGGTCTCAGGTATTGGTTCTTA<br>CTACGGTTACACAGGTTATGCAGACTCCGTGAAGGG<br>CCGGTTCACCATCTCCCGTGACAATTCCAAGAACAC<br>GCTGTATCTGCAAATGAACAGCCTGCGTGCCGAGGA<br>CACGGCTGTATATTATTGTGCGCGCGCTTACTACGA<br>CTACAACTACTACTACGCTTACTTTGACTATTGGGGC<br>CAGGGAACCCTGGTCACCGTCTCCTCAGGTGGAGG<br>CGGTTCAGGCGGAGGTGGATCCGGCGGTGGCGGAT<br>CGGACATCCAGATGACCCAGTCTCCATCCTCCCTGA<br>GCGCATCTGTAGGAGACCGCGTCACCATCACTTGCC<br>GGGCAAGTCAGAGCATTAGCAGCTATTTAAATTGGT<br>ATCAGCAGAAACCAGGGAAAGCCCCTAAGCTCCTGA<br>TCTATGCTGCATCCAGTTTGCAAAGTGGGGTCCCAT<br>CACGTTTCAGTGGCAGTGGAAGCGGGACAGATTTCA<br>CTCTCACCATCAGCAGTCTGCAACCTGAAGATTTTG<br>CAACTTATTACTGTCAACAGTCTGTTCCGCACTACCC<br>GTTCACTTTTGGCCAGGGGACCAAGCTGGAGATCAA<br>ACGC |
| 157 | Fusion of:<br>VH1: 1482 (bold underlined)<br>IgG1 constant domains (italics)<br>Linker (underlined)<br>VH2: 1204 (bold)<br>VL2: 1205 (bold, italics) | <u>EVQLLESGGGLVQPGGSLRLSCAASGFTFSSYAMSW</u><br><u>VRQAPGKGLEWVSYISYYSGYTYYADSVKGRFTISRD</u><br><u>NSKNTLYLQMNSLRAEDTAVYYCARGYGYLDYWGQ</u><br><u>GTLVTVSS</u>*ASTKGPSVFPLAPSSKSTSGGTAALGCLVK*<br>*DYFPEPVTVSWNSGALTSGVHTFPAVLQSSGLYSLSS*<br>*VVTVPSSSLGTQTYICNVNHKPSNTKVDKKVEPKSCDK*<br>*THTCPPCPAPELLGGPSVFLFPPKPKDTLMISRTPEVT*<br>*CVVVDVSHEDPEVKFNWYVDGVEVHNAKTKPREEQY*<br>*NSTYRVVSVLTVLHQDWLNGKEYKCKVSNKALPAPIEK*<br>*TISKAKGQPREPQVYTLPPSRDELTKNQVSLTCLVKGF*<br>*YPSDIAVEWESNGQPENNYKTTPPVLDSDGSFFLYSKL*<br>*TVDKSRWQQGNVFSCSVMHEALHNHYTQKSLSLSPG*<br>*K*<u>GGGGSGGGGSGGGGS</u>EVQLLESGGGLVQPGGSLR<br>LSCAASGFTFSSYYMGWVRQAPGKGLEWVSGIGSYY<br>GYTGYADSVKGRFTISRDNSKNTLYLQMNSLRAEDTA<br>VYYCARAYYDYNYYYAYFDYWGQGTLVTVSS<u>GGGGS</u><br><u>GGGGSGGGGS</u>*DIQMTQSPSSLSASVGDRVTITCRAS*<br>*QSISSYLNWYQQKPGKAPKLLIYAASSLQSGVPSRFS*<br>*GSGSGTDFTLTISSLQPEDFATYYCQQSVPHYPFTFG*<br>*QGTKLEIKR*<br>This sequence typically expressed together with a light chain sequence comprising VL1 1483 (SEQ ID NO: 103) fused to kappa sequence (SEQ ID NO: 136) to assemble a 1482/1483-1204/1205 bispecific antibody. |
| 158 | Nucleotide sequence encoding SEQ ID NO: 157 | GAGGTGCAGCTGTTGGAGAGCGGGGAGGCTTGGT<br>ACAGCCTGGGGGGTCCCTGCGCCTCTCCTGTGCAG<br>CCAGCGGATTCACCTTTAGCAGCTATGCCATGAGCT<br>GGGTCCGCCAGGCTCCAGGGAAGGGGCTGGAGTG<br>GGTCTCATACATTTCTTACTACTCTGGTTACACATAC<br>TATGCAGACTCCGTGAAGGGCCGGTTCACCATCTCC<br>CGTGACAATTCCAAGAACACGCTGTATCTGCAAATG<br>AACAGCCTGCGTGCCGAGGACACGGCTGTATATTAT<br>TGTGCGCGCGGTTACGGTTACTTGGACTATTGGGGC<br>CAGGGAACCCTGGTCACCGTCTCCTCAGGTGAGTTa<br>aCgtacgctagcaagctttctggggcaggccaggcctgaccttggctttggg |

TABLE F-continued

Exemplary sequences

| SEQ ID NO. | DESIGNATION | SEQUENCE |
|---|---|---|
| | | gcagggagggggctaaggtgaggcaggtggcgccagccaggtgcacac |
| | | ccaatgcccatgagcccagacactggacgctgaacctcgcggacagttaa |
| | | gaacccaggggcctctgcgccctgggcccagctctgtcccacaccgcggtc |
| | | acatggcaccacctctcttgcagCCTCCACCAAGGGCCCATCG |
| | | GTCTTCCCCCTGGCACCCTCCTCCAAGAGCACCTCT |
| | | GGGGGCACAGCGGCCCTGGGCTGCCTGGTCAAGG |
| | | ACTACTTCCCCGAACCGGTGACGGTGTCGTGGAACT |
| | | CAGGCGCCCTGACCAGCGGCGTGCACACCTTCCCG |
| | | GCTGTCCTACAGTCCTCAGGACTCTACTCCCTCAGC |
| | | AGCGTGGTGACCGTGCCCTCCAGCAGCTTGGGCAC |
| | | CCAGACCTACATCTGCAACGTGAATCACAAGCCCAG |
| | | CAACACCAAGGTGGACAAGAAAGTTGgtgagaggccagc |
| | | acagggagggagggtgtctgctggaagccaggctcagcgctcctgcctgga |
| | | cgcatcccggctatgcagccccagtccagggcagcaaggcaggccccgtc |
| | | tgcctcttcaccggaggcctctgcccgccccactcatgctcagggagaggg |
| | | tcttctggcttttccccaggctctgggcaggcacaggctaggtgccctaacc |
| | | caggccctgcacacaaaggggcaggtgctgggctcagacctgccaagag |
| | | ccatatccgggaggaccctgccctgacctaagcccaccccaaaggccaa |
| | | actctccactccctcagctcggacaccttctctcctcccagattccagtaactcc |
| | | caatcttctctctgcagAGCCCAAATCTTGTGACAAAACTCAC |
| | | ACATGCCCACCGTGCCCAGgtaagccagcccaggcctcgccct |
| | | ccagctcaaggcgggacaggtgcccctagagtagcctgcatccagggacag |
| | | gccccagccgggtgctgacacgtccacctccatctcttcctcagCACCTG |
| | | AACTCCTGGGGGGACCGTCAGTCTTCCTCTTCCCCC |
| | | CAAAACCCAAGGACACCCTCATGATCTCCCGGACCC |
| | | CTGAGGTCACATGCGTGGTGGTGGACGTGAGCCAC |
| | | GAAGACCCTGAGGTCAAGTTCAACTGGTACGTGGAC |
| | | GGCGTGGAGGTGCATAATGCCAAGACAAAGCCGCG |
| | | GGAGGAGCAGTACAACAGCACGTACCGTGTGGTCA |
| | | GCGTCCTCACCGTCCTGCACCAGGACTGGCTGAAT |
| | | GGCAAGGAGTACAAGTGCAAGGTCTCCAACAAAGCC |
| | | CTCCCAGCCCCCATCGAGAAAACCATCTCCAAAGCC |
| | | AAAGgtgggacccgtggggtgcgagggccacatggacagaggccggct |
| | | cggcccaccctctgccctgagagtgaccgctgtaccaacctctgtccctacag |
| | | GGCAGCCCCGAGAACCACAGGTGTACACCCTGCCC |
| | | CCATCCCGGGATGAGCTGACCAAGAACCAGGTCAG |
| | | CCTGACCTGCCTGGTCAAAGGCTTCTATCCCAGCGA |
| | | CATCGCCGTGGAGTGGGAGAGCAATGGGCAGCCGG |
| | | AGAACAACTACAAGACCACGCCTCCCGTGCTGGACT |
| | | CCGACGGCTCCTTCTTCCTCTACAGCAAGCTCACCG |
| | | TGGACAAGAGCAGGTGGCAGCAGGGGAACGTCTTC |
| | | TCATGCTCCGTGATGCATGAGGCTCTGCACAACCAC |
| | | TACACGCAGAAGAGCCTCTCCCTGTCTCCGGGTAAA |
| | | GGAGGAGGAGGAAGCGGAGGAGGAGGAAGCGGAG |
| | | GAGGAGGAAGCGAGGTGCAGCTGCTCGAGAGCGG |
| | | GGGAGGCTTGGTACAGCCTGGGGGGTCCCTGCGCC |
| | | TCTCCTGTGCAGCCAGCGGATTCACCTTTTCTTCTTA |
| | | CTACATGGGTTGGGTCCGCCAGGCTCCAGGGAAGG |
| | | GGCTGGAGTGGGTCTCAGGTATTGGTTCTTACTACG |
| | | GTTACACAGGTTATGCAGACTCCGTGAAGGGCCGGT |
| | | TCACCATCTCCCGTGACAATTCCAAGAACACGCTGT |
| | | ATCTGCAAATGAACAGCCTGCGTGCCGAGGACACG |
| | | GCTGTATATTATTGTGCGCGCGCTTACTACGACTACA |
| | | ACTACTACTACGCTTACTTTGACTATTGGGGCCAGG |
| | | GAACCCTGGTCACCGTCTCCTCAGGTGGAGGCGGT |
| | | TCAGGCGGAGGTGGATCCGGCGGTGGCGGATCGG |
| | | ACATCCAGATGACCCAGTCTCCATCCTCCCTGAGCG |
| | | CATCTGTAGGAGACCGCGTCACCATCACTTGCCGGG |
| | | CAAGTCAGAGCATTAGCAGCTATTTAAATTGGTATCA |
| | | GCAGAAACCAGGGAAAGCCCCTAAGCTCCTGATCTA |
| | | TGCTGCATCCAGTTTGCAAAGTGGGGTCCCATCACG |
| | | TTTCAGTGGCAGTGGAAGCGGGACAGATTTCACTCT |
| | | CACCATCAGCAGTCTGCAACCTGAAGATTTTGCAAC |
| | | TTATTACTGTCAACAGTCTGTTCCGCACTACCCGTTC |
| | | ACTTTTGGCCAGGGGACCAAGCTGGAGATCAAACGC |

TABLE F-continued

Exemplary sequences

| SEQ ID NO. | DESIGNATION | SEQUENCE |
|---|---|---|
| 159 | Fusion of:<br>VH1: 1520 (bold underlined)<br>Ig G1 constant domains (italics)<br>Linker (underlined)<br>VH2: 1204 (bold)<br>VL2: 1205 (bold, italics) | <u>EVQLLESGGGLVQPGGSLRLSCAASGFTFSSYAMSW</u><br><u>VRQAPGKGLEWVSAISGSGGSTYYADSVKGRFTISRD</u><br><u>NSKNTLYLQMNSLRAEDTAVYYCARYYYSHGYYVYG</u><br><u>TLDYWGQGTLVTVSS</u>_ASTKGPSVFPLAPSSKSTSGGT_<br>_AALGCLVKDYFPEPVTVSWNSGALTSGVHTFPAVLQS_<br>_SGLYSLSSVVTVPSSSLGTQTYICNVNHKPSNTKVDKK_<br>_VEPKSCDKTHTCPPCPAPELLGGPSVFLFPPKPKDTLM_<br>_ISRTPEVTCVVVDVSHEDPEVKFNWYVDGVEVHNAKT_<br>_KPREEQYNSTYRVVSVLTVLHQDWLNGKEYKCKVSNK_<br>_ALPAPIEKTISKAKGQPREPQVYTLPPSRDELTKNQVSL_<br>_TCLVKGFYPSDIAVEWESNGQPENNYKTTPPVLDSDG_<br>_SFFLYSKLTVDKSRWQQGNVFSCSVMHEALHNHYTQK_<br>_SLSLSPGK_<u>GGGGSGGGGSGGGGS</u>EVQLLESGGGLV<br>QPGGSLRLSCAASGFTFSSYYMGWVRQAPGKGLEW<br>VSGIGSYYGYTGYADSVKGRFTISRDNSKNTLYLQMN<br>SLRAEDTAVYYCARAYYDYNYYAYFDYWGQGTLVT<br>VSS<u>GGGGSGGGGSGGGGS</u>_DIQMTQSPSSLSASVGD_<br>_RVTITCRASQSISSYLNWYQQKPGKAPKLLIYAASSLQ_<br>_SGVPSRFSGSGSGTDFTLTISSLQPEDFATYYCQQSV_<br>_PHYPFTFGQGTKLEIKR_<br>This sequence typically expressed together with a light chain sequence comprising VL1 1135 (SEQ ID NO: 97) fused to kappa sequence (SEQ ID NO: 136) to assemble a 1520/1135-1204/1205 bispecific antibody. |
| 160 | Nucleotide sequence encoding SEQ ID NO: 159 | GAGGTGCAGCTGTTGGAGAGCGGGGGAGGCTTGGT<br>ACAGCCTGGGGGGTCCCTGCGCCTCTCCTGTGCAG<br>CCAGCGGATTCACCTTTAGCAGCTATGCCATGAGCT<br>GGGTCCGCCAGGCTCCAGGGAAGGGGCTGGAGTG<br>GGTCTCAGCTATTAGTGGTAGTGGTGGTAGCACATA<br>CTATGCAGACTCCGTGAAGGGCCGGTTCACCATCTC<br>CCGTGACAATTCCAAGAACACGCTGTATCTGCAAAT<br>GAACAGCCTGCGTGCCGAGGACACGGCTGTATATTA<br>TTGTGCGCGCTACTACTACTCTCATGGTTACTACGTT<br>TACGGTACTTTGGACTATTGGGGCCAGGGAACCCTG<br>GTCACCGTCTCCTCAGGTGAGTTaaCgtacgctagcaagctt<br>tctggggcaggccaggcctgaccttggctttggggcaggagggggctaag<br>gtgaggcaggtggcgccagccaggtgcacacccaatgccccatgagccca<br>gacactggacgctgaacctcgcggacagttaagaacccaggggcctctgc<br>gccctgggcccagctctgtcccacaccgcggtcacatggcaccacctctcttg<br>cagCCTCCACCAAGGGCCCATCGGTCTTCCCCCTGG<br>CACCCTCCTCCAAGAGCACCTCTGGGGGCACAGCG<br>GCCCTGGGCTGCCTGGTCAAGGACTACTTCCCCGA<br>ACCGGTGACGGTGTCGTGGAACTCAGGCGCCCTGA<br>CCAGCGGCGTGCACACCTTCCCGGCTGTCCTACAG<br>TCCTCAGGACTCTACTCCCTCAGCAGCGTGGTGACC<br>GTGCCCTCCAGCAGCTTGGGCACCCAGACCTACATC<br>TGCAACGTGAATCACAAGCCCAGCAACACCAAGGTG<br>GACAAGAAAGTTGgtgagaggccagcacagggaggagggtgtc<br>tgctggaagccaggctcagcgctcctgcctggacgcatcccggctatgcagc<br>cccagtccagggcagcaaggcaggccccgtctgcctcttcacccggaggc<br>ctctgcccgccccactcatgctcagggagagggtcttctggcttttttccccagg<br>ctctgggcaggcacaggctaggtgcccctaacccaggccctgcacacaaa<br>ggggcaggtgctgggctcagacctgccaagagcatatccggaggaccc<br>tgcccctgacctaagcccacccaaaggccaaactctccactccctcagctc<br>ggacaccttctctcctcccagattccagtaactcccaatcttctctctgcagAG<br>CCCAAATCTTGTGACAAAACTCACACATGCCCACCG<br>TGCCCAGgtaagccagcccaggcctcgccctccagctcaaggcggga<br>caggtgcccctagagtagcctgcatccagggacaggccccagccgggtgct<br>gacacgtccacctccatctcttcctcagCACCTGAACTCCTGGGG<br>GGACCGTCAGTCTTCCTCTTCCCCCCAAAACCCAAG<br>GACACCCTCATGATCTCCCGGACCCCTGAGGTCACA<br>TGCGTGGTGGTGGACGTGAGCCACGAAGACCCTGA<br>GGTCAAGTTCAACTGGTACGTGGACGGCGTGGAGG<br>TGCATAATGCCAAGACAAAGCCGCGGGAGGAGCAG<br>TACAACAGCACGTACCGTGTGGTCAGCGTCCTCACC<br>GTCCTGCACCAGGACTGGCTGAATGGCAAGGAGTA<br>CAAGTGCAAGGTCTCCAACAAAGCCCTCCCAGCCCC<br>CATCGAGAAAACCATCTCCAAAGCCAAAGgtgggacccg<br>tggggtgcgagggccacatggacagaggccggctcggcccaccctctgcc<br>ctgagagtgaccgctgtaccaacctctgtccctacagGGCAGCCCCG |

TABLE F-continued

Exemplary sequences

| SEQ ID NO. | DESIGNATION | SEQUENCE |
|---|---|---|
| | | AGAACCACAGGTGTACACCCTGCCCCCATCCCGGG<br>ATGAGCTGACCAAGAACCAGGTCAGCCTGACCTGCC<br>TGGTCAAAGGCTTCTATCCCAGCGACATCGCCGTGG<br>AGTGGGAGAGCAATGGGCAGCCGGAGAACAACTAC<br>AAGACCACGCCTCCCGTGCTGGACTCCGACGGCTC<br>CTTCTTCCTCTACAGCAAGCTCACCGTGGACAAGAG<br>CAGGTGGCAGCAGGGGAACGTCTTCTCATGCTCCG<br>TGATGCATGAGGCTCTGCACAACCACTACACGCAGA<br>AGAGCCTCTCCCTGTCTCCGGGTAAAGGAGGAGGA<br>GGAAGCGGAGGAGGAGGAAGCGGAGGAGGAGGAA<br>GCGAGGTGCAGCTGCTCGAGAGCGGGGAGGCTT<br>GGTACAGCCTGGGGGGTCCCTGCGCCTCTCCTGTG<br>CAGCCAGCGGATTCACCTTTTCTTCTTACTACATGGG<br>TTGGGTCCGCCAGGCTCCAGGGAAGGGGCTGGAGT<br>GGGTCTCAGGTATTGGTTCTTACTACGGTTACACAG<br>GTTATGCAGACTCCGTGAAGGGCCGGTTCACCATCT<br>CCCGTGACAATTCCAAGAACACGCTGTATCTGCAAA<br>TGAACAGCCTGCGTGCCGAGGACACGGCTGTATATT<br>ATTGTGCGCGCTTACTACGACTACAACTACTACTA<br>CGCTTACTTTGACTATTGGGGCCAGGGAACCCTGGT<br>CACCGTCTCCTCAGGTGGAGGCGGTTCAGGCGGAG<br>GTGGATCCGGCGGTGGCGGATCGGACATCCAGATG<br>ACCCAGTCTCCATCCTCCCTGAGCGCATCTGTAGGA<br>GACCGCGTCACCATCACTTGCCGGGCAAGTCAGAG<br>CATTAGCAGCTATTTAAATTGGTATCAGCAGAAACCA<br>GGGAAAGCCCCTAAGCTCCTGATCTATGCTGCATCC<br>AGTTTGCAAAGTGGGGTCCCATCACGTTTCAGTGGC<br>AGTGGAAGCGGGACAGATTTCACTCTCACCATCAGC<br>AGTCTGCAACCTGAAGATTTTGCAACTTATTACTGTC<br>AACAGTCTGTTCCGCACTACCCGTTCACTTTTGGCC<br>AGGGGACCAAGCTGGAGATCAAACGC |
| 161 | Fusion of:<br>VH1: 1526 (bold underlined)<br>Ig G1 constant domains (italics)<br>Linker (underlined)<br>VH2: 1204 (bold)<br>VL2: 1205 (bold, italics) | EVQLLESGGGLVQPGGSLRLSCAASGFTFSGYSMYW<br>VRQAPGKGLEWVSGIGYSGYGTYYADSVKGRFTISRD<br>NSKNTLYLQMNSLRAEDTAVYYCARYYFHDYAAYSL<br>DYWGQGTLVTVSS_ASTKGPSVFPLAPSSKSTSGGTAA_<br>_LGCLVKDYFPEPVTVSWNSGALTSGVHTFPAVLQSSG_<br>_LYSLSSVVTVPSSSLGTQTYICNVNHKPSNTKVDKKVE_<br>_PKSCDKTHTCPPCPAPELLGGPSVFLFPPKPKDTLMIS_<br>_RTPEVTCVVVDVSHEDPEVKFNWYVDGVEVHNAKTKP_<br>_REEQYNSTYRVVSVLTVLHQDWLNGKEYKCKVSNKAL_<br>_PAPIEKTISKAKGQPREPQVYTLPPSRDELTKNQVSLTC_<br>_LVKGFYPSDIAVEWESNGQPENNYKTTPPVLDSDGSF_<br>_FLYSKLTVDKSRWQQGNVFSCSVMHEALHNHYTQKSL_<br>_SLSPGK_<u>GGGGSGGGGSGGGGS</u>EVQLLESGGGLVQP<br>GGSLRLSCAASGFTFSSYYMGWVRQAPGKGLEWVS<br>GIGSYYGYTGYADSVKGRFTISRDNSKNTLYLQMNSL<br>RAEDTAVYYCARAYYDYNYYYAYFDYWGQGTLVTVS<br>S<u>GGGGSGGGGSGGGGS</u>_DIQMTQSPSSLSASVGDRV_<br>_TITCRASQSISSYLNWYQQKPGKAPKLLIYAASSLQSG_<br>_VPSRFSGSGSGTDFTLTISSLQPEDFATYYCQQSVPH_<br>_YPFTFGQGTKLEIKR_<br>This sequence typically expressed together with a light chain sequence comprising VL1 1527 (SEQ ID NO: 119) fused to kappa sequence (SEQ ID NO: 136) to assemble a 1526/1527-1204/1205 bispecific antibody. |
| 162 | Nucleotide sequence encoding SEQ ID NO: 161 | GAGGTGCAGCTGTTGGAGAGCGGGGGAGGCTTGGT<br>ACAGCCTGGGGGGTCCCTGCGCCTCTCCTGTGCAG<br>CCAGCGGATTCACCTTTTCTGGTTACTCTATGTACTG<br>GGTCCGCCAGGCTCCAGGGAAGGGGCTGGAGTGG<br>GTCTCAGGTATTGGTTACTCTGGTTACGGTACATACT<br>ATGCAGACTCCGTGAAGGGCCGGTTCACCATCTCCC<br>GTGACAATTCCAAGAACACGCTGTATCTGCAAATGA<br>ACAGCCTGCGTGCCGAGGACACGGCTGTATATTATT<br>GTGCGCGCTACTACTTCCATGACTACGCTGCTTACT<br>CTTTGGACTATTGGGGCCAGGGAACCCTGGTCACC<br>GTCTCCTCA<br>GGTGAGTTaaCgtacgctagcaagcttctggggcaggccaggcctg<br>accttggctttggggcagggaggggctaaggtgaggcaggtggcgccag<br>ccaggtgcacacccaatgcccatgagcccagacactggacgctgaacctc<br>gcggacagttaagaacccaggggcctctgcgccctgggcccagctctgtcc |

TABLE F-continued

Exemplary sequences

| SEQ ID NO. | DESIGNATION | SEQUENCE |
|---|---|---|
| | | cacaccgcggtcacatggcaccacctctcttgcagCCTCCACCAAG GGCCCATCGGTCTTCCCCCTGGCACCCTCCTCCAAG AGCACCTCTGGGGGCACAGCGGCCCTGGGCTGCCT GGTCAAGGACTACTTCCCCGAACCGGTGACGGTGT CGTGGAACTCAGGCGCCCTGACCAGCGGCGTGCAC ACCTTCCCGGCTGTCCTACAGTCCTCAGGACTCTAC TCCCTCAGCAGCGTGGTGACCGTGCCCTCCAGCAG CTTGGGCACCCAGACCTACATCTGCAACGTGAATCA CAAGCCCAGCAACACCAAGGTGGACAAGAAAGTTGg tgagaggccagcacagggagggagggtgtctgctggaagccaggctcag cgctcctgcctggacgcatcccggctatgcagccccagtccagggcagcaa ggcaggcccgtctgcctcttcacccggaggcctctgcccgcccactcatg ctcagggagagggtcttctggcttttcccaggctctgggcaggcacaggct aggtgccctaacccaggccctgcacacaaaggggcaggtgctgggctca gacctgccaagagccatatccgggaggaccctgcccctgacctaagccca ccccaaaggccaaactctccactccctcagctcggacacctttctctcctccca gattccagtaactcccaatcttctctctgcagAGCCCAAATCTTGTGA CAAAACTCACACATGCCCACCGTGCCCAGgtaagccag cccaggcctcgcctccagctcaaggcgggacaggtgccctagagtagcct gcatccagggacaggccccagccgggtgctgacacgtccacctccatctctt cctcagCACCTGAACTCCTGGGGGGACCGTCAGTCTT CCTCTTCCCCCCAAAACCCAAGGACACCCTCATGAT CTCCCGGACCCCTGAGGTCACATGCGTGGTGGTGG ACGTGAGCCACGAAGACCCTGAGGTCAAGTTCAACT GGTACGTGGACGGCGTGGAGGTGCATAATGCCAAG ACAAAGCCGCGGGAGGAGCAGTACAACAGCACGTA CCGTGTGGTCAGCGTCCTCACCGTCCTGCACCAGG ACTGGCTGAATGGCAAGGAGTACAAGTGCAAGGTCT CCAACAAAGCCCTCCCAGCCCCCATCGAGAAAACCA TCTCCAAAGCCAAAGgtgggacccgtggggtgcgagggccacat ggacagaggccggctcggcccaccctctgccctgagagtgaccgctgtacc aacctctgtccctacagGGCAGCCCCGAGAACCACAGGTGT ACACCCTGCCCCCATCCCGGGATGAGCTGACCAAG AACCAGGTCAGCCTGACCTGCCTGGTCAAAGGCTTC TATCCCAGCGACATCGCCGTGGAGTGGGAGAGCAA TGGGCAGCCGGAGAACAACTACAAGACCACGCCTC CCGTGCTGGACTCCGACGGCTCCTTCTTCCTCTACA GCAAGCTCACCGTGGACAAGAGCAGGTGGCAGCAG GGGAACGTCTTCTCATGCTCCGTGATGCATGAGGCT CTGCACAACCACTACACGCAGAAGAGCCTCTCCCTG TCTCCGGGTAAAGGAGGAGGAGGAAGCGGAGGAGG AGGAAGCGGAGGAGGAGGAAGCGAGGTGCAGCTG CTCGAGAGCGGGGGAGGCTTGGTACAGCCTGGGG GGTCCCTGCGCCTCTCCTGTGCAGCCAGCGGATTC ACCTTTTCTTCTTACTACATGGGTTGGGTCCGCCAG GCTCCAGGGAAGGGGCTGGAGTGGGTCTCAGGTAT TGGTTCTTACTACGGTTACACAGGTTATGCAGACTCC GTGAAGGGCCGGTTCACCATCTCCCGTGACAATTCC AAGAACACGCTGTATCTGCAAATGAACAGCCTGCGT GCCGAGGACACGGCTGTATATTATTGTGCGCGCGCT TACTACGACTACAACTACTACTACGCTTACTTTGACT ATTGGGGCCAGGGAACCCTGGTCACCGTCTCCTCA GGTGGAGGCGGTTCAGGCGGAGGTGGATCCGGCG GTGGCGGATCGGACATCCAGATGACCCAGTCTCCAT CCTCCCTGAGCGCATCTGTAGGAGACCGCGTCACC ATCACTTGCCGGGCAAGTCAGAGCATTAGCAGCTAT TTAAATTGGTATCAGCAGAAACAGGGAAAGCCCCT AAGCTCCTGATCTATGCTGCATCCAGTTTGCAAAGT GGGGTCCCATCACGTTTCAGTGGCAGTGGAAGCGG GACAGATTTCACTCTCACCATCAGCAGTCTGCAACC TGAAGATTTTGCAACTTATTACTGTCAACAGTCTGTT CCGCACTACCCGTTCACTTTTGGCCAGGGGACCAAG CTGGAGATCAAACGC |

TABLE F-continued

Exemplary sequences

| SEQ ID NO. | DESIGNATION | SEQUENCE |
|---|---|---|
| 163 | Fusion of:<br>VH1: 1542 (bold underlined)<br>IgG1 constant domains (italics)<br>Linker (underlined)<br>VH2: 1204 (bold)<br>VL2: 1205 (bold, italics) | EVQLLESGGGLVQPGGSLRLSCAASGFTFGSSSMYW<br>VRQAPGKGLEWVSGIGYYSYSTSYADSVKGRFTISRD<br>NSKNTLYLQMNSLRAEDTAVYYCARGYPHHYFDYWG<br>QGTLVTVSS_ASTKGPSVFPLAPSSKSTSGGTAALGCLV<br>KDYFPEPVTVSWNSGALTSGVHTFPAVLQSSGLYSLS<br>SVVTVPSSSLGTQTYICNVNHKPSNTKVDKKVEPKSCD<br>KTHTCPPCPAPELLGGPSVFLFPPKPKDTLMISRTPEV<br>TCVVVDVSHEDPEVKFNWYVDGVEVHNAKTKPREEQ<br>YNSTYRVVSVLTVLHQDWLNGKEYKCKVSNKALPAPIE<br>KTISKAKGQPREPQVYTLPPSRDELTKNQVSLTCLVKG<br>FYPSDIAVEWESNGQPENNYKTTPPVLDSDGSFFLYSK<br>LTVDKSRWQQGNVFSCSVMHEALHNHYTQKSLSLSP<br>GK_<u>GGGGSGGGGSGGGGS</u>EVQLLESGGGLVQPGGSL<br>RLSCAASGFTFSSYYMGWVRQAPGKGLEWVSGIGSY<br>YGYTGYADSVKGRFTISRDNSKNTLYLQMNSLRAEDT<br>AVYYCARAYYDYNYYYAYFDYWGQGTLVTVSS<u>GGGG<br>SGGGGSGGGGS</u>_DIQMTQSPSSLSASVGDRVTITCRA<br>SQSISSYLNWYQQKPGKAPKLLIYAASSLQSGVPSRF<br>SGSGSGTDFTLTISSLQPEDFATYYCQQSVPHYPFTFG<br>QGTKLEIKR_<br>This sequence typically expressed together with a light chain sequence comprising VL1 1135 (SEQ ID NO: 97) fused to kappa sequence (SEQ ID NO: 136) to assemble a 1542/1135-1204/1205 bispecific antibody. |
| 164 | Nucleotide sequence encoding SEQ ID NO: 163 | GAGGTGCAGCTGTTGGAGAGCGGGGGAGGCTTGGT<br>ACAGCCTGGGGGGTCCCTGCGCCTCTCCTGTGCAG<br>CCAGCGGATTCACCTTTGGTTCTTCTTCTATGTACTG<br>GGTCCGCCAGGCTCCAGGGAAGGGGCTGGAGTGG<br>GTCTCAGGTATTGGTTACTACTCTTACTCTACATCTT<br>ATGCAGACTCCGTGAAGGGCCGGTTCACCATCTCCC<br>GTGACAATTCCAAGAACACGCTGTATCTGCAAATGA<br>ACAGCCTGCGTGCCGAGGACACGGCTGTATATTATT<br>GTGCGCGCGGTTACCCGCATCATTACTTTGACTATT<br>GGGGCCAGGGAACCCTGGTCACCGTCTCCTCAGGT<br>GAGTTaaCgtacgctagcaagctttctggggcaggccaggcctgaccttg<br>gcttgggcagggaggggctaaggtgaggcaggtggcgccagccag<br>gtgcacacccaatgcccatgagcccagacactggacgctgaacctcgcgg<br>acagttaagaacccaggggcctctgcgccctgggcccagctctgtcccaca<br>ccgcggtcacatggcaccacctctcttgcagCCTCCACCAAGGGC<br>CCATCGGTCTTCCCCCTGGCACCCTCCTCCAAGAGC<br>ACCTCTGGGGGCACAGCGGCCCTGGGCTGCCTGGT<br>CAAGGACTACTTCCCCGAACCGGTGACGGTGTCGT<br>GGAACTCAGGCGCCCTGACCAGCGGCGTGCACACC<br>TTCCCGGCTGTCCTACAGTCCTCAGGACTCTACTCC<br>CTCAGCAGCGTGGTGACCGTGCCCTCCAGCAGCTT<br>GGGCACCCAGACCTACATCTGCAACGTGAATCACAA<br>GCCCAGCAACACCAAGGTGGACAAGAAAGTTGgtgag<br>aggccagcacagggagggagggtgtctgctggaagccaggctcagcgctc<br>ctgcctggacgcatcccggctatgcagcccagtccagggcagcaaggca<br>ggcccgtctgcctcttcacccggaggcctctgccgcccactcatgctcag<br>ggagagggtcttctggcttttttcccaggctctgggcaggcacaggctaggtg<br>cccctaacccaggccctgcacacaaaggggcaggtgctgggctcagacct<br>gccaagagccatatccgggaggaccctgcccctgacctaagcccaccca<br>aaggccaaactctccactccctcagctcggacaccttctctcctcccagattcc<br>agtaactcccaatcttctctctgcagAGCCCAAATCTTGTGACAA<br>AACTCACACATGCCCACCGTGCCCAGgtaagccagccca<br>ggcctcgccctccagctcaaggcgggacaggtgccctagagtagcctgcat<br>ccaggacaggcccagccgggtgctgacacgtccacctccatctcttcctc<br>agCACCTGAACTCCTGGGGGGACCGTCAGTCTTCCT<br>CTTCCCCCCAAAACCCAAGGACACCCTCATGATCTC<br>CCGGACCCCTGAGGTCACATGCGTGGTGGTGGACG<br>TGAGCCACGAAGACCCTGAGGTCAAGTTCAACTGGT<br>ACGTGGACGGCGTGGAGGTGCATAATGCCAAGACA<br>AAGCCGCGGGAGGAGCAGTACAACAGCACGTACCG<br>TGTGGTCAGCGTCCTCACCGTCCTGCACCAGGACTG<br>GCTGAATGGCAAGGAGTACAAGTGCAAGGTCTCCAA<br>CAAAGCCCTCCCAGCCCCCATCGAGAAAACCATCTC<br>CAAAGCCAAAGgtgggacccgtggggtgcgagggccacatggaca<br>gaggccggctcggcccaccctctgccctgagagtgaccgctgtaccaacct<br>ctgtccctacagGGCAGCCCCGAGAACCACAGGTGTACA |

TABLE F-continued

Exemplary sequences

| SEQ ID NO. | DESIGNATION | SEQUENCE |
|---|---|---|
| | | CCCTGCCCCCATCCCGGGATGAGCTGACCAAGAAC CAGGTCAGCCTGACCTGCCTGGTCAAAGGCTTCTAT CCCAGCGACATCGCCGTGGAGTGGGAGAGCAATGG GCAGCCGGAGAACAACTACAAGACCACGCCTCCCG TGCTGGACTCCGACGGCTCCTTCTTCCTCTACAGCA AGCTCACCGTGGACAAGAGCAGGTGGCAGCAGGGG AACGTCTTCTCATGCTCCGTGATGCATGAGGCTCTG CACAACCACTACACGCAGAAGAGCCTCTCCCTGTCT CCGGGTAAAGGAGGAGGAGGAAGCGGAGGAGGAG GAAGCGGAGGAGGAGGAAGCGAGGTGCAGCTGCTC GAGAGCGGGGGAGGCTTGGTACAGCCTGGGGGGT CCCTGCGCCTCTCCTGTGCAGCCAGCGGATTCACCT TTTCTTCTTACTACATGGGTTGGGTCCGCCAGGCTC CAGGGAAGGGGCTGGAGTGGGTCTCAGGTATTGGT TCTTACTACGGTTACACAGGTTATGCAGACTCCGTG AAGGGCCGGTTCACCATCTCCCGTGACAATTCCAAG AACACGCTGTATCTGCAAATGAACAGCCTGCGTGCC GAGGACACGGCTGTATATTATTGTGCGCGCGCTTAC TACGACTACAACTACTACTACGCTTACTTTGACTATT GGGGCCAGGGAACCCTGGTCACCGTCTCCTCAGGT GGAGGCGGTTCAGGCGGAGGTGGATCCGGCGGTG GCGGATCGGACATCCAGATGACCCAGTCTCCATCCT CCCTGAGCGCATCTGTAGGAGACCGCGTCACCATCA CTTGCCGGGCAAGTCAGAGCATTAGCAGCTATTTAA ATTGGTATCAGCAGAAACCAGGGAAAGCCCCTAAGC TCCTGATCTATGCTGCATCCAGTTTGCAAAGTGGGG TCCCATCACGTTTCAGTGGCAGTGGAAGCGGGACA GATTTCACTCTCACCATCAGCAGTCTGCAACCTGAA GATTTTGCAACTTATTACTGTCAACAGTCTGTTCCGC ACTACCCGTTCACTTTTGGCCAGGGGACCAAGCTGG AGATCAAACGC |

TABLE G

Exemplary sequences

| SEQ ID NO. | DESIGNATION | SEQUENCE |
|---|---|---|
| 165 | Fusion of: VL1: 1135 (bold underlined) kappa constant domains (italics) (i.e. fusion of SEQ ID NOS: 97 and 136) | DIQMTQSPSSLSASVGDRVTITCRAS QSISSYLNWYQQKPGKAPKLLIYAAS SLQSGVPSRFSGSGSGTDFTLTISSL QPEDFATYYCQQSYSTPYTFGQGTKL EIK_RTVAAPSVFIFPPSDEQLKSGTA SVVCLLNNFYPREAKVQWKVDNALQS GNSQESVTEQDSKDSTYSLSSTLTLS KADYEKHKVYACEVTHQGLSSPVTKS FNRGEC_ May assemble with any one of SEQ ID NOs: 149, 153, 159 or 163 to form a 1164/1135-1204/1205, 1168/1135-1204/1205, 1520/1135-1204/1205 or 1542/1135-1204/1205 bispecific antibody. |
| 166 | Nucleotide encoding SEQ ID NO: 165 | GACATCCAGATGACCCAGTCTCCATC CTCCCTGAGCGCATCTGTAGGAGACC GCGTCACCATCACTTGCCGGGCAAGT CAGAGCATTAGCAGCTATTTAAATTG GTATCAGCAGAAACCAGGGAAAGCCC CTAAGCTCCTGATCTATGCTGCATCC AGTTTGCAAAGTGGGGTCCCATCACG TTTCAGTGGCAGTGGAAGCGGGACAG ATTTCACTCTCACCATCAGCAGTCTG CAACCTGAAGATTTTGCAACTTATTA CTGTCAACAGAGTTACAGTACCCCTT ATACTTTTGGCCAGGGGACCAAGCTG GAGATCAAACgtgagtcgtacgctag caagcttgatatcgaattctaaactc tgaggggtcggatgacgtggccatt ctttgcctaaagcattgagtttactg caaggtcagaaaagcatgcaaagccc tcagaatggctgcaaagagctccaac aaaacaatttagaactttattaagga ataggggaagctaggaagaaactca aaacatcaagattttaaatacgcttc ttggtctccttgctataattatctgg gataagcatgctgttttctgtctgtc cctaacatgccctgtgattatccgca aacaacacacccaagggcagaacttt gttacttaaacaccatcctgtttgct tctttcctcagGAACTGTGGCTGCAC CATCTGTCTTCATCTTCCCGCCATCT GATGAGCAGTTGAAATCTGGAACTGC CTGTTGTGTGCCTGCTGAATAACT TCTATCCCAGAGAGGCCAAAGTACAG TGGAAGGTGGATAACGCCCTCCAATC GGGTAACTCCCAGGAGAGTGTCACAG AGCAGGACAGCAAGGACAGCACCTAC AGCCTCAGCAGCACCCTGACGCTGAG CAAAGCAGACTACGAGAAACACAAAG TCTACGCCTGCGAAGTCACCCATCAG GGCCTGAGCTCGCCCGTCACAAAGAG CTTCAACAGGGGAGAGTGT |

TABLE G-continued

Exemplary sequences

| SEQ ID NO. | DESIGNATION | SEQUENCE |
|---|---|---|
| 167 | Fusion of: VL1: 1167 (bold underlined) kappa constant domains (italics) (i.e. fusion of SEQ ID NOS: 89 and 136) | DIQMTQSPSSLSASVGDRVTITCRAS QSISSYLNWYQQKPGKAPKLLIYAAS SLQSGVPSRFSGSGSGTDFTLTISSL QPEDFATYYCQQYYWYGLSTFGQGTK LEIK_RTVAAPSVFIFPPSDEQLKSGT ASVVCLLNNFYPREAKVQWKVDNALQ SGNSQESVTEQDSKDSTYSLSSTLTL SKADYEKHKVYACEVTHQGLSSPVTK SFNRGEC_ May assemble with SEQ ID NO: 151 to form a 1166/1167-1204/1205 bispecific antibody. |
| 168 | Nucleotide encoding SEQ ID NO: 167 | _GACATCCAGATGACCCAGTCTCCATC CTCCCTGAGCGCATCTGTAGGAGACC GCGTCACCATCACTTGCCGGGCAAGT CAGAGCATTAGCAGCTATTTAAATTG GTATCAGCAGAAACCAGGGAAAGCCC CTAAGCTCCTGATCTATGCTGCATCC AGTTTGCAAAGTGGGGTCCCATCACG TTTCAGTGGCAGTGGAAGCGGGACAG ATTTCACTCTCACCATCAGCAGTCTG CAACCTGAAGATTTTGCAACTTATTA CTGTCAACAGTACTACTGGTACGGTC TGTCCACTTTTGGCCAGGGGACCAAG CTGGAGATCAAACGTGAGTC_gtacgc tagcaagcttgatatcgaattctaaa ctctgaggggtcggatgacgttggcc attctttgcctaaagcattgagttta ctgcaaggtcagaaaagcatgcaaag ccctcagaatggctgcaaagagctcc aacaaaacaatttagaactttattaa ggaataggggaagctaggaagaaac tcaaaacatcaagatttttaaatacgc ttcttggtctccttgctataattatc tgggataagcatgctgttttctgtct gtccctaacatgccctgtgattatcc gcaaacaacacacccaagggcagaac tttgttacttaaacaccatcctgttt gcttcttcctcag_GAACTGTGGCTG CACCATCTGTCTTCATCTTCCCGCCA TCTGATGAGCAGTTGAAATCTGGAAC TGCCTCTGTTGTGTGCCTGCTGAATA ACTTCTATCCCAGAGAGGCCAAAGTA CAGTGGAAGGTGGATAACGCCCTCCA ATCGGGTAACTCCCAGGAGAGTGTCA CAGAGCAGGACAGCAAGGACAGCACC TACAGCCTCAGCAGCACCCTGACGCT GAGCAAAGCAGACTACGAGAAACACA AAGTCTACGCCTGCGAAGTCACCCAT CAGGGCCTGAGCTCGCCCGTCACAAA GAGCTTCAACAGGGGAGAGTGT |
| 169 | Fusion of: VL1: 1171 (bold underlined) kappa constant domains (italics) (i.e. fusion of SEQ ID NOS: 93 and 136) | DIQMTQSPSSLSASVGDRVTITCRAS QSISSYLNWYQQKPGKAPKLLIYAAS SLQSGVPSRFSGSGSGTDFTLTISSL QPEDFATYYCQQGHGSYPHTFGQGTK LEIK_RTVAAPSVFIFPPSDEQLKSGT ASVVCLLNNFYPREAKVQWKVDNALQ SGNSQESVTEQDSKDSTYSLSSTLTL SKADYEKHKVYACEVTHQGLSSPVTK SFNRGEC_ May assemble with SEQ ID NO: 155 to form a 1170/1171-1204/1205 bispecific antibody |
| 170 | Nucleotide encoding SEQ ID NO: 169 | _GACATCCAGATGACCCAGTCTCCATC CTCCCTGAGCGCATCTGTAGGAGACC GCGTCACCATCACTTGCCGGGCAAGT CAGAGCATTAGCAGCTATTTAAATTG GTATCAGCAGAAACCAGGGAAAGCCC CTAAGCTCCTGATCTATGCTGCATCC AGTTTGCAAAGTGGGGTCCCATCACG TTTCAGTGGCAGTGGAAGCGGGACAG ATTTCACTCTCACCATCAGCAGTCTG CAACCTGAAGATTTTGCAACTTATTA CTGTCAACAGGGTCATGGTTCTTACC CGCACACTTTTGGCCAGGGGACCAAG CTGGAGATCAAACGTGAGTC_gtacgc tagcaagcttgatatcgaattctaaa ctctgaggggtcggatgacgttggcc attctttgcctaaagcattgagttta ctgcaaggtcagaaaagcatgcaaag ccctcagaatggctgcaaagagctcc aacaaaacaatttagaactttattaa ggaataggggaagctaggaagaaac tcaaaacatcaagatttttaaatacgc ttcttggtctccttgctataattatc tgggataagcatgctgttttctgtct gtccctaacatgccctgtgattatcc gcaaacaacacacccaagggcagaac tttgttacttaaacaccatcctgttt gcttcttcctcag_GAACTGTGGCTG CACCATCTGTCTTCATCTTCCCGCCA TCTGATGAGCAGTTGAAATCTGGAAC TGCCTCTGTTGTGTGCCTGCTGAATA ACTTCTATCCCAGAGAGGCCAAAGTA CAGTGGAAGGTGGATAACGCCCTCCA ATCGGGTAACTCCCAGGAGAGTGTCA CAGAGCAGGACAGCAAGGACAGCACC TACAGCCTCAGCAGCACCCTGACGCT GAGCAAAGCAGACTACGAGAAACACA AAGTCTACGCCTGCGAAGTCACCCAT CAGGGCCTGAGCTCGCCCGTCACAAA GAGCTTCAACAGGGGAGAGTGT |
| 171 | Fusion of: VL1: 1483 (bold underlined) kappa constant domains (italics) (i.e. fusion of SEQ ID NOS: 103 and 136) | DIQMTQSPSSLSASVGDRVTITCRAS QSISSYLNWYQQKPGKAPKLLIYAAS SLQSGVPSRFSGSGSGTDFTLTISSL QPEDFATYYCQQYGSLLTFGQGTKLE IK_RTVAAPSVFIFPPSDEQLKSGTAS VVCLLNNFYPREAKVQWKVDNALQSG NSQESVTEQDSKDSTYSLSSTLTLSK ADYEKHKVYACEVTHQGLSSPVTKSF NRGEC_ May assemble with SEQ ID NO: 157 to form a 1482/1483-1204/1205 bispecific antibody |
| 172 | Nucleotide encoding SEQ ID NO: 171 | GACATCCAGATGACCCAGTCTCCATC CTCCCTGAGCGCATCTGTAGGAGACC GCGTCACCATCACTTGCCGGGCAAGT CAGAGCATTAGCAGCTATTTAAATTG GTATCAGCAGAAACCAGGGAAAGCCC CTAAGCTCCTGATCTATGCTGCATCC AGTTTGCAAAGTGGGGTCCCATCACG TTTCAGTGGCAGTGGAAGCGGGACAG ATTTCACTCTCACCATCAGCAGTCTG CAACCTGAAGATTTTGCAACTTATTA CTGTCAACAGTACGGTTCTCTGCTCA CTTTTGGCCAGGGGACCAAGCTGGAG ATCAAACGTGAGTCgtacgctagcaa gcttgatatcgaattctaaactctga ggggtcggatgacgttggccattctt tgcctaaagcattgagtttactgcaa ggtcagaaaagcatgcaaagcccttca gaatggctgcaaagagctccaacaaa acaatttagaactttattaaggaata ggggaagctaggaagaaactcaaaa catcaagatttttaaatacgcttcttg gtctccttgctataattatctgggat aagcatgctgttttctgtctgtccct aacatgccctgtgattatccgcaaac aacacacccaagggcagaactttgtt acttaaacaccatcctgtttgcttct ttcctcagGAACTGTGGCTGCACCAT CTGTCTTCATCTTCCCGCCATCTGAT

TABLE G-continued

Exemplary sequences

| SEQ ID NO. | DESIGNATION | SEQUENCE |
|---|---|---|
| | | GAGCAGTTGAAATCTGGAACTGCCTC TGTTGTGTGCCTGCTGAATAACTTCT ATCCCAGAGAGGCCAAAGTACAGTGG AAGGTGGATAACGCCCTCCAATCGGG TAACTCCCAGGAGAGTGTCACAGAGC AGGACAGCAAGGACAGCACCTACAGC CTCAGCAGCACCCTGACGCTGAGCAA AGCAGACTACGAGAAACACAAAGTCT ACGCCTGCGAAGTCACCCATCAGGGC CTGAGCTCGCCCGTCACAAAGAGCTT CAACAGGGGAGAGTGT |
| 173 | Fusion of: VL1: 1527 (bold underlined) kappa constant domains (italics) (i.e. fusion of SEQ ID NOS: 119 and 136) | DIQMTQSPSSLSASVGDRVTITCRAS QSISSYLNWYQQKPGKAPKLLIYAAS SLQSGVPSRFSGSGSGTDFTLTISSL QPEDFATYYCQQYGSDSLLTFGQGTK LEIK_RTVAAPSVFIFPPSDEQLKSGT ASVVCLLNNFYPREAKVQWKVDNALQ SGNSQESVTEQDSKDSTYSLSSTLTL SKADYEKHKVYACEVTHQGLSSPVTK SFNRGEC_ May assemble with SEQ ID NO: 161 to form 1526/1527-1204/1205 bispecific antibody |
| 174 | Nucleotide encoding SEQ ID NO: 173 | GACATCCAGATGACCCAGTCTCCATC CTCCCTGAGCGCATCTGTAGGAGACC GCGTCACCATCACTTGCCGGGCAAGT CAGAGCATTAGCAGCTATTTAAATTG GTATCAGCAGAAACCAGGGAAAGCCC CTAAGCTCCTGATCTATGCTGCATCC AGTTTGCAAAGTGGGGTCCCATCACG TTTCAGTGGCAGTGGAAGCGGGACAG ATTTCACTCTCACCATCAGCAGTCTG CAACCTGAAGATTTTGCAACTTATTA CTGTCAACAGTACGGTTCTGATTCTC TGCTCACTTTTGGCCAGGGGACCAAG CTGGAGATCAAACGTGAGTCgtacgc tagcaagcttgatatcgaattctaaa ctctgaggggtcggatgacgtggcc attctttgcctaaagcattgagttta ctgcaaggtcagaaaagcatgcaaag ccctcagaatggctgcaaagagctcc aacaaaacaatttagaactttattaa ggaataggggaagctaggaagaaac tcaaaacatcaagattttaaatacgc ttcttggtctccttgctataattatc tgggataagcatgctgttttctgtct gtccctaacatgccctgtgattatcc gcaaacaacacacccaagggcagaac tttgttacttaaacaccatcctgttt gcttctttcctcagGAACTGTGGCTG CACCATCTGTCTTCATCTTCCCGCCA TCTGATGAGCAGTTGAAATCTGGAAC TGCCTCTGTTGTGTGCCTGCTGAATA ACTTCTATCCCAGAGAGGCCAAAGTA CAGTGGAAGGTGGATAACGCCCTCCA ATCGGGTAACTCCCAGGAGAGTGTCA CAGAGCAGGACAGCAAGGACAGCACC TACAGCCTCAGCAGCACCCTGACGCT GAGCAAAGCAGACTACGAGAAACACA AAGTCTACGCCTGCGAAGTCACCCAT CAGGGCCTGAGCTCGCCCGTCACAAA GAGCTTCAACAGGGGAGAGTGT |

TABLE H

Exemplary CD137 binding domains and bispecific polypeptides for CD137 and CTLA-4

| SEQ ID NO. | CHAIN NO. | TYPE | SEQUENCE |
|---|---|---|---|
| 177 | 1205, light chain VL | aa | DIQMTQSPSSLSASVGDRVTITCRASQSISSYLNWYQ QKPGKAPKLLIYAASSLQSGVPSRFSGSGSGTDFTLT ISSLQPEDFATYYCQQSVPHYPFTFGQGTKLEIK |
| 178 | 1205, light chain VL | nt | GACATCCAGATGACCCAGTCTCCATCCTCCCTGAGCG CATCTGTAGGAGACCGCGTCACCATCACTTGCCGGGC AAGTCAGAGCATTAGCAGCTATTTAAATTGGTATCAG CAGAAACCAGGGAAAGCCCCTAAGCTCCTGATCTATG CTGCATCCAGTTTGCAAAGTGGGGTCCCATCACGTTT CAGTGGCAGTGGAAGCGGGACAGATTTCACTCTCACC ATCAGCAGTCTGCAACCTGAAGATTTTGCAACTTATT ACTGTCAACAGTCTGTTCCGCACTACCCGTTCACTTT TGGCCAGGGGACCAAGCTGGAGATCAAA |
| 179 | 1204, heavy chain VH | aa | EVQLLESGGGLVQPGGSLRLSCAASGFTFSSYYMGWV RQAPGKGLEWVSGIGSYYGYTGYADSVKGRFTISRDN SKNTLYLQMNSLRAEDTAVYYCARAYYDYNYYYAYFD YWGQGTLVTVSS |
| 180 | 1204, heavy chain VH | nt | GAGGTGCAGCTGTTGGAGAGCGGGGGAGGCTTGGTAC AGCCTGGGGGGTCCCTGCGCCTCTCCTGTGCAGCCAG CGGATTCACCTTTTCTTCTTACTACATGGGTTGGGTC CGCCAGGCTCCAGGGAAGGGGCTGGAGTGGGTCTCAG GTATTGGTTCTTACTACGGTTACACAGGTTATGCAGA CTCCGTGAAGGGCCGGTTCACCATCTCCCGTGACAAT TCCAAGAACACGCTGTATCTGCAAATGAACAGCCTGC GTGCCGAGGACACGGCTGTATATTATTGTGCGCGCGC TTACTACGACTACAACTACTACTACGCTTACTTTGAC TATTGGGGCCAGGGAACCCTGGTCACCGTCTCCTCA |

TABLE H-continued

Exemplary CD137 binding domains and
bispecific polypeptides for CD137 and CTLA-4

| SEQ ID NO. | CHAIN NO. | TYPE | SEQUENCE |
|---|---|---|---|
| 181 | 1214 (VH) | aa | EVQLLESGGGLVQPGGSLRLSCAASGFTFSSYAMSWV RQAPGKGLEWVSSIGSGGGYTGYADSVKGRFTISRDN SKNTLYLQMNSLRAEDTAVYYCARVGHPFDYWGQGTL VTVSS |
| 182 | 1214 (VH) | nt | GAGGTGCAGCTGTTGGAGAGCGGGGGAGGCTTGGTAC AGCCTGGGGGGTCCCTGCGCCTCTCCTGTGCAGCCAG CGGATTCACCTTTAGCAGCTATGCCATGAGCTGGGTC CGCCAGGCTCCAGGGAAGGGGCTGGAGTGGGTCTCAT CTATTGGTTCTGGTGGTGGTTACACAGGTTATGCAGA CTCCGTGAAGGGCCGGTTCACCATCTCCCGTGACAAT TCCAAGAACACGCTGTATCTGCAAATGAACAGCCTGC GTGCCGAGGACACGGCTGTATATTATTGTGCGCGCGT TGGTCATCCGTTTGACTATTGGGGCCAGGGAACCCTG GTCACCGTCTCCTCA |
| 183 | 1215 (VL) | aa | DIQMTQSPSSLSASVGDRVTITCRASQSISSYLNWYQ QKPGKAPKLLIYAASSLQSGVPSRFSGSGSGTDFTLT ISSLQPEDFATYYCQQDAYPHTFGQGTKLEIK |
| 184 | 1215 (VL) | nt | GACATCCAGATGACCCAGTCTCCATCCTCCCTGAGCG CATCTGTAGGAGACCGCGTCACCATCACTTGCCGGGC AAGTCAGAGCATTAGCAGCTATTTAAATTGGTATCAG CAGAAACCAGGGAAAGCCCCTAAGCTCCTGATCTATG CTGCATCCAGTTTGCAAAGTGGGGTCCCATCACGTTT CAGTGGCAGTGGAAGCGGGACAGATTTCACTCTCACC ATCAGCAGTCTGCAACCTGAAGATTTTGCAACTTATT ACTGTCAACAGGACGCTTACCCGCACACTTTTGGCCA GGGGACCAAGCTGGAGATCAAA |
| 185 | 1618 (VH) | aa | EVQLLESGGGLVQPGGSLRLSCAASGFTFSYGSMYWV RQAPGKGLEWVSSISSGSGSTYYADSVKGRFTISRDN SKNTLYLQMNSLRAEDTAVYYCARSSYYGSYYSIDYW GQGTLVTVSS |
| 186 | 1618 (VH) | nt | GAGGTGCAGCTGTTGGAGAGCGGGGGAGGCTTGGTAC AGCCTGGGGGGTCCCTGCGCCTCTCCTGTGCAGCCAG CGGATTCACCTTTTCTTACGGTTCTATGTACTGGGTC CGCCAGGCTCCAGGGAAGGGGCTGGAGTGGGTCTCAT CTATTTCTTCTGGTTCTGGTTCTACATACTATGCAGA CTCCGTGAAGGGCCGGTTCACCATCTCCCGTGACAAT TCCAAGAACACGCTGTATCTGCAAATGAACAGCCTGC GTGCCGAGGACACGGCTGTATATTATTGTGCGCGCTC TTCTTACTACGGTTCTTACTACTCTATTGACTATTGG GGCCAGGGAACCCTGGTCACCGTCTCCTCA |
| 187 | 1619 (VL) | aa | DIQMTQSPSSLSASVGDRVTITCRASQSISSYLNWYQ QKPGKAPKLLIYAASSLQSGVPSRFSGSGSGTDFTLT ISSLQPEDFATYYCQQYYDNLPTFGQGTKLEIK |
| 188 | 1619 (VL) | nt | GACATCCAGATGACCCAGTCTCCATCCTCCCTGAGCG CATCTGTAGGAGACCGCGTCACCATCACTTGCCGGGC AAGTCAGAGCATTAGCAGCTATTTAAATTGGTATCAG CAGAAACCAGGGAAAGCCCCTAAGCTCCTGATCTATG CTGCATCCAGTTTGCAAAGTGGGGTCCCATCACGTTT CAGTGGCAGTGGAAGCGGGACAGATTTCACTCTCACC ATCAGCAGTCTGCAACCTGAAGATTTTGCAACTTATT ACTGTCAACAGTACTACGACAACCTGCCCACTTTTGG CCAGGGGACCAAGCTGGAGATCAAA |
| 189 | 1620 (VH) | aa | EVQLLESGGGLVQPGGSLRLSCAASGFTFSGYYMYWV RQAPGKGLEWVSGISSSGSYTYYADSVKGRFTISRDN SKNTLYLQMNSLRAEDTAVYYCARSVGPYFDYWGQGT LVTVSS |
| 190 | 1620 (VH) | nt | GAGGTGCAGCTGTTGGAGAGCGGGGGAGGCTTGGTAC AGCCTGGGGGGTCCCTGCGCCTCTCCTGTGCAGCCAG CGGATTCACCTTTTCTGGTTACTACATGTACTGGGTC CGCCAGGCTCCAGGGAAGGGGCTGGAGTGGGTCTCAG GTATTTCTTCTTCTGGTTCTTACACATACTATGCAGA |

TABLE H-continued

Exemplary CD137 binding domains and
bispecific polypeptides for CD137 and CTLA-4

| SEQ ID NO. | CHAIN NO. | TYPE | SEQUENCE |
|---|---|---|---|
| | | | CTCCGTGAAGGGCCGGTTCACCATCTCCCGTGACAAT
TCCAAGAACACGCTGTATCTGCAAATGAACAGCCTGC
GTGCCGAGGACACGGCTGTATATTATTGTGCGCGCTC
TGTTGGTCCGTACTTGACTATTGGGGCCAGGGAACC
CTGGTCACCGTCTCCTCA |
| 191 | 1621 (VL) | aa | DIQMTQSPSSLSASVGDRVTITCRASQSISSYLNWYQ
QKPGKAPKLLIYAASSLQSGVPSRFSGSGSGTDFTLT
ISSLQPEDFATYYCQQGVGPYTFGQGTKLEIK |
| 192 | 1621 (VL) | nt | GACATCCAGATGACCCAGTCTCCATCCTCCCTGAGCG
CATCTGTAGGAGACCGCGTCACCATCACTTGCCGGGC
AAGTCAGAGCATTAGCAGCTATTTAAATTGGTATCAG
CAGAAACCAGGGAAAGCCCCTAAGCTCCTGATCTATG
CTGCATCCAGTTTGCAAAGTGGGGTCCCATCACGTTT
CAGTGGCAGTGGAAGCGGGACAGATTTCACTCTCACC
ATCAGCAGTCTGCAACCTGAAGATTTTGCAACTTATT
ACTGTCAACAGGGTGTTGGTCCGTACACTTTTGGCCA
GGGGACCAAGCTGGAGATCAAA |
| 193 | 1626 (VH) | aa | EVQLLESGGGLVQPGGSLRLSCAASGFTFGGYSMYWV
RQAPGKGLEWVSSIGGYYYSTYYADSVKGRFTISRDN
SKNTLYLQMNSLRAEDTAVYYCARSYYGSIDYWGQGT
LVTVSS |
| 194 | 1626 (VH) | nt | GAGGTGCAGCTGTTGGAGAGCGGGGGAGGCTTGGTAC
AGCCTGGGGGGTCCCTGCGCCTCTCCTGTGCAGCCAG
CGGATTCACCTTTGGTGGTTACTCTATGTACTGGGTC
CGCCAGGCTCCAGGGAAGGGGCTGGAGTGGGTCTCAT
CTATTGGTGGTTACTACTACTCTACATACTATGCAGA
CTCCGTGAAGGGCCGGTTCACCATCTCCCGTGACAAT
TCCAAGAACACGCTGTATCTGCAAATGAACAGCCTGC
GTGCCGAGGACACGGCTGTATATTATTGTGCGCGCTC
TTACTACGGTTCTATTGACTATTGGGGCCAGGGAACC
CTGGTCACCGTCTCCTCA |
| 195 | 1627 (VL) | aa | DIQMTQSPSSLSASVGDRVTITCRASQSISSYLNWYQ
QKPGKAPKLLIYAASSLQSGVPSRFSGSGSGTDFTLT
ISSLQPEDFATYYCQQGTGYGPLTFGQGTKLEIK |
| 196 | 1627 (VL) | nt | GACATCCAGATGACCCAGTCTCCATCCTCCCTGAGCG
CATCTGTAGGAGACCGCGTCACCATCACTTGCCGGGC
AAGTCAGAGCATTAGCAGCTATTTAAATTGGTATCAG
CAGAAACCAGGGAAAGCCCCTAAGCTCCTGATCTATG
CTGCATCCAGTTTGCAAAGTGGGGTCCCATCACGTTT
CAGTGGCAGTGGAAGCGGGACAGATTTCACTCTCACC
ATCAGCAGTCTGCAACCTGAAGATTTTGCAACTTATT
ACTGTCAACAGGGTACTGGTTACGGTCCGCTCACTTT
TGGCCAGGGGACCAAGCTGGAGATCAAA |
| 197 | 1761 =
1205 Light
chain VL, with
constant kappa
sequence, linker
and CD86
mutant 1040
inclusive intron
sequence | nt | GACATCCAGATGACCCAGTCTCCATCCTCCCTGAGCG
CATCTGTAGGAGACCGCGTCACCATCACTTGCCGGGC
AAGTCAGAGCATTAGCAGCTATTTAAATTGGTATCAG
CAGAAACCAGGGAAAGCCCCTAAGCTCCTGATCTATG
CTGCATCCAGTTTGCAAAGTGGGGTCCCATCACGTTT
CAGTGGCAGTGGAAGCGGGACAGATTTCACTCTCACC
ATCAGCAGTCTGCAACCTGAAGATTTTGCAACTTATT
ACTGTCAACAGTCTGTTCCGCACTACCCGTTCACTTT
TGGCCAGGGGACCAAGCTGGAGATCAAACGTgagtcg
tacgctagcaagcttgatatcgaattctaaactctga
gggggtcggatgacgtggccattctttgcctaaagca
ttgagtttactgcaaggtcagaaaagcatgcaaagcc
ctcagaatggctgcaaagagctccaacaaaacaattt
agaactttattaaggaatagggggaagctaggaagaa
actcaaaacatcaagatttaaatacgcttcttggtc
tccttgctataattatctgggataagcatgctgtttt
ctgtctgtccctaacatgccctgtgattatccgcaaa
caacacacccaagggcagaactttgttacttaaacac
catcctgtttgcttcttttcctcagGAACTGTGGCTGC
ACCATCTGTCTTCATCTTCCCGCCATCTGATGAGCAG
TTGAAATCTGGAACTGCCTCTGTTGTGTGCCTGCTGA
ATAACTTCTATCCCAGAGAGGCCAAAGTACAGTGGAA
GGTGGATAACGCCCTCCAATCGGGTAACTCCCAGGAG
AGTGTCACAGAGCAGGACAGCAAGGACAGCACCTACA |

TABLE H-continued

Exemplary CD137 binding domains and
bispecific polypeptides for CD137 and CTLA-4

| SEQ ID NO. | CHAIN NO. | TYPE | SEQUENCE |
|---|---|---|---|
| | | | GCCTCAGCAGCACCCTGACGCTGAGCAAAGCAGACTA CGAGAAACACAAAGTCTACGCCTGCGAAGTCACCCAT CAGGGCCTGAGCTCGCCCGTCACAAAGAGCTTCAACA GGGGAGAGTGTAGCGGAGGAGGAGGAAGCGGAGGAGG AGGAAGCGCCCCCCTCAAAATCCAAGCGTACTTCAAC GAAACTGCAGACTTACCGTGTCAGTTTGCCAATTCGC AGAATCTGAGCCTGAGCGAACTGGTGGTTTTCTGGCA GGATCAGGAGAACCTGGTTCTGAACGAAGTCTATCTG GGCAAAGAGCGGTTCGACAGCGTGGACAGCAAGTATA TGGGCCGCACCAGCTTTGATAGCGACAGCTGGACCCT GCGTCTGCACAATCTGCAAATCAAAGATAAGGGTAGG TACCAGTGCATTATCCACCATAAGAAGCCGACGGGTA TGATTAATATTCACCAAATGAACTCCGAGTTGTCTGT CCTGGCG |
| 198 | 1761 = 1205 light chain VL, with constant kappa sequence, linker (underlined) and CD86 mutant 1040 | aa | DIQMTQSPSSLSASVGDRVTITCRASQSISSYLNWYQ QKPGKAPKLLIYAASSLQSGVPSRFSGSGSGTDFTLT ISSLQPEDFATYYCQQSVPHYPFTFGQGTKLEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC<u>SGGGGSG GGGSAP</u>LKIQAYFNETADLPCQFANSQNLSLSELVVF WQDQENLVLNEVYLGKERFDSVDSKYMGRTSFDSDSW TLRLHNLQIKDKGRYQCIIHHKKPTGMINIHQMNSEL SVLA LIGHT CHAIN PREFERABLY ASSEMBLES WITH A HEAVY CHAIN COMPRISING THE 1204 VH SEQUENCE THUS, COMPLETE MOLECULE MAY BE DESIGNATED 1204/1761 |
| 199 | 1763 = 1215 Light chain VL, with constant kappa sequence, linker and CD86 mutant 1040 | nt | GACATCCAGATGACCCAGTCTCCATCCTCCCTGAGCG CATCTGTAGGAGACCGCGTCACCATCACTTGCCGGGC AAGTCAGAGCATTAGCAGCTATTTAAATTGGTATCAG CAGAAACCAGGGAAAGCCCCTAAGCTCCTGATCTATG CTGCATCCAGTTTGCAAAGTGGGGTCCCATCACGTTT CAGTGGCAGTGGAAGCGGGACAGATTTCACTCTCACC ATCAGCAGTCTGCAACCTGAAGATTTTGCAACTTATT ACTGTCAACAGGACGCTTACCCGCACACTTTTGGCCA GGGGACCAAGCTGGAGATCAAACGTgagtcgtacgct agcaagcttgatatcgaattctaaactctgagggggt cggatgacgtggccattctttgcctaaagcattgagt ttactgcaaggtcagaaaagcatgcaaagccctcaga atggctgcaaagagctccaacaaaacaatttagaact ttattaaggaatagggggaagctaggaagaaactcaa aacatcaagattttaaatacgcttcttggtctccttg ctataattatctgggataagcatgctgttttctgtct gtccctaacatgccctgtgattatccgcaaacaacac acccaagggcagaactttgttacttaaacaccatcct gtttgcttctttcctcagGAACTGTGGCTGCACCATC TGTCTTCATCTTCCCGCCATCTGATGAGCAGTTGAAA TCTGGAACTGCCTCTGTTGTGTGCCTGCTGAATAACT TCTATCCCAGAGAGGCCAAAGTACAGTGGAAGGTGGA TAACGCCCTCCAATCGGGTAACTCCCAGGAGAGTGTC ACAGAGCAGGACAGCAAGGACAGCACCTACAGCCTCA GCAGCACCCTGACGCTGAGCAAAGCAGACTACGAGAA ACACAAAGTCTACGCCTGCGAAGTCACCCATCAGGGC CTGAGCTCGCCCGTCACAAAGAGCTTCAACAGGGGAG AGTGTAGCGGAGGAGGAGGAAGCGGAGGAGGAGGAAG CGCCCCCCTCAAAATCCAAGCGTACTTCAACGAAACT GCAGACTTACCGTGTCAGTTTGCCAATTCGCAGAATC TGAGCCTGAGCGAACTGGTGGTTTTCTGGCAGGATCAG GAGAACCTGGTTCTGAACGAAGTCTATCTGGGCAAAG AGCGGTTCGACAGCGTGGACAGCAAGTATATGGGCCG CACCAGCTTTGATAGCGACAGCTGGACCCTGCGTCTG CACAATCTGCAAATCAAAGATAAGGGTAGGTACCAGT GCATTATCCACCATAAGAAGCCGACGGGTATGATTAA TATTCACCAAATGAACTCCGAGTTGTCTGTCCTGGCG |

TABLE H-continued

Exemplary CD137 binding domains and
bispecific polypeptides for CD137 and CTLA-4

| SEQ ID NO. | CHAIN NO. | TYPE | SEQUENCE |
|---|---|---|---|
| 200 | 1763 = 1215 Light chain VL, with constant kappa sequence, linker (underlined) and CD86 mutant 1040 | aa | DIQMTQSPSSLSASVGDRVTITCRASQSISSYLNWYQ QKPGKAPKLLIYAASSLQSGVPSRFSGSGSTDFTLT ISSLQPEDFATYYCQQDAYPHTFGQGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC<u>SGGGGSGGG GSAP</u>LKIQAYFNETADLPCQFANSQNLSLSELVVFWQ DQENLVLNEVYLGKERFDSVDSKYMGRTSFDSDSWTL RLHNLQIKDKGRYQCIIHHKKPTGMINIHQMNSELSV LA<br>LIGHT CHAIN PREFERABLY ASSEMBLES WITH A HEAVY CHAIN COMPRISING THE 1214 VH SEQUENCE THUS, COMPLETE MOLECULE MAY BE DESIGNATED 1214/1763 |
| 201 | 1765 = 1619 Light chain VL, with constant kappa sequence, linker and CD86 mutant 1040 | nt | GACATCCAGATGACCCAGTCTCCATCCTCCCTGAGCG CATCTGTAGGAGACCGCGTCACCATCACTTGCCGGGC AAGTCAGAGCATTAGCAGCTATTTAAATTGGTATCAG CAGAAACCAGGGAAAGCCCCTAAGCTCCTGATCTATG CTGCATCCAGTTTGCAAAGTGGGGTCCCATCACGTTT CAGTGGCAGTGGAAGCGGGACAGATTTCACTCTCACC ATCAGCAGTCTGCAACCTGAAGATTTTGCAACTTATT ACTGTCAACAGTACTACGACAACCTGCCCACTTTTGG CCAGGGGACCAAGCTGGAGATCAAACGTgagtcgtac gctagcaagcttgatatcgaattctaaactctgaggg ggtcggatgacgtggccattctttgcctaaagcattg agtttactgcaaggtcagaaaagcatgcaaagccctc agaatggctgcaaagagctccaacaaaacaatttaga actttattaaggaatagggggaagctaggaagaaact caaaacatcaagatttaaatacgcttcttggtctcc ttgctataattatctgggataagcatgctgttttctg tctgtccctaacatgccctgtgattatccgcaaacaa cacacccaagggcagaactttgttacttaaacaccat cctgtttgcttctttcctcagGAACTGTGGCTGCACC ATCTGTCTTCATCTTCCCGCCATCTGATGAGCAGTTG AAATCTGGAACTGCCTCTGTTGTGTGCCTGCTGAATA ACTTCTATCCCAGAGAGGCCAAAGTACAGTGGAAGGT GGATAACGCCCTCCAATCGGGTAACTCCCAGGAGAGT GTCACAGAGCAGGACAGCAAGGACAGCACCTACAGCC TCAGCAGCACCCTGACGCTGAGCAAAGCAGACTACGA GAAACACAAAGTCTACGCCTGCGAAGTCACCCATCAG GGCCTGAGCTCGCCCGTCACAAAGAGCTTCAACAGGG GAGAGTGTAGCGGAGGAGGAAGCGGAGGAGGAGG AAGCGCCCCCCTCAAAATCCAAGCGTACTTCAACGAA ACTGCAGACTTACCGTGTCAGTTTGCCAATTCGCAGA ATCTGAGCCTGAGCGAACTGGTGGTTTTCTGGCAGGA TCAGGAGAACCTGGTTCTGAACGAAGTCTATCTGGGC AAAGAGCGGTTCGACAGCGTGGACAGCAAGTATATGG GCCGCACCAGCTTTGATAGCGACAGCTGGACCCTGCG TCTGCACAATCTGCAAATCAAAGATAAGGGTAGGTAC CAGTGCATTATCCACCATAAGAAGCCGACGGGTATGA TTAATATTCACCAAATGAACTCCGAGTTGTCTGTCCT GGCG |
| 202 | 1765 = 1619 Light chain VL, with constant kappa sequence, linker (underlined) and CD86 mutant 1040 | aa | DIQMTQSPSSLSASVGDRVTITCRASQSISSYLNWYQ QKPGKAPKLLIYAASSLQSGVPSRFSGSGSTDFTLT ISSLQPEDFATYYCQQYYDNLPTFGQGTKLEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC<u>SGGGGSGG GGSAP</u>LKIQAYFNETADLPCQFANSQNLSLSELVVFW QDQENLVLNEVYLGKERFDSVDSKYMGRTSFDSDSWT LRLHNLQIKDKGRYQCIIHHKKPTGMINIHQMNSELS VLA<br>LIGHT CHAIN PREFERABLY ASSEMBLES WITH A HEAVY CHAIN COMPRISING THE 1618 VH SEQUENCE THUS, COMPLETE MOLECULE MAY BE DESIGNATED 1618/1765 |

TABLE H-continued

Exemplary CD137 binding domains and
bispecific polypeptides for CD137 and CTLA-4

| SEQ ID NO. | CHAIN NO. | TYPE | SEQUENCE |
|---|---|---|---|
| 203 | 1767 = 1621 Light chain VL, with constant kappa sequence, linker and CD86 mutant 1040 | nt | GACATCCAGATGACCCAGTCTCCATCCTCCCTGAGCG CATCTGTAGGAGACCGCGTCACCATCACTTGCCGGGC AAGTCAGAGCATTAGCAGCTATTTAAATTGGTATCAG CAGAAACCAGGGAAAGCCCCTAAGCTCCTGATCTATG CTGCATCCAGTTTGCAAAGTGGGGTCCCATCACGTTT CAGTGGCAGTGGAAGCGGGACAGATTTCACTCTCACC ATCAGCAGTCTGCAACCTGAAGATTTTGCAACTTATT ACTGTCAACAGGGTGTTGGTCCGTACACTTTTGGCCA GGGGACCAAGCTGGAGATCAAACGTgagtcgtacgct agcaagcttgatatcgaattctaaactctgagggggt cggatgacgtggccattctttgcctaaagcattgagt ttactgcaaggtcagaaaagcatgcaaagccctcaga atggctgcaaagagctccaacaaaacaatttagaact ttattaaggaataggggggaagctaggaagaaactcaa aacatcaagattttaaatacgcttcttggtctccttg ctataattatctgggataagcatgctgttttctgtct gtccctaacatgccctgtgattatccgcaaacaacac acccaagggcagaactttgttacttaaacaccatcct gtttgcttctttcctcagGAACTGTGGCTGCACCATC TGTCTTCATCTTCCCGCCATCTGATGAGCAGTTGAAA TCTGGAACTGCCTCTGTTGTGTGCCTGCTGAATAACT TCTATCCCAGAGAGGCCAAAGTACAGTGGAAGGTGGA TAACGCCCTCCAATCGGGTAACTCCCAGGAGAGTGTC ACAGAGCAGGACAGCAAGGACAGCACCTACAGCCTCA GCAGCACCCTGACGCTGAGCAAAGCAGACTACGAGAA ACACAAAGTCTACGCCTGCGAAGTCACCCATCAGGGC CTGAGCTCGCCCGTCACAAAGAGCTTCAACAGGGGAG AGTGTAGCGGAGGAGGAGGAAGCGGAGGAGGAGGAAG CGCCCCCCTCAAAATCCAAGCGTACTTCAACGAAACT GCAGACTTACCGTGTCAGTTTGCCAATTCGCAGAATC TGAGCCTGAGCGAACTGGTGGTTTTCTGGCAGGATCA GGAGAACCTGGTTCTGAACGAAGTCTATCTGGGCAAA GAGCGGTTCGACAGCGTGGACAGCAAGTATATGGGCC GCACCAGCTTTGATAGCGACAGCTGGACCCTGCGTCT GCACAATCTGCAAATCAAAGATAAGGGGTAGGTACCA TGCATTATCCACCATAAGAAGCCGACGGGTATGATTA ATATTCACCAAATGAACTCCGAGTTGTCTGTCCTGGC G |
| 204 | 1767 = 1621 Light chain VL, with constant kappa sequence, linker (underlined) and CD86 mutant 1040 | aa | DIQMTQSPSSLSASVGDRVTITCRASQSISSYLNWYQ QKPGKAPKLLIYAASSLQSGVPSRFSGSGSGTDFTLT ISSLQPEDFATYYCQQGVGPYTFGQGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC<u>SGGGGSGGG GSAPL</u>KIQAYFNETADLPCQFANSQNLSLSELVVFWQ DQENLVLNEVYLGKERFDSVDSKYMGRTSFDSDSWTL RLHNLQIKDKGRYQCIIHHKKPTGMINIHQMNSELSV LA<br>LIGHT CHAIN PREFERABLY ASSEMBLES WITH A HEAVY CHAIN COMPRISING THE 1620 VH SEQUENCE THUS, COMPLETE MOLECULE MAY BE DESIGNATED 1620/1767 |
| 205 | 1769 = 1627 Light chain VL, with constant kappa sequence, linker (underlined) and CD86 mutant 1040 | nt | GACATCCAGATGACCCAGTCTCCATCCTCCCTGAGCG CATCTGTAGGAGACCGCGTCACCATCACTTGCCGGGC AAGTCAGAGCATTAGCAGCTATTTAAATTGGTATCAG CAGAAACCAGGGAAAGCCCCTAAGCTCCTGATCTATG CTGCATCCAGTTTGCAAAGTGGGGTCCCATCACGTTT CAGTGGCAGTGGAAGCGGACAGATTTCACTCTCACC ATCAGCAGTCTGCAACCTGAAGATTTTGCAACTTATT ACTGTCAACAGGGTACTGGTTACGGTCCGCTCACTTT TGGCCAGGGGACCAAGCTGGAGATCAAACGTgagtcg tacgctagcaagcttgatatcgaattctaaactctga ggggtcggatgacgtggccattctttgcctaaagca ttgagtttactgcaaggtcagaaaagcatgcaaagcc ctcagaatggctgcaaagagctccaacaaaacaattt agaactttattaaggaataggggggaagctaggaagaa actcaaaacatcaagattttaaatacgcttcttggtc tccttgctataattatctgggataagcatgctgtttt ctgtctgtccctaacatgccctgtgattatccgcaaa caacacccaagggcagaactttgttacttaaacac catcctgtttgcttctttcctcagGAACTGTGGCTGC |

TABLE H-continued

Exemplary CD137 binding domains and
bispecific polypeptides for CD137 and CTLA-4

| SEQ ID NO. | CHAIN NO. | TYPE | SEQUENCE |
|---|---|---|---|
| | | | ACCATCTGTCTTCATCTTCCCGCCATCTGATGAGCAG TTGAAATCTGGAACTGCCTCTGTTGTGTGCCTGCTGA ATAACTTCTATCCCAGAGAGGCCAAAGTACAGTGGAA GGTGGATAACGCCCTCCAATCGGGTAACTCCCAGGAG AGTGTCACAGAGCAGGACAGCAAGGACAGCACCTACA GCCTCAGCAGCACCCTGACGCTGAGCAAAGCAGACTA CGAGAAACACAAAGTCTACGCCTGCGAAGTCACCCAT CAGGGCCTGAGCTCGCCCGTCACAAAGAGCTTCAACA GGGGAGAGTGTAGCGGAGGAGGAGGAAGCGGAGGAGG AGGAAGCGCCCCCCTCAAAATCCAAGCGTACTTCAAC GAAACTGCAGACTTACCGTGTCAGTTTGCCAATTCGC AGAATCTGAGCCTGAGCGAACTGGTGGTTTTCTGGCA GGATCAGGAGAACCTGGTTCTGAACGAAGTCTATCTG GGCAAAGAGCGGTTCGACAGCGTGGACAGCAAGTATA TGGGCCGCACCAGCTTTGATAGCGACAGCTGGACCCT GCGTCTGCACAATCTGCAAATCAAAGATAAGGGTAGG TACCAGTGCATTATCCACCATAAGAAGCCGACGGGTA TGATTAATATTCACCAAATGAACTCCGAGTTGTCTGT CCTGGCG |
| 206 | 1769 = 1627 Light chain VL, with constant kappa sequence, linker (underlined) and CD86 mutant 1040 | aa | DIQMTQSPSSLSASVGDRVTITCRASQSISSYLNWYQ QKPGKAPKLLIYAASSLQSGVPSRFSGSGSGTDFTLT ISSLQPEDFATYYCQQGTGYGPLTFGQGTKLEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC<u>SGGGGSG GGGSAP</u>LKIQAYFNETADLPCQFANSQNLSLSELVVF WQDQENLVLNEVYLGKERFDSVDSKYMGRTSFDSDSW TLRLHNLQIKDKGRYQCIIHHKKPTGMINIHQMNSEL SVLA<br>LIGHT CHAIN PREFERABLY ASSEMBLES WITH A HEAVY CHAIN COMPRISING THE 1626 VH SEQUENCE THUS, COMPLETE MOLECULE MAY BE DESIGNATED 1626/1769 |

TABLE I(1)

Exemplary CD137 CDR sequences

| Antibody | CDRH1 | CDRH2 | CDRH3 |
|---|---|---|---|
| 1204/1205 | GFTFSSYY (SEQ ID NO: 207) | IGSYYGYT (SEQ ID NO: 212) | ARAYYDYNYYYAYFDY (SEQ ID NO: 217) |
| 1214/1215 | GFTFSSYA (SEQ ID NO: 208) | IGSGGGYT (SEQ ID NO: 213) | ARVGHPFDY (SEQ ID NO: 218) |
| 1618/1619 | GFTFSYGS (SEQ ID NO: 209) | ISSGSGST (SEQ ID NO: 214) | ARSSYYGSYYSIDY (SEQ ID NO: 219) |
| 1620/1621 | GFTFSGYY (SEQ ID NO: 210) | ISSSGSYT (SEQ ID NO: 215) | ARSVGPYFDY (SEQ ID NO: 220) |
| 1626/1627 | GFTFGGYS (SEQ ID NO: 211) | IGGYYYST (SEQ ID NO: 216) | ARSYYGSIDY (SEQ ID NO: 221) |

TABLE I(2)

Exemplary CD137 CDR sequences

| Antibody | CDRL1 | CDRL2 | CDRL3 |
|---|---|---|---|
| 1204/1205 | QSISSY (SEQ ID NO: 80) | AAS (SEQ ID NO: 81) | QQSVPHYPFT (SEQ ID NO: 222) |
| 1214/1215 | QSISSY (SEQ ID NO: 80) | AAS (SEQ ID NO: 81) | QQDAYPHT (SEQ ID NO: 223) |
| 1618/1619 | QSISSY (SEQ ID NO: 80) | AAS (SEQ ID NO: 81) | QQYYDNLPT (SEQ ID NO: 224) |
| 1620/1621 | QSISSY (SEQ ID NO: 80) | AAS (SEQ ID NO: 81)) | QQGVGPYT (SEQ ID NO: 225) |
| 1626/1627 | QSISSY (SEQ ID NO: 80) | AAS (SEQ ID NO: 81)) | QQGTGYGPLT (SEQ ID NO: 226) |

Other Sequences (human CTLA-4)
SEQ ID NO: 1
MHVAQPAVVLASSRGIASFVCEYASPGKATEVRVTVLRQADSQVTEVCAATYMMGNELTFLDDSI

CTGTSSGNQVNLTIQGLRAMDTGLYICKVELMYPPPYYLGIGNGTQIYVIAKEKKPSYNRGLCEN

APNRARM (human CD28)
SEQ ID NO: 2
MLRLLLALNLFPSIQVTGNKILVKQSPMLVAYDNAVNLSCKYSYNLFSREFRASLHKGLDSAVEV

CVVYGNYSQQLQVYSKTGFNCDGKLGNESVTFYLQNLYVNQTDIYFCKIEVMYPPPYLDNEKSNG

TIIHVKGKHLCPSPLFPGPSKPFWVLVVVGGVLACYSLLVTVAFIIFWVRSKRSRLLHSDYMNMT

PRRPGPTRKHYQPYAPPRDFAAYRS

SEQ ID NO: 3
APLKIQAYFNETADLPCQFANSQNQSLSELVVFWQDQENLVLNEVYLGKEKFDSVHSKYMGRTSF

DSDSWTLRLHNLQIKDKGLYQCIIHHKKPTGMIRIHQMNSELSVLA

SEQ ID NO: 4
MDPQCTMGLSNILFVMAFLLSGAAPLKIQAYFNETADLPCQFANSQNQSLSELVVFWQDQENLVL

NEVYLGKEKFDSVHSKYMGRTSFDSDSWTLRLHNLQIKDKGLYQCIIHHKKPTGMIRIHQMNSEL

SVLANFSQPEIVPISNITENVYINLTCSSIHGYPEPKKMSVLLRTKNSTIEYDGIMQKSQDNVTE

LYDVSISLSVSFPDVTSNMTIFCILETDKTRLLSSPFSIELEDPQPPPDHIP

SEQ ID NO: 5
APLKIQAYFNETADLPCQFANSQNQSLSELVVFWQDQENLVLNEVYLGKEKFDSVASKYMGRTSF

DSDSWTLRLHNLQIKDKGLYQCIIHHKKPTGMIRIHQMNSELSVLA (human CD86)
SEQ ID NO: 44
MDPQCTMGLSNILFVMAFLLSGAAPLKIQAYFNETADLPCQFANSQNQSLSELVVFWQDQENLVL

NEVYLGKEKFDSVHSKYMGRTSFDSDSWTLRLHNLQIKDKGLYQCIIHHKKPTGMIRIHQMNSEL

SVLANFSQPEIVPISNITENVYINLTCSSIHGYPEPKKMSVLLRTKNSTIEYDGIMQKSQDNVTE

LYDVSISLSVSFPDVTSNMTIFCILETDKTRLLSSPFSIELEDPQPPPDHIPWITAVLPTVIICV

MVFCLILWKWKKKKRPRNSYKCGTNTMEREESEQTKKREKIHIPERSDEAQRVFKSSKTSSCDKS

DTCF (murine CTLA-4)
SEQ ID NO: 45
MACLGLRRYKAQLQLPSRTWPFVALLTLLFIPVFSEAIQVTQPSVVLASSHGVASFPCEYSPSHN

TDEVRVTVLRQTNDQMTEVCATTFTEKNTVGFLDYPFCSGTFNESRVNLTIQGLRAVDTGLYLCK

VELMYPPPYFVGMGNGTQIYVIDPEPCPDSDFLLWILVAVSLGLFFYSFLVSAVSLSKMLKKRSP

LTTGVYVKMPPTEPECEKQFQPYFIPIN (murine CD28)

SEQ ID NO: 46

MTLRLLFLALNFFSVQVTENKILVKQSPLLVVDSNEVSLSCRYSYNLLAKEFRASLYKGVNSDVE

VCVGNGNFTYQPQFRSNAEFNCDGDFDNETVTFRLWNLHVNHTDIYFCKIEFMYPPPYLDNERSN

GTIIHIKEKHLCHTQSSPKLFWALVVVAGVLFCYGLLVTVALCVIWTNSRRNRLLQVTTMNMTPR

RPGLTRKPYQPYAPARDFAAYRP (human OX40)

SEQ ID NO: 51

MCVGARRLGRGPCAALLLLGLGLSTVTGLHCVGDTYPSNDRCCHECRPGNGMVSRCSRSQNTVCR

PCGPGFYNDVVSSKPCKPCTWCNLRSGSERKQLCTATQDTVCRCRAGTQPLDSYKPGVDCAPCPP

GHFSPGDNQACKPWTNCTLAGKHTLQPASNSSDAICEDRDPPATQPQETQGPPARPITVQPTEAW

PRTSQGPSTRPVEVPGGRAVAAILGLGLVLGLLGPLAILLALYLLRRDQRLPPDAHKPPGGGSFR

TPIQEEQADAHSTLAKI

SEQ ID NO: 140 gcttccacca agggcccatc cgtcttcccc ctggcgccct gctccaggag cacctccgag agcacagccg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacgaagacc tacacctgca acgtagatca caagcccagc aacaccaagg tggacaagag agttgagtcc aaatatggtc cccatgccc accttgccca gcacctgagt tcctgggggg accatcagtc ttcctgttcc cccaaaaccc aaggacact ctcatgatct cccggacccc tgaggtcacg tgcgtggtgg tggacgtgag ccaggaagac cccgaggtcc agttcaactg gtacgtggat ggcgtggagg tgcataatgc caagacaaag ccgcgggagg agcagttcaa cagcacgtac cgtgtggtca gcgtcctcac cgtcctgcac caggactggc tgaacggcaa ggagtacaag tgcaaggtct ccaacaaagg cctcccgtcc tccatcgaga aaaccatctc aaagccaaa gggcagcccc gagagccaca ggtgtacacc ctgcccccat cccaggagga gatgaccaag aaccaggtca gcctgacctg cctggtcaaa ggcttctacc ccagcgacat cgccgtggag tgggagagca atgggcagcc ggagaacaac tacaagacca cgcctcccgt gctggactcc gacggctcct tcttcctcta cagcaggcta accgtggaca agagcaggtg gcaggagggg aatgtcttct catgctccgt gatgcatgag gctctgcaca accgctacac acagaagagc ctctccctgt ctctgggtaa a

SEQ ID NO: 141 agctttctgg ggcaggccgg gcctgacttt ggctggggc agggagggg ctaaggtgac gcaggtggcg ccagccaggt gcacacccaa tgcccatgag cccagacact ggaccctgca tggaccatcg cggatagaca agaaccgagg ggcctctgcg ccctgggccc agctctgtcc cacaccgcgg tcacatggca ccacctctct tgcagcttcc accaagggcc catccgtctt cccctggcg ccctgctcca ggagcacctc cgagagcaca gccgccctgg gctgcctggt caaggactac ttccccgaac cggtgacggt gtcgtggaac tcaggcgccc tgaccagcgg cgtgcacacc ttcccggctg tcctacagtc ctcaggactc tactccctca gcagcgtggt gaccgtgccc tccagcagct gggcacgaa gacctacacc tgcaacgtag atcacaagcc cagcaacacc aaggtggaca gagagttgg tgagaggcca gcagggagg ggagggtgtc -continued

```
tgctggaagc caggctcagc cctcctgcct ggacgcaccc cggctgtgca gccccagccc agggcagcaa ggcatgcccc atctgtctcc tcacccggag ccctctgacc acccactca tgctcaggga gagggtcttc tggattttc caccaggctc ccggcaccac aggctggatg cccctacccc aggccctgcg catacagggc aggtgctgcg ctcagacctg ccaagagcca tatccgggag gaccctgccc ctgacctaag cccacccaa aggccaaact ctccactccc tcagctcaga caccttctct cctcccagat ctgagtaact cccaatcttc tctctgcaga gtccaaatat ggtcccccat gcccaccttg cccaggtaag ccaacccagg cctcgccctc cagctcaagg cgggacaggt gccctagagt agcctgcatc cagggacagg ccccagccgg gtgctgacgc atccacctcc atctcttcct cagcacctga gttcctgggg ggaccatcag tcttcctgtt ccccccaaaa cccaaggaca ctctcatgat ctcccggacc cctgaggtca cgtgcgtggt ggtggacgtg agccaggaag accccgaggt ccagttcaac tggtacgtgg atggcgtgga ggtgcataat gccaagacaa agccgcggga ggagcagttc aacagcacgt accgtgtggt cagcgtcctc accgtcctgc accaggactg gctgaacggc aaggagtaca agtgcaaggt ctccaacaaa ggcctcccgt cctccatcga gaaaaccatc tccaaagcca aaggtgggac ccacggggtg cgagggccac acggacagag gccagctcgg cccaccctct gccctgggag tgaccgctgt gccaacctct gtccctacag ggcagccccg agagccacag gtgtacaccc tgcccccatc ccaggaggag atgaccaaga accaggtcag cctgacctgc ctggtcaaag gcttctaccc cagcgacatc gccgtggagt gggagagcaa tgggcagccg gagaacaact acaagaccac gcctcccgtg ctggactccg acggctcctt cttcctctac agcaggctaa ccgtggacaa gagcaggtgg caggagggga atgtcttctc atgctccgtg atgcatgagg ctctgcacaa ccgctacaca cagaagagcc tctccctgtc tctgggtaaa tgagtgccag ggccggcaag ccccgctcc ccgggctctc ggggtcgcgc gaggatgctt ggcacgtacc ccgtctacat acttcccagg cacccagcat ggaaataaag cacccaccac tgccctgggc ccctgtgaga ctgtgatggt tctttccacg ggtcaggccg agtctgaggc ctgagtgaca tgagggaggc agagcgggtc ccactgtccc cacactgg SEQ ID NO: 142
gcttccacca agggcccatc cgtcttcccc ctggcgccct gctccaggag cacctccgag agcacagccg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacgaagacc tacacctgca acgtagatca caagcccagc aacaccaagg tggacaagag agttgagtcc aaatatggtc cccatgccc atcatgccca gcacctgagt tcctgggggg accatcagtc ttcctgttcc cccaaaacc caaggacact ctcatgatct cccggacccc tgaggtcacg tgcgtggtgg tggacgtgag ccaggaagac cccgaggtcc agttcaactg gtacgtggat ggcgtggagg tgcataatgc caagacaaag ccgcgggagg agcagttcaa cagcacgtac cgtgtggtca gcgtcctcac cgtcctgcac caggactggc tgaacggcaa ggagtacaag tgcaaggtct ccaacaaagg cctcccgtcc tccatcgaga aaaccatctc caaagccaaa gggcagcccc gagagccaca ggtgtacacc ctgcccccat cccaggagga gatgaccaag aaccaggtca gcctgacctg cctggtcaaa ggcttctacc ccagcgacat cgccgtggag tgggagagca atgggcagcc ggagaacaac tacaagacca cgcctcccgt gctggactcc gacggctcct tcttcctcta cagcaggcta accgtggaca agagcaggtg gcaggagggg
```

-continued aatgtcttct catgctccgt gatgcatgag gctctgcaca accactacac acagaagagc ctctccctgt ctctgggtaa a SEQ ID NO: 143
agctttctgg ggcaggccgg gcctgacttt ggctgggggc agggaggggg ctaaggtgac gcaggtggcg ccagccaggt gcacacccaa tgcccatgag cccagacact ggaccctgca tggaccatcg cggatagaca agaaccgagg ggcctctgcg ccctgggccc agctctgtcc cacaccgcgg tcacatggca ccacctctct tgcagcttcc accaagggcc catccgtctt ccccctggcg ccctgctcca ggagcacctc cgagagcaca gccgccctgg gctgcctggt caaggactac ttccccgaac cggtgacggt gtcgtggaac tcaggcgccc tgaccagcgg cgtgcacacc ttcccggctg tcctacagtc ctcaggactc tactccctca gcagcgtggt gaccgtgccc tccagcagct tgggcacgaa gacctacacc tgcaacgtag atcacaagcc cagcaacacc aaggtggaca gagagttgg tgagaggcca gcacagggag ggagggtgtc tgctggaagc caggctcagc cctcctgcct ggacgcaccc cggctgtgca gccccagccc agggcagcaa ggcatgcccc atctgtctcc tcacccggag gcctctgacc accccactca tgctcaggga gagggtcttc tggatttttc caccaggctc ccggcaccac aggctggatg cccctacccc aggccctgcg catacagggc aggtgctgcg ctcagacctg ccaagagcca tatccgggag gaccctgccc ctgacctaag cccaccccaa aggccaaact ctccactccc tcagctcaga caccttctct cctcccagat ctgagtaact cccaatcttc tctctgcaga gtccaaatat ggtcccccat gcccatcatg cccaggtaag ccaacccagg cctcgccctc cagctcaagg cgggacaggt gccctagagt agcctgcatc cagggacagg ccccagccgg gtgctgacgc atccacctcc atctcttcct cagcacctga gttcctgggg ggaccatcag tcttcctgtt ccccccaaaa cccaaggaca ctctcatgat ctcccggacc cctgaggtca cgtgcgtggt ggtggacgtg agccaggaag accccgaggt ccagttcaac tggtacgtgg atggcgtgga ggtgcataat gccaagacaa agccgcggga ggagcagttc aacagcacgt accgtgtggt cagcgtcctc accgtcctgc accaggactg gctgaacggc aaggagtaca agtgcaaggt ctccaacaaa ggcctcccgt cctccatcga aaaaccatc tccaaagcca aaggtgggac ccacggggtg cgagggccac acggacagag gccagctcgg cccaccctct gccctgggag tgaccgctgt gccaacctct gtccctacag gcagccccg agagccacag gtgtacaccc tgcccccatc ccaggaggag atgaccaaga accaggtcag cctgacctgc ctggtcaaag gcttctaccc cagcgacatc gccgtggagt gggagagcaa tgggcagccg gagaacaact acaagaccac gcctcccgtg ctggactccg acggctcctt cttcctctac agcaggctaa ccgtggacaa gagcaggtgg caggagggga atgtcttctc atgctccgtg atgcatgagg ctctgcacaa ccactacaca cagaagagcc tctccctgtc tctgggtaaa tgagtgccag gccggcaag ccccgctcc ccggctctc ggggtcgcgc gaggatgctt ggcacgtacc ccgtctacat acttcccagg cacccagcat ggaaataaag caccaccac tgccctgggc cctgtgaga ctgtgatggt tctttccacg ggtcaggccg agtctgaggc ctgagtgaca tgagggaggc agagcgggtc ccactgtccc cacactgg SEQ ID NO: 145
gcctccacca agggcccatc ggtcttcccc ctggcaccct cctccaagag cacctctggg ggcacagcgg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacccagacc -continued

```
tacatctgca acgtgaatca caagcccagc aacaccaagg tggacaagaa agttgagccc aaatcttgtg acaaaactca cacatgccca ccgtgcccag cacctgaact cctgggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag ggcagccccg agaaccacag gtgtacaccc tgcccccatc ccgggatgag ctgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggtaaa
```

SEQ ID NO: 146
```
gcctccacca agggcccatc ggtcttcccc ctggcaccct cctccaagag cacctctggg ggcacagcgg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacccagacc tacatctgca acgtgaatca caagcccagc aacaccaagg tggacaagaa agttggtgag aggccagcac agggagggag ggtgtctgct ggaagccagg ctcagcgctc ctgcctggac gcatcccggc tatgcagccc cagtccaggg cagcaaggca ggccccgtct gcctcttcac ccggaggcct ctgcccgccc cactcatgct cagggagagg gtcttctggc tttttcccca ggctctgggc aggcacaggc taggtgcccc taacccaggc cctgcacaca aaggggcagg tgctgggctc agacctgcca agagccatat ccgggaggac cctgcccctg acctaagccc accccaaagg ccaaactctc cactccctca gctcggacac tttctctcct cccagattcc agtaactccc aatcttctct ctgcagagcc caaatcttgt gacaaaactc acacatgccc accgtgccca ggtaagccag cccaggcctc gccctccagc tcaaggcggg acaggtgccc tagagtagcc tgcatccagg gacaggcccc agccgggtgc tgacacgtcc acctccatct cttcctcagc acctgaactc ctgggggac cgtcagtctt cctcttcccc ccaaaaccca aggacaccct catgatctcc cggacccctg aggtcacatg cgtggtggtg gacgtgagcc acgaagaccc tgaggtcaag ttcaactggt acgtggacgg cgtggaggtg cataatgcca agacaaagcc gcgggaggag cagtacaaca gcacgtaccg tgtggtcagc gtcctcaccg tcctgcacca ggactggctg aatggcaagg agtacaagtg caaggtctcc aacaaagccc tcccagcccc catcgagaaa accatctcca agccaaagg tgggacccgt ggggtgcgag ggccacatgg acagaggccg gctcggccca cctctgccc tgagagtgac cgctgtacca acctctgtcc ctacagggca gccccgagaa ccacaggtgt acaccctgcc cccatcccgg gatgagctga ccaagaacca ggtcagcctg acctgcctgg tcaaaggctt ctatcccagc gacatcgccg tggagtggga gagcaatggg cagccggaga caactacaa gaccacgcct cccgtgctgg actccgacgg ctccttcttc ctctacagca agctcaccgt ggacaagagc aggtggcagc aggggaacgt cttctcatgc tccgtgatgc atgaggctct gcacaaccac tacacgcaga gagcctctc cctgtctccg ggtaaa
```

```
                                                SEQ ID NO: 147
cgaactgtgg ctgcaccatc tgtcttcatc ttcccgccat ctgatgagca gttgaaatct ggaactgcct ctgttgtgtg cctgctgaat aacttctatc ccagagaggc caaagtacag tggaaggtgg ataacgccct ccaatcgggt aactcccagg agagtgtcac agagcaggac agcaaggaca gcacctacag cctcagcagc accctgacgc tgagcaaagc agactacgag aaacacaaag tctacgcctg cgaagtcacc catcagggcc tgagctcgcc cgtcacaaag agcttcaaca ggggagagtg t
```

(Human CD137, amino acid sequence: >gi|571321|gb|AAA53133.1| 4-1BB [Homo sapiens])

```
                                                SEQ ID NO: 148
MGNSCYNIVATLLLVLNFERTRSLQDPCSNCPAGTFCDNNRNQICSPCPPNSFSSAGGQRTCDIC

RQCKGVFRTRKECSSTSNAECDCTPGFHCLGAGCSMCEQDCKQGQELTKKGCKDCCFGTFNDQKR

GICRPWTNCSLDGKSVLVNGTKERDVVCGPSPADLSPGASSVTPPAPAREPGHSPQIISFFLALT

STALLFLLFFLTLRFSVVKRGRKKLLYIFKQPFMRPVQTTQEEDGCSCRFPEEEEGGCEL
```

```
                                                SEQ ID NO: 175
gcttccacca agggcccatc cgtcttcccc ctggcgccct gctccaggag cacctccgag agcacagccg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacgaagacc tacacctgca acgtagatca caagcccagc aacaccaagg tggacaagag agttgagtcc aaatatggtc cccccatgcc cactgccca gcacctgagt tcctgggggg accatcagtc ttcctgttcc cccaaaacc caaggacact ctcatgatct cccggacccc tgaggtcacg tgcgtggtgg tggacgtgag ccaggaagac cccgaggtcc agttcaactg gtacgtggat ggcgtggagg tgcataatgc caagacaaag ccgcgggagg agcagttcaa cagcacgtac cgtgtggtca gcgtcctcac cgtcctgcac caggactggc tgaacggcaa ggagtacaag tgcaaggtct ccaacaaagg cctcccgtcc tccatcgaga aaaccatctc caaagccaaa gggcagcccc gagagccaca ggtgtacacc ctgcccccat cccaggagga gatgaccaag aaccaggtca gcctgacctg cctggtcaaa ggcttctacc ccagcgacat cgccgtggag tgggagagca atgggcagcc ggagaacaac tacaagacca cgcctcccgt gctggactcc gacggctcct tcttcctcta cagcaggcta accgtggaca agagcaggtg gcaggagggg aatgtcttct catgctccgt gatgcatgag gctctgcaca accactacac acagaagagc ctctccctgt ctctgggtaa a
```

```
                                                SEQ ID NO: 176
agctttctgg ggcaggccgg gcctgacttt ggctggggc agggaggggg ctaaggtgac gcaggtggcg ccagccaggt gcacacccaa tgcccatgag cccagacact ggaccctgca tggaccatcg cggatagaca agaaccgagg ggcctctgcg ccctgggccc agctctgtcc cacaccgcgg tcacatggca ccacctctct tgcagcttcc accaagggcc catccgtctt cccctggcg ccctgctcca ggagcacctc cgagagcaca gccgccctgg gctgcctggt caaggactac ttccccgaac cggtgacggt gtcgtggaac tcaggcgccc tgaccagcgg cgtgcacacc ttcccggctg tcctacagtc ctcaggactc tactccctca gcagcgtggt gaccgtgccc tccagcagct gggcacgaa gacctacacc tgcaacgtag atcacaagcc cagcaacaca aaggtggaca agagagttgg tgagaggcca gcacagggag ggagggtgtc tgctggaagc caggctcagc cctcctgcct ggacgcaccc cggctgtgca gccccagccc
```

```
-continued
agggcagcaa ggcatgcccc atctgtctcc tcaccggag gcctctgacc accccactca tgctcaggga gagggtcttc tggattttc caccaggctc ccggcaccac aggctggatg cccctacccc aggccctgcg catacagggc aggtgctgcg ctcagacctg ccaagagcca tatccgggag gaccctgccc ctgacctaag cccaccccaa aggccaaact ctccactccc tcagctcaga caccttctct cctcccagat ctgagtaact cccaatcttc tctctgcaga gtccaaatat ggtcccccat gcccaccttg cccaggtaag ccaacccagg cctcgccctc cagctcaagg cgggacaggt gccctagagt agcctgcatc cagggacagg ccccagccgg gtgctgacgc atccacctcc atctcttcct cagcacctga gttcctgggg ggaccatcag tcttcctgtt cccccaaaa cccaaggaca ctctcatgat ctcccggacc cctgaggtca cgtgcgtggt ggtggacgtg agccaggaag accccgaggt ccagttcaac tggtacgtgg atggcgtgga ggtgcataat gccaagacaa agccgcggga ggagcagttc aacagcacgt accgtgtggt cagcgtcctc accgtcctgc accaggactg gctgaacggc aaggagtaca agtgcaaggt ctccaacaaa ggcctcccgt cctccatcga gaaaaccatc tccaaagcca aaggtgggac ccacggggtg cgagggccac acggacagag gccagctcgg cccaccctct gccctgggag tgaccgctgt gccaacctct gtccctacag ggcagccccg agagccacag gtgtacaccc tgccccatc ccaggaggag atgaccaaga accaggtcag cctgacctgc ctggtcaaag gcttctaccc cagcgacatc gccgtggagt gggagagcaa tgggcagccg gagaacaact acaagaccac gcctcccgtg ctggactccg acggctcctt cttcctctac agcaggctaa ccgtggacaa gagcaggtgg caggagggga atgtcttctc atgctccgtg atgcatgagg ctctgcacaa ccactacaca cagaagagcc tctccctgtc tctgggtaaa tgagtgccag ggccggcaag cccccgctcc ccgggctctc ggggtcgcgc gaggatgctt ggcacgtacc ccgtctacat acttcccagg cacccagcat ggaaataaag cacccaccac tgccctgggc ccctgtgaga ctgtgatggt tctttccacg ggtcaggccg agtctgaggc ctgagtgaca tgagggaggc agagcgggtc ccactgtccc cacactgg
```

EXAMPLES

The present invention is further illustrated by the following examples which should not be construed as further limiting. The contents of all figures and all references, patents and published patent applications cited throughout this application are expressly incorporated herein by reference.

Example 1—CTLA-4 Binding Domains

CTLA-4 binding domain polypeptides were selected and expressed as described in WO 2014/207063 (see Examples) and were assayed for binding to CTLA-4 by at least one of ELISA and surface plasmon resonance as described below.

Binding ELISA 96-well flat bottom high binding plates (Greiner, #655074) were coated with either CTLA4-Fc (Fitzgerald, #30R-CD152) or CD28-Fc (R&D systems, 342-CD) by incubating overnight at 4° C. The plates were washed (Wash buffer: PBS+0.05% Tween 20 (PBST) Medicago, #09-9410-100) and then blocked in PBST+3% BSA (Merck, #1.12018.0100). The plates were washed again and sample or controls (serially diluted ⅕ from 200-0.001 μg/ml) were added to the wells. The samples were incubated for 1 h at room temperature and then washed. Detection antibody, goat-anti-human IgG Fcγ-HRP (Jackson, #109-035-098) was added and the plates were subsequently developed using SuperSignal Pico Chemiluminescent substrate (Thermo Scientific, #37069) and detected with an Envision reader (Perkin Elmer). EC50 values were calculated for both CTLA4 and CD28. The binding ratio (EC50 binding ratio=[EC50 for CD28]=[EC50 for CTLA-4]) was calculated for each polypeptide and is shown in Table 1.1.

Surface Plasmon Resonance

Either CTLA4-Fc (Fitzgerald, #30R-CD152) or CD28-Fc (R&D Systems, 342-CD) was immobilized to the Biacore™ sensor chip, CM5, using conventional amine coupling. The CD86 mutant molecules and controls (serially diluted ½ 100-1.5 nM) were analyzed for binding in HBS-P (GE, BR-1003-68) ata flow rate of 30 μl/ml. The association was followed for 3 minutes and the dissociation for 10 minutes. Regeneration was performed twice using 5 mM NaOH for 30 seconds. The kinetic parameters and the affinity constants were calculated using BIAevaluation 4.1 software (Table 1.3).

Inhibition ELISA 96-well flat bottom plate high binding plates (Greiner, #655074) were coated with wildtype CD86-Fc (R&D Systems, #7625-B2) by incubating overnight at 4° C. The plates were washed (Wash buffer: PBS+0.05% Tween 20 (PBST) Medicago, #09-9410-100) and then blocked in PBST+3%

BSA (Merck, #1.12018.0100). The sample (CD86 mutant or wild type protein; serially diluted ¼ from 30000 to 0.3 ng/ml) was incubated with biotinylated-CTLA4 (Fitzgerald, #30R-CD152) in room temperature 1 h, the mixture was then added to the blocked wells in the ELISA plate. Detection was performed with Streptavidin-HRP (Pierce, #21126) and the plates were subsequently developed using SuperSignal Pico Chemiluminescent substrate (Thermo Scientific, #37069) and detected with Envision reader (Perkin Elmer). The results are shown in FIG. 2. IC50 values were calculated and are shown in the tables below. All molecules tested showed better IC50 value than both wild type and H79A, the IC of the best mutant CD86 molecule was improved over 100-fold compared to wild type. Results for exemplary molecules 900, 901, 904, 906, 907, 908, 910, 915 and 938 are shown in Table 1.1. Kd binding ratio=[Kd for CD28]=[Kd for CTLA-4]. The full amino acid sequences for exemplary molecules 900, 901, 904, 906, 907, 908, 910, 915 and 938 are provided as SEQ ID NOs: 6 to 14, respectively.

TABLE 1.1

| Sample | Mutated positions and amino acid change relative to wild-type (positions numbered as in FIG. 4) | EC50 binding ratio | Kd binding ratio |
|---|---|---|---|
| 900 | H79D, L107I, I111V, T118S, M120L, I121V, R122K, Q125E | 3.5 | ND* |
| 901 | Q48L, S49T, L107I, I111V, R122K, Q125E, A134T | 17.2 | 2.7 |
| 904 | V54I, K74R, S77A, H79D, L107I, T118S, I121V, R122K, N127D | 12.2 | 6.8 |
| 906 | F32I, Q48L, K74R, H79D, L107F, M120L, I121V, R122K, Q125E | 16.2 | 0.8 |
| 907 | R122K, Q125E | 30.5 | 5.6 |
| 908 | L107I, I121V, R122K, Q125E | 6.2 | 4.7 |
| 910 | H79D, L107I, I121V, R122K, Q125E | 7.7 | 5.1 |
| 915 | V64I, H79D, L107F, T118S, M120L, R122K, N127D | 9.9 | 1.9 |
| 938 | V64I, L107I, I121V, R122K | 2.0 | 5.5 |
| Wild type | | 3.4 | 1.6 |

*No detectable binding was seen in the BIAcore ™ analysis nor binding ELISA

Results for exemplary molecules 1038, 1039, 1040, 1041, 1042, 1043, 1044, 1045, 1046 and 1047 are shown in Tables 1.2 and 1.3, and in FIGS. 2 and 3. The full amino acid sequences for exemplary molecules 1038, 1039, 1040, 1041, 1042, 1043, 1044, 1045, 1046 and 1047 are provided as SEQ ID NOs: 15 to 24, respectively.

TABLE 1.2

| Sample | EC50 | Sample | IC50 |
|---|---|---|---|
| 1038 | 0.14 | — | — |
| 1039 | 0.039 | — | — |
| 1040 | 0.0076 | 1040 | 0.049 |
| 1041 | 0.087 | 1041 | 3.1 |
| 1042 | 0.29 | 1042 | 4.3 |
| 1043 | 0.035 | 1043 | 4.0 |
| 1044 | 0.029 | 1044 | 1.4 |
| 1045 | 0.047 | 1045 | 2.6 |
| 1046 | 0.019 | 1046 | 1.1 |
| 1047 | 0.037 | 1047 | 0.98 |
| Wild type | 0.51 | Wild type | 15 |
| Prior Art | 0.81 | H79A | 25 |
| Negative control | No activity | Negative control | No activity |

TABLE 1.3

| Sample | Mutated positions and amino acid change (positions numbered as in FIG. 4) | ka (1/Ms) | kd (1/s) | $K_D$ (nM) |
|---|---|---|---|---|
| 1038 | Q48L, H79D, L107I, I121V, R122K, Q125E | 1.0e6 | 0.012 | 12 |
| 1039 | Q48L, H79S, L107I, T118S, I121V, R122K, N127D | 1.0e6 | 8.5e-3 | 8 |
| 1040 | Q48L, K74R, H79D, L107R, R122N | 1.0e6 | 3.2e-3 | 3 |
| 1041 | F32L, Q48L, H79D, L107I, M120L, I121V, R122K, 125E | 7.0e5 | 8.4e-3 | 12 |
| 1042 | Q48L, K74I, H79S, L107I, T118S, I121V, R122K, N127D | 4.4e5 | 0.011 | 25 |
| 1043 | Q48L, H79D, L107I, R122K, Q125E | 1.1e6 | 0.011 | 10 |
| 1044 | Q48L, S49T, H79S, L107I, R122K, Q125E, N127S | 1.1e6 | 9.4e-3 | 8 |
| 1045 | Q48L, S49T, H79D, M120L, I121V, R122K, Q125E | 9.4e5 | 8.3e-3 | 9 |
| 1046 | H79D, K103E, L107I, T118S, I121V, R122K, N127D | 1.4e6 | 8.0e-3 | 6 |
| 1047 | Q48L, H79D, L107I, M120L, I121V, R122K, Q125E | 8.5e5 | 8.4e-3 | 10 |
| Wild type | | 4.6e5 | 0.023 | 50 |
| H79A | | 3.4e5 | 0.022 | 63 |

Example 2—Cross Reactivity to Murine CTLA-4 of Exemplary Polypeptide from Clone 1040

The relative affinity for murine and human CTLA-4 of an exemplary mutant CD86 molecule 1040 was investigated using an inhibition ELISA binding assay. The 1040 molecule used in these experiments was conjugated to an anti-CD40 antibody as part of a bispecific molecule. The CTLA-4 binding properties of the CD86 molecule are not affected by this conjugation (data not shown).

In brief, 96-well flat bottom plate high binding plates (Greiner #655074) were coated with human CTLA-4 (Fitzgerald) incubating overnight at 4° C. The plates were washed (Wash buffer: PBS+0.05% Tween 20 (PBST) Medicago #09-9410-100) and then blocked in PBST+3% BSA (Merck, #1.12018.0100).

The sample (exemplary CD86 mutant) was pre-incubated at room temperature for 1 hour with soluble biotinylated human CTLA4 (Fitzgerald #30R-CD152) or soluble murine CTLA-4 (R&D systems) at different concentrations (serial dilutions ¼ from 30000 to 0.3 ng/ml).

The mixture was then added to the blocked wells in the ELISA plate. Detection was performed with Streptavidin-HRP (Pierce, #21126) and the plates were subsequently developed using SuperSignal Pico Chemiluminescent substrate (Thermo Scientific, #37069) and detected with Envision reader (Perkin Elmer). The results are shown in FIG. 5. The observed inhibition curves with murine and human CTLA-4 demonstrate that the binding affinity of the exemplary CD86 mutant (1040) to the two forms of CTLA-4 is of a similar magnitude. The other clones tested in Example 1 were also found to bind to murine CTLA-4 (data not shown).

Example 3—Characterisation of OX40 Antibodies

Characteristics of exemplary OX40 antibodies are summarised in Table 3.1 below.

by incubating with commercial OX40 antibody (huOX40, BD Biosciences) for 30 min at 4° C. and then detected with a-huIgG-PE (Jackson Immunoresearch) 30 min 4° C. For the assay, the transfected cells were incubated with the test

TABLE 3.1

| Antibody | CDR H3 length (IMGT) | Dose response ELISA (IgG) | T-cell agonist | *M. mulatta* OX40 binding | huOX40 binding FACS (CHO) | Hydrophathy index | Isoelectric point | Dissociation constant $K_D$ (M) | Association rate constant ka (1/Ms) | Association rate constant kd (1/s) |
|---|---|---|---|---|---|---|---|---|---|---|
| 1166/1167 | 10 | <1 nM | Yes | Yes | Yes | −0.392 | 9.11 | 3.22E−10 | 9.01E+04 | 2.90E−05 |
| 1170/1171 | 10 | <1 nM | Yes | Yes | Yes | −0.415 | 9.11 | 2.50E−10 | 1.45E+06 | 3.63E−04 |
| 1164/1135 | 11 | <1 nM | Yes | Yes | Yes | −0.398 | 9.21 | 3.08E−10 | 2.51E+05 | 7.73E−05 |
| 1168/1135 | 11 | <1 nM | Yes | Yes | Yes | −0.404 | 9.19 | 3.27E−10 | 5.18E+05 | 1.69E−04 |
| 1482/1483 | 9 | <1 nM | Yes | Yes | Yes | −0.381 | 9.19 | 7.53E−10 | 7.76E+05 | 5.84E−04 |
| 1490/1135 | 11 | <1 nM | Yes | Yes | Yes | −0.407 | 9.18 | 3.07E−10 | 3.87E+06 | 1.19E−03 |
| 1514/1515 | 14 | <1 nM | Yes | Yes | Yes | −0.399 | 9.11 | 6.40E−10 | 2.57E+05 | 1.64E−04 |
| 1520/1135 | 17 | <1 nM | Yes | Yes | Yes | −0.394 | 9.18 | 5.55E−10 | 6.20E+05 | 3.44E−04 |
| 1524/1525 | 10 | <1 nM | Yes | Yes | Yes | −0.391 | 9.11 | 8.11E−10 | 1.71E+06 | 1.39E−03 |
| 1526/1527 | 15 | <1 nM | Yes | Yes | Yes | −0.388 | 8.99 | 4.30E−10 | 4.35E+05 | 1.87E−04 |
| 1542/1135 | 11 | <1 nM | Yes | Yes | Yes | −0.411 | 9.2 | 4.63E−10 | 2.16E+05 | 1.00E−04 |

Two anti-OX40 antibodies were synthesised solely for use as reference antibodies for the purposes of comparison in these studies. They are designated herein as "72" or "72/76", and "74" or "74/78", respectively.

Measurement of Kinetic Constants by Surface Plasmon Resonance

Figure 6:
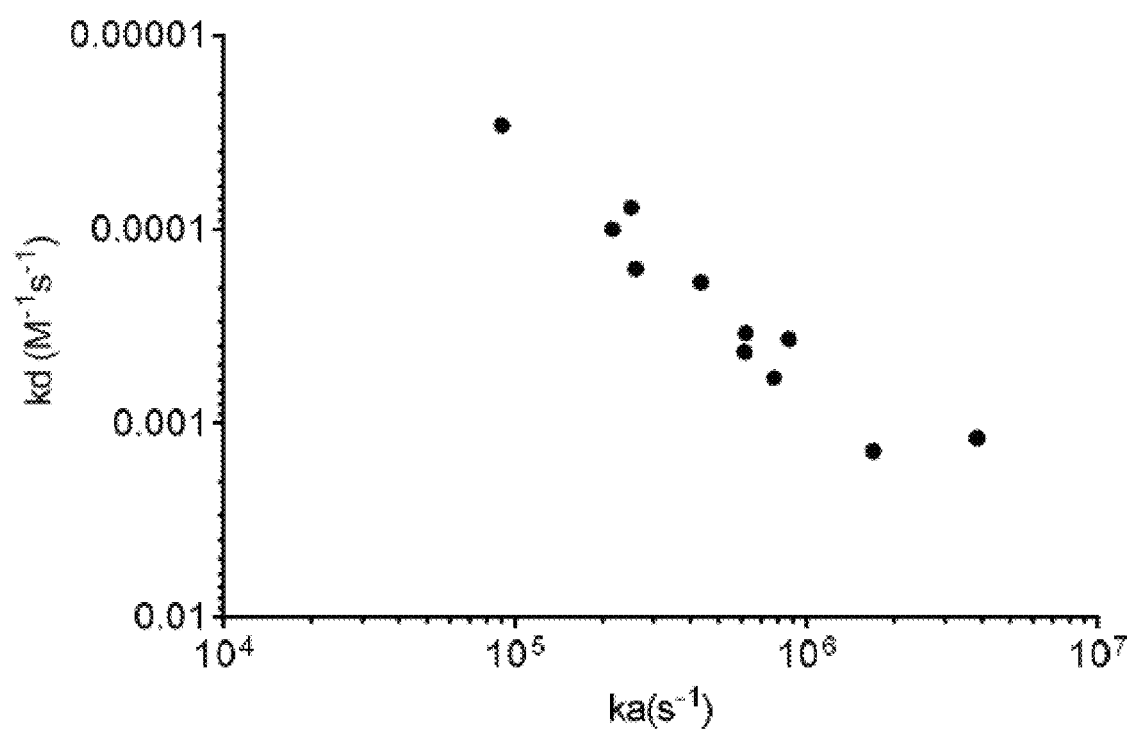
FIG. 6 is a plot of dissociation rate constant versus association rate constant for exemplary anti-OX40 antibodies, as determined by surface plasmon resonance.

Human OX40 (R&D systems, #3358_OX) was immobilized to the Biacore™ sensor chip, CM5, using conventional amine coupling. The tested antibodies and controls (serially diluted ⅓ or ½ 100-2 nM) were analyzed for binding in HBS-P (GE, #BR-1003-68) at a flow rate of 30 μl/ml. The association was followed for 3 minutes and the dissociation for 20 minutes. Regeneration was performed twice using 50 mM NaOH for 60 seconds. The kinetic parameters and the affinity constants were calculated using 1:1 Langmuir model with drifting baseline. The tested antibodies were overall in the subnanomolar-nanomolar range with varying on and off rates (FIG. 6 and Table 3.1). Most of the antibodies had affinities <5 nM. The kinetic parameters and the affinity constants were calculated using BIAevaluation 4.1 software.

Measurement by ELISA of Binding to Human and Murine OX40, and to CD137 and CD40 by ELISA ELISA plates were coated with human OX40 (R&D Systems, 3388-OX), CD40 (Ancell), or CD137 (R&D Systems) at 0.1 or 0.5 μg/ml. The ELISA plates were washed with PBST and then blocked with PBST+2% BSA for 1 h at room temperature and then washed again with PBST. The antibodies were added in dilution series to the ELISA plates for 1 h at room temperature and then washed with PBST. Binding was detected using goat anti human kappa light chain HRP, incubated for 1 h at room temperature. SuperSignal Pico Luminescent was used as substrate and luminescence was measured using Fluostar Optima.

All the tested OX40 antibodies bound to human OX40 and displayed EC50 value below 1 nM. The antibodies did not bind to murine OX40 or to the other TNFR super family members tested (data not shown).

Measurement of Binding to Human OX40 Over-Expressed on CHO Cells

The extracellular part of human OX40 was fused to the transmembrane and intracellular part of hCD40 and cloned into pcDNA3.0. The vector was subsequently stably transfected into CHO cells. Expression of OX40 was confirmed antibodies and controls for 30 min at 4° C. and then detected with a-huIgG-PE (Jackson Immunoresearch) 30 min 4° C. Cells were analyzed by flow cytometry with FACS Verse (BD Biosciences).

Figure 7:
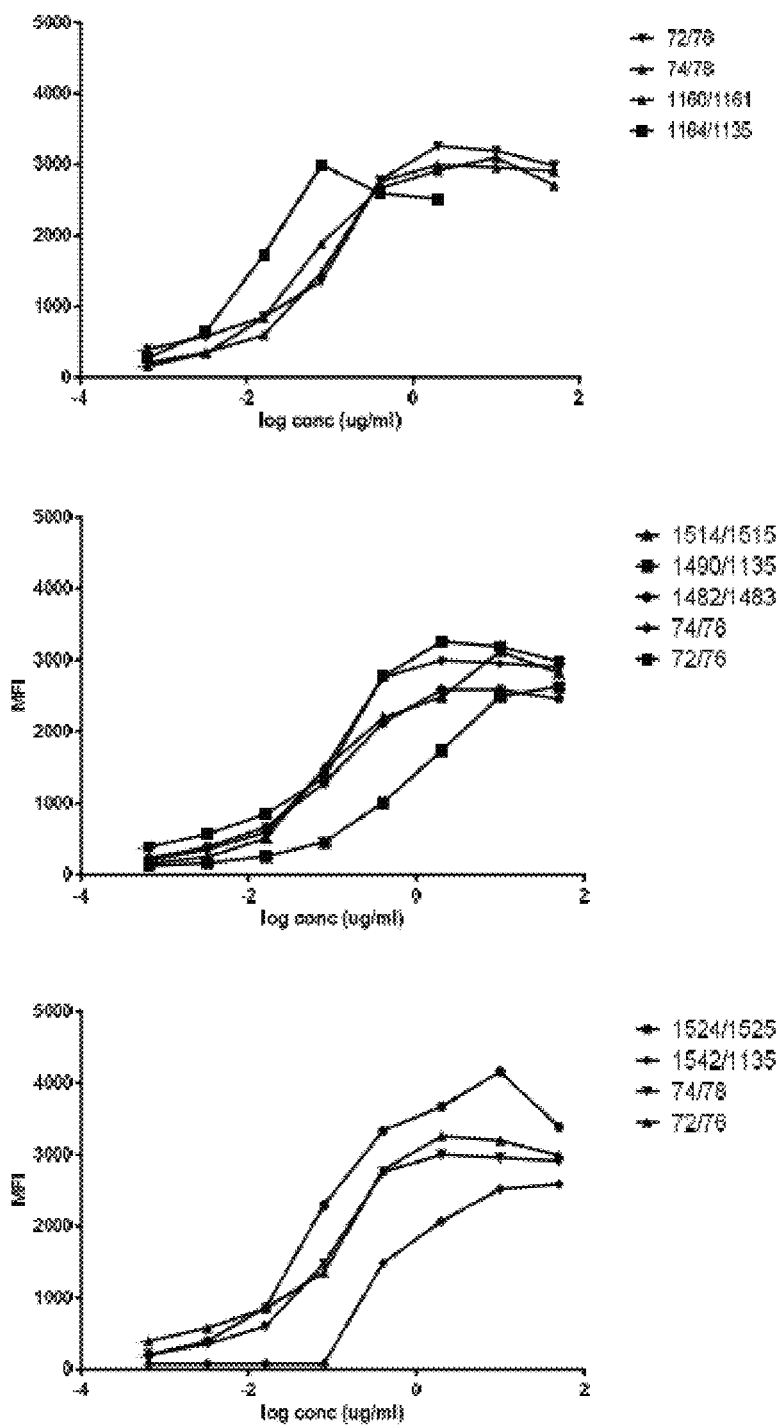
FIG. 7 shows binding of exemplary anti-OX40 antibodies to human OX40 overexpressed on CHO cells, measured by flow cytometry.

All clones bound to hOX40 overexpressed on CHO cells in a dose dependent manner (FIG. 7).

Example 4—Sequence Analysis of OX40 Antibodies

The CDR sequences of both the heavy and light chain variable regions were analysed for each antibody. Table 4.1 illustrates the analysis as conducted for the VH CDR3 sequences. Positions in Table 4.1 are defined according to IMGT numbering system. The following patterns were identified.

The VH regions all comprise:
(a) a heavy chain CDR1 sequence which is 8 amino acids in length and comprises the consensus sequence: "G, F, T, F, G/Y/S, G/Y/S, Y/S, Y/S/A";
(b) a heavy chain CDR2 sequence which is 8 amino acids in length and comprises the consensus sequence: "I, G/Y/S/T, G/S/Y, S/Y, G/S/Y, G/S/Y, G/S/Y, T"; and
(c) a heavy chain CDR3 sequence which is 9 to 17 amino acids in length and which comprises the consensus sequence of : "A, R, G/Y/S/H, G/Y/F/V/D, G/Y/P/F, -/H/S, -/N/D/H, -/Y/G, -/Y, -/Y, -/VV/A/V, -/A/Y, -/D/A/Y/G/H/N, Y/S/W/A/T, UM/I/F, D, Y".

The VL regions all comprise:
(a) a light chain CDR1 sequence which consists of the sequence: "Q, S, I, S, S, Y";
(b) a light chain CDR2 sequence which consists of the sequence: "A, A, S";
(c) a light chain CDR3 sequence which is 8 to 10 amino acids in length and comprises the consensus sequence: "Q,Q, S/Y/G, -/Y/H/G, -/S/Y/G/D, S/Y/G/D , S/Y/G/T, P/L, Y/S/H/L/F, T".

Within the consensus sequence for the heavy chain CDR3, two sub-families were identified. Each antibody in the first sub-family comprises a VH CDR3 sequence of 10 amino acids in length which comprises the consensus sequence "A, R, Y/H, D, Y, A/Y/G, S/W/A, M/L, D, Y". Antibodies in this family are referred to as family Z and are identified as such in Table 4.1. Each antibody in the second sub-family comprises a VH CDR3 sequence of 11 amino acids in length which comprises the consensus sequence "A, R, G/Y, V/F/Y, P, H, G/Y/H, Y, F/I, D, Y". Antibodies in this family are referred to as family P and are identified as such in Table 4.1. Antibodies of family Z or P are preferred. Antibodies having a VH sequence in family P typically also include a VL sequence with a CDR3 sequence of "Q, Q, S, Y, S, T, P, Y, T", a CDR1 sequence "Q,S,I,S,S,Y" and a CDR2 sequence of "A,A,S". Accordingly antibodies with a VL region comprising these three CDR sequences are preferred.

TABLE 4.1

| VH | 105 | 106 | 107 | 108 | 109 | 110 | 111 | 111.1 | 111.2 | 112.2 | 112.1 | 112 | 113 | 114 | 115 | 116 | 117 | CDRH3 LENGTH | FAM-ILY |
|---|---|---|---|---|---|---|---|---|---|---|---|---|---|---|---|---|---|---|---|
| 1482 | A | R | G | Y | G | | | | | | | | | Y | L | D | Y | 9 | |
| 1166 | A | R | Y | D | Y | | | | | | | | A | S | M | D | Y | 10 | Z |
| 1170 | A | R | Y | D | Y | | | | | | | | Y | W | M | D | Y | 10 | Z |
| 1524 | A | R | H | D | Y | | | | | | | | G | A | L | D | Y | 10 | Z |
| 1164 | A | R | G | V | P | H | | | | | | | G | Y | F | D | Y | 11 | P |
| 1168 | A | R | Y | F | P | H | | | | | | | Y | Y | F | D | Y | 11 | P |
| 1490 | A | R | Y | Y | P | H | | | | | | | H | Y | I | D | Y | 11 | P |
| 1542 | A | R | G | Y | P | H | | | | | | | H | Y | F | D | Y | 11 | P |
| 1514 | A | R | S | G | Y | S | N | | | | W | A | N | S | F | D | Y | 14 | |
| 1526 | A | R | Y | Y | F | H | D | Y | | | A | A | Y | S | L | D | Y | 15 | |
| 1520 | A | R | Y | Y | Y | S | H | G | Y | Y | V | Y | G | T | L | D | Y | 17 | |

Example 5—Domain Mapping of OX40 Antibodies

The extracellular part of OX40 consists of four domains, each of which can be subdivided into two modules. Genes of OX40 human/mouse chimeras were synthesized using standard laboratory techniques. The different chimeras were designed by exchanging domains or modules of the human OX40 with corresponding mouse OX40. The chimeras were designed based on evaluation of the human and mouse sequences and 3D investigation of human OX40. The synthesized genes were assigned project specific ID numbers (see Table 5.1). The constructs were cloned into pcDNA3.1 vector (Invitrogen).

The mouse/human chimeras were transiently transfected into FreeStyle 293-F cells (Invitrogen), incubated 48 hours in FreeStyle 293 expression medium (Invitrogen) 37C, 8% $CO_2$, 135 rpm. The transfected cells were incubated with human OX40 antibodies, human OX4OL (hOX4OL, RnD Systems), mouse OX4OL (mOX4OL, RnD Systems) and controls for 30 min 4° C. and then detected with a-huIgG-PE (Jackson Immunoresearch) 30 min 4° C. Cells were analyzed with FACS Verse (BD Biosciences). Binding to the different chimeric constructs were calculated as relative (mean fluorescence intensity) MFI compared to the binding of the isotype control. Results are shown in Table 5.2.

None of the human OX40 antibodies tested bind to murine OX40. Accordingly, if a given antibody does not bind to a particular chimera, this indicates that the antibody is specific for one of the domains which has been replaced with a murine domain in that chimera.

TABLE 5.1

Identity of chimeric constructs

| ID construct | Description of coding region of the chimeric DNA constructs |
|---|---|
| 1544 | Human OX40 with mouse domains 1A, 1B and 2A (aa 30-81) |
| 1545 | Human OX40 with mouse domains 1B, 2A and 2B (aa 43-107) |
| 1546 | Human OX40 with mouse domains 2A, 2B and module 3 (aa 66-126) |

TABLE 5.1-continued

Identity of chimeric constructs

| ID construct | Description of coding region of the chimeric DNA constructs |
|---|---|
| 1547 | Human OX40 with mouse domain 2B, module 3 and domain 4A (aa 83-141) |
| 1548 | Human OX40 with mouse module 3 and domains 4A and 4B (aa 108-167) |
| 1549 | Human OX40 with mouse domains 1A and 4B and region non-annotated extracellular region (aa 30-65 and aa 127-214) |
| 84 | Construct containing the full length OX40 sequence |
| 57 | Empty vector (negative control) |

At least four separate binding patterns were identified.
Pattern A:
Antibodies 1170/1171, 1524/1525, and 1526/1527 display a similar binding pattern and depend on residues in the same domains for binding. Amino acid residues critical for binding are likely located in module B in domain 2, and in module A of domain 2. The majority of the antibodies with CDRH3 family "Z" bind according to pattern A (1166/1167 being the exception), indicating that antibodies with this type of CDRH3 are predisposed to bind this epitope.
Pattern B:
Antibodies 1168/1135, 1542/1135, 1520/1135, 1490/1135, 1482/1483 and 1164/1135 display a similar binding pattern and depend mainly on residues located in Domain 3 for binding. All antibodies with CDRH3 family "P" binds with this pattern, demonstrating that the similarity in CDRH3 sequence reveals a common binding epitope.

Pattern C:

Antibody 1166/1167 has a unique binding pattern and likely depends on residues located in module A and module B in domain 2 for binding. However, both modules must be exchanged simultaneously to abolish binding, suggesting a structurally complex epitope.

Pattern D:

Antibody 1514/1515 displays a unique binding profile and likely depends mostly on amino acids located in module B in domain 2 for binding.

Reference antibody 72 binds according to pattern B. The binding pattern of the human OX40 ligand is similar to pattern C.

TABLE 5.2

Results from domain mapping experiment

| Chimeric OX40 construct | Antibody | | | | | | | | | | |
|---|---|---|---|---|---|---|---|---|---|---|---|
| | 1490/ 1135 | 1170/ 1171 | 1524/ 1525 | 1526/ 1527 | 1482/ 1483 | 1514/ 1515 | 1164/ 1135 | 1168/ 1135 | 1520/ 1135 | 1542/ 1135 | 1166/ 1167 | polyclonal antibody |
| 1544 | 4.2 | 2.0 | 1.5 | 1.1 | 8.4 | 11.6 | 14.0 | 13.2 | 9.4 | 7.1 | 14.2 | 50.9 |
| 1545 | 28.9 | 1.0 | 0.9 | 1.3 | 44.4 | 1.2 | 37.3 | 46.6 | 32.6 | 40.2 | 1.0 | 58.6 |
| 1546 | 1.0 | 0.8 | 0.9 | 0.9 | 0.9 | 0.9 | 0.9 | 0.9 | 0.9 | 0.9 | 0.8 | 30.0 |
| 1547 | 1.1 | 2.3 | 1.0 | 1.0 | 1.0 | 1.1 | 1.0 | 1.0 | 0.9 | 1.0 | 15.2 | 43.9 |
| 1548 | 1.1 | 20.3 | 15.4 | 12.7 | 1.1 | 17.2 | 1.0 | 1.0 | 1.1 | 1.2 | 15.8 | 31.7 |
| 1549 | 5.9 | 12.1 | 11.2 | 8.5 | 8.7 | 10.6 | 14.1 | 15.1 | 8.5 | 13.0 | 11.3 | 26.3 |
| 84 | 14.2 | 33.4 | 31.4 | 21.4 | 24.9 | 25.9 | 27.5 | 29.6 | 25.4 | 29.4 | 27.6 | 53.2 |
| 57 | 1.0 | 1.0 | 1.0 | 1.0 | 1.0 | 1.1 | 1.0 | 0.9 | 1.0 | 1.1 | 1.0 | 1.2 |

Example 6—Cross Reactivity with *Macaca Mulatta*

The extracellular part of OX40 from *Macaca mulatta* was fused to the transmembrane and intracellular part of hCD40 and cloned into pcDNA3.0. The vector was subsequently stably transfected into HEK cells (macOX40-HEK).

Expression of OX40 was confirmed by incubating with commercial OX40 antibody (huOX40, BD Biosciences) for 30 min at 4° C. and then detected with a-huIgG-PE (Jackson Immunoresearch) 30 min 4° C. For the assay, the transfected cells were incubated with the test antibodies and controls for 30 min at 4° C. and then detected with a-huIgG-PE (Jackson Immunoresearch) 30 min 4° C. Cells were analyzed by flow cytometry with FACS Verse (BD Biosciences).

As shown in Table 6.1 below, tested antibodies bind to *Macaca mulatta* OX40 with EC50 values comparable to those achieved for human OX40, suggesting that Macaca mulatta will be suitable for use in toxicology studies.

*Macaca mulatta* is genetically very similar to *Macaca fascicularis* (cynomolgus monkey) making it very likely that cynomolgus monkey is also a suitable species for toxicology studies.

TABLE 6.1

Binding to human and monkey OX40 (95% confidence intervals)

| OX40 antibody | Binding to *M mulatta* OX40, EC50 (µg/ml) | Binding to human OX40, EC50 (µg/ml) |
|---|---|---|
| 1166/1167 | 0.1595 to 0.2425 | 0.1415 to 0.2834 |
| 1168/1135 | 0.09054 to 0.1939 | 0.06360 to 0.1308 |
| 1482/1483 | 0.1565 to 0.3120 | 0.08196 to 0.1822 |
| 1520/1135 | 0.1632 to 0.3587 | 0.09247 to 0.2749 |
| 1526/1527 | 0.2921 to 0.5888 | 0.1715 to 0.4292 |
| 1542/1135 | 0.7221 to 1.414 | 0.3223 to 0.5525 |

Example 7—Agonistic Activity in a Human T Cell Assay

Human T cells were obtained by negative T cell selection kit from Miltenyi from PBMC from leucocyte filters obtained from the blood bank (Lund University Hospital). The OX40 antibodies were coated to the surface of a 96 well culture plate (Corning Costar U-shaped plates (#3799) and cultured with a combination of immobilized anti-CD3 antibody (UCHT1), at 3 µg/ml, and soluble anti-CD28 antibody (CD28.2), at 5 µg/ml. Anti-CD3 was pre-coated overnight at 4° C. On the following day, after one wash with PBS, the OX40 antibodies were coated 1-2 h at 37° C. After 72 h incubation in a moisture chamber at 37° C., 5% $CO_2$ the IL-2 levels in the supernatant were measured.

Figure 8:
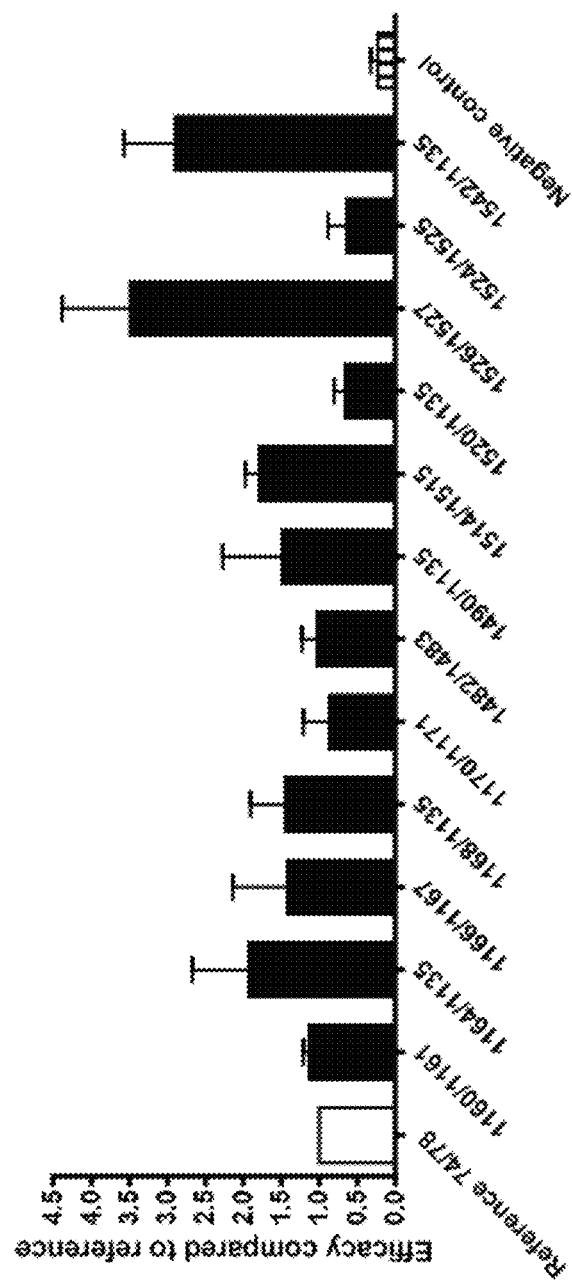
FIG. 8 shows the level of IL-2 production by T cells when incubated in vitro with different exemplary anti-OX40 antibodies. The y-axis is the ratio of the top value of IL-2 production by a tested antibody/the top value of a reference antibody. Mean and SEM values from at least 4 donors are shown.

The ability of the antibodies to stimulate human T cells to produce IL-2 was compared with the reference antibody 74 and the relative activity is displayed in FIG. 8. The majority of the antibodies provided T cell activation levels that were comparable with the reference antibody. A number of antibodies provided higher levels of T cell activation.

Bispecific Molecules

In the following Examples, tested bispecific molecules are referred to by number, e.g. 1164/1141. This means that the molecule comprises the amino acid sequences of the respective VH and VL regions shown in Tables B and D. For example, 1164/1141 comprises the heavy chain VH region sequence 1164 shown in Table B (SEQ ID NO: 99), and the bispecific chain number 1141 shown in Table D (SEQ ID NO: 129). The specified VH region sequence of a given molecule is typically provided linked (as part of a single contiguous polypeptide chain) to the IgG1 heavy chain constant region sequence of SEQ ID NO: 135. This sequence is typically present at the C terminal end of a specified VH region sequence of Table B.

Example 8—Affinity of Exemplary Bispecific Molecules for Binding to Single Targets Measurement of Kinetic Constants by Surface Plasmon Resonance Human OX40 (R&D systems, #3358_OX) was immobilized to the Biacore™ sensor chip, CM5, using conventional amine coupling. The tested antibodies and controls (serially diluted ⅓ or ½ 100-2 nM) were analyzed for binding in HBS-P (GE, #BR-1003-68) at a flow rate of 30 µl/ml. The association was followed for 3 minutes and the dissociation for 20 minutes. Regeneration was performed twice using 50 mM NaOH for 30 seconds. The kinetic parameters and the affinity constants were calculated using 1:1 Langmuir model with drifting baseline. The tested molecules had varying on and off rates with generally lower affinity for OX40 than the corresponding monomeric antibodies, but were still in the nanomolar range (Table 8.1).

TABLE 8.1

| BsAb | ka (1/Ms) | kd (1/s) | KD (nM) |
|---|---|---|---|
| 1164/1141 | 8.87E+04 | 1.72E-04 | 1.94 |
| 1168/1141 | 2.84E+05 | 3.05E-04 | 1.07 |
| 1166/1261 | 7.04E+04 | 1.12E-04 | 1.59 |
| 1170/1263 | 5.18E+05 | 6.39E-04 | 1.23 |

Measurement by ELISA

ELISA plates were coated with human with CTLA-4 (BMS, Orencia) or human OX40 (R&D Systems, 3388-OX) at 0.4 or 0.5 µg/ml, respectively. The ELISA plates were washed with PBST and then blocked with PBST+2% BSA for 1 h at room temperature and then washed again with PBST. The bispecific molecules were added in dilution series to the plates and incubated for 1 h at room temperature. The ELISA plates were washed, and binding was detected using goat anti human kappa light chain HRP for 1 h at room temperature. SuperSignal Pico Luminescent was used as substrate and luminescence was measured using Fluostar Optima.

Figure 9:
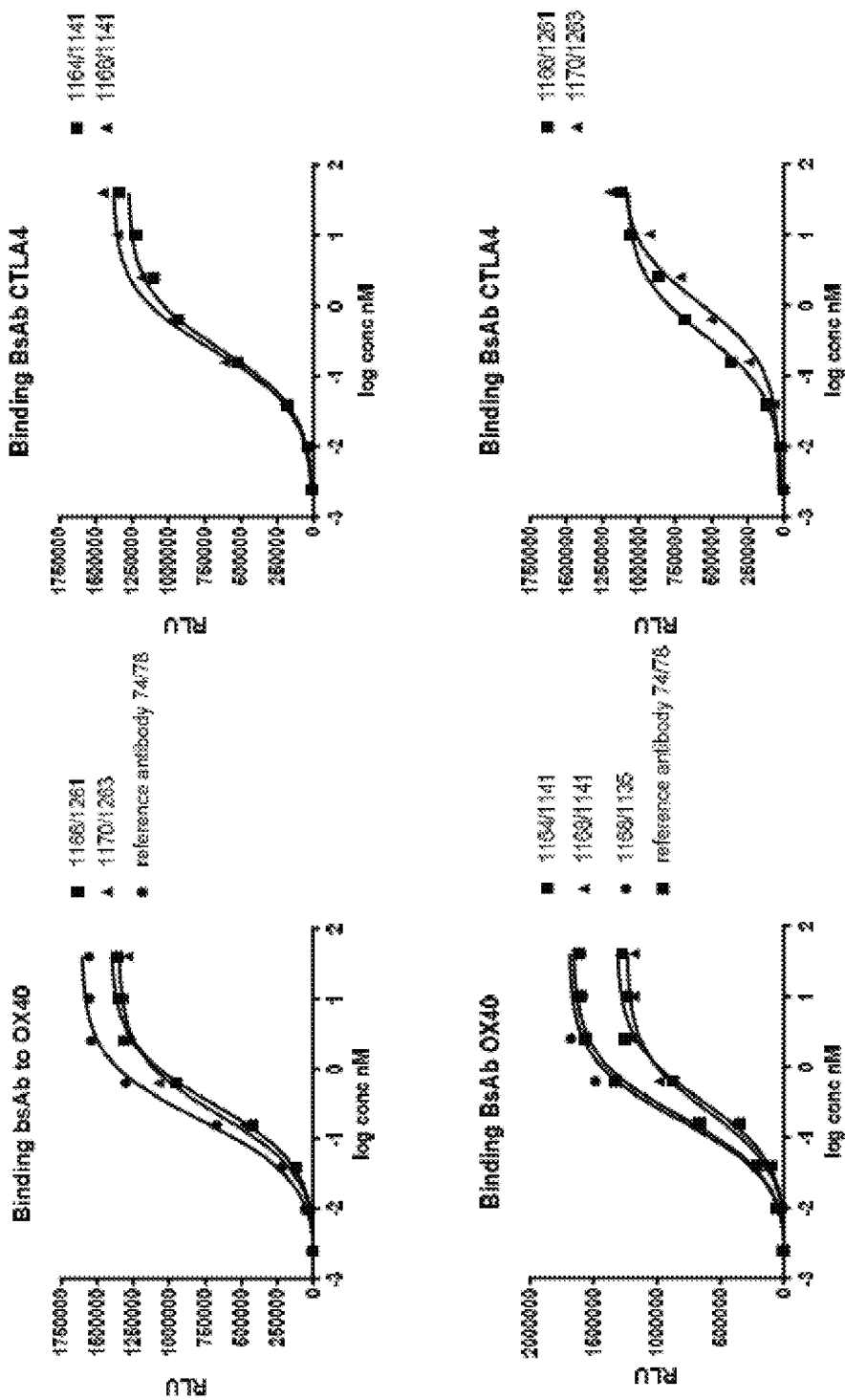
FIG. 9 shows results of an ELISA assay for binding of exemplary bispecific molecules to individual targets OX40 and CTLA4.

All the tested bispecific molecules bound to both targets and the EC50 values are in the range that would be expected based on their affinity as monospecific antibodies (FIG. 9).

Example 9—Dual Binding to Both Targets of Exemplary Bispecific Molecules

Measurement by Surface Plasmon Resonance

Human OX40 (R&D systems, #3358_OX) was immobilized to the Biacore™ sensor chip, CM5, using conventional amine coupling. The tested bispecific molecules (0.5 µM or 0.25 µM) and controls were run over the chip at a flow rate of 30 µl/ml. The association was followed for 3 minutes and the dissociation for 3 minutes. CTLA4-Fc (BMS, Orencia) was then injected and association followed for 3 minutes and the dissociation for 3 minutes. As a control a blank PBS was injected instead of CTLA4.

Figure 10:
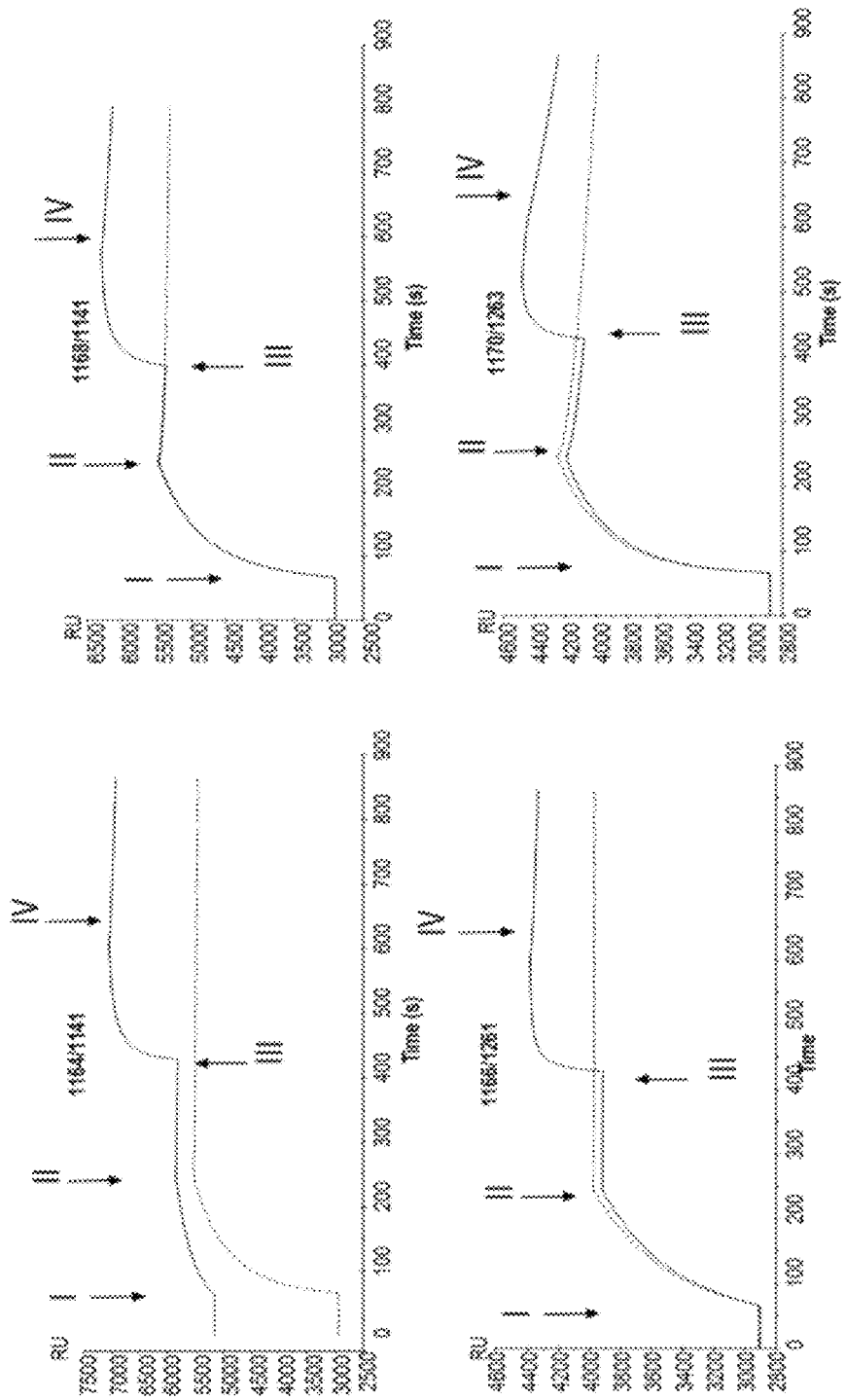
FIG. 10 shows results of surface plasmon resonance analysis of binding of exemplary bispecific molecules to both OX40 and CTLA4. The different bispecific antibodies were passed over the sensor (start indicated by I)). At near saturation of the surface, buffer was applied (II) and subsequently CTLA-4 (III) was passed over the sensor surface generating a second association phase, represented by the full line. After three minutes, buffer (IV) was applied, and the following dissociation phase reflects dissociation of both CTLA-4 and OX40 Ab. As a control, only buffer, with no CTLA-4 was added, represented by the dotted line.

All the tested bispecific molecules bound to both targets simultaneously, as is shown in FIG. 10).

Measurement by ELISA

ELISA plates were coated with OX40-Fc (R&D systems, #3358_OX) (0.4 µg/ml) over night at 4° C. The ELISA plates were washed with PBST and then blocked with PBST+2% BSA for 1 h at room temperature and then washed again with PBST. Bispecific molecules were added in dilutions to the plates and incubated for 1 h at room temperature. The ELISA plates were washed and biotinylated CTLA-4 (1 µg/ml) was added and incubated on the plates at room temperature. The plates were washed and HRP-labelled streptavidin was used for detection of binding. SuperSignal Pico Luminescent was used as substrate and luminescence was measured using Fluostar Optima.

Binding to both targets was confirmed for all tested bispecific molecules. As is shown in FIG. 11, the tested bispecific molecules could be detected at a concentration 0.1 nM, which corresponds to 0.015 µg/ml. The relative values in the assay correspond well to the affinities measured by surface plasmon resonance.

Example 10—Agonistic Activity of Exemplary Bispecific Molecules in a Human CD4 T Cell Assay Human CD4 T cells were isolated by negative CD4 T cell selection (Miltenyi, human CD4+ T cell Isolation Kit 130-096-533) of PBMC from leucocyte filters obtained from the blood bank (Lund University Hospital). CTLA-4 (Orencia, 2.5 µg/ml) and anti-CD3 (UCHT-1, 1 ug/ml) was coated to the surface of a 96-well culture plate (non-tissue cultured treated, U-shaped 96-well plates (Nunc, VWR #738-0147) over night at 4° C. By coating with both CTLA-4 and CD3, the assay provides an experimental model of a tumor microenvironment with over-expressed CTLA-4. CTLA-4 was omitted from some wells as a control.

Bispecific molecules to be tested were added soluble in a serial dilution to the wells and compared at the same molar concentrations with controls. Two different controls were used for each bispecific molecule tested. The first control is a bispecific molecule designated 1756/1757 (an isotype control antibody fused to the 1040 CTLA4 binding region=binds CTLA4 but not OX40). The second control is a mixture of the bispecific 1756/1757 control and the monospecific OX40 antibody, which corresponds to the tested bispecific molecule. After 72 h of incubation in a moisture chamber at 37° C., 5% CO2, IL-2 levels were measured in the supernatant.

Figure 12:
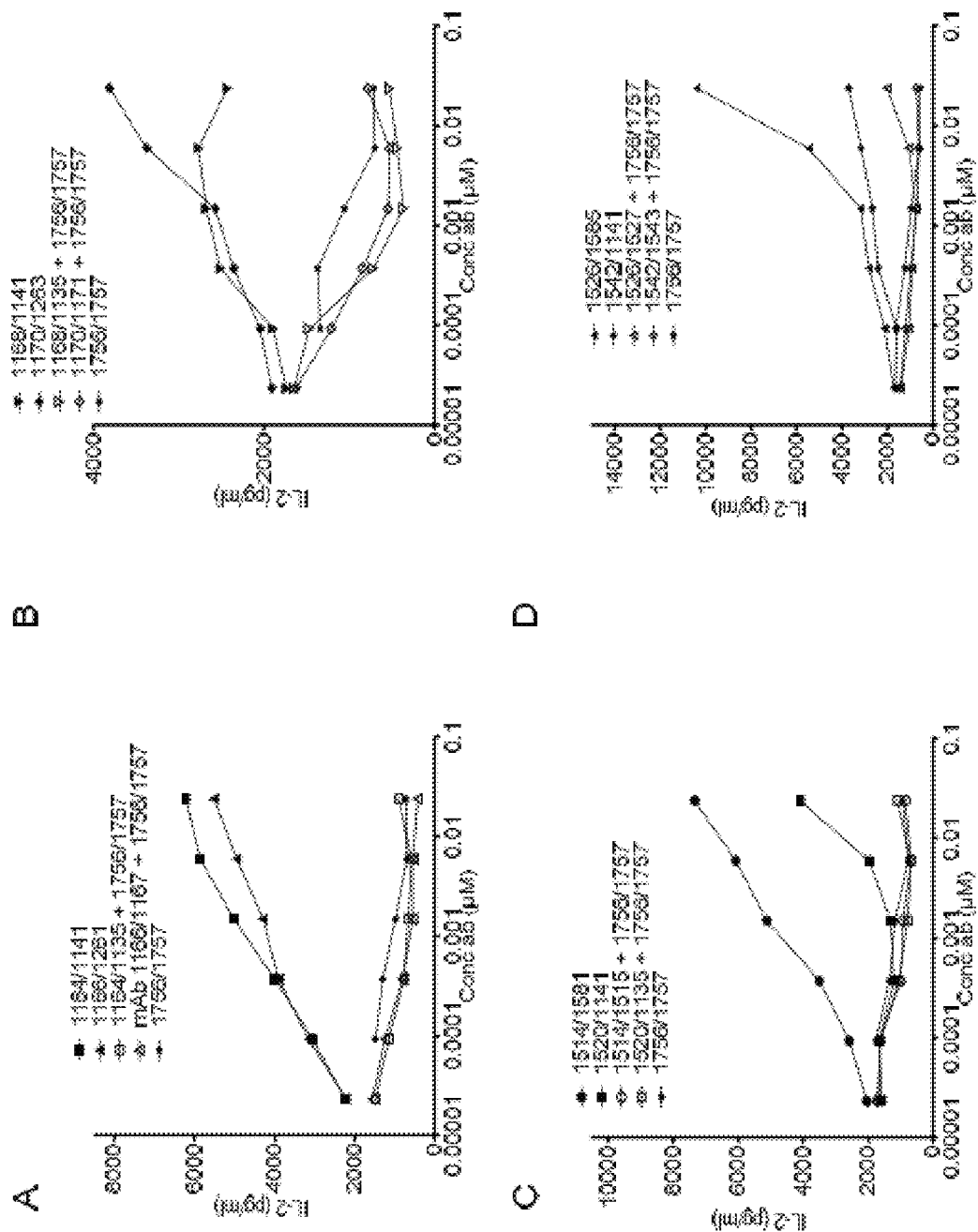
FIG. 12 shows the level of IL-2 production by T cells when incubated in vitro with different exemplary bispecific molecules in a titration series: A) 1164/1141 and 1166/1141 B) 1168/1141 and 1170/1263 C) 1514/1581 and 1520/1141 D) 1526/1585 and 1542/1141 or a combination of the two corresponding monospecific antibodies for each target (monoclonal OX40 antibodies or the CTLA-4-binding domain coupled to an isotype IgG antibody: 1756/1757). The assay was performed in U-shaped non-tissue cultured treated 96-well plates coated with CD3 (UCHT1) and CTLA-4 (Orencia). Mean out of 4 donors is presented.
Figure 13:
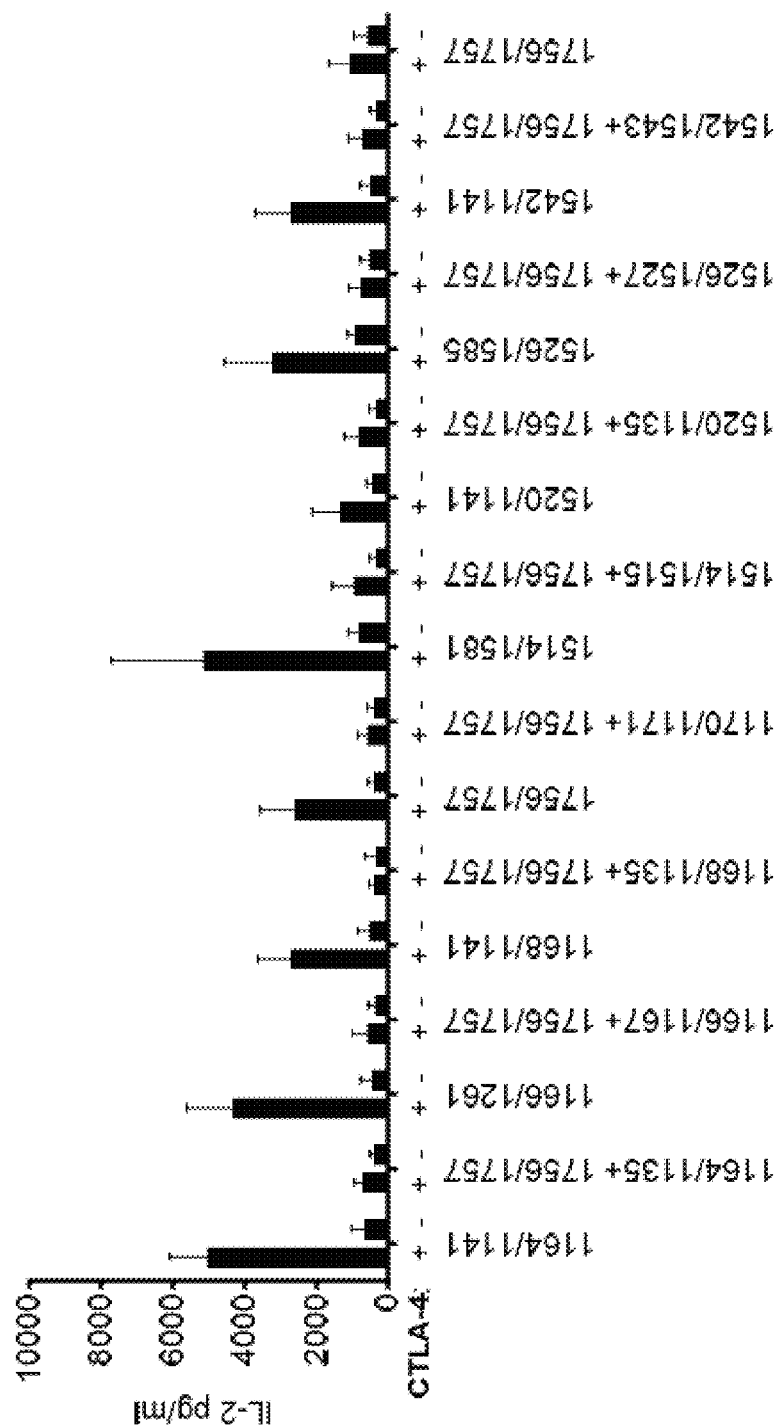
FIG. 13 shows the level of IL-2 production by T cells when incubated in vitro with different exemplary bispecific molecules at 1.49 nM or a combination of the corresponding monospecific antibodies for each target (a-OX40 mAbs or the CTLA-4-domain coupled to an isotype antibody: 1756/1757). The assay was performed in U-shaped non-tissue cultured treated 96-well plates coated with anti-CD3 (UCHT1) with or without CTLA-4 (Orencia), indicated by + or −. Mean and SD out of 4 donors is presented.

As shown in FIG. 12, there is a dose-dependent effect of the bispecific molecules, which induce an increase in human T cell activation (measured by an increase in IL-2 production) when cultured in plates coated with CTLA-4. The controls do not. FIG. 13 shows the results of the same assay when conducted at a fixed concentration for the bispecific antibodies and controls (1.5 nM) in the presence or absence of CTLA-4. The increase in T cell activation is not seen in the absence of CTLA-4. The fold change in IL-2 levels induced by each bispecific molecule compared to the corresponding combination of monospecific molecules is shown in Table 10.1. The mean value of IL-2 produced (pg/ml) for each bispecific molecule or control is shown in Table 10.2.

Since this assay represents an experimental model of a tumor microenvironment with over-expressed CTLA-4, the results suggest that the tested bispecific molecules can be expected to have a greater effect than monospecific antibodies in such a microenvironment.

TABLE 10.1

Fold change in IL-2 level induced by bispecific molecule compared to the corresponding combination of the monospecific molecules at 1.5 nM

| 1164/1141 | 1166/1261 | 1168/1141 | 1170/1141 | 1514/1581 | 1520/1141 |
|---|---|---|---|---|---|
| 7.6 | 7.8 | 7.2 | 4.7 | 5.5 | 1.7 |

TABLE 10.2

Mean IL-2 level (pg/ml) induced at 1.5 nM bispecific antibody or control

|  | 1164/1141 | 1166/1261 | 1164/1135 + 1756/1757 | 1166/1167 + 1756/1757 | 1168/1141 | 1170/1141 | 1168/1135 + 1756/1757 | 1170/1171 + 1756/1757 | 1514/1581 | 1520/1141 |
|---|---|---|---|---|---|---|---|---|---|---|
| Mean | 5024 | 4292 | 665 | 550 | 2681 | 2575 | 371 | 552 | 5109 | 1303 |
| SD | 1058 | 1333 | 273 | 456 | 954 | 992 | 162 | 285 | 2600 | 812 |

|  | 1514/1515 + 1756/1757 | 1520/1135 + 1756/1757 | 1526/1585 | 1542/1141 | 1526/1527 + 1756/1757 | 1542/1543 + 1756/1757 | 1756/1757 |
|---|---|---|---|---|---|---|---|
| Mean | 927 | 774 | 3200 | 2671 | 746 | 697 | 1047 |
| SD | 653 | 451 | 1350 | 1016 | 346 | 418 | 601 |

Example 11—Stability of Exemplary Bispecific Molecules

The melting point of the antibodies was analyzed by differential scanning fluorimetry (DSF). Antibody samples in PBS were mixed with SYPRO Orange which was diluted 1000-fold. Thermal scanning between 25 and 95° C. was performed in a real-time PCR machine with measurements made each degree. A reference antibody 250/251 was used for comparison and the difference in melting temperature Tm ($\Delta T_m$) relative to the reference was determined. $T_m$ differences of more than 1.1° C. compared to the reference are considered statistically significant. As shown in Table 11.1, all tested bispecific molecules displayed good thermostability with values of 65° C. or above.

TABLE 11.1

| Antibody | Melting temperature (° C.) |
|---|---|
| 1168/1141 | 65.6 |
| 1164/1141 | 65.5 |
| 1160/1259 | 68.5 |
| 1166/1261 | 67.8 |
| 1170/1263 | 66.4 |
| 1514/1581 | 65.3 |
| 1520/1141 | 65.0 |
| 1526/1585 | 67.6 |
| 1542/1141 | 66.3 |

Example 12—Characterisation of CD137 Antibodies

General chemical properties of an exemplary CD137 antibody (referred to as 1204/1205) were determined by routine analysis and are shown in Table 12.1.

TABLE 12.1

| Antibody | pI | net charge (in oxidizing conditions) pH 5.5 | net charge (in oxidizing conditions) pH 7.4 | Hydrophathy (GRAVY index) whole mAb | Hydrophathy (GRAVY index) CDRs according to IMGT | Melting Temperature (C. °) Tm1 |
|---|---|---|---|---|---|---|
| 1204/1205 | 9.05 | 32.9 | 7.4 | −0.401 | −0.465 | 68 |

Measurement of Kinetic Constants by Surface Plasmon Resonance

Human CD137 (R&D systems) was immobilized to the Biacore™ sensor chip, CM5, using conventional amine coupling. The tested antibodies and controls (serially diluted 1/2 10-0.63 nM) were analyzed for binding in HBS-P (GE, #BR-1003-68) at a flow rate of 30 µl/ml. The association was followed for 5 minutes and the dissociation for 15 minutes. Regeneration was performed twice using 10 mM Glycine pH 1.7 for 30 seconds. The kinetic parameters and the affinity constants were calculated using 1:1 Langmuir model. As a representative example, the 1204/1205 anti-CD137 antibody has an affinity in the low nanomolar range. See Table 12.2.

TABLE 12.2

| Dissociation constant $K_D$ (M) | 1.1E−09 |
|---|---|
| Association rate constant $k_a$ (1/Ms) | 2.5E+05 |
| Dissociation rate constant $k_d$ (1/s) | 2.8E−04 |

Measurement by ELISA of Binding to Human CD137

Binding of CD137 mAb to recombinant human CD137 was determined by sandwich ELISA. Briefly, ELISA plates (Greiner #655074) were coated with recombinant human CD137-Fc (R&D #838-4B) at 0.5 µg/ml, or alternatively 0.05 µg/ml at 4° C. overnight or 37° C. for 1 hour. The plates were washed three times with PBS+0.05% Tween 20 (PBST) and blocked with PBST+1% BSA. The CD137 antibodies to be tested were added in serial dilution series and the incubated for 1 h at room temperature prior to wash with PBST. Binding was detected using HRP-conjugated goat-anti-human kappa light chain (AbD Serotec #STAR127P) and developed with SuperSignal ELISA Pico Chemiluminescent substrate (Pierce #37069) measured using a Fluostar Optima. EC50 values of the various mAb were determined in 2-6 separate experiments.

As a representative example, the 1204/1205 anti-CD137 antibody has an EC50 value of approximately 0.3 nM when assessed by this method. See Table 12.3.

TABLE 12.3

| Clone name | Mean (nM) | SD | n |
|---|---|---|---|
| 1204/1205 | 0.34 | 0.058 | 6 | n = number of data points, including separate experiments and different antibody batches in same experiment Measurement of Binding to Human or Cynomolgus CD137 Over-Expressed on CHO Cells The extracellular part of human or cynomolgus CD137 was fused to the transmembrane and intracellular part of hCD40 and cloned into pcDNA3.0. The vector was subsequently stably transfected into CHO cells. Expression of CD137 was confirmed by incubating with commercial CD137 antibody (huCD137-PE, BD Biosciences #555956) for 30 min at 4° C.

For the assay, the transfected cells were incubated with the test antibodies and controls for at least 1 hr at 4° C. to saturate binding. In order to minimize antibody internalization, 0.05% sodium azide was used in the incubation buffer and all work was performed on ice. Detection was achieved using an anti-hIgG-PE antibody (109-115-098, Jackson Immunoresearch laboratories) incubated for 30 min at 4° C. Directly after staining, the cells were fixed with a paraformaldehyde solution (10× concentrate BD CellFIX, BD biosciences #340181). Cells were analyzed by flow cytometry using FACSVerse (BD Biosciences). The median fluorescence intensity (MFI) for each sample was determined and the dose response data was analyzed using Graph Pad Prism. In order to fit MFI data in Graph Pad MFI data was normalized for each antibody, where 0% was defined as the lowest value and 100% was the highest value in the dose titration for each antibody.

Figure 14:
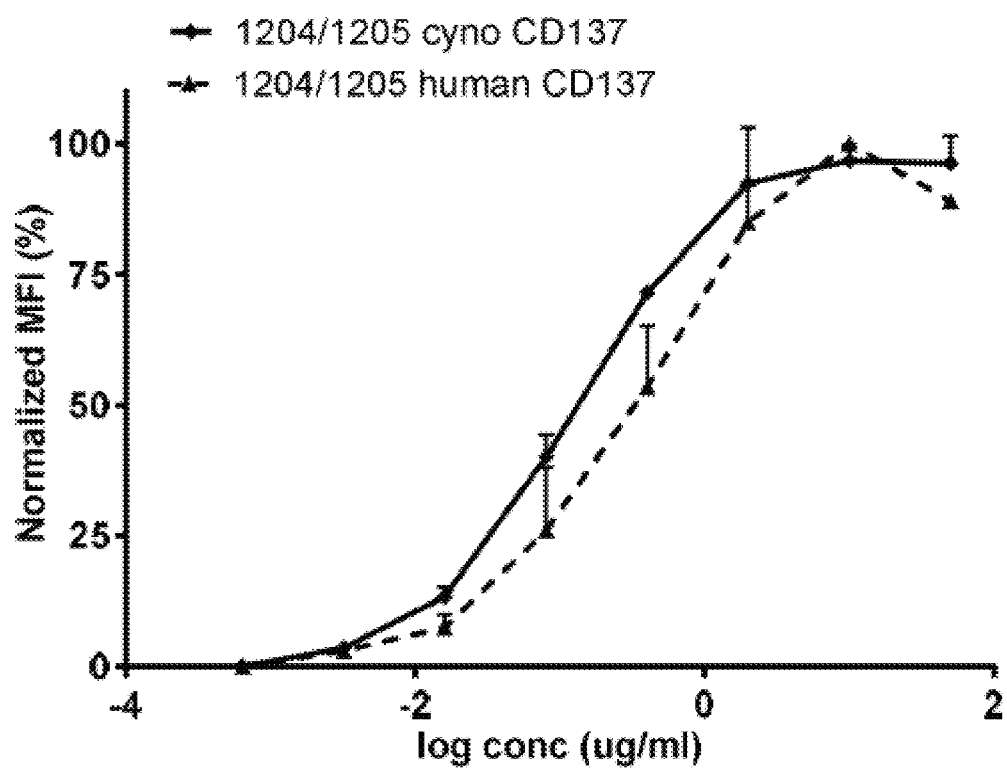
FIG. 14 shows binding of exemplary anti-CD137 antibody 1204/1205 to human and cynomolgus monkey CD137 overexpressed on CHO cells, measured by flow cytometry.

Binding to human and cynomolgus monkey CD137 was confirmed in two separate experiments for exemplary antibody 1204/1205. The binding affinities were very similar between cynomolgus monkey and human CD137 (FIG. 14, Table 12.4)

TABLE 12.4

95% confidence intervals for the EC50 determined as an average from two experiments of normalized data.

| Clone name | Binding to human CD137, EC50 (µg/mL) | Binding to cyno CD137, EC50 (µg/mL) |
| --- | --- | --- |
| 1204/1205 | 0.23-0.39 | 0.11-0.16 |

Agonistic Activity of CD137 Antibodies in a Human T Cell Assay

Agonistic activity of CD137 mAb was evaluated in a T cell assay based on primary human CD8$^+$ T cells. Briefly, CD8$^+$ T cells were separated from human peripheral blood mononuclear cells by MACS separation (Miltenyi #130-096-495) according to the manufacturer's protocol. Cells were incubated in 96-well microtiter plates (NuncThermo Scientific #268200), pre-coated with anti-CD3 mAb (clone OKT3, Affymetrix eBioscience #16-0037) and titrated concentrations of the CD137 mAb to be tested. Following 72 or 96 hour incubation, culture medium was harvested and IFN-γ levels were determined by ELISA (BD #555142). Each clone was analyzed in multiple donors and compared to a reference CD137 mAb 111/112 and an isotype control (62/63).

Due to large intra-donor variations the stimulation index (SI, fold induction by mAb compared to isotype control) was determined for each sample and normalized to the stimulation index for the reference antibody 111/112.

Figure 15:
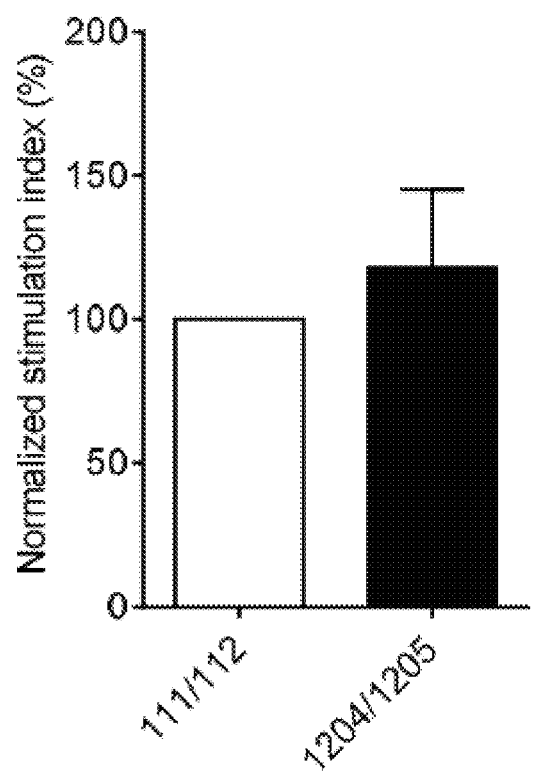
FIG. 15 shows the normalized stimulation index of IFNγ production of exemplary anti-CD137 antibody 1204/1205 compared with reference antibody 111/112 in a CD8 T cell agonist assay.
Figure 16:
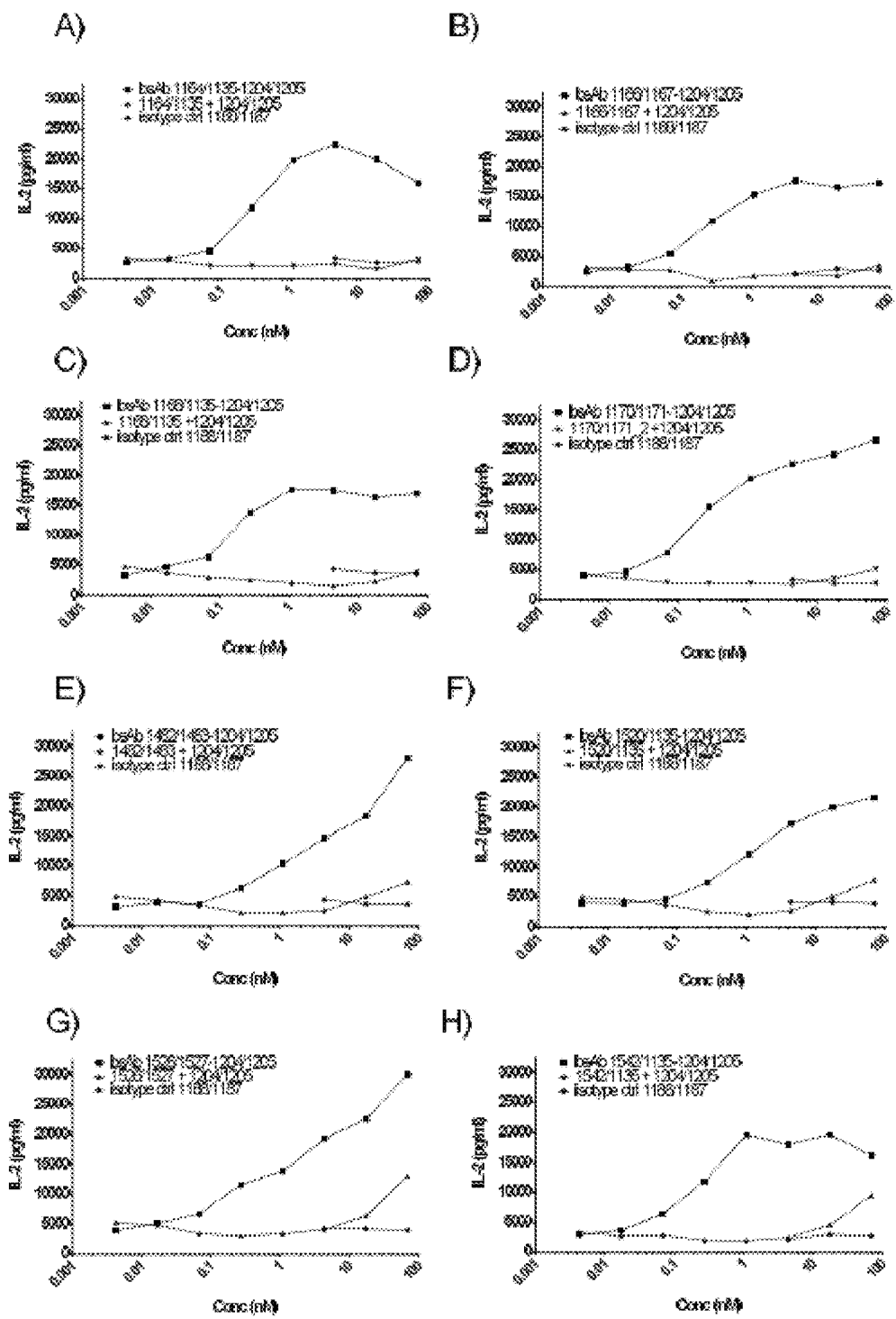
FIG. 16 shows the level of IL-2 production by T cells when incubated in vitro with different exemplary bispecific molecules in a titration series: A) 1164/1135-1204/1205. B) 1166/1167-1204/1205, C) 1168/1135-1204/1205, D) 1170/1171-1204/1205, E) 1482/1483-1204/1205, F) 1520/1135-1204/1205, G) 1526/1527-1204/1205, H) 1542/1135-1204/1205; or a combination of the two corresponding monospecific antibodies for each target. An isotype control 1188/1187 (IgG1) is used as a negative control in all experiments. The cells were cultured for 72 h in U-shaped non-tissue cultured treated 96-well plates coated with anti-CD3 antibody (UCHT1). Mean IL-2 levels of 2 donors is presented.

The exemplary 1204/1205 antibody induced activation of T cells that was comparable or better compared to the reference antibody 111/112. Mean normalized SI±SD of 8 donors is presented in FIG. 15. Table 12.5 indicates the absolute IFN-γ levels induced by CD137 stimulation.

TABLE 12.5

IFN-γ production levels induced by the various mAb

| Ab Clone name | Mean IFN-γ (pg/ml) | Min IFN-γ (pg/ml) | Max IFN-γ (pg/ml) | No. of repeated experiments |
| --- | --- | --- | --- | --- |
| 62/63 | 2502 | 337 | 8526 | 13 |
| 111/112 | 42268 | 2256 | 136802 | 12 |
| 1204/1205 | 64430 | 13062 | 153136 | 8 |

Sequence Information
VH CDR1=GFTFSSYY (SEQ ID NO: 207)
VH CDR2=IGSYYGYT (SEQ ID NO: 212)
VH CDR3=ARAYYDYNYYYAYFDY (SEQ ID NO: 217)
VL CDR1=QSISSY (SEQ ID NO: 80)
VL CDR2=AAS (SEQ ID NO: 81)
VL CDR3=QQSVPHYPFT (SEQ ID NO: 222)

TABLE 12.6

| 1205, light chain VL aa sequence | DIQMTQSPSSLSASVGDRVTITCRASQSISSY LNWYQQKPGKAPKLLIYAASSLQSGVPSRFSG SGSGTDFTLTISSLQPEDFATYYCQQSVPHYP FTFGQGTKLEIK (SEQ ID NO: 177) |
| --- | --- |
| 1205, light chain VL nt sequence | GACATCCAGATGACCCAGTCTCCATCCTCCCT GAGCGCATCTGTAGGAGACCGCGTCACCATCA CTTGCCGGGCAAGTCAGAGCATTAGCAGCTAT TTAAATTGGTATCAGCAGAAACCAGGGAAAGC CCCTAAGCTCCTGATCTATGCTGCATCCAGTT TGCAAAGTGGGGTCCCATCACGTTTCAGTGGC AGTGGAAGCGGGACAGATTTCACTCTCACCAT CAGCAGTCTGCAACCTGAAGATTTTGCAACTT ATTACTGTCAACAGTCTGTTCCGCACTACCCG TTCACITTTGGCCAGGGGACCAAGCTGGAGAT CAAA (SEQ ID NO: 178) |
| 1204, heavy chain VH aa sequence | EVQLLESGGGLVQPGGSLRLSCAASGFTFSSY YMGWVRQAPGKGLEWVSGIGSYYGYTGYADSV KGRFTISRDNSKNTLYLQMNSLRAEDTAVYYC ARAYYDYNYYYAYFDYWGQGTLVTVSS (SEQ ID NO: 179) |
| 1204, heavy chain VH nt sequence | GAGGTGCAGCTGTTGGAGAGCGGGGGAGGCTT GGTACAGCCTGGGGGGTCCCTGCGCCTCTCCT GTGCAGCCAGCGGATTCACCTTTTCTTCTTAC TACATGGGTTGGGTCCGCCAGGCTCCAGGGAA GGGGCTGGAGTGGGTCTCAGGTATTGGTTCTT ACTACGGTTACACAGGTTATGCAGACTCCGTG AAGGGCCGGTTCACCATCTCCCGTGACAATTC CAAGAACACGCTGTATCTGCAAATGAACAGCC TGCGTGCCGAGGACACGGCTGTATATTATTGT GCGCGCGCTTACTACGACTACAACTACTACTA CGCTTACTTTGACTATTGGGGCCAGGGAACCC TGGTCACCGTCTCCTCA (SEQ ID NO: 180) |

Example 13—Domain Mapping of CD137 Antibodies

The extracellular part of CD137 consists of four domains, which can be further subdivided into two modules. Genes of CD137 human/mouse chimeras were synthesized using standard laboratory techniques. The different chimeras were designed by exchanging domains or modules of the human CD137 with corresponding mouse CD137. The chimeras were designed based on evaluation of the human and mouse sequences and 3D investigation of human CD137. The synthesized genes were assigned project specific ID numbers (see Table 13.1). The constructs were cloned into pcDNA3.1 vector (Invitrogen) and transiently transfected into FreeStyle 293-F cells (Invitrogen). The transfected cells were incubated with CD137 antibodies and control antibodies, followed by incubation with anti-human IgG-PE (Jackson Immunoresearch) for detection and analyzed with FACS Verse (BD Biosciences). Binding to the different chimeric constructs was calculated as relative MFI compared to the binding of the isotype control, followed by normalization to the full-length human CD137 construct to minimize the effect of affinity differences between individual antibodies.

The results for binding of exemplary antibody 1204/1205 to the different constructs are shown in Table 13.2. As indicated by these results, antibody 1204/1205 is mainly dependent on domain 2. In addition, some loss of binding is also seen for construct 1555, indicating an impact of domain 1 as well.

TABLE 13.1

CD137 constructs used for the domain mapping

| Sequence | Description |
|---|---|
| 1550 (1407) | Human CD137 with mouse domains 1, 2A and 2B (aa 24-86) |
| 1551 (1408) | Human CD137 with mouse domains 2A, 2B and 3A (aa 47-96) |
| 1552 (1409) | Human CD137 with mouse domains 2B, 3A and 3B (aa 64-118) |
| 1553 (1410) | Human CD137 with mouse domains 3A, 3B and 4A (aa 87-133) |
| 1554 (1411) | Human CD137 with mouse domains 3B, 4A and 4B (aa 97-159) |
| 1555 (1412) | Human CD137 with mouse domains 1 and 4B and region of unknown function (aa 24-46 and aa 139-186) |
| 1030 | Full length human CD137 |

(wherein the number in parentheses identifies the same CD137 construct, but corresponds to an alternative clone numbering system used in the figures)

TABLE 13.2

Binding of antibody 1204/1205 to the different CD137 constructs measured by flow cytometry. Median fluorescence intensity (MFI) for mAb sample/isotype control, normalized to full-length human CD137.

| Sequence | Relative binding |
|---|---|
| 1550 | 0.07 |
| 1551 | 0.11 |
| 1552 | 0.13 |
| 1553 | 0.85 |
| 1554 | 0.73 |
| 1555 | 0.28 |
| 1030 | 1 |

BISPECIFIC ANTIBODIES

Example 14—Agonistic Activity of Exemplary Bispecific Molecules In Vitro

Human CD3 positive T cells were purified from Ficoll separated PBMCs (obtained from leucocyte filters from the blood bank of the Lund University Hospital) using negative selection (Pan T cell Isolation Kit, human, Miltenyi, 130-096-535). 50 µl of anti-CD3 (clone: UCHT-1, BD, concentration: 1 µg/ml) diluted in PBS was coated to the surface of non-tissue culture treated, U-shaped 96-well plates (Nunc, VWR #738-0147) over night at 4° C. Bispecific anti-OX40/anti-CD137 polypeptides were added in a serial dilution to the wells and compared at the same molar concentrations as controls. Two different controls were used for each bispecific molecule tested. The first control is an isotype control antibody specific for GFP (designated 1188-1187). The second control is a mixture of the monospecific OX40 and CD137 antibodies corresponding to the tested bispecific. After 72 h of incubation in a moisture chamber at 37° C., 5% CO2, IL-2 levels were measured in the supernatant.

Figure 17:
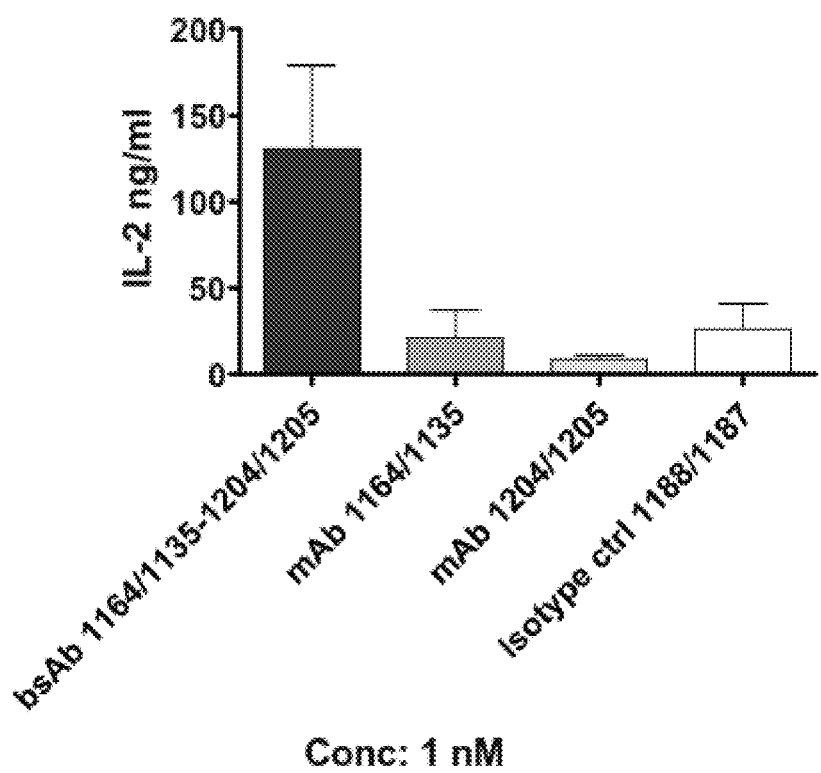
FIG. 17 shows the level of IL-2 production by peripheral blood mononuclear cells when incubated in vitro with exemplary bispecific molecule 1164/1135-1204/1205 at 1 nM, compared to the corresponding monospecific antibodies for each target: anti-OX40 mAb 1164/1135 or mAb anti-CD137 1204/1205 or an isotype control 1188/1187 (IgG1). The cells were cultured for 48 h in U-shaped non-tissue cultured treated 96-well plates coated with anti-CD3 antibody (UCHT1). Mean IL-2 levels of 2 donors is presented.

As shown in FIG. 16A-H, there is a dose-dependent effect of the bispecific molecules, which induce an increase in human T cell activation (measured by an increase in IL-2 production) when cultured in plates coated with anti-CD3. The controls do not. FIG. 17 shows the results of a similar assay when conducted at a fixed concentration for the exemplary bispecific antibody 1164/1135-1204/1205 and controls (1 nM). In this assay Human PBMC were obtained from leucocyte concentrates from the blood bank of the Lund University Hospital) using Ficoll density separation. 50 µl of anti-CD3 (clone: UCHT-1, BD, concentration: 1 µg/ml) diluted in PBS was coated to the surface of a non-tissue cultured treated, U-shaped 96-well plates (Nunc, VWR #738-0147) over night at 4° C. The bispecific anti-OX40/anti-CD137 antibody 1164/1135-1204/1205 was added soluble to the wells together with PBMCs and compared at the same molar concentration (1 nM) with an isotype control 1188-1187 or its corresponding monospecific OX40 and CD137 antibodies. After 48 h of incubation in a moisture chamber at 37° C., 5% CO2, IL-2 levels were measured in the supernatants. The bispecific antibody induces significantly higher T cell activation than controls even in a mixed population of different cells (PBMCs).

Since this assay represents an experimental model of a tumor microenvironment where both OX40 and CD137 are relatively overexpressed, the results suggest that the tested bispecific molecules can be expected to have a greater effect than monospecific antibodies in such a microenvironment.

Example 15—Dual Binding to Both Targets of Exemplary Bispecific Molecules

Measurement by ELISA

ELISA plates were coated with OX40-Fc (R&D systems, #3388_OX) (0.4 µg/ml, 50 µl/well) over night at 4° C. The ELISA plates were washed with PBST and then blocked with PBST+2% BSA for 1 h at room temperature. After 3 washes with PBST, bispecific antibodies and controls were added at different concentrations, from 50 nM to $6.4 \times 10^{-4}$ nM and incubated for 1 h at room temperature. The ELISA plates were washed and biotinylated CD137-Fc at (1 µg/ml) was added and incubated on the plates for 1 h at room temperature. The plates were washed three times with PBST and HRP-labelled streptavidin was used for detection of binding (1 h incubation at room temperature). The plates were washed 6 times with PBST and then SuperSignal Pico Luminescent was used as substrate and luminescence was measured using Fluostar Optima according to the manufacturers' protocols.

Figure 18:
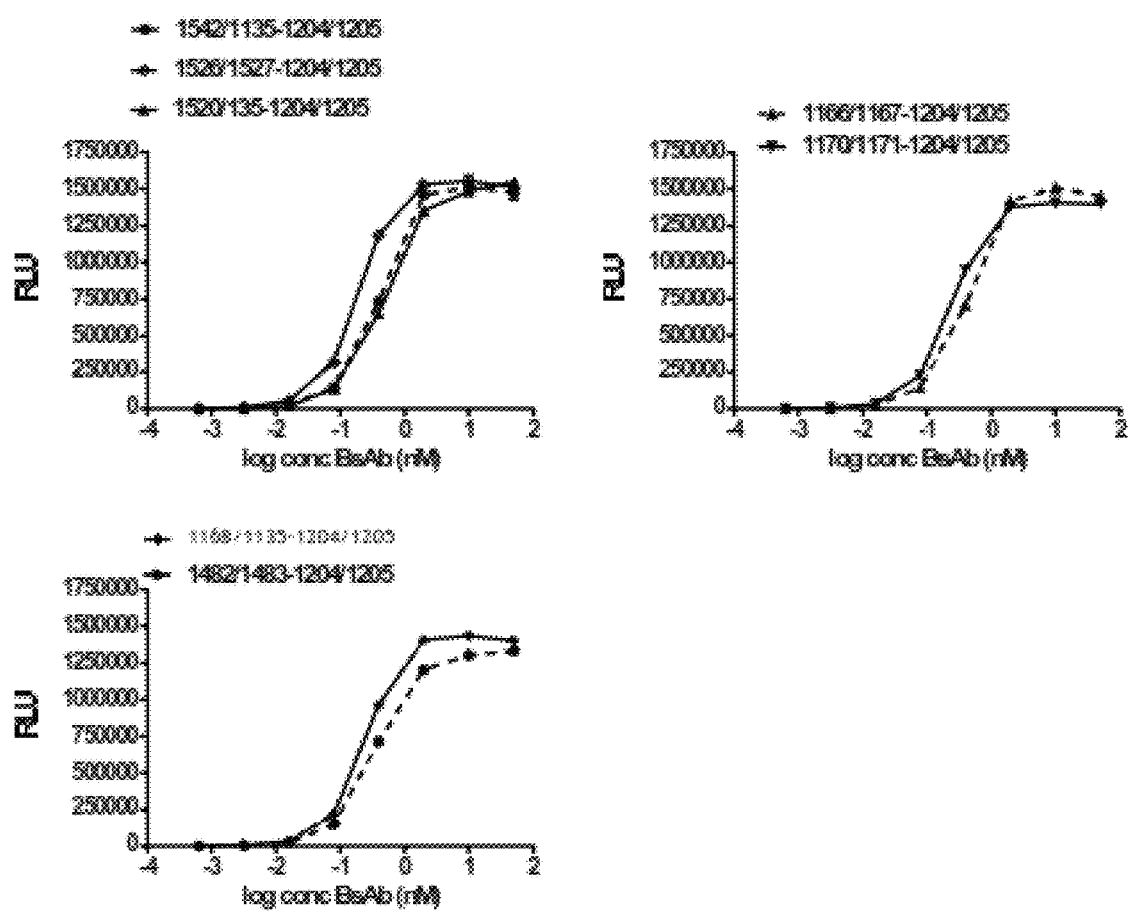
FIG. 18 shows results of an ELISA assay showing binding of exemplary bispecific molecules to both OX40 and CD137 simultaneously.
Figure 19:
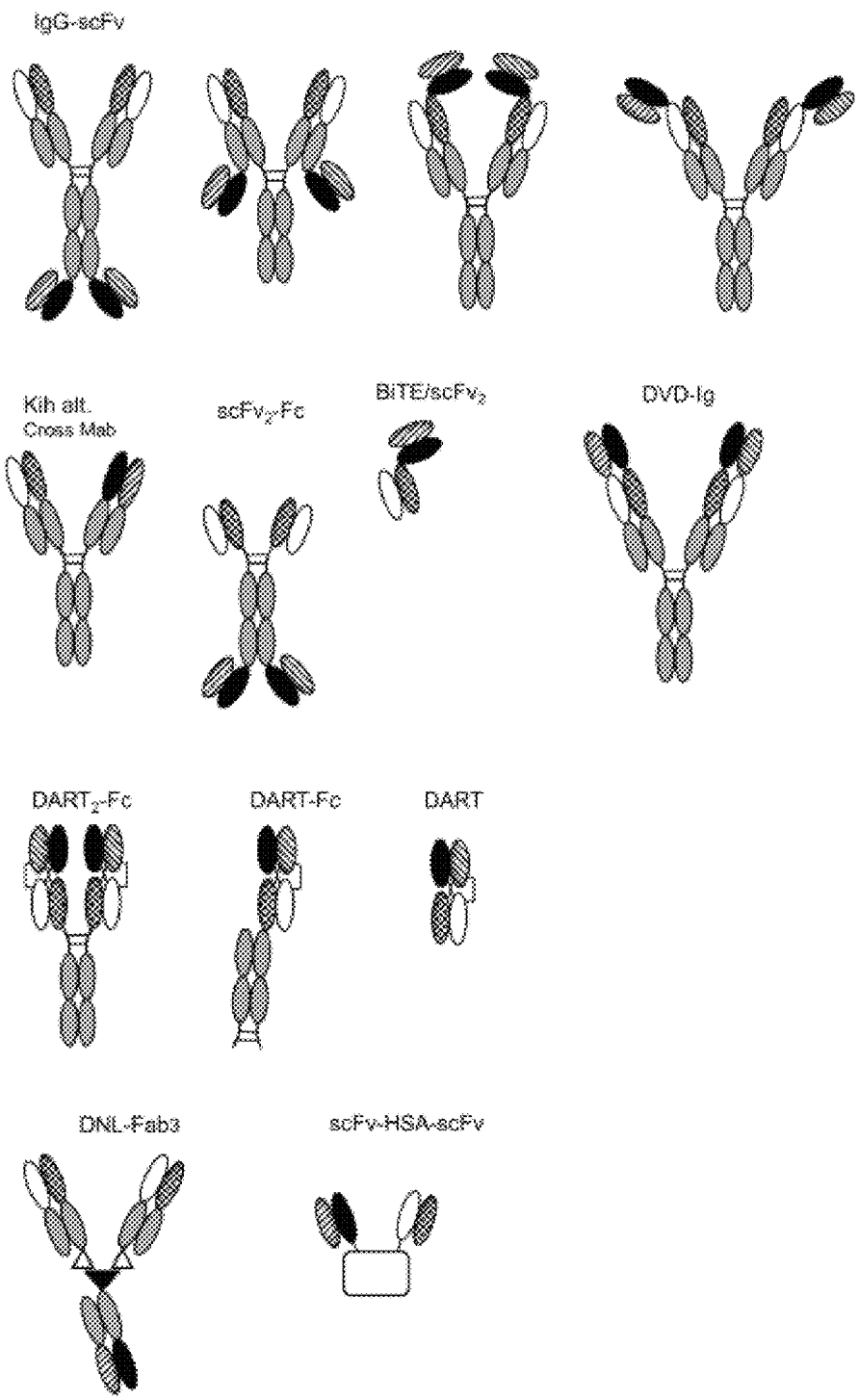
FIG. 19 shows a schematic representation of the structure of exemplary formats for bispecific antibodies of the invention. In each format, the constant regions are shown as filled light grey; variable heavy chain regions VH1 are shown as checkered black and white; variable light chain regions VL1 are shown as filled white; variable heavy chain regions VH2 are shown as filled black; and variable light chain regions VL2 are shown as white with diagonal lines. OX40 binding domains (binding domain 1) are typically represented as a pair of a checkered black and white domain with a filled white domain (VH1/VL1); CD137 binding domains (binding domain 2) are typically represented as a pair of a filled black domain and a white domain with diagonal lines (VH2/VL2). However, in all of the formats shown, it will be appreciated that binding domains 1 and 2 may be switched. That is, an OX40 binding domain may occur in a position shown in this figure for a CD137 domain, and vice versa. Furthermore, binding domain 2 may occur in different variable heavy and light chain orders, i.e. either in VH2/VL2 or VL2/VH2 order.

Binding to both targets was confirmed for all tested bispecific molecules as is shown in FIG. 18. Each of the bispecific antibodies was detectable at $8 \times 10^{-2}$ nM. The bispecific antibodies also bind to both targets when the assay is reversed (coating CD137 and using soluble biotinylated OX40 for detection (data not shown).

Example 16—Selection of CD137 Antibodies from Alligator GOLD™ Library and Overview of Tested Clones Phage display selections were performed using a human antibody (scFv) library, Alligator GOLD. Selections towards recombinant CD137 in soluble form, coated onto the surface of beads or tubes, or expressed on the surface of CD137-transfected cells were performed. CTLA4-Fc and an irrelevant His-tagged protein were used as non-targets included in excess in the selections. Prior to each selection round, the phage stocks were pre-selected towards biotinylated beriglobin, CTLA4-Fc, beads or CD137 negative cells to remove unspecific binders.

To identify specific binders from the phage selection, approximately 4500 individual clones were screened in phage format using ELISA coated with either recombinant target (CD137-Fc) or non-target (CTLA4-Fc) protein, followed by confirmation as soluble scFv for some clones. Clones exhibiting specific binding to CD137 were sequenced and unique clones were produced as IgG for further characterization.

Five human CD137 antibodies with agonistic properties have been characterized and described herein (summarized in Table 16.1). The tested antibodies are comparable to clinically active reference antibodies in a functional T cell assay. Four different classes of antibodies were identified based on epitope domain mapping studies. Both CD137 blocking and non-blocking antibodies were obtained.

TABLE 16.1

Summary of the CD137 antibodies

| Antibody | T cell agonist | Cynomolgus CD137 cross-reactivity | Target Specificity | EC50 cell binding (CHO transfectants) (µg/mL) | ka (1/Ms) | kd (1/s) | KD (M) | CD137L block | Domain binding |
|---|---|---|---|---|---|---|---|---|---|
| 1204/1205 | Yes | Yes | OK | 0.23-0.39 | 3E+05 | 3E−04 | 1E−09 | Yes | 2 |
| 1214/1215 | Yes | Yes | OK | 0.89-1.28 | 5E+04 | 3E−05 | 7E−10 | No | ND |
| 1618/1619 | Yes | Yes | OK | 0.11-0.19 | 1E+06 | 1E−04 | 1E−10 | No | 1 |
| 1620/1621 | Yes | Yes | OK | 0.20-0.42 | 4E+05 | 5E−04 | 1E−09 | Yes | 3B-4A |
| 1626/1627 | Yes | Yes | OK | 0.38-0.67 | 2E+05 | 3E−04 | 1E−09 | No | ND |

Example 17—Characteristics of CD137 Antibodies—Binding to Human CD137 Measured by ELISA Binding of CD137 antibodies to recombinant human CD137 was determined by sandwich ELISA. Briefly, ELISA plates (Greiner #655074) coated with recombinant human CD137-Fc (R&D #838-4B) were incubated with serial dilutions of the various CD137 antibodies to be investigated. CD137 antibodies were detected using HRP-conjugated goat-anti-human kappa light chain (AbD Serotec #STAR127P) and developed with SuperSignal ELISA Pico Chemiluminescent substrate (Pierce #37069). EC50 values of the various antibodies were determined in multiple separate experiments.

Two different reference antibodies have been used in this study, designated 1811/1812 and 1813/1814.

Reference antibody 1811/1812 is a CD137 agonist that binds to domain 1 of CD137 and does not block the ligand. It binds to its target with high affinity and specificity. An antibody with this sequence has been evaluated in clinical trials.

Reference antibody 1813/1814 is and antibody that binds to domain 3-4 on CD137. It binds to its target with high affinity and specificity. An antibody with this sequence has been evaluated in clinical trials.

The majority of the antibodies exhibit EC50 values in a similar range as those of the reference antibodies, i.e. sub nM or low nM. Data is summarized in Table 17.1.

TABLE 17.1

EC50 values (nM) of Alligator-GOLD-derived CD137 antibodies determined by ELISA for human CD137.

| Clone name | Mean | SD | n |
|---|---|---|---|
| 1811/1812 | 0.75 | 0.137 | 8 |
| 1813/1814 | 0.33 | 0.069 | 5 |
| 1204/1205 | 0.34 | 0.058 | 6 |
| 1214/1215 | 0.98 | 0.124 | 6 |
| 1618/1619 | 0.35 | 0.018 | 4 |
| 1620/1621 | 0.38 | 0.137 | 2 |
| 1626/1627 | 0.22 | 0.057 | 2 | n = number of data points.

Example 18—Characteristics of CD137 Antibodies—Binding to Human and Cynomolgus CD137 Measured by Flow Cytometry Binding and EC50 to human and cynomolgus (*Macaca fascicularis*) CD137 was determined using flow cytometry of CHO cells transfected with human CD137, cynomolgus CD137 or empty vector. The extracellular part of human or cynomolgus CD137 was fused to the transmembrane and intracellular part of human CD40 and cloned into pcDNA3.0. The vector was subsequently stably transfected into CHO cells. Expression of CD137 was confirmed by flow cytometry using CD137 antibody (human CD137-PE, BD Biosciences #555956) for 30 min at 4° C. CD137-transfected and empty vector-transfected cells were incubated with CD137 antibodies for at least 1 h at 4° C. to saturate the binding. In order to minimize antibody internalization, 0.05% sodium azide was used in the incubation buffer and all work was performed on ice. The CD137 antibodies were detected using PE-conjugated anti-hIgG antibody (109-115-098, Jackson Immunoresearch laboratories), incubated for 30 min at 4° C. Directly after staining the cells were fixed with a paraformaldehyde solution (10× concentrate BD CellFIX, BD biosciences #340181). Cells were analyzed by flow cytometry using FACSVerse (BD Biosciences). The median fluorescence intensity (MFI) for each sample was determined and the dose response data was analysed using Graph Pad Prism.

MFI data was normalized for each antibody, where 0% is defined as the lowest value and 100% is the highest value in the dose titration for each antibody. EC50 and 95% confidence interval were calculated with Graph-Pad Prism based on data from the two experiments (non-linear regression (curve fit), constraints set to 0 and 100).

Figure 20:
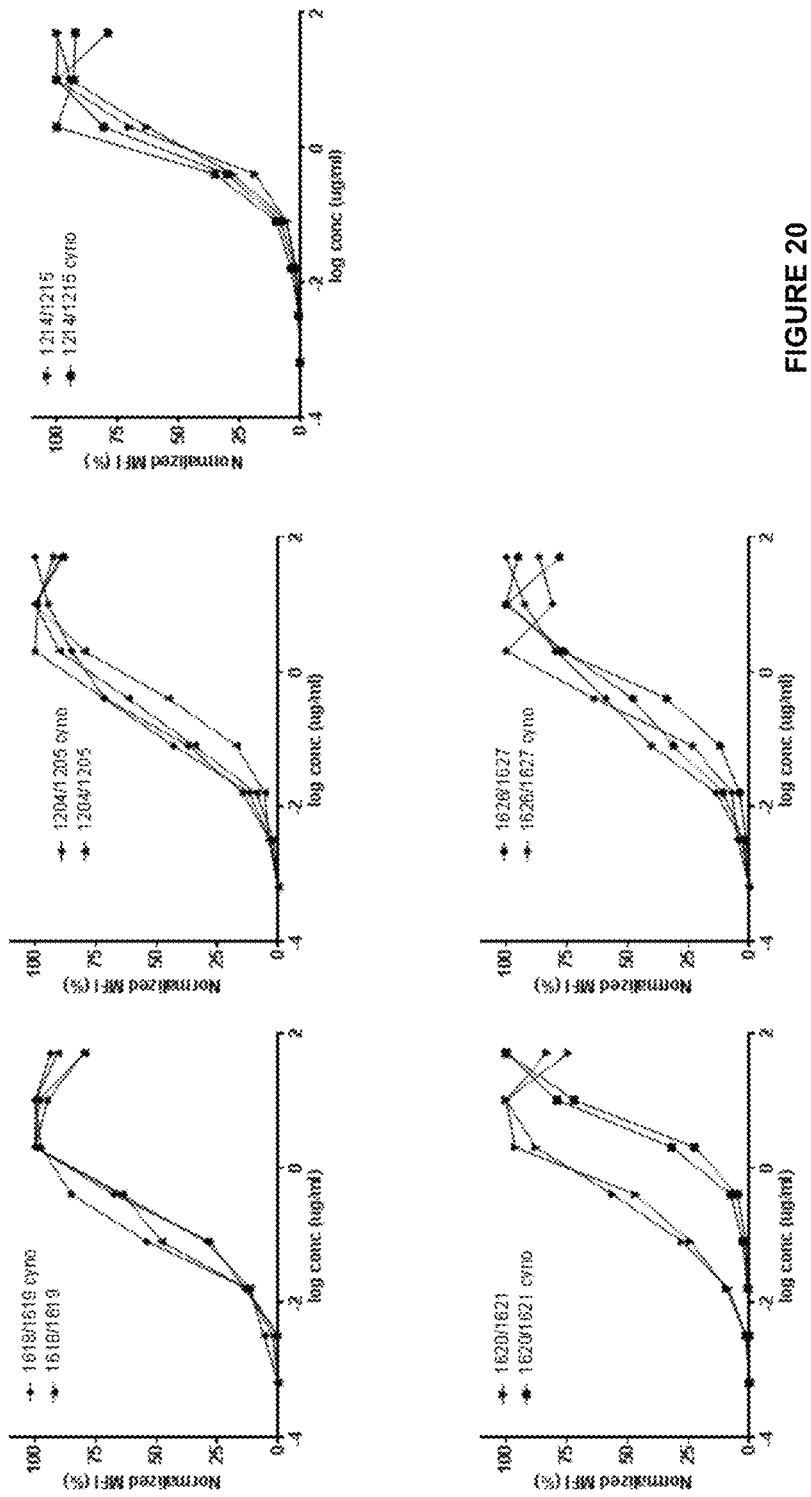
FIG. 20 shows binding of the different CD137 antibodies to human CD137 and cynomolgus CD137 expressed on cells and measured by flow cytometry.

Binding to CHO-huCD137, CHO-cyCD137 and CHO-pcDNA was confirmed in two separate experiments (FIG. 20). All CD137 antibodies bind relatively well to human CD137 with EC50 comparable with the two reference antibodies 1181/1812 and 1813/1814. All CD137 antibodies tested bind well to cynomolgus CD137, except for reference antibody 1811/1812 which does not bind at all and clone 1620/1621 which binds weakly and does not reach a complete saturation. The binding pattern has also been confirmed on stimulated primary cynomolgus PBL.

The EC50 determination is presented as 95% confidence intervals for each CD137 antibody tested in order to include the inter and intra assay variations (Table 18.1)

TABLE 18.1

95% confidence intervals for the EC50 of each CD137 antibody determined as an average from two experiments of normalized data.

| Clone name | Binding to human CD137, EC50 (µg/mL) | Binding to cyno CD137, EC50 (µg/mL) | Ratio, cyno:human |
|---|---|---|---|
| 1204/1205 | 0.23-0.39 | 0.11-0.16 | 0.43 |
| 1214/1215 | 0.89-1.28 | 0.41-0.80 | 0.54 |
| 1618/1619 | 0.11-0.19 | 0.086-0.15 | 0.77 |
| 1620/1621 | 0.20-0.42 | 3-5* | 14* |
| 1626/1627 | 0.38-0.67 | 0.16-0.27 | 0.41 |

Example 19—Characteristics of CD137 Antibodies—Affinity Measured by Biacore

Human CD137 (R&D systems) was immobilized to the Biacore™ sensorchip, CM5, using conventional amine coupling. The tested antibody and control (serially diluted 1/2 10-0.63 nM) were analyzed for binding in HBS-P (GE, #BR-1003-68) at a flow rate of 30 µl/ml. The association was followed for 5 minutes and the dissociation for 15 minutes. Regeneration was performed twice using 10 mM Glycine pH 1.7 for 30 seconds. The kinetic parameters and the affinity constants were calculated using 1:1 Langmuir model.

Results and Conclusions

The affinities of the antibodies were in the nanomolar to sub-nanomolar range (Table 19.1) measured using bivalent antibodies flowed over CD137 coated on the chip surface.

TABLE 19.1

Kinetic parameters measured by surface plasmon resonance

| Sample | ka (1/Ms) | kd (1/s) | KD (M) |
|---|---|---|---|
| 1204 | 2.54E+05 | 2.80E-04 | 1.10E-09 |
| 1214 | 4.54E+04 | 3.17E-05 | 6.99E-10 |
| 1618 | 1.02E+06 | 1.10E-04 | 1.07E-10 |
| 1620 | 3.92E+05 | 5.19E-04 | 1.32E-09 |
| 1626 | 2.32E+05 | 2.94E-04 | 1.27E-09 |

Example 20—Characteristics of CD137 Antibodies—Target Specificity of the CD137 Antibodies Determination of unspecific binding of CD137 antibodies to other TNFR superfamily members (CD40 and OX40) was evaluated to detect potential propensity to cross react to non-target proteins.

ELISA plates (Greiner #655074) were coated with 50 µl/well of recombinant human OX40 (R&D #1493-CD), CD4O-Fc (Ancell #504-820) or CD137 (R&D #838-4B) diluted to a final concentration of 0.5 µg/ml in PBS for 1 h at 37° C. or overnight at 4° C. Plates were washed with PBS+0.05% TWEEN20 (PBST), followed by block with PBST+1% bovine serum albumin (BSA). Antibody samples were prepared as serial 1/10 dilutions from 10-0.01 µg/ml in PBST+1% BSA and incubated for 1 h in room temperature, followed by detection using a horse radish peroxidase-conjugated anti-human kappa light chain antibody (AbD Serotec #STAR127P) and developed using SuperSignal ELISA Pico Chemiluminescent substrate (Pierce Thermo-Scientific #37069).

Results and Conclusions

TABLE 20.1

Summary of CD137 antibody unspecific binding to OX40 and CD40

| pAb | Binding to OX40 and CD40 |
|---|---|
| 1204/1205 | No |
| 1214/1215 | No |
| 1618/1619 | No |
| 1620/1621 | No |
| 1626/1627 | No |

No binding to OX40 or CD40 of the CD137 antibodies was detected. An overview of antibodies analyzed, and results from the two experiments is shown in Table 20.1.Table Further, binding to primary PBL from multiple blood donors was tested. The binding to PBL was similar to Reference antibodies. No relevant unspecific binding to non-target proteins was detected.

Example 21—Characteristics of CD137 Antibodies—Domain Mapping of Antibodies Binding to CD137

The ability of each antibody to bind to a panel of human/mouse CD137 chimeras expressed on the surface of transfected cells was analyzed by flow cytometry.

The chimeras were designed by exchanging domains or modules of the human CD137 with the corresponding mouse domain (FIG. 21). Genes of CD137 human/mouse chimeras were synthesized (GenScript) and constructs cloned into pcDNA3.1 vector (Invitrogen) and transiently transfected into FreeStyle 293-F cells (Invitrogen). The transfected cells were incubated with CD137 antibodies and control antibodies, followed by incubation with anti-human IgG-PE (Jackson Immunoresearch) for detection and analyzed with FACS Verse (BD Biosciences). Binding to the different chimeric constructs was calculated as relative MFI compared to the binding of the isotype control, followed by normalization to the full-length human CD137 construct to minimize the effect of affinity differences between individual antibodies.

Results and Conclusions 6 binding patterns can be observed as described below. Data is summarized in Table 21.1.

Pattern A

Antibody 1618/1619 is dependent on domain 1.

Pattern B

Antibody 1204/1205 is mainly dependent on domain 2. In addition, some loss of binding is also seen for construct 1555, indicating an impact of domain 1 as well.

Pattern C

Antibody 1620/1621 appears to be mainly dependent on domains 3B-4A. However, loss of binding is seen for all constructs, making this pattern quite similar to pattern D.

Pattern D

For antibodies 1214/1215 and 1626/1627, no clear dependence on particular CD137 domains could be demonstrated. Instead, these antibodies exhibited extensive loss of binding for all chimeras.

TABLE 21.1

Domain mapping of CD137 antibodies. The table displays relative binding to different CD137 constructs in which part of the human CD137 sequence has been exchanged to the murine CD137 sequence. Median fluorescence intensity (MFI) for antibody sample/isotype control, normalized to full-length human CD137.

| | Group | | | | | |
|---|---|---|---|---|---|---|
| | A | B | C | | D | |
| | | | Domain | | | |
| | 1 | 2 | 3B-4A | | Unclear | |
| | | | | | Clone | |
| | | | | | 1214/1215 | |
| | 1618/1619 | 1204/1205 | 1620/1621 | 1626/1627 | Exp 1 | Exp 2 |
| 1550 (1407) | 0.11 | 0.07 | 0.17 | 0.10 | 0.06 | 0.14 |
| 1551 (1408) | 0.67 | 0.11 | 0.33 | 0.11 | 0.07 | 0.15 |
| 1552 (1409) | 1.20 | 0.13 | 0.18 | 0.11 | 0.32 | 0.13 |
| 1553 (1410) | 1.24 | 0.85 | 0.17 | 0.14 | 0.41 | 0.15 |
| 1554 (1411) | 1.01 | 0.73 | 0.17 | 0.12 | 0.26 | 0.15 |
| 1555 (1412) | 0.12 | 0.28 | 0.32 | 0.29 | 0.30 | 0.45 |
| 1030* | 1 | 1 | 1 | 1 | 1 | 1 |

*Full-length CD137
(wherein the number in parentheses identifies the same CD137 construct, but corresponds to an alternative clone numbering system used in the figures)

Example 22—Characteristics of CD137 Antibodies—CD137 Ligand Blocking

The aim was to determine if the CD137 antibodies block the CD137 ligand (CD137L) binding.

In the previous domain mapping experiment the CD137 antibodies were divided in different groups based on their binding to similar subdomains of the CD137 antigen. If the CD137 antibodies bind to epitopes close to the ligand binding region, binding to the antigen can lead to partly or total block of ligand biding. Binding close to the CD137 ligand binding epitope may also affect the ligand binding due to steric hindrance or conformational changes of the CD137 ligand binding epitope. All CD137 antibodies were titrated against a fixed concentration of CD137L for evaluation of ligand blocking properties.

CHO-cells transfected with human CD137 were used for the ligand competition. The extracellular part of human CD137 was fused to the transmembrane and intracellular part of hCD40 and cloned into pcDNA3.0. The vector was subsequently stably transfected into CHO cells. The expression of CD137 was confirmed by staining with commercial antibody targeting CD137.

The CHO-huCD137 were pre-incubated with CD137 monoclonal antibodies, titrating down from a predetermined saturating concentration (25, 2.5 and 0.25 µg/ml), for 1 h at +4C before the addition of CD137 ligand at a concentration at EC50. After co-incubation for another 30 min at +4C, the cells were washed and bound CD137 ligand was detected with anti-FLAG-APC (Cell signaling technology). Before analyzation the cells were fixed with paraformaldehyde (10× concentrate BD CellFIX, BD biosciences). Analyzation was performed with FACSverse and the MFI (Median Fluorescence Intensity) was calculated with FlowJo software.

Results and Conclusions

Figure 22:
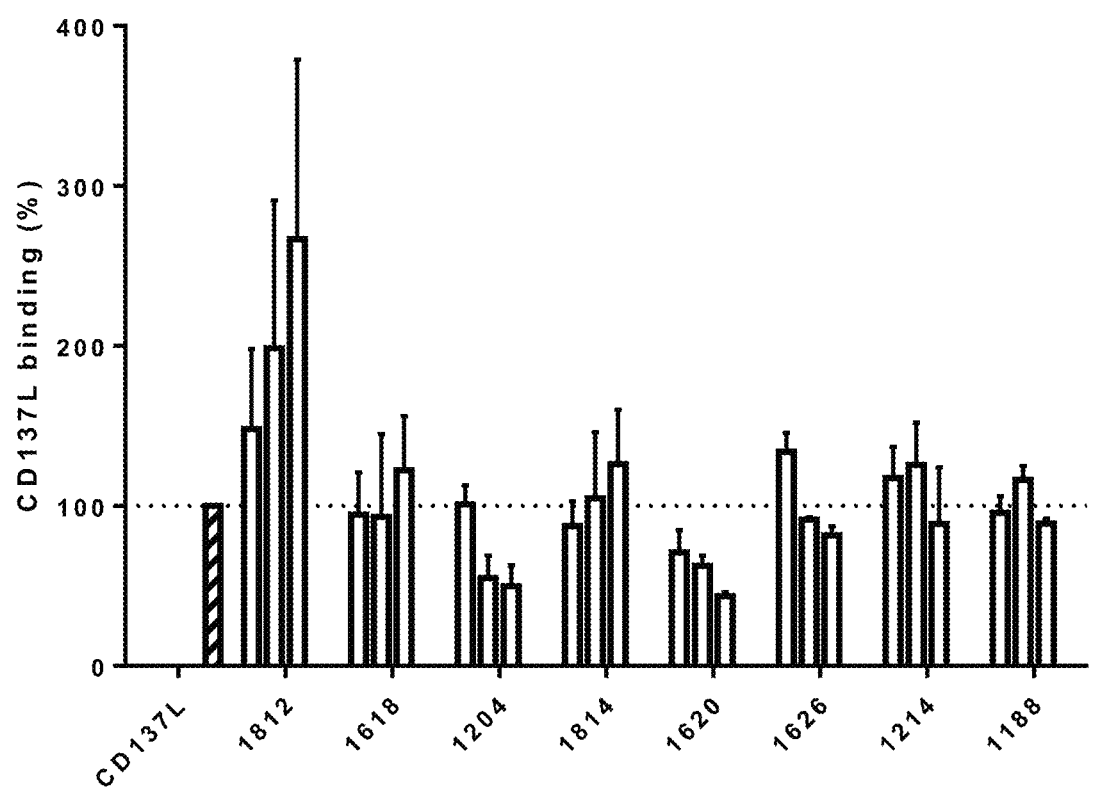
FIG. 22 shows the results from an example were the ability to block CD137L binding was evaluated. 100% binding reflects no blocking. Signals below 100% reflects blocking of the binding (antibody concentration from left to right 0.25, 2.5 and 25 µg/ml).

The CD137L blocking experiment was performed two times. It can be concluded that not all CD137 mAbs tested were blocking the CD137 ligand binding (Table 22.1, FIG. 22). CD137 mAbs belonging to group B and C (1204 and 1620), binding to domain 2B-4A, were blocking the CD137L. Antibody 1814 has been reported to block the CD137L, however, this could not be verified in our CD137L blocking assay. 1812 and 1618, belonging to group A which bound to domain 1, did not block CD137 ligand, but instead synergistically increased the CD137L binding. Antibodies 1626 and 1214, did not block the CD137L in the two experiments performed.

TABLE 22.1

Maximal CD137 ligand competition of the CD137 antibodies, mean out of two experiments

| Group (domain mapping) | CD137 mAb | CD137L, max inhib. |
|---|---|---|
| A | 1618/1619 | −22% |
| B | 1204/1205 | 50% |
| C | 1620/1621 | 56% |
| D | 1626/1627 | 18% |
| D | 1214/1215 | 11% |

Example 23—Characteristics of CD137 Antibodies—Competition ELISA

By competing each CD137 antibody with each another, it is possible to determine antibodies binding to similar epitopes based on their blocking pattern. The competition ELISA is performed by co-incubating biotinylated CD137 antibodies with non-biotinylated CD137 antibodies when binding to coated CD137-Fc. Competition is defined as loss of signal from the biotinylated CD137 antibody. Low competition values could either be due to no competition between the antibodies or binding kinetics of the antibodies. Binding of one antibody could also lead to steric hindrance or conformational changes when binding the antigen which affects the binding of the other CD137 antibody.

CD137 antibodies were biotinylated (EZ-link NHS-LC-Biotin, ThermoFisher) and intact binding properties to CD137-Fc was verified with ELISA by comparing EC50 between biotinylated and non-biotinylated anti-CD137 mAbs. Non-biotinylated anti-CD137 (anti-CD137) was pre-incubated to CD137-Fc at concentrations 30 times higher than the determined EC50 for 0.5 h. Without washing, anti-CD137-bio was added and co-incubated for another 1 h. The binding of anti-CD137-bio was detected with Streptavidin-HRP (Pierce). Competition was calculated as the relative number by dividing the binding measured to other antibodies relative to its maximum competition (competing with itself). The relative values obtained were normalized against the maximum blocking capacity (Table 23.1).

TABLE 23.1

Summary of CD137 antibody competition ELISA from two experiments
Values are presented as % competition with CD137-bio

| | Group comp ELISA | | | | |
|---|---|---|---|---|---|
| | X | Y | | | |
| | Group (domain mapping) | | | | |
| | A | B | C | D | |
| | 1618/1619 | 1204/1205 | 1620/1621 | 1626/1627 | 1214/1215 |
| 1812-bio | 100 | 5 | 4 | 0 | 4 |
| 1814-bio | 21 | 74 | 61 | 57 | 99 |
| 1214-bio | 6 | 92 | 80 | 77 | 99 |
| 1618-bio | 88 | 3 | 10 | 16 | 9 |
| 1620-bio | 7 | 93 | 82 | 79 | 100 |
| 1626-bio | 24 | 100 | 97 | 100 | 99 |
| 1204-bio | 28 | 88 | 66 | 66 | 97 |

Results and Conclusions

The competition ELISA was performed twice. In both experiments, several of the CD137 mAbs did not fully compete with itself. When normalizing the relative competition values for each antibody a competition pattern emerged (Table 23.1). The antibodies 1812 and 1618 that belongs to domain mapping group A, displayed a unique pattern in the competition ELISA (group X). The other CD137 antibodies analyzed had a similar blocking pattern (group Y). Differences in binding kinetics may explain some of the minor variations in the binding patterns among the antibodies of group Y, although it cannot be excluded that the small variations within group Y reflects actual differences in the epitope binding.

Example 24—Characteristics of CD137 Antibodies—In Vitro Efficacy of CD137 Antibodies The aim was to identify CD137 antibodies with agonistic activity.

Agonistic activity of CD137 antibodies was evaluated in a T cell assay based on primary human CD8+ T cells. Briefly, CD8+ T cells were separated from human peripheral blood mononuclear cells by MACS separation (Miltenyi #130-096-495) according to the manufacturer's protocol. Cells were incubated in 96-well microtiter plates (Nunc-Thermo Scientific #268200), pre-coated with anti-CD3 antibody (clone OKT3, Affymetrix eBioscience #16-0037) and titrated concentrations of the CD137 antibody to be tested. Following 72 or 96 hour incubation, culture medium was harvested and IFN-γ levels were determined by ELISA (BD #555142).

Each clone was analyzed in at least 6 donors and compared to the reference CD137 antibody 1811/1812 and the negative control antibody.

Due to large intra-donor variations the stimulation index (SI, fold induction by antibody compared to negative control) was determined for each sample and normalized to the stimulation index for the reference antibody 1811/1812.

Results and Conclusions

Figure 23:
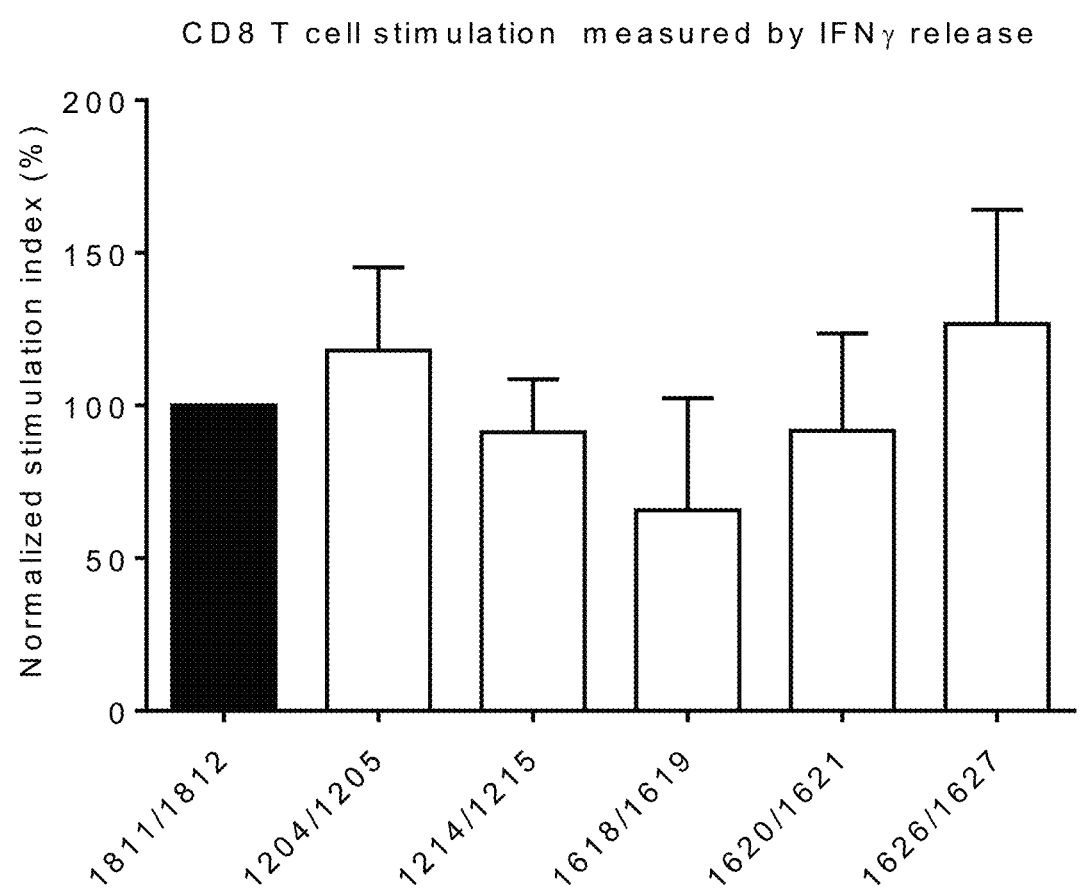
FIG. 23 shows the ability of monospecific CD137 antibodies to stimulate CD8 T cells as measured by IFNγ release.

Several clones with efficacy comparable to the reference 1811/1812 were identified (see FIG. 23).

Table 24.1 indicates the absolute IFN-γ levels induced by CD137 stimulation. However, all antibodies were not analyzed head-to-head in all donors, and the normalized SI is more relevant for comparison of the efficacy. The antibodies were evaluated in an IgG1 format, and the efficacy was measured using antibodies coated to the surface of the wells, which may influence the efficacy.

TABLE 24.1

IFN-γ production levels induced by the various antibodies.

| Clone name | Mean IFN-γ (pg/ml) | Min IFN-γ (pg/ml) | Max IFN-γ (pg/ml) | n |
|---|---|---|---|---|
| Ctrl IgG | 2502 | 337 | 8526 | 13 |
| 1204/1205 | 64430 | 13062 | 153136 | 8 |
| 1214/1215 | 51836 | 8208 | 122163 | 8 |
| 1618/1619 | 33604 | 7380 | 111196 | 8 |
| 1620/1621 | 52448 | 7727 | 123127 | 8 |
| 1626/1627 | 15097 | 4159 | 32163 | 6 |

BISPECIFIC ANTIBODIES

Example 25—Bispecific Antibodies Targeting CD137 and CTLA4—Binding to Both Targets in Dual ELISA Aim: To evaluate and confirm the ability of the bispecific antibodies to bind to both targets using ELISA.

Material and Methods

ELISA plates were coated with rhCD137-Fc (rh4-1BB, 0.5 µg/ml) over night at 4° C. Bispecific antibodies were added in dilutions and detected by addition of biotinylated CTLA-4 (1 µg/ml) followed by HRP-labelled streptavidin (0.167 µg/ml). SuperSignal Pico Luminescent was used as substrate and luminescence was measured using Fluostar Optima.

Results

The bispecific antibodies could be detected at approximately 0.1 nM, and displayed EC50 values of approximately 0.5-1 nM in this assay (see FIG. 24). The results show that the bispecific CD137-CTLA-4 antibodies can bind to both targets simultaneously Example 26—Bispecific Antibodies Targeting CD137 and CTLA4—Activation Ability in the Context of Cells Expressing CTLA-4

Aim

To determine the ability to activate immune cells in the context of cells expressing CTLA-4. The aim is to achieve higher activation (efficacy and potency) when CTLA-4 is present.

Material and Methods

Human CD8 positive T cells were obtained using negative selection (Miltenyi, human CD8+ T cell Isolation Kit, 130-096-495) of PBMC from leucocyte filters obtained from the blood bank (Lund University Hospital). CTLA-4 (Orencia, 2.5 µg/ml) and anti-CD3 (OKT-3, 3 ug/ml) was coated to the surface of a 96 well U-shaped culture plate (Nunc, VWR, #738-0147, non-tissue culture treated) over night at 4° C. Bispecific antibodies and controls were added to the wells. The IFNγ levels in the supernatant was measured after 96 h of incubation in a moisture chamber at 37° C., 5% $CO_2$.

Results

Figure 25:
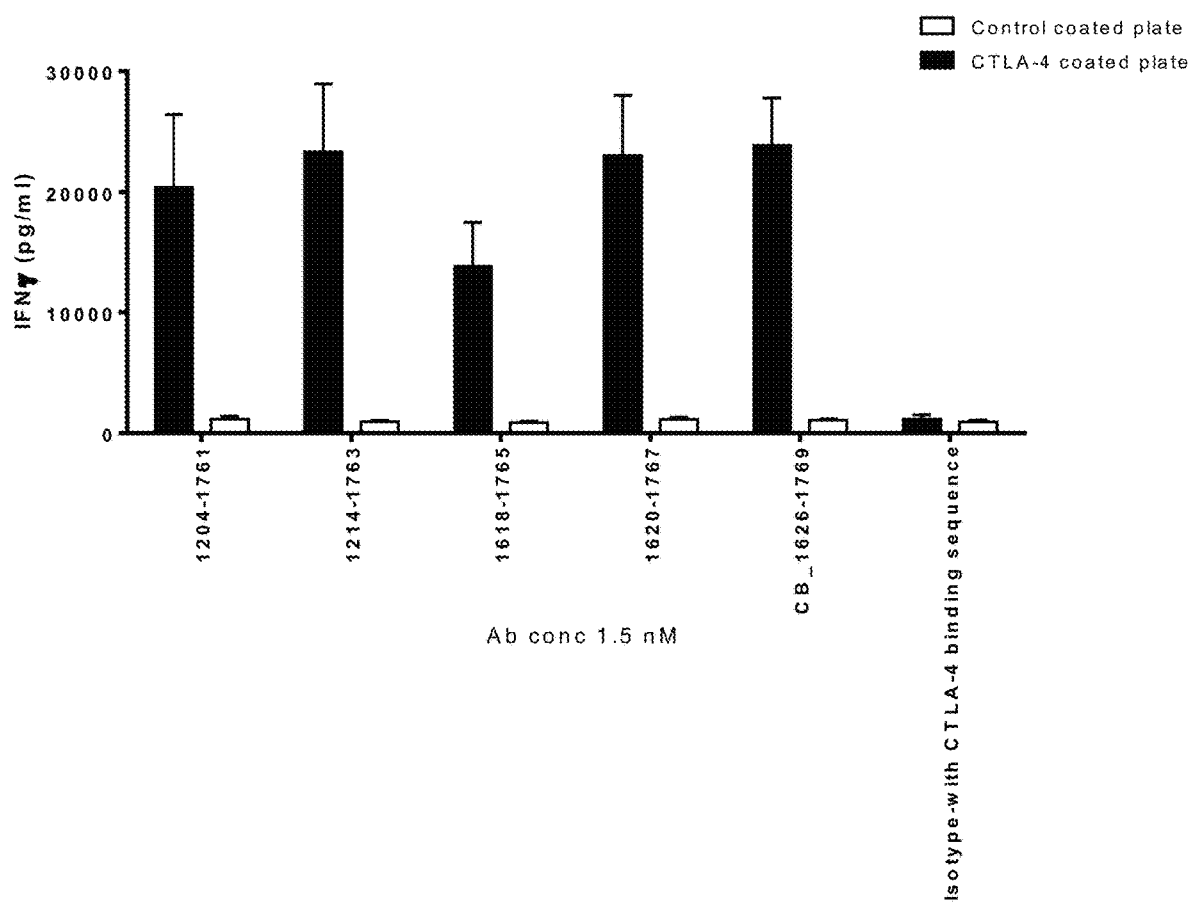
FIG. 25 shows IFNγ levels in supernatants measured from human CD8 positive T cells stimulated with 1.5 nM CD137-CTLA4 bispecific antibodies or an isotype control with CTLA-4 binding only. The assay was performed on plates coated with CD3 with or without CTLA-4.
Figure 26:
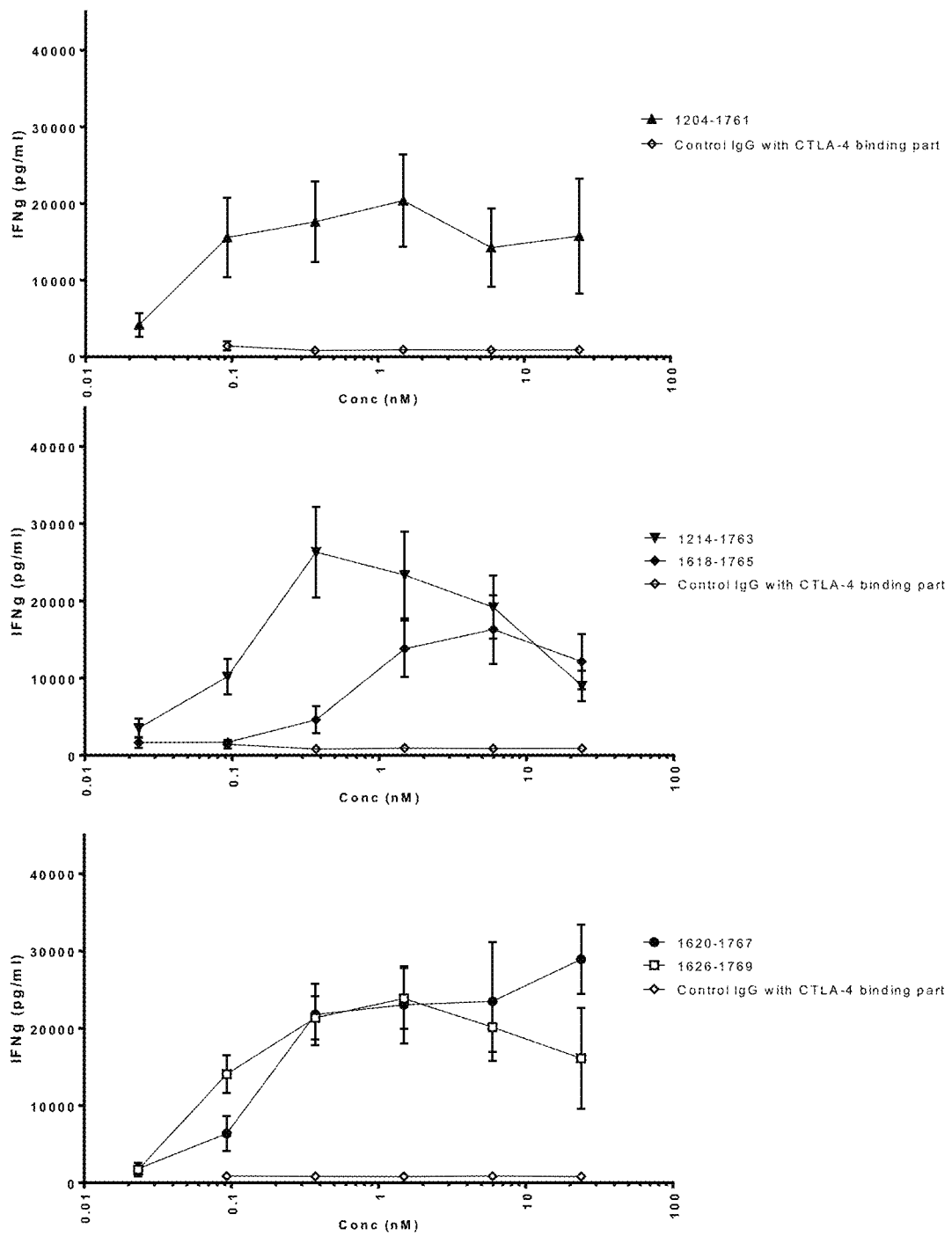
FIG. 26 shows full dilution curve of IFNγ levels in supernatants measured from human CD8 positive T cells stimulated with CD137-CTLA4 bispecific antibodies (at different concentrations) or an isotype control with CTLA-4 binding only. The assay was performed on plates coated with CD3 with CTLA-4.

The results (FIG. 25, FIG. 26) show that the bispecific antibodies activate T cells only when cultured on plates coated with CTLA-4. The in vitro assay represents an experimental model of the situation in the tumor microenvironment where CTLA-4 is relatively overexpressed. The Example 27—Synergism in Induction of ADCC by Exemplary Bispecific Antibodies Targeting CTLA4 and OX40 (Compared to Effect Of Monospecific Antibodies, Alone or in Combination)

Materials and Methods

Assessment of Antibody-Dependent Cell-Mediated Cytotoxicity (ADCC)

Jurkat cells engineered to stably express FcγRIIIa receptor (V158 variant) and an NFAT response element driving expression of firefly luciferase (Promega Corporation) were used as effector cells in the assessment of ADCC. Antibodies were titrated in duplicate wells in a 96-well opaque luminescence plate, and effector cells and target cells expressing both OX40 and CTLA4 were added in a ratio of 5:1. After 6 h incubation in a 37° C., 95% $O_2$ humidified incubator, luciferase assay substrate (Promega Corporation) was added to all wells including medium control wells (for blank subtraction), and luminescence was detected on a FLUOstar Optima microplate reader (BMG LabTech). Fold-induced ADCC was calculated as: (target lysis−blank)/(spontaneous lysis−blank). Top values were calculated based on log (agonist) vs. response (three parameters) curve fit using Prism 6.0 (Graphpad, La Jolla, Calif., USA).

Antibodies

"1166/1167" =monospecific OX40 antibody

"Control IgG with CTLA-4 binding part"=monospecific CTLA4 binding domain fused to an IgG protein "1166/1261"=exemplary bispecific antibody targeting OX40 and CTLA4 (containing the identical OX40 and CTLA-4 binding part as the monospecific binders described above).

"Ctrl IgG"=negative isotype control

Results

Exemplary Bispecific Antibody 1166/1261 Exhibits Superior Induction of ADCC

Figure 27:
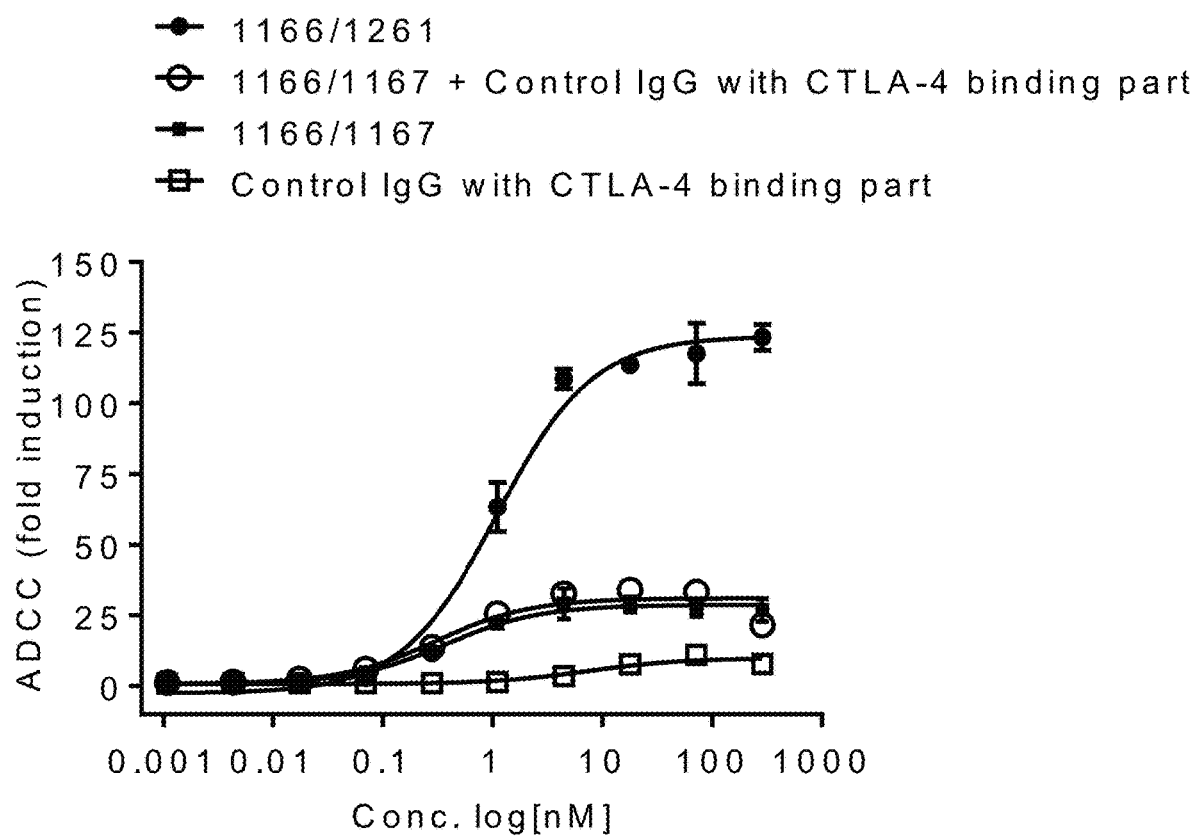
FIG. 27 shows induction of ADCC at different concentration by monospecific CTLA-4 (Control IgG with CTLA-4 binding part, i.e. domain) and OX40 (1166/1167) binding molecules, alone and in combination, compared to ADCC induced by an exemplary bispecific antibody targeting CTLA-4 and OX40.

As shown in FIG. 27, detectable levels of ADCC were induced by all tested components. The negative isotype control did not induce any ADCC (data not shown). Most notably, the bispecific 1166/1261 antibody induced ~123-fold ADCC compared to control. The monospecific OX40 antibody (1166/1167) induced ~29-fold and the monospecific CTLA-4 binding domain (62/376) induced ~10-fold ADCC, whereas the mixture of the two monospecific components (1166/1167+62/376) induced ~31-fold ADCC.

There is thus an unexpected and marked synergy obtained by the bispecific molecule binding to OX40 and CTLA-4.

Example 28—Bispecific Antibodies Targeting OX40 and CTLA4—Specific Binding to Cells Expressing Both OX40 and CTLA4

Background

The aim of this study was to determine the binding efficacy and EC50 of 1166/1261 and the corresponding monospecific binding entities to cells expressing both OX40 and CTLA4 using flow cytometry. The bispecific antibody is designed to bind both OX40 and CTLA4 simultaneously. For this purpose, we used transfected CHO cells with a stable expression of our targets. CHO P4 cells have a high expression level of both OX40 and CTLA4.

Methods and Results

Double-transfected CHO cells expressing both OX40 and CTLA4 were originally sorted by FACS (Beckton Dickinson) into a cell pool expressing high levels of both targets (denoted CHO P4). Target expression was kept stable by culturing the cells under selection pressure of geneticine and zeocine. Untransfected CHO wild-type cells were used as controls.

Cells were stained with decreasing concentrations of 1166/1261 (an exemplary bispecific antibody targeting OX40 and CTLA4), or the two monospecific binders 1166/1167 (OX40 specific monoclonal antibody) and Control IgG with CTLA-4 binding part (monospecific CTLA4 binding IgG fusion protein) (200 nM-0.0034 nM), followed by PE-conjugated anti-human IgG. Fluorescence was detected using a FACSverse instrument, and the acquisition was analysed using FlowJo software. The median fluorescent intensity (MFI) was determined for each staining.

Figure 28:
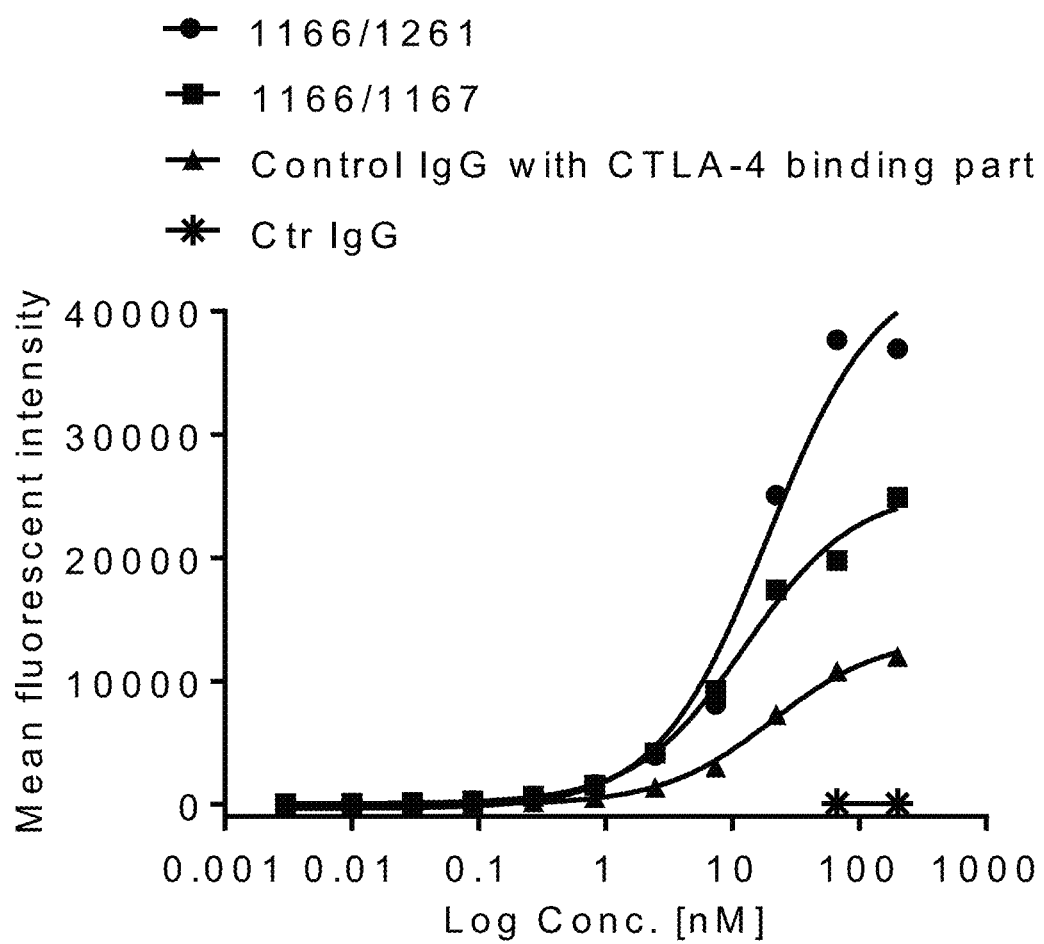
FIG. 28. CHO cells expressing both CTLA-4 and OX40 were stained with decreasing concentrations of 1166/1261, or the two monospecific binders 1166/1167 (OX40 specific monoclonal antibody) and control IgG with CTLA-4 binding part (monospecific CTLA4 binding IgG fusion protein) (200 nM-0.0034 nM), followed by PE-conjugated anti-human IgG. Fluorescence was detected using flow cytometry. 'Ctr IgG' is a negative isotype control.

Binding efficacy curves for CHO P4 are presented in FIG. 28 (one representative experiment out of three). 1166/1261 binds to cells with high expression of OX40 and CTLA4 better than 1166/1167 or the Control IgG with a CTLA-4 binding entity. This is probably an additive effect of 1166/1261 being able to bind two targets simultaneously.

Example 29—Bispecific Antibodies Targeting OX40 and CTLA4—Dual Binding of Cells Expressing OX40 and CTLA4 Measured by Flow Cytometry Aim Measure simultaneous binding by 1166/1261 to both OX40 and CTLA4 over-expressed on cells by measuring the number of aggregated cells using flow cytometry.

Materials and Methods

CHO-OX40 cells and HEK-CTLA4 cells were intracellularly stained with the fluorescent dyes PKH-67 (green fluorescent dye) respectively PKH-26 (red fluorescent dye) (Sigma-Aldrich). After verifying homogenously stained cell population, the cells were mixed and incubated with either 1166/1261 (an exemplary bispecific antibody targeting OX40 and CTLA4) or a combination of the two monoclonal antibodies 1166/1167 (a monospecific anti-OX40 antibody) and a control IgG comprising a CTLA4-binding domain. After staining the cells were immediately fixed and the number of aggregated, double-positive cells were quantified using FACS-verse (BD biosciences). Data analyses and non-linear regression was performed using Graph Pad Prism v6.

Results and Conclusions

Figure 29:
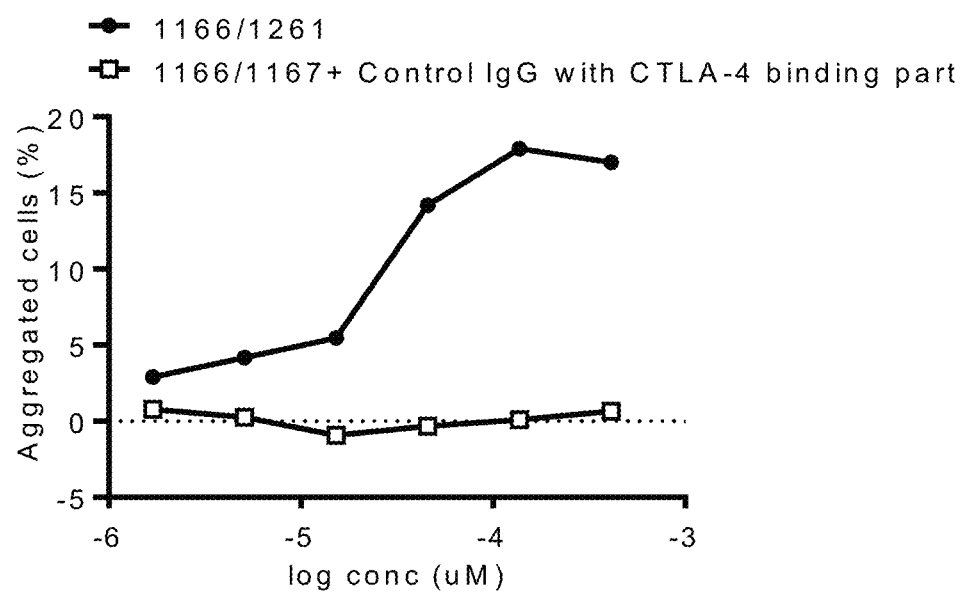
FIG. 29. HEK-CTLA4 and CHO-OX40 were stained with PKH26 and PKH67 respectively and incubated with 1166/1261 or a combination of the two monospecific OX40 and CTLA-4 binding molecules (1166/1167 and Control IgG with CTLA-4 binding part). The percentage of double-positive/aggregated cells were quantified using flow cytometry (representative experiment).

Exemplary bispecific antibody 1166/1261 increases the number of aggregated cells with increasing concentration (FIG. 29) (one representative experiment out of two).

Example 30—Bispecific Antibodies Targeting OX40 and CTLA4—Pharmacokinetics in Mice Material and Methods Antibodies 1166/1261 (an exemplary bispecific antibody targeting OX40 and CTLA4)

1166/1167 (a monospecific control antibody targeting OX40)

In Vivo Studies

Female C57BL/6 (7-8 w) mice from Taconic's Denmark were used in the experiments. All experiments were done by approval of Malmö/Lund ethical committee.

The mice were injected intraperitoneally with 100 μg of each antibody and blood was drawn either via vena saphena or at termination via vena cava into heparinized tubes after 0 h, 1 h, 4 h, 8 h, 24 h, 72 h and after 1 week. 3 mice were used for each time-point. Blood was spun at 2500 rpm for 30 min and plasma was frozen to −80° C. for further analysis.

Assays for Determination of 1166/1261 and 1166/1167 Levels in Plasma

Two different assays were used. A single target ELISA (ELISA1) and a dual ELISA (ELISA2). Briefly the assays consisted of the following steps. White high-binding flat-bottom, LIA plates (Greiner Bio-One, Austria) were coated over night with 0.8 μg/mL human OX40-Fc (RnD Systems, MN, USA). After washing with Washing buffer (phosphatase buffer saline supplemented with 0.05% Tween 20 (PBST), Medicago, Sweden) the wells were blocked using PBST with 2% bovine serum albumin (BSA) (Merck, Germany) for 1 hour at ambient room temperature (ART) with shaking and washed again before plasma samples diluted 1:200 and 1:5000 in assay buffer (PBST+0.5% BSA) together with calibration curve samples (1166/1261, conc. 6-0.0012 μg/mL) were added. After incubation at ART for 1 h with shaking and subsequent washing, secondary reagent was added, consisting of either human anti-kappa-antibody horse radish peroxidase conjugated (HRP) (AbD Serotec, UK) for the single target ELISA or biotinylated human CTLA-4-Fc (Orencia) at 1 μg/mL followed by streptavidin-HRP (Thermo Fisher Scientific, MN, USA) according to the manufacturer's instructions for the dual ELISA. Signal was obtained using HRP substrate SuperSignal Pico Luminescence (Thermo Fisher Scientific). Luminescence measurements were collected after 10 minutes incubation in darkness with shaking using a Flurostar Optima (MBG Labtech, Germany).The data was analyzed by using GraphPad Prism program.

Results

Figure 30:
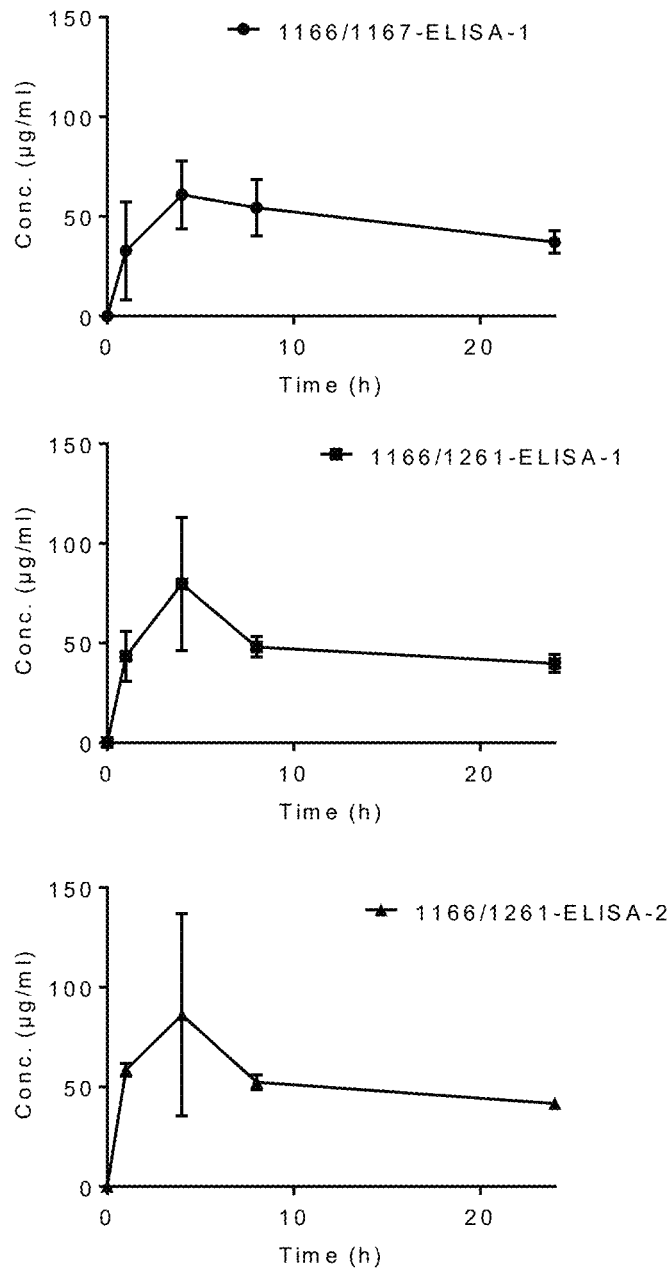
FIG. 30. Plasma levels of the bispecific OX40-CTLA-4 antibody 1166/1261 and the monospecific OX40 antibody 1166/1167 measured at different time points following administration. Two different ELISA methods were used, ELISA-1, where OX40 was coated on the wells and anti-Fc was used to detect binding and ELISA-2, where OX40 was coated on the wells and biotinylated CTLA-4 was used for detection.

Samples collected at the different time points after injection with 1166/1261 and 1166/1167 were analyzed with only single target ELISA or single target and dual ELISA for determination of the plasma levels of 1166/1261 and 1166/1167 respectively. The results show that the levels of 1166/1261 and 1166/1167 in plasma increased around the first 4 hours after peritoneal injection and then reduced (FIG. 30 upper panel). Detectable levels of both 1166/1261 and 1166/1167 are present in plasma after one week (FIG. 30 middle and lower panels).

The levels of 1166/1261 in plasma are similar to the levels obtained for the monoclonal antibody 1166/1167 indicating that 1166/1261 exhibits a good half-life in vivo, comparable to that of an equivalent monospecific anti-OX40 antibody.

References

Hemerle T., Wulhfard S., Neri D., (2012) A critical evaluation of the tumor-targeting properties of bispecific antibodies based on quantitative biodistribution data. Protein Engineering and Design, 25, pp 851-854.

Example 31—Bispecific Antibodies Targeting OX40 and CTLA4—In Vivo Anti-Tumor Effect in HT-29 Colon Cancer Model Summary The anti-tumor effect of 1166/1261 (an exemplary bispecific antibody targeting OX40 and CTLA4) was investigated using hPBMC humanized immunodefiecient mice and subcutaneous tumor models of HT-29 colon carcinoma.

1166-1261 demonstrated statistically significant tumor volume inhibition.

Material and Methods

Female SCID-Beige mice (6-9 w) from Taconic's Denmark were used in the experiments. All experiments were done by approval of Malmö/Lund ethical committee.

HT-29 colon cancer were obtained from ATCC and cultivated according to ATCC recommendations. The HT-29 cell line growing in log phase was injected subcutaneously ($4 \times 10^6$ cells in 100-200 μL at day 0 (D0)). Human PBMC ($7 \times 10^6$ in 200 μL) isolated from leukocyte concentrates was injected intraperitoneally at the same day. Intraperitoneal treatments (667 pmol) were done at days 6, 13, and 20.

Leukocyte concentrates were obtained from Lund University Hospital.

Tumor was measured with a caliper in width, length and height of which the tumor volume calculated (w/2×l/2×h/2×pi×(4/3)). The animals were terminated before the tumor volume reached 2 cm$^3$, at wounding, or affected health of the mice.

The data were analyzed by Mann-Whitney test using the GraphPad Prism program. Responder donors were considered those donors that were responsive to the reference antibody 1874. Minimum of 10% average tumor inhibition during the exponential tumor growth period was considered as a response.

Results

Figure 31:
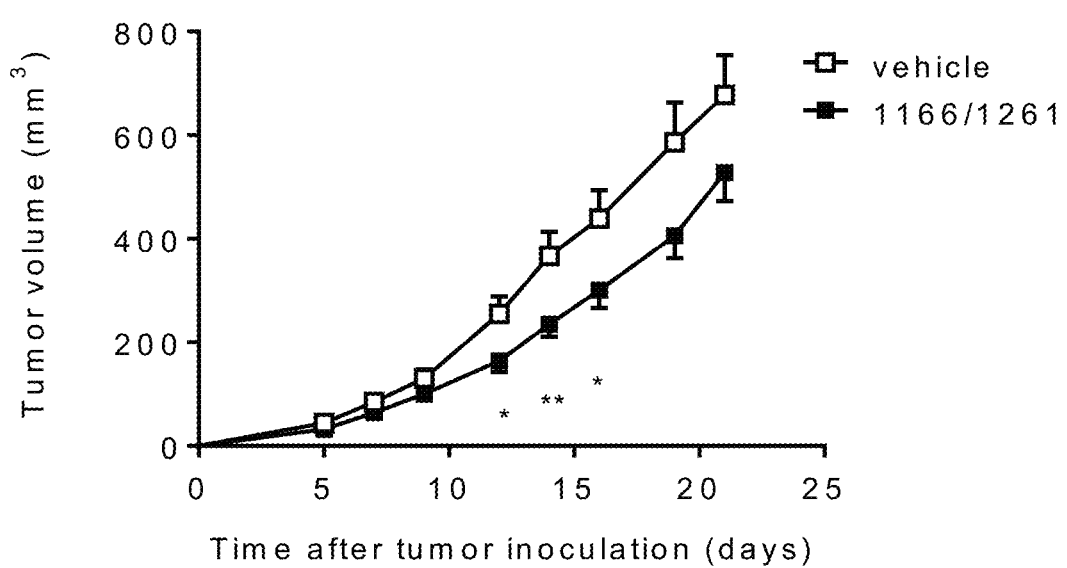
FIG. 31. HT-29 colon carcinoma cells ($4 \times 10^6$) were inoculated subcutaneously to the right hind flank/back at day 0. Human PBMC cells ($7 \times 10^6$) were administered intraperitoneally on the same day. The treatments were done by intraperitoneal injections (667 nmol/dose) on days 6, 13, and 20. N(mice)=5/donor, n(donor=4), pooled data from HT29 responders.

Pooled data from mice engrafted with responder donors (4 donors from two separate experiments) demonstrated statistically significant anti-tumor efficacy at days 12-16 in the form of inhibition of tumor growth when treated with the 1166/1261 antibody (p=0.0469 to p=0.0074, Mann-Whitney non parametric, 2-tail) in comparison to the vehicle group (ZZ). The percentage of tumor volume inhibition ranged from 22-36% with 1166/1261 between days 10 and 21 (see FIG. 31 and Table 31.1).

In conclusion, the anti-tumor effect of 1166/1261 was investigated using hPBMC humanized immunodeficient mice and subcutaneous tumor models of HT-29 colon carcinoma. 1166/1261 demonstrated statistically significant tumor volume inhibition.

TABLE 31.1

Statistical analysis and percent tumor inhibition

| Day after tumor inoculation | Tumor growth inhibition (tumor volume) compared to vehicle (%) | p-value (Mann-Whitney 2-tail) |
|---|---|---|
| D10 | 22.8 | 0.1298 |
| D12 | 35.4 | 0.0315 |
| D14 | 35.9 | 0.0074 |
| D16 | 31.5 | 0.0469 |
| D19 | 30.8 | 0.1059 |
| D21 | 22.1 | 0.1067 |

Example 32—Bispecific Antibodies Targeting OX40 and CTLA4—In Vivo Anti-Tumor Effect in Raji Lymphoma Model Summary The anti-tumor effect of 1166/1261 (an exemplary bispecific antibody targeting OX40 and CTLA4) was investigated using hPBMC humanized immunodeficient mice and subcutaneous tumor models of Raji B-cell lymphoma.

1166/1261 demonstrated statistically significant tumor volume inhibition.

Material and Methods

Female SCID-Beige mice (6-9 w) from Taconic's Denmark were used in the experiments. All experiments were done by approval of Malmö/Lund ethical committee.

Raji B-cell lymphoma was obtained from ATCC and cultivated according to ATCC recommendations. The Raji cell line growing in log phase was injected subcutaneously ($10 \times 10^6$ cells) together with human PBMC ($10 \times 10^6$ in 200 µL), isolated from buffy coats. Intraperitoneal treatments (667 pmol) were done at days 0, 7, and 14.

Buffy coats were obtained from Kalmar University Hospital.

Tumor size was measured with a caliper in width, length and height of which the tumor volume calculated (w/2×l/2×h/2×pi×(4/3)). The animals were terminated before the tumor volume reached 2 cm$^3$, at wounding, or affected health of the mice.

The data were analyzed by Mann-Whitney test using the GraphPad Prism program. Responder donors were considered those donors that were responsive to the reference antibody 1874. Minimum of 10% average tumor inhibition during the exponential tumor growth period was considered as a response.

Results and Conclusions

Pooled data from experimental groups with responding donors, the bispecific 1166/1261 antibody demonstrated statistically significant anti-tumor efficacy at days 14 and 21 (p=0.0068 and p=0.0288, Mann-Whitney, 2-tail) in comparison to the vehicle (Table 32.1).

TABLE 32.1

Statistical analysis and percent tumor inhibition

| Day after tumor inoculation | Tumor volume in vehicle-treated animals | Tumor volume in animals treated with 1166/1261 | Tumor growth inhibition (tumor volume) compared to vehicle (%) | p-value (Mann-Whitney 2-tail) |
|---|---|---|---|---|
| D10 | 14.2 | 13.8 | 6.1 | 0.6842 |
| D12 | 35.7 | 21.5 | 39.9 | 0.0603 |
| D14 | 61.8 | 33.6 | 45.7 | 0.0068 |
| D17 | 105.3 | 76.0 | 27.8 | 0.3527 |
| D19 | 205.1 | 133.3 | 35 | 0.0524 |
| D21 | 314.8 | 187.0 | 40.6 | 0.0288 |
| D24 | 467.5 | 299.9 | 37.2 | 0.054 |
| D26 | 529.7 | 360.1 | 32 | 0.063 |

The invention claimed is:

1. An antibody or antigen-binding fragment thereof specific for CD137, wherein the antibody or antigen binding fragment thereof comprises a heavy chain variable region which comprises three complementarity determining regions (CDRs) of SEQ ID NO: 185 and a light chain variable region which comprises three CDRs of SEQ ID NO: 187.

2. The antibody or antigen-binding fragment thereof of claim 1, wherein the three CDRs of the heavy chain variable region comprise SEQ ID NOs: 209, 214, and 219, and wherein the three CDRs of the light chain variable region comprise SEQ ID NOs: 80, 81, and 224.

3. The antibody or antigen-binding fragment thereof of claim 1, wherein the heavy chain variable region comprises SEQ ID NO: 185, and wherein the light chain variable region comprises SEQ ID NO: 187.

4. The antibody or antigen-binding fragment thereof of claim 1, wherein the antigen-binding fragment is selected from the group consisting of: an Fv fragment, a single Fv fragment, a disulphide-bonded Fv fragment, a Fab-like fragment, a Fab fragment, a Fab' fragment, a F(ab)$_2$ fragment, and domain antibodies.

5. The antibody or antigen-binding fragment thereof of claim 1 comprising a human Fc region.

6. The antibody or antigen-binding fragment thereof of claim 5, wherein said human Fc region is an IgG1, IgG2, IgG3 or IgG4 Fc region.

7. The antibody or antigen-binding fragment thereof of claim 1 which binds to human CD137 with a $K_D$ of less than $10 \times 10^{-9}$M.

8. The antibody or antigen-binding fragment thereof of claim 1 which induces an increase in the activity of a CD8+ T cell.

9. The antibody or antigen-binding fragment thereof of claim 8, wherein said increase in CD8+ T cell activity is an increase in proliferation, IFN-γ production and/or IL-2 production by the CD8+ T cell.

10. The antibody or antigen-binding fragment thereof of claim 1 conjugated to an additional therapeutic moiety.

11. The antibody or antigen-binding fragment thereof of claim 10, wherein said additional therapeutic agent is a cytotoxic moiety or a drug.

12. A composition comprising the antibody or antigen-binding fragment thereof of claim 1 and at least one pharmaceutically acceptable diluent or carrier.

13. A bispecific antibody comprising a first antibody or antigen-binding fragment thereof specific for a first epitope and a second antibody or antigen-binding fragment thereof specific for a second epitope, wherein said first antibody or antigen-binding fragment thereof is the antibody or antigen-binding fragment thereof of claim 1.

14. The bispecific antibody of claim 13, wherein said first antibody or antigen-binding fragment thereof and said second antibody or antigen-binding fragment thereof are joined via a peptide linker.

15. The bispecific antibody of claim 14, wherein said peptide linker comprises the amino acid sequence SGGGGSGGGGS (SEQ ID NO: 47), SGGGGSGGGGSAP (SEQ ID NO: 48), NFSQP (SEQ ID NO: 49), KRTVA (SEQ ID NO: 50), GGGGSGGGGSGGGGS (SEQ ID NO: 144) or (SG)m, where m=1 to 7.

* * * * *